US012714752B2

(12) United States Patent
Robillard et al.

(10) Patent No.: US 12,714,752 B2
(45) Date of Patent: Aug. 25, 2026

(54) COMPOUNDS COMPRISING A LINKER FOR INCREASING TRANSCYCLOOCTENE STABILITY

(71) Applicant: Tagworks Pharmaceuticals B.V., Eindhoven (NL)

(72) Inventors: Marc Stefan Robillard, Eindhoven (NL); Raffaella Rossin, Eindhoven (NL); Ronny Mathieu Versteegen, Eindhoven (NL)

(73) Assignee: Tagworks Pharmaceuticals B.V., Nijmegen (NL)

( * ) Notice: Subject to any disclaimer, the term of this patent is extended or adjusted under 35 U.S.C. 154(b) by 1047 days.

(21) Appl. No.: 17/052,925

(22) PCT Filed: May 6, 2019

(86) PCT No.: PCT/NL2019/050272
§ 371 (c)(1),
(2) Date: Nov. 4, 2020

(87) PCT Pub. No.: WO2019/212357
PCT Pub. Date: Nov. 7, 2019

(65) Prior Publication Data
US 2021/0308207 A1 Oct. 7, 2021

(30) Foreign Application Priority Data
May 4, 2018 (EP) .................................... 18170937

(51) Int. Cl.
*A61K 38/07* (2006.01)
*A61K 47/54* (2017.01)
(Continued)

(52) U.S. Cl.
CPC .......... *A61K 47/6803* (2017.08); *A61K 38/07* (2013.01); *A61K 47/545* (2017.08);
(Continued)

(58) Field of Classification Search
CPC ................ A61K 38/07; A61K 47/6889; A61K 47/6851; A61K 47/545; A61K 47/6817; A61P 35/00
See application file for complete search history.

(56) References Cited

U.S. PATENT DOCUMENTS

| | | | |
|---|---|---|---|
| 4,486,414 | A | 12/1984 | Pettit |
| 4,486,444 | A | 12/1984 | Shepard |

(Continued)

FOREIGN PATENT DOCUMENTS

| | | |
|---|---|---|
| WO | 2010/051530 | 5/2010 |
| WO | 2010/119382 | 10/2010 |

(Continued)

OTHER PUBLICATIONS

Rossin R, van Duijnhoven SM, Ten Hoeve W, Janssen HM, Kleijn LH, Hoeben FJ, Versteegen RM, Robillard MS. Triggered Drug Release from an Antibody-Drug Conjugate Using Fast "Click-to-Release" Chemistry in Mice. Bioconjug Chem. Jul. 20, 2016;27(7): 1697-706. (Year: 2016).*

(Continued)

*Primary Examiner* — Clinton A Brooks
*Assistant Examiner* — Josmalen M. Ramos-Lewis
(74) *Attorney, Agent, or Firm* — Foley & Lardner LLP

(57) ABSTRACT

Disclosed are compounds having a linker for increasing trans-cyclooctene stability. The linker of the invention is a three-arm linker. In some embodiments, one arm of the linker is attached to a trans-cyclooctene moiety, another arm is attached to a compound selected from the group consisting of antibodies, proteins, peptides, and peptoids, and the third arm extends into the solution.

18 Claims, 14 Drawing Sheets

Specification includes a Sequence Listing.

(51) Int. Cl.
*A61K 47/68* (2017.01)
*A61P 35/00* (2006.01)
(52) U.S. Cl.
CPC .... *A61K 47/68031* (2023.08); *A61K 47/6817* (2017.08); *A61K 47/6851* (2017.08); *A61K 47/6889* (2017.08); *A61P 35/00* (2018.01)

(56) References Cited

U.S. PATENT DOCUMENTS

| | | | |
|---|---|---|---|
| 4,879,278 | A | 11/1989 | Pettit et al. |
| 4,986,988 | A | 1/1991 | Pettit et al. |
| 5,138,036 | A | 8/1992 | Pettit et al. |
| 5,198,560 | A | 3/1993 | Kadow et al. |
| 5,410,024 | A | 4/1995 | Pettit et al. |
| 5,504,191 | A | 4/1996 | Pettit et al. |
| 5,521,284 | A | 5/1996 | Pettit et al. |
| 5,530,097 | A | 6/1996 | Pettit et al. |
| 5,599,902 | A | 2/1997 | Pettit et al. |
| 5,635,483 | A | 6/1997 | Pettit et al. |
| 5,663,149 | A | 9/1997 | Pettit et al. |
| 5,665,860 | A | 9/1997 | Pettit et al. |
| 5,780,588 | A | 7/1998 | Pettit et al. |
| 6,034,065 | A | 3/2000 | Pettit et al. |
| 6,239,104 | B1 | 5/2001 | Pettit et al. |
| 6,323,315 | B1 | 11/2001 | Pettit et al. |
| 7,005,132 | B2 | 2/2006 | Cubicciotti |
| 9,421,274 | B2 | 8/2016 | Robillard et al. |
| 9,427,482 | B2 | 8/2016 | Rossin et al. |
| 9,463,256 | B2 | 10/2016 | Lub et al. |
| 9,913,921 | B2 | 3/2018 | Robillard et al. |
| 9,931,408 | B2 | 4/2018 | Robillard et al. |
| 10,004,810 | B2 | 6/2018 | Robillard et al. |
| 10,376,594 | B2 | 8/2019 | Robillard et al. |
| 10,927,139 | B2 | 2/2021 | Robillard et al. |
| 10,967,069 | B2 | 4/2021 | Robillard et al. |
| 2009/0023916 | A1 | 1/2009 | Fox et al. |
| 2015/0297741 | A1 | 10/2015 | Robillard |

FOREIGN PATENT DOCUMENTS

| | | | |
|---|---|---|---|
| WO | 2010/119389 | 10/2010 | |
| WO | 2012/012612 | 1/2012 | |
| WO | 2012/049624 | 4/2012 | |
| WO | 2012/085789 | 6/2012 | |
| WO | 2012/156919 | 11/2012 | |
| WO | 2012156918 A1 | 11/2012 | |
| WO | 2014/065860 | 5/2014 | |
| WO | 2014/081301 | 5/2014 | |
| WO | 2014/081303 | 5/2014 | |
| WO | 2016/025480 | 2/2016 | |
| WO | 2018/004338 | 1/2018 | |
| WO | WO-2018004338 A1 * | 1/2018 | .......... C07D 257/08 |

OTHER PUBLICATIONS

Ferreira VFC, Oliveira BL, et al In Vivo Pretargeting Based on Cysteine-Selective Antibody Modification with IEDDA Bioorthogonal Handles for Click Chemistry. Bioconjug Chem. Jan. 20, 2021;32(1):121-132. (Year: 2021).* van Duijnhoven SM, Rossin R, van den Bosch SM, Wheatcroft MP, Hudson PJ, Robillard MS. Diabody Pretargeting with Click Chemistry In Vivo. J Nucl Med. Sep. 2015;56(9):1422-8. doi: 10.2967/jnumed. 115.159145. (Year: 2015).*

Rossin R, van Duijnhoven SM, Ten Hoeve W, Janssen HM, Kleijn LH, Hoeben FJ, Versteegen RM, Robillard MS. Triggered Drug Release from an Antibody-Drug Conjugate Using Fast "Click-to-Release" Chemistry in Mice. Bioconjug Chem. Jul. 20, 2016;27(7):1697-706. doi: 10.1021/acs.bioconjchem.6b00231. (Year: 2016).*

Ajay et al., "Diversity-Oriented Synthesis of cis-3,4-Dihydroxylated Piperidine and Its Higher Saturated and Unsaturated Homologues from d-Ribose and Their Glycosidase-Inhibition Study", Synlett, 2016, Vo. 27, No. 19, pp. 2721-2725.

Alley, S; Okeley N; Senter, PD; et al. "Antibody-drug conjugates: targeted drug delivery for cancer." Current Opinion in Chemical Biology, (2010), 14:529-537.

Atfah, M., "Diels-Alder Reactions of 3,6-Diphenyl-1,2,3,4,5-Tetrazinenad 3,6-Di(2-Pyridyl)-1,2,4,5,-tetrazine with some 1-Morpholinocycloalkenes," J. Heterocyclic Chem, 26, 717 (1989).

Audebert, P. et al. "Synthesis of new substituted tetrazines: electrochemical and spectroscopic properties". New Journal Chem. (2004), 28, 387-392.

Banker, G.S. et al, "B. Prodrugs", Modern Pharmaceutics, 3ed, Marcel Dekker, New York, 1996, p. 451 and 596.

Blackman, M.L. et al. "The tetrazine ligation: fast bioconjugation based on inverse-electron-demand Diels-Alder reactivity". Journal of American Chemical Society, (2008), 130(41), 13518-13519.

Blencowe, C.A. et al. "Self-immolative linkers in polymeric delivery systems". Polymer Chemistry, (2011 ), 2, 773-790.

Cere, V. et al. "Olefin Inversion. Protection of the sulfide function in the stereospecific synthesis of trans-Thiacyclooct-4-ene". Journal of Organic Chemistry, (1980), 45, 261-264.

Choe, Y.H. et al. "Anticancer drug delivery systems: multi-loaded N4-acyl poly(ethylene glycol) prodrugs of ara-C. II. Efficacy in ascites and solid tumors". Journal of Controlled Release, (2002), 79, 55-70.

Devaraj, N.K. et al. "Fast and sensitive pretargeted labeling of cancer cells via tetrazine/trans-cyclooctene cycloaddition". Angewandte Chemie International Edition, (2009), 48(38): 7013-1016.

Devaraj, N.K. et al. "Tetrazine-based cycloadditions: Application to Pretargeted live cell imaging", Bioconjugate Chem., (2008), 19(12), 2297-2299.

Geldard, J.F. et al. "The organic chemistry of a new weak field tridentate chelating agent. 3,5-Di(2-pyridyl)-1,2,4-triazole". Journal Organic Chemistry. (1965), 30, 318-319.

Grakauskas, V.A. et al. "Some 3,6-unsymmetrically disubstituted 1,2,4,5-Tetrazines". Journal American Chemical Society, (1958), 80, 3155-3159.

Greenwald, R.B. et al. "Drug delivery systems employing 1,4-or 1,6-elimination: Poly(ethylene glycol) prodrugs of amine-containing compounds". Journal Med. Chem. (1999), 42, 3657-3667.

Haba, K. et al. "Single-triggered trimeric prodrugs". Angewandte Chemie International Edition. (2005), 44, 726-730.

Haun, Jered B. et al, "Bioorthogonal Chemistry Amplifies Nanoparticle Binding and Enhances the Sensitivity of Cell Detection", Nature Nanotechnology, vol. 5, Sep. 2010, pp. 660-665.

Ingold, C.K. et al. "The Nature of the Alternating effect in carbon chains. Part XXII. An attempt further to define the probable mechanism of orientation in aromatic substitution". Journal Chem. Society. (1927), 2918-2926.

International Preliminary Report on Patentability for International Application No. PCT/IB2012/052446, Nov. 19, 2013, 10 Pages.

International Search Report and Written Opinion for Corresponding International Application No. PCT/NL2013/050850 (9 Pages) (Feb. 11, 2014).

International Search Report and Written Opinion for Corresponding International Application No. PCT/NL2019/050271 (10 Pages) ( Oct. 23, 2019).

International Search Report and Written Opinion for Corresponding International Application No. PCT/NL2020/050386 (17 Pages) (Nov. 5, 2020).

International Search Report and Written Opinion for Corresponding International Application No. PCT/NL2020/050387 (9 Pages) (Aug. 25, 2020).

International Search Report and Written Opinion for Corresponding International Application No. PCT/NL2020/050388 (9 Pages) (Aug. 19, 2020).

International Search Report and Written Opinion for International Application No. PCT/IB2012/052446, Oct. 23, 2012, 14 Pages.

Kaim, W. et al. "The new tetrafunctional (pi) acceptor ligand 3,6-Bis(2'-pyrimidyl)-1,2,4,5-tetrazine(bmtz): Diruthenium complexes of bmtz and of its 1,4-Dihydro form". Z. Naturforsch, 50b, 123-127 (1995).

(56) References Cited

OTHER PUBLICATIONS

Klopman, G. et al. "Computer automated log P calculations based on an extended group contribution approach". Journal Chem. Inf. Comput. Sci. (1994), 34, 752-781.
Mohsin, H. et al. "Radiolanthanide-labeled monoclonal antibody CC49 for radioimmunotherapy of cancer: biological comparison of DOTA conjugates and 149Pm, 166Ho, and 177Lu". Bioconjugate Chem. (2006), 17, 485-492.
Prevost, M. et al. "Insertions of silylenes into vinyl epoxides: Diastereoselective synthesis of functionalized, optically active trans-Dioxasilacyclooctenes". Journal of the American Chemical Society, (2009), 131, 14182-14182.
Rossin et al., "Triggered Drug Release from an Antibody—Drug Conjugate Using Fast "Click-to-Release" Chemistry In Mice", Bioconjugate Chemistry, 2016, vol. 27, No. 7, pp. 1697-1706.
Rossin, R. et al. "In vivo chemistry for pretargeted tumor imaging in live mice". Angewandte Chemie International Edition, (2010), 49, 3375-3378.
Thakur, A. et al. "Cancer therapy with bispecific antibodies: Clinical experience". Current Opinion in Molecular Therapeutics, (2010), 12(3), 340-349.
Thalhammer, F. et al. Reaktivitat Einfacher Offenkettiger Und Cyclischer Dienophile Bei Diels-alder-reaktionen mil inversem elektronenbedarf. Tetrahedron Letters (1990), 31 (47), 6851-6854. (See English abstract.).
Thomas, J., et al., "Proligands with protease-regulated binding activity identified from cell-displayed prodomain libraries," Protein Science 2009, vol. 18:2053-2059.
Thompson, S. et al. "The construction and in vitro testing of photo-activalable cancer targeting folaled anti-CD3 conjugates". Biochemical and Biophysical Research Communications, (2008), 366, 526-531.
Tranoy-Opalinski, I. et al. "Design of self-Immolative linkers for tumour activated prodrug therapy". Anti-Cancer Agents in Medicinal Chemistry, (2008), 8, 618-637.
Van Brakel, R. et al. "A doxorubicin prodrug activated by the staudinger reaction". Bioconjugate Chem. (2008), 19, 714-718.
Viswanadhan, V.N. et al. "Atomic physicochemical parameters for three dimensional structure directed quantitative structure-activity relationships. 4. Additional parameters for hydrophobic and dispersive interactions and their application for an automated superposition of certain naturally occuring nucleoside antibiotics". Journal Chem. Inf. Comput. Sci. (1989), 29, 163-172.
White et al., "Synthesis of Polyhydroxylated Pyrrolizidine Alkaloids of the Alexine Family by Tandem Ring-Closing Metathesis-Transannular Cyclization. (+)-Australine", Journal of Organic Chemistry, 2000, vol. 65, No. 26, pp. 9129-9142.
Whitham, G.H. et al. "trans-Cycloalkenes. Part I. (1 RS,2RS)-Irans-Cyclo-oct-2-en-1-ol". Journal Chem. Society, (1971), 883-886.
Whitham, G.H. et al. "trans-Cycloalkenes. Part II. Application of the Dioxolan Olefin Synthesis to the Stereospecific Formation of trans-Cyclo-octene Derivatives. (1 SR,2RS)-Irans-Cyclo-oct-2-en-1-ol". Journal Chem. Society, (1971), 886-890.
Whitham, G.H. et al. "trans-Cycloalkenes. Part III. Stereochemistry and mechanism of some reactions of diastereoisomeric 3-substituted trans-cyclo-octenes". Journal Chem. Society, (1971), 891-896.
Wiessler, Manfred; et al. "Extension of the PNA world by functionalized PNA monomers eligible candidates for inverse Diels Alder Click Chemistry", Int. Journal of Medical Science, Jun. 27, 2010, 7(4):213-223.
Wijnen, J.W. et al. "Substitute effects on an inverse electron demand hetero diels-alder reaction in aqueous solution and organic solvents: cycloaddition of substituted styrenes to Di(2-pyridyl)-1,2,4,5-tetrazine". Journal of Organic Chemistry, (1996), 61, 2001-2005.
Wolff, Manfred E. "Burgers Medicinal Chemistry", 5ed, Part 1 John Wiley & Sons, 1995, pp. 975-977.
Xia, Y. et al. "Shape-Controlled Synthesis of Metal Nanocrystals: Simple Chemistry Meets Complex Physics?", Angewandte Chemie International Edition (2009), 48, 1-5.
Rossin et al., "Highly Reactive trans-Cyclooctene Tags with Improved Stability for Diels—Alder Chemistry in Living Systems", Bioconjugate Chemistry, 2013, vol. 24, No. 7, pp. 1210-1217.
International Search Report and Written Opinion for Corresponding International Application No. PCT/NL2019/050272 (9 Pages) (Oct. 9, 2019).

* cited by examiner

COMPOUNDS COMPRISING A LINKER FOR INCREASING TRANSCYCLOOCTENE STABILITY

CROSS-REFERENCE TO RELATED APPLICATIONS

This application is a 371 of PCT/NL2019/050272, filed May 6, 2019, which claims the benefit of European Patent Application No. 18170937.9, filed May 4, 2018.

FIELD OF THE INVENTION

The invention disclosed herein relates to compounds comprising a trans-cyclooctene group of which the stability is increased by another group within the same compound and kits comprising said compounds.

BACKGROUND OF THE INVENTION

Selective chemical reactions that are orthogonal to the diverse functionality of biological systems are called bio-orthogonal reactions and occur between two abiotic groups with exclusive mutual reactivity. These can be used to selectively modify biochemical structures, such as proteins or nucleic acids, which typically proceed in water and at near-ambient temperature, and may be applied in complex chemical environments, such as those found in living organisms.

Bio-orthogonal reactions are broadly useful tools with applications that span synthesis, materials science, chemical biology, diagnostics, and medicine.

Especially prominent application areas for biorthogonal reactions include drug delivery agents and prodrugs for pharmaceutical applications, as well as various reversible bioconjugates and sophisticated spectroscopic bioprobes for applications in the field of biological analysis.

One prominent bioorthogonal reaction is the inverse-electron-demand Diels Alder (IEDDA) reaction between a trans-cyclooctene (TCO) and a tetrazine (TZ). In previous studies the IEDDA reaction was used for pretargeted radioimmunoimaging, treating tumor-bearing mice with trans-cyclooctene (TCO)-tagged antibody or antibody fragments, followed one or more days later by administration and selective conjugation of a radiolabeled tetrazine probe to the TCO tag of the tumor-bound antibody [R. Rossin, M. S. Robillard, Curr. Opin. Chem. Biol. 2014, 21, 161-169].

Based on the IEDDA conjugation a release reaction has been developed, which was termed the IEDDA pyridazine elimination, a “click-to-release” approach that affords instantaneous and selective release upon conjugation [R. M. Versteegen, R. Rossin, W. ten Hoeve, H. M. Janssen, M. S. Robillard, Angew. Chem. Int. Ed. 2013, 52, 14112-14116]. IEDDA reactions between tetrazines (i.e. diene) and alkenes (i.e. dienophile) afford 4,5-dihydropyridazines, which usually tautomerize to 1,4- and 2,5-dihydropyridazines. It was demonstrated that the 1,4-dihydropyridazine product derived from a TCO containing a carbamate-linked doxorubicin (Dox) at the allylic position and tetrazine is prone to eliminate $CO_2$ and Dox via an electron cascade mechanism eventually affording aromatic pyridazine. The triggered release has been demonstrated in PBS (phosphate buffered saline), serum, cell culture and in mice and holds promise for a range of applications in medicine, chemical biology, and synthetic chemistry, including triggered drug release, biomolecule uncaging and capture&release strategies.

In an initial step of an IEDDA reaction, a diene reacts with a drug-bearing TCO to form a conjugate. This is referred to as the click conjugation step. Next, via one or multiple mechanisms, the drug is preferably released from the TCO. It will be understood that a high yield in the click conjugation step, i.e. a high click conjugation yield, does not necessarily result in a high yield of released drug, i.e. a high drug release yield.

The IEDDA pyridazine elimination has been applied in triggered drug release from antibody-drug conjugates (ADCs) capable of participating in an IEDDA reaction. ADCs are a promising class of biopharmaceuticals that combine the target-specificity of monoclonal antibodies (mAbs) or mAb fragments with the potency of small molecule toxins. Classical ADCs are designed to bind to an internalizing cancer cell receptor leading to uptake of the ADC and subsequent intracellular release of the drug by enzymes, thiols, or lysosomal pH. Routing the toxin to the tumour, while minimizing the peripheral damage to healthy tissue, allows the use of highly potent drugs resulting in improved therapeutic outcomes. The use of the IEDDA pyridazine elimination for ADC activation allows the targeting of non-internalizing receptors, as the drug is cleaved chemically instead of biologically.

In general prodrugs, which may comprise ADCs, are an interesting application for the IEDDA pyridazine elimination reaction, in which a drug is deactivated, bound or masked by a moiety, and is reactivated, released or unmasked after an IEDDA reaction has taken place.

Background art for the aforementioned technology further includes WO2012/156919, WO2012156918A1, WO 2014/081303, and US20150297741. Herein a dienophile is used as a chemically cleavable group. The group is attached to a Construct in such a way that the release of the dienophile from the Construct can be provoked by allowing the dienophile to react with a diene. The dienophile is an eight-membered non-aromatic cyclic alkenylene group, particularly a TCO group.

From the viewpoint of bio-orthogonality the chemistry works well.

However, the trans-cyclooctene linker deactivates over time in aqueous solutions, in particular in biological environments. Without wishing to be bound by theory, it is believed that this deactivation occurs through trans-cis isomerization in the trans-cyclooctene linker. Isomerization towards cis-cyclooctene releases ring strain, resulting in a much slower IEDDA reaction when a diene is added. The deactivation of the trans-cyclooctene occurs both in circulation in vivo and in serum in vitro. Without wishing to be bound by theory, it is believed that this deactivation via trans-cis isomerization occurs through interactions with copper, for example derived from copper-containing proteins such as albumin.

Increasing the stability of TCO’s by reducing the trans-cis isomerization is desired both in vivo and in vitro. In particular, the increase of TCO stability is preferred in vivo. In some applications, the TCO is part of an ADC which is first injected in the blood stream of a subject and may be targeted to a certain part of the body, e.g. a tumor. Then, a certain percentage of the ADC is immobilized at the targeted spot, while another percentage is cleared by the body. After several hours or days, an activator comprising a diene is added to release a drug from the ADC, preferably only at the targeted spot.

In one aspect, an optimal rate of clearance of the ADC is desired. Under optimal conditions, the ADC is cleared slowly enough to allow it to circulate within the body and be immobilized at the targeted spot. At the same time, the ADC should be cleared from the body fast enough so that the diene can be applied to the subject after a reasonable waiting period following ADC injection without the diene reacting with ADC still circulating in the blood.

In another aspect, it is preferred that the reaction rate between the diene and the TCO is high.

In yet another aspect, a high drug release yield is preferably obtained when the diene and the TCO have reacted in an initial click conjugation step.

As in some applications the TCO-comprising ADC will be in a subject for several hours or days before the diene can be administered, it is preferred that the TCO is as stable as possible in vivo on this timescale. In one aspect, it is desired that drug-releasing TCO's are developed that have prolonged deactivation half-lives in vivo. In another aspect, it is desired that groups on and/or modifications of drug-releasing TCO's are developed that increase the half-lives of the TCO, particularly in vivo.

An earlier publication showed that changing a spacer comprising a polyethyleneglycol (PEG) 12 group between an antibody and a TCO to a very short group increased the in vivo deactivation half-life of the TCO [R. Rossin, S. M. van den Bosch, W. ten Hoeve, M. Carvelli, R. M. Versteegen, J. Lub, M. S. Robillard, Bioconjug. Chem. 2013, 24, 1210-1217]. This study related to TCO's with hydrogens on the vinylic and allylic positions, and not to drug release from the TCO.

In another publication, it was shown that the TCO half-life in vivo decreased compared to the 2013 Bioconjug. Chem. publication mentioned above, when a drug was coupled to the allylic position of the TCO [R. Rossin, S. M. J. van Duijnhoven, W. ten Hoeve, H. M. Janssen, L. H. J. Kleijn, F. J. M. Hoeben, R. M. Versteegen, M. S. Robillard, Bioconj. Chem., 2016 27, 1697-1706]. In this study, an ADC with a short, equatorial spacer between the antibody and the TCO was used with in addition an axially positioned methyl group, and its structure was comparable with the structures used in the publication [R. Rossin, S. M. van den Bosch, W. ten Hoeve, M. Carvelli, R. M. Versteegen, J. Lub, M. S. Robillard, Bioconjug. Chem. 2013, 24, 1210-1217], apart from the fact that in the latter study, no drug was attached to the TCO.

It is desired that compounds are developed that address one or more of the abovementioned problems and/or desires.

SUMMARY OF THE INVENTION

In one aspect, the invention pertains to compounds according to Formula (1):

Formula (1)

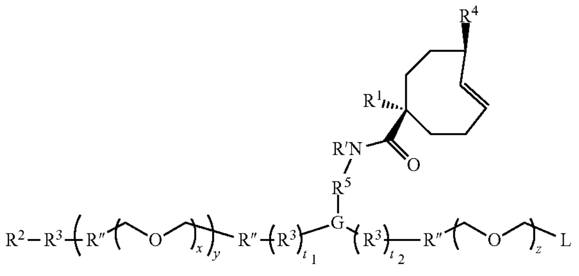

wherein $t_1$ is 0 or 1, wherein $t_2$ is 0 or 1, wherein x is an integer in a range of from 1 to 12, wherein y is 0 or 1, wherein z is an integer in a range of from 6 to 48, wherein L is selected from the group consisting of $—CH_2—OCH_3$, $—CH_2—OH$, $—CH_2—C(O)OH$, —C(O)OH, wherein L is preferably-$CH_2—OCH_3$, wherein when at least one of $t_1$ or $t_2$ is 0, then G is selected from the group consisting of CR', $C_5$-$C_6$ arenetriyl, $C_4$-$C_5$ heteroarenetriyl, $C_3$-$C_6$ cycloalkanetriyl, and $C_4$-$C_6$ cycloalkenetriyl, wherein when both $t_1$ and $t_2$ are 1, then G is selected from the group consisting of CR', N, $C_5$-$C_6$ arenetriyl, $C_4$-$C_5$ heteroarenetriyl, $C_3$-$C_6$ cycloalkanetriyl, and $C_4$-$C_6$ cycloalkenetriyl, wherein for G, the arenetriyl, heteroarenetriyl, cycloalkanetriyl, and cycloalkenetriyl are optionally further substituted with groups selected from the group consisting of —Cl, —F, —Br, —I, —OR', $—N(R')_2$, —SR', $—SO_3H$, $—PO_3H$, $—PO_4H_2$, $—NO_2$, $—CF_3$ and $—R_1$, and optionally contain one or more heteroatoms selected from the group consisting of —O—, —S—, —NR'—, —P—, and —Si—, wherein the N, S, and P atoms are optionally oxidized, wherein the N atoms are optionally quaternized, wherein $R^1$ is selected from the group consisting of hydrogen, $C_1$-$C_6$ alkyl groups, $C_6$ aryl groups, $C_4$-$C_5$ heteroaryl groups, $C_3$-$C_6$ cycloalkyl groups, $C_5$-$C_{12}$ alkyl(hetero)aryl groups, $C_5$-$C_{12}$ (hetero)arylalkyl groups, $C_4$-$C_{12}$ alkylcycloalkyl groups, $—N(R')_2$, —OR', —SR', $—SO_3H$, —C(O)OR', and $Si(R')_3$, wherein for $R^1$ the alkyl groups, (hetero)aryl groups, cycloalkyl groups, alkyl(hetero)aryl groups, (hetero) arylalkyl groups, alkylcycloalkyl groups are optionally substituted with a moiety selected from the group consisting of —Cl, —F, —Br, —I, $NO_2$, $SO_3H$, $PO_3H$, $—PO_4H_2$, —OR', $—N(R')_2$, $—CF_3$, =O, =NR', —SR', and optionally contain one or more heteroatoms selected from the group consisting of —O—, —S—, —NR'—, —P—, and —Si—, wherein the N, S, and P atoms are optionally oxidized, wherein the N atoms are optionally quaternized, wherein $R^2$ is selected from the group consisting of N-maleimidyl groups, halogenated N-alkylamido groups, sulfonyloxy N-alkylamido groups, vinyl sulfone groups, activated carboxylic acids, benzenesulfonyl halides, ester groups, carbonate groups, sulfonyl halide groups, thiol groups or derivatives thereof, $C_{2-6}$ alkenyl groups, $C_{2-6}$ alkynyl groups, $C_{7-18}$ cycloalkynyl groups, $C_{5-18}$ heterocycloalkynyl groups, bicyclo[6.1.0]non-4-yn-9-yl] groups, $C_{4-12}$ cycloalkenyl groups, azido groups, phosphine groups, nitrile oxide groups, nitrone groups, nitrile imine groups, isonitrile groups, diazo groups, ketone groups, (O-alkyl) hydroxylamino groups, hydrazine groups, halogenated N-maleimidyl groups, aryloxymaleimides, dithiophenolmaleimides, bromo- and dibromopyridazinediones, 2,5-dibromohexanediamide groups, alkynone groups, 3-arylpropiolonitrile groups, 1,1-bis(sulfonylmethyl)-methylcarbonyl groups or elimination derivatives thereof, carbonyl halide groups, allenamide groups, 1,2-quinone groups, isothiocyanate groups, aldehyde groups, triazine groups, squaric acids, 2-imino-2-methoxyethyl groups, (oxa)norbornene groups, (imino)sydnones, methylsulfonyl phenyloxadiazole groups, aminooxy groups, 2-amino benzamidoxime groups, groups reactive in the Pictet-Spengler ligation and hydrazino-Pictet-Spengler (HIPS) ligation, wherein each individual $R_3$ is selected from the group consisting of $C_1$-$C_{12}$ alkylene groups, $C_2$-$C_{12}$ alkenylene groups, $C_2$-$C_{12}$ alkynylene groups, $C_6$ arylene groups, $C_4$-$C_5$ heteroarylene groups, $C_3$-$C_8$ cycloalkylene groups, $C_5$-$C_8$cycloalkenylene groups, $C_5$-$C_{12}$ alkyl(hetero)arylene groups, $C_5$-$C_{12}$ (hetero)arylalkylene groups, $C_4$-$C_{12}$ alkylcycloalkylene groups, $C_4$-$C_{12}$ cycloalkylalkylene groups, wherein each individual $R_5$ is selected from the group consisting of $C_1$-$C_8$alkylene groups, $C_2$-$C_8$ alkenylene groups, $C_2$-$C_8$ alkynylene groups, $C_6$ arylene groups, $C_4$-$C_5$ heteroarylene groups, $C_3$-$C_6$ cycloalkylene groups, $C_5$-$C_5$ cycloalkenylene groups, $C_5$-$C_{12}$ alkyl (hetero)arylene groups, $C_5$-$C_{12}$ (hetero)arylalkylene groups, $C_4$-$C_{12}$ alkylcycloalkylene groups, $C_4$-$C_{12}$ cycloalkylalkylene groups, wherein for $R_3$ and $R^5$ the alkylene groups, alkenylene groups, alkynylene groups, (hetero)arylene groups, cycloalkylene groups, cycloalkenylene groups, alkyl (hetero)arylene groups, (hetero)arylalkylene groups, alkylcycloalkylene groups, cycloalkylalkylene groups, are optionally substituted with a moiety selected from the group consisting of —Cl, —F, —Br, —I, —OR', —N(R')$_2$, =O, =NR', —SR', —$SO_3H$, —$PO_3H$, —$PO_4H_2$, —$NO_2$ and —Si(R')$_3$, and optionally contain one or more heteroatoms selected from the group consisting of —O—, —S—, —NR'—, —P—, and —Si—, wherein the N, S, and P atoms are optionally oxidized, wherein the N atoms are optionally quaternized, wherein each R' is independently selected from the group consisting of hydrogen, $C_1$-$C_6$ alkylene groups, $C_2$-$C_6$ alkenylene groups, $C_2$-$C_6$ alkynylene groups, $C_6$ arylene, $C_4$-$C_5$ heteroarylene, $C_3$-$C_6$ cycloalkylene groups, $C_5$-$C_8$ cycloalkenylene groups, $C_5$-$C_{12}$ alkyl (hetero)arylene groups, $C_5$-$C_{12}$ (hetero)arylalkylene groups, $C_4$-$C_{12}$ alkylcycloalkylene groups, and $C_4$-$C_{12}$ cycloalkylalkylene groups, wherein for R' the alkylene groups, alkenylene groups, alkynylene groups, (hetero)arylene groups, cycloalkylene groups, cycloalkenylene groups, alkyl(hetero) arylene groups, (hetero)arylalkylene groups, alkylcycloalkylene groups, cycloalkylalkylene groups are optionally substituted with a moiety selected from the group consisting of —Cl, —F, —Br, —I, —OH, —$NH_2$, —O, —SH, —$SO_3H$, —$PO_3H$, —$PO_4H_2$, —$NO_2$, and optionally contain one or more heteroatoms selected from the group consisting of —O—, —S—, —NH—, —P—, and —Si, wherein the N, S, and P atoms are optionally oxidized, wherein each R" is independently selected from the group consisting of

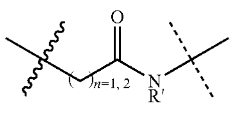
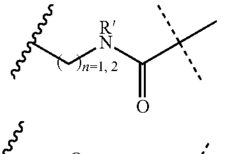
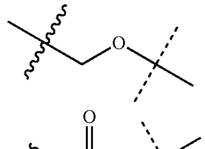
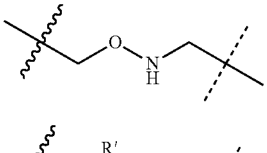
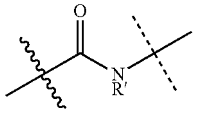
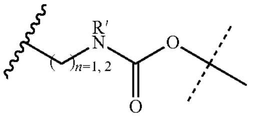

-continued

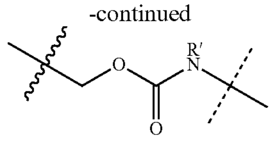
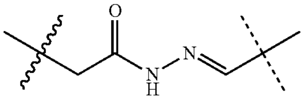
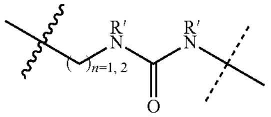
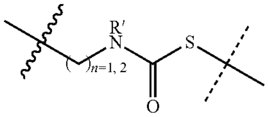
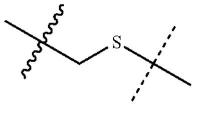
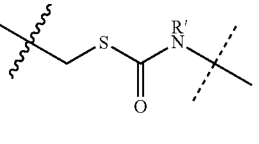
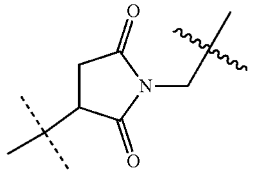
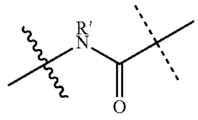
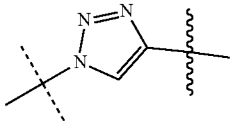
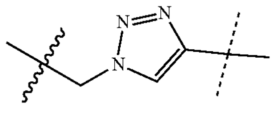
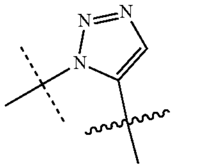
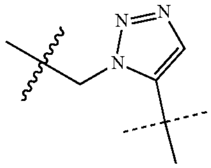
, wherein the wiggly line depicts a bond to an ethylene glycol group or optionally to the $R^3$ adjacent to $R^2$ when y is 0, and the dashed line depicts a bond to $R^3$ or G, wherein $R^4$ is selected from the group consisting of —OH, —OC(O)Cl, —OC(O)O—N-succinimidyl, —OC(O) O-4-nitrophenyl, —OC(O)O-tetrafluorophenyl, —OC (O)O-pentafluorophenyl, —OC(O)—$C^A$, —OC(S)—$C^A$, —O-($L^C$($C^A$), ($C^A$)$_s$($C^A$)$_n$-$C^A$, and —$C^A$, wherein n is an integer in range of from 0 to 2, wherein each s is independently 0 or 1, wherein $L^C$ is a self-immolative linker, wherein $C^A$ denotes a Construct A, wherein said Construct A is a drug, wherein, when $R^4$ is —OC(O)—$C^A$ or —OC(S)—$C^A$, $C^A$ is bound to the —OC(O)— or —OC(S)— of $R^4$ via an atom selected from the group consisting of O, S, and N, preferably a secondary or a tertiary N, wherein this atom is part of $C^A$, wherein, when $R^4$ is —O-($L^C$($C^A$)$_s$($C^A$)$_s$)$_n$-$C^A$ and n is 0, $C^A$ is bound to the —O— moiety of $R^4$ on the allylic position of the trans-cyclooctene ring of Formula (1) via a group selected from the group consisting of —C(O)—, and —C(S)—, wherein this group is part of $C^A$, wherein, when $R^4$ is —O-($L^C$($C^A$)$_s$($C^A$)$_s$)$_n$-$C^A$ and n is 1, $L^C$ is bound to the —O— moiety on the allylic position of the trans-cyclooctene ring of Formula (1) via a group selected from the group consisting of —C($Y^{C2}$)$Y^{C1}$—, and a carbon atom, preferably an aromatic carbon, wherein this group is part of $L^C$, wherein $Y^{C1}$ is selected from the group consisting of —O—, —S—, and —$NR^6$—, wherein $Y^{C2}$ is selected from the group consisting of O and S, wherein, when $R^4$ is —O-($L^C$($C^A$), $(C^A)_s)_n$-$C^A$, and n is 1, then $C^A$ is bound to Le via a moiety selected from the group consisting of —O—, —S—, and —N—, preferably a secondary or a tertiary N, wherein said moiety is part of $C^A$, wherein, when $R^4$ is —$C^A$, then $C^A$ is bound to the allylic position of the trans-cyclooctene of Formula (1) via an-O-atom, wherein this atom is part of $C^A$, wherein $R^6$ is selected from the group consisting of hydrogen, $C_1$-$C_4$ alkyl groups, $C_2$-$C_4$ alkenyl groups, and $C_{4-6}$ (hetero)aryl groups, wherein for $R^6$ the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$ and —$NO_2$ and optionally contain at most two heteroatoms selected from the group consisting of —O—, —S—, —NH—, —P—, and —Si—, wherein the N, S, and P atoms are optionally oxidized, and pharmaceutically accepted salts thereof.

In another aspect, the invention pertains to compounds selected from the group consisting of antibodies, proteins, peptoids and peptides, modified with at least one compound as defined herein.

In yet another aspect, the invention pertains to compounds selected from the group consisting of antibodies, proteins, peptoids and peptides comprising at least one moiety M selected from the group consisting of —OH, —NHR', —$CO_2H$, —SH, —S—S—, —$N_3$, terminal alkynyl, terminal alkenyl, —C(O)R', $C_8$-$C_{12}$ (hetero)cycloalkynyl, nitrone, nitrile oxide, (imino)sydnone, isonitrille, (oxa)norbornene before modification with a compound according to Formula (1), wherein the compound selected from the group consisting of antibodies, proteins, peptoids and peptides satisfies Formula (2) after modification with at least one compound according to Formula (1):

Formula (2)

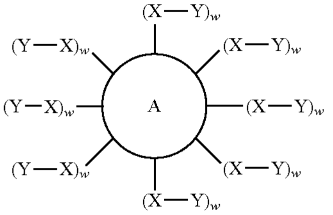

wherein moiety A is selected from the group consisting of antibodies, proteins peptoids and peptides, wherein each individual w is 0 or 1, wherein at least one w is 1, wherein each moiety Y is independently selected from moieties according to Formula (3), wherein at least one moiety Y satisfies said Formula (3):

Formula (3)

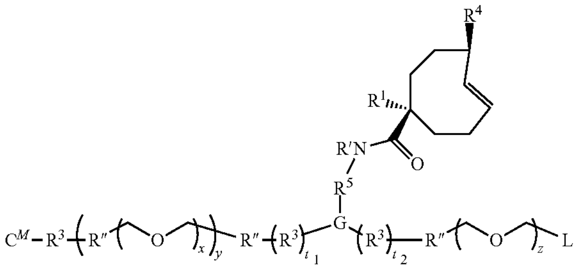

wherein moiety X is part of moiety A and was a moiety M before modification of moiety A, wherein moiety $C^M$ is part of moiety Y and was a moiety $R^2$ as defined herein for compounds according to Formula (1) before modification of moiety A, wherein when moiety X is —S—, then $C^M$ is selected from the group consisting of

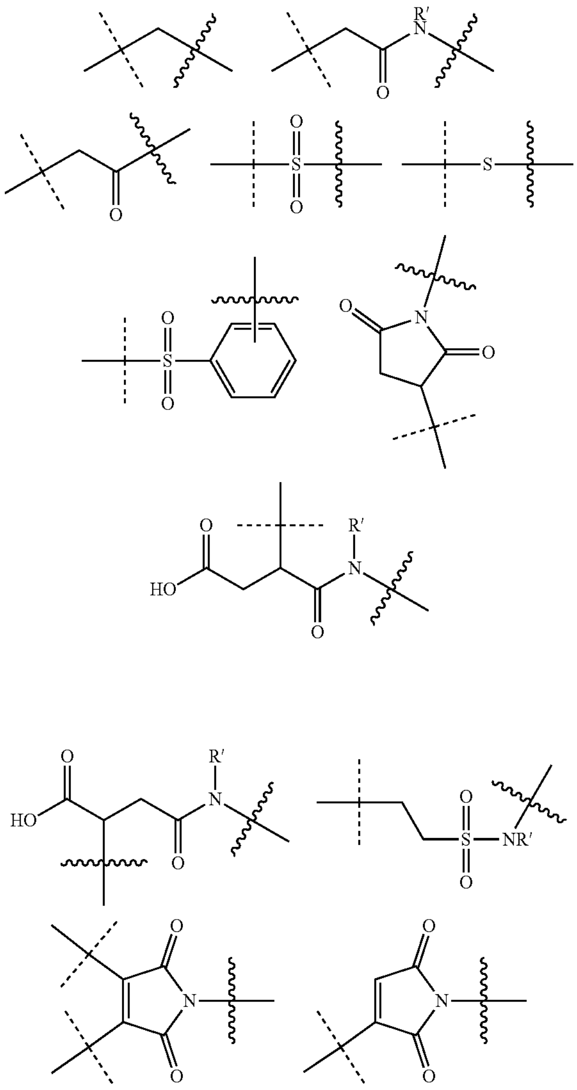

-continued

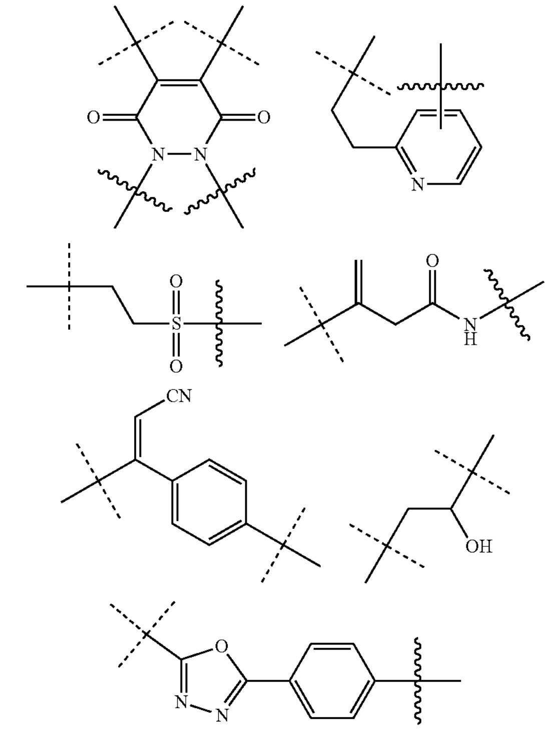

wherein the wiggly line denotes a bond to the remaining part of moiety Y, and wherein the dashed line denotes a bond to moiety X, wherein when moiety X is —NR'—, then $C^M$ is selected from the group consisting of

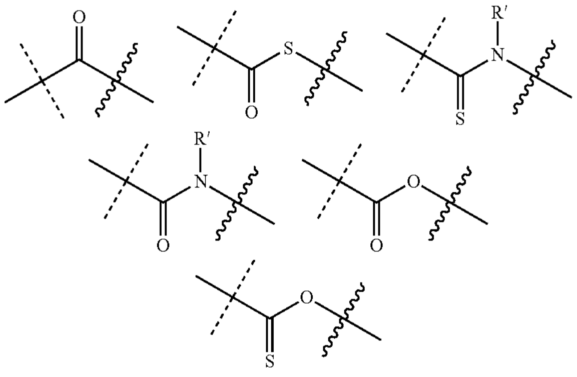

wherein the wiggly line denotes a bond to the remaining part of moiety Y, and wherein the dashed line denotes a bond to moiety X, wherein when moiety X is —C— derived from a moiety M that was —C(O)R' or —C(O)R'—, then $C^M$ is selected from the group consisting of

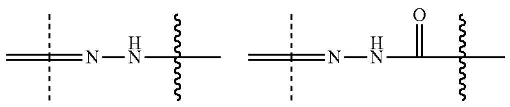

-continued

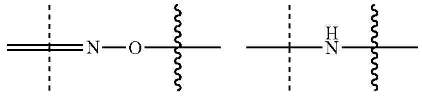

wherein the wiggly line denotes a bond to the remaining part of moiety Y, and wherein the dashed line denotes a bond to moiety X, wherein when moiety X is —C(O)— derived from a moiety M that was —C(O)OH, then $C^M$ is selected from the group consisting of

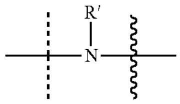

wherein the wiggly line denotes a bond to the remaining part of moiety Y, and wherein the dashed line denotes a bond to moiety X, wherein when moiety X is —O—, then $C^M$ is selected from the group consisting of

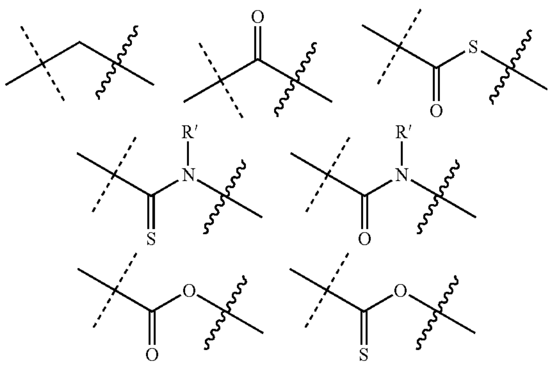

wherein the wiggly line denotes a bond to the remaining part of moiety Y, and wherein the dashed line denotes a bond to moiety X, wherein when moiety X is derived from a moiety M that was —$N_3$ and that was reacted with an $R^2$ that comprised an alkyne group, then X and $C^M$ together form a moiety $C^X$, wherein $C^X$ comprises a triazole ring.

In still another aspect, the invention pertains to kits comprising a compound according to any one of Formulae (1), (2), or (3), wherein said kit further comprises a diene, preferably a tetrazine.

In a further aspect, the invention pertains to kits comprising a compound according to any one of Formulae (1), (2), or (3), and a diene, preferably a tetrazine, for use in the treatment of patients.

BRIEF DESCRIPTION OF THE FIGURES

FIG. 4 shows in (B) Biodistribution of $^{177}$Lu-labeled 2.12 in selected organs and tissues 1 h post-injection. Data represent the mean with SD (n=4).

DETAILED DESCRIPTION OF THE INVENTION

Figure 1:
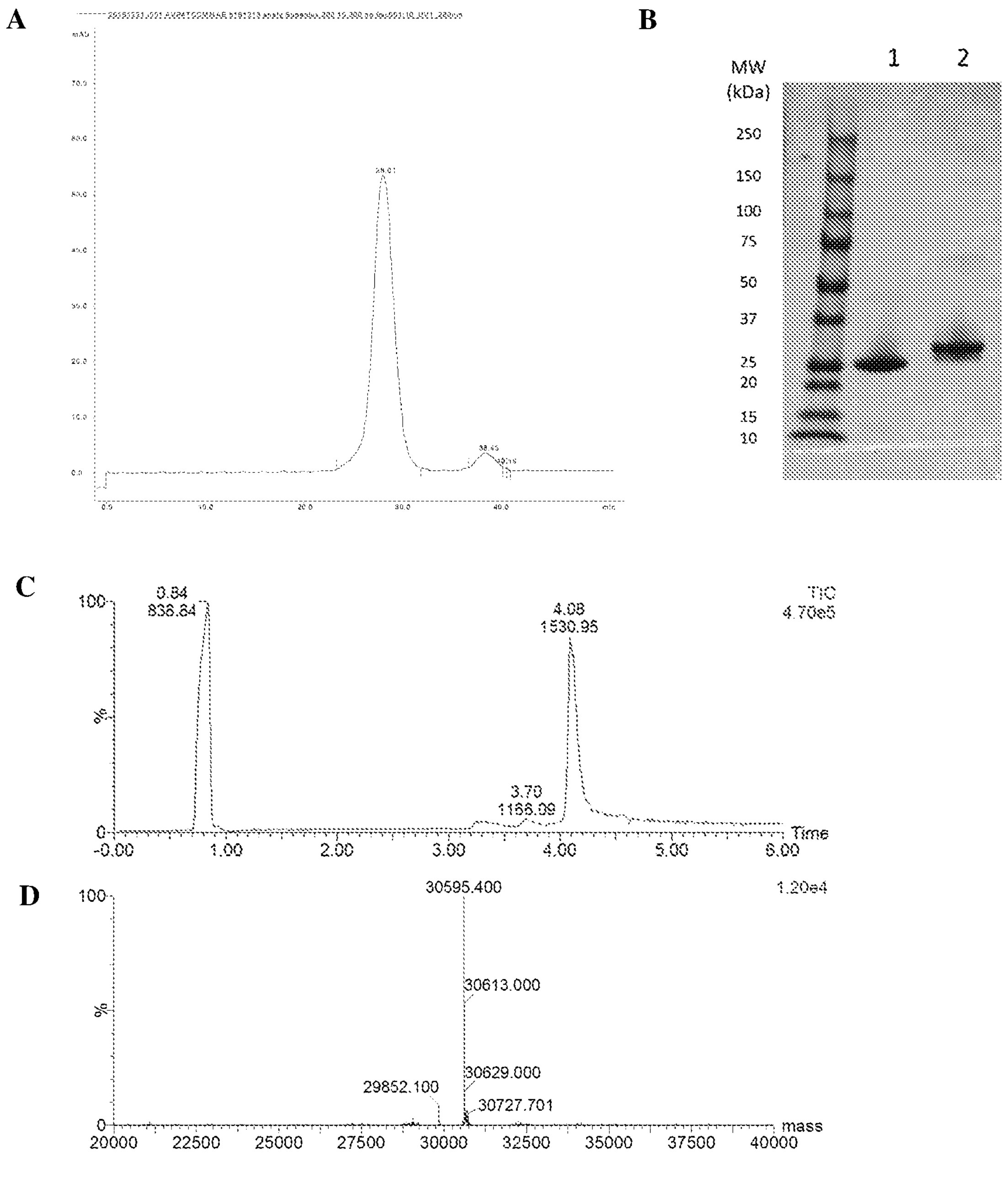
FIG. 1 shows tc-ADC characterization. (A) Size exclusion chromatography. (B) SDS-PAGE analysis; left lane: MW marker; 1: AVP0458 (ca. 25 kDa MW monomer); 2: tc-ADC (ca. 31 kDa MW monomer). (C) HPLC-QTOF-MS analysis: (C) HPLC chromatogram, (D) MS spectrum after deconvolution, showing mass of the diabody monomer with DAR of 2.

The invention, in a broad sense, is based on the judicious insight that compounds comprising a three-armed linker increase the stability of a TCO, in particular in vivo. Of this three-armed linker, one arm of said linker is attached to the TCO. A second arm is either short or comprises a polyethyleneglycol group and ends with a moiety that is suitable for conjugation to a natural or non-natural amino acid or derivatives thereof. In some embodiments, the second arm of the three-armed linker is linked to an antibody, protein, peptide, or peptoid, preferably a nanobody, diabody or an antibody. A third arm of the three-armed linker comprises an oligo-ethyleneglycol.

Without wishing to be bound by theory, it is believed that the oligoethyleneglycol in the third arm of the three-armed linker shields the TCO, which leads to slower deactivation, possibly deactivation through trans-cis isomerization to the cis-cyclooctene.

In one aspect, the TCOs of the invention give a good reaction with dienes, in particular tetrazines, in particular in vivo. In another aspect, high click conjugation yields and high drug release yields are obtained, both in vitro and in vivo.

In yet another aspect, in embodiments where the TCO is coupled to a protein, antibody, peptoid or peptide, preferably a diabody, the three-armed linker allows tuning of the clearance rate of such a protein, peptoid or peptide.

Definitions

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where an indefinite or definite article is used when referring to a singular noun e.g. "a" or "an", "the", this includes a plural of that noun unless something else is specifically stated.

The verb "to comprise", and its conjugations, as used in this description and in the claims is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

Thus, the scope of the expression "a device comprising means A and B" should not be limited to devices consisting only of components A and B. It means that with respect to the present invention, the only relevant components of the device are A and B.

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer, unless stated otherwise. When the structure of a compound is depicted as a specific diastereomer, it is to be understood that the invention of the present application is not limited to that specific diastereomer, unless stated otherwise.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer, unless stated otherwise.

The compounds disclosed in this description and in the claims may further exist as exo and endo diastereoisomers. Unless stated otherwise, the description of any compound in the description and in the claims is meant to include both the individual exo and the individual endo diastereoisomers of a compound, as well as mixtures thereof. When the structure of a compound is depicted as a specific endo or exo diastereomer, it is to be understood that the invention of the present application is not limited to that specific endo or exo diastereomer, unless stated otherwise.

Unless stated otherwise, the compounds of the invention and/or groups thereof may be protonated or deprotonated. It will be understood that it is possible that a compound may bear multiple charges which may be of opposite sign. For example, in a compound containing an amine and a carboxylic acid, the amine may be protonated while simultaneously the carboxylic acid is deprotonated.

In several formulae, groups or substituents are indicated with reference to letters such as "A", "B", "X", "Y", and various (numbered) "R" groups.

In addition, the number of repeating units may be referred to with a letter, e.g. n in-$(CH_2)_n$—. The definitions of these letters are to be read with reference to each formula, i.e. in different formulae these letters, each independently, can have different meanings unless indicated otherwise.

In several chemical formulae and texts below reference is made to "alkyl", "heteroalkyl", "aryl", "heteroaryl", "alkenyl", "alkynyl", "alkylene", "alkenylene", "alkynylene", "arylene", "cycloalkyl", "cycloalkenyl", "cycloakynyl", arenetriyl, and the like. The number of carbon atoms that these groups have, excluding the carbon atoms comprised in any optional substituents as defined below, can be indicated by a designation preceding such terms (e.g. "$C_1$-$C_8$alkyl" means that said alkyl may have from 1 to 8 carbon atoms). For the avoidance of doubt, a butyl group substituted with a-$OCH_3$ group is designated as a $C_4$ alkyl, because the carbon atom in the substituent is not included in the carbon count.

Unsubstituted alkyl groups have the general formula $C_nH_{2n+1}$ and may be linear or branched. Optionally, the alkyl groups are substituted by one or more substituents further specified in this document. Examples of alkyl groups include methyl, ethyl, propyl, 2-propyl, t-butyl, 1-hexyl, 1-dodecyl, etc. Unless stated otherwise, an alkyl group optionally contains one or more heteroatoms independently selected from the group consisting of O, $NR_5$, S, P, and Si, wherein the N, S, and P atoms are optionally oxidized and the N atoms are optionally quaternized. In preferred embodiments, up to two heteroatoms may be consecutive, such as in for example —$CH_2$—NH—OCH; and —$CH_2$—O—Si$(CH_3)_3$. In some preferred embodiments the heteroatoms are not directly bound to one another. Examples of heteroalkyls include —CH $CH_2$—O—$CH_3$, —$CH_2CH_2$—NH—$CH_3$, —$CH_2CH_2$—S(O)—$CH_3$, —CH—CH—O—$CH_3$, —Si$(CH_3)_3$. In preferred embodiments, a $C_1$-$C_4$ alkyl contains at most 2 heteroatoms.

A cycloalkyl group is a cyclic alkyl group. Unsubstituted cycloalkyl groups comprise at least three carbon atoms and have the general formula $C_2H_{2n-1}$. Optionally, the cycloalkyl groups are substituted by one or more substituents further specified in this document. Examples of cycloalkyl groups include cyclopropyl, cyclobutyl, cyclopentyl and cyclohexyl. Unless stated otherwise, a cycloalkyl group optionally contains one or more heteroatoms independently selected from the group consisting of O, $NR_5$, S, P, and Si, wherein the N, S, and P atoms are optionally oxidized and the N atoms are optionally quaternized.

An alkenyl group comprises one or more carbon-carbon double bonds, and may be linear or branched. Unsubstituted alkenyl groups comprising one C—C double bond have the general formula $C_nH_{2n-1}$. Unsubstituted alkenyl groups comprising two C—C double bonds have the general formula $C_nH_{2n-3}$. An alkenyl group may comprise a terminal carbon-carbon double bond and/or an internal carbon-carbon double bond. A terminal alkenyl group is an alkenyl group wherein a carbon-carbon double bond is located at a terminal position of a carbon chain. An alkenyl group may also comprise two or more carbon-carbon double bonds. Examples of an alkenyl group include ethenyl, propenyl, isopropenyl, t-butenyl, 1,3-butadienyl, 1,3-pentadienyl, etc. Unless stated otherwise, an alkenyl group may optionally be substituted with one or more, independently selected, substituents as defined below. Unless stated otherwise, an alkenyl group optionally contains one or more heteroatoms independently selected from the group consisting of O, $NR_5$, S, P, and Si, wherein the N, S, and P atoms are optionally oxidized and the N atoms are optionally quaternized.

An alkynyl group comprises one or more carbon-carbon triple bonds, and may be linear or branched. Unsubstituted alkynyl groups comprising one C—C triple bond have the general formula $C_nH_{2n-3}$. An alkynyl group may comprise a terminal carbon-carbon triple bond and/or an internal carbon-carbon triple bond. A terminal alkynyl group is an alkynyl group wherein a carbon-carbon triple bond is located at a terminal position of a carbon chain. An alkynyl group may also comprise two or more carbon-carbon triple bonds. Unless stated otherwise, an alkynyl group may optionally be substituted with one or more, independently selected, substituents as defined below. Examples of an alkynyl group include ethynyl, propynyl, isopropynyl, t-butynyl, etc. Unless stated otherwise, an alkynyl group optionally contains one or more heteroatoms independently selected from the group consisting of O, $NR_5$, S, P, and Si, wherein the N, S, and P atoms are optionally oxidized and the N atoms are optionally quaternized.

An aryl group refers to an aromatic hydrocarbon ring system that comprises six to twenty-four carbon atoms, more preferably six to twelve carbon atoms, and may include monocyclic and polycyclic structures. When the aryl group is a polycyclic structure, it is preferably a bicyclic structure. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-tert-butylphenyl.

Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl. Heteroaryl groups preferably comprise five to sixteen carbon atoms and contain between one to five heteroatoms.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and an alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

A cycloalkenyl group is a cyclic alkenyl group. An unsubstituted cycloalkenyl group comprising one double bond has the general formula $C_nH_{2n-3}$. Optionally, a cycloalkenyl group is substituted by one or more substituents further specified in this document. An example of a cycloalkenyl group is cyclopentenyl. Unless stated otherwise, a cycloalkenyl group optionally contains one or more heteroatoms independently selected from the group consisting of O, NRs, S, P, and Si, wherein the N, S, and P atoms are optionally oxidized and the N atoms are optionally quaternized.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl. Unless stated otherwise, a cycloalkynyl group optionally contains one or more heteroatoms independently selected from the group consisting of O, $NR_5$, S, P, and Si, wherein the N, S, and P atoms are optionally oxidized and the N atoms are optionally quaternized.

When referring to a (hetero)aryl group the notation is meant to include an aryl group and a heteroaryl group. An alkyl(hetero)aryl group refers to an alkylaryl group and an alkylheteroaryl group. A (hetero)arylalkyl group refers to an arylalkyl group and a heteroarylalkyl group. In general, when (hetero) is placed before a group, it refers to both the variant of the group without the prefix hetero- as well as the group with the prefix hetero-.

Herein, the prefix hetero-denotes that the group contains one or more heteroatoms selected from the group consisting of O, N, S, P, and Si. It will be understood that groups with the prefix hetero- by definition contain heteroatoms. Hence, it will be understood that if a group with the prefix hetero- is part of a list of groups that is defined as optionally containing heteroatoms, that for the groups with the prefix hetero- it is not optional to contain heteroatoms, but is the case by definition.

Herein, it will be understood that when the prefix hetero- is used for combinations of groups, the prefix hetero-only refers to the one group before it is directly placed. For example, heteroarylalkyl denotes the combination of a heteroaryl group and an alkyl group, not the combination of a heteroaryl and a heteroalkyl group. As such, it will be understood that when the prefix hetero- is used for a combination of groups that is part of a list of groups that are indicated to optionally contain heteroatoms, it is only optional for the group within the combination without the prefix hetero- to contain a heteroatom, as it is not optional for the group within the combination with the prefix hetero- by definition (see above). For example, if heteroarylalkyl is part of a list of groups indicated to optionally contain heteroatoms, the heteroaryl part is considered to contain heteroatoms by definition, while for the alkyl part it is optional to contain heteroatoms.

Herein, the prefix cyclo-denotes that groups are cyclic. It will be understood that when the prefix cyclo- is used for combinations of groups, the prefix cyclo-only refers to the one group before it is directly placed. For example, cycloalkylalkenylene denotes the combination of a cycloalkylene group (see the definition of the suffix -ene below) and an alkenylene group, not the combination of a cycloalkylene and a cycloalkenylene group.

In general, when (cyclo) is placed before a group, it refers to both the variant of the group without the prefix cyclo- as well as the group with the prefix cyclo-.

Herein, the suffix-ene denotes divalent groups, i.e. that the group is linked to at least two other moieties. An example of an alkylene is propylene ($—CH_2—CH_2—CH_2—$), which is linked to another moiety at both termini. It is understood that if a group with the suffix-ene is substituted at one position with —H, then this group is identical to a group without the suffix. For example, an alkylene substituted with —H is identical to an alkyl group. I.e. propylene, $—CH_2—CH_2—CH_2—$, substituted with —H at one terminus, $—CH_2—CH_2—CH_2—H$, is logically identical to propyl, $—CH_2—CH_2—CH_3$.

Herein, when combinations of groups are listed with the suffix-ene, it refers to a divalent group, i.e. that the group is linked to at least two other moieties, wherein each group of the combination contains one linkage to one of these two moieties. As such, for example alkylarylene is understood as a combination of an arylene group and an alkylene group. An example of an alkylarylene group is -phenyl-$CH_2$—, and an example of an arylalkylene group is —$CH_2$-phenyl-.

Herein, the suffix-triyl denotes trivalent groups, i.e. that the group is linked to at least three other moieties. An example of an arenetriyl is depicted below:

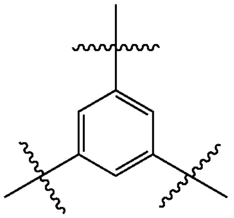

wherein the wiggly lines denote bonds to different groups of the main compound.

It is understood that if a group with the suffix-triyl is substituted at one position with —H, then this group is identical to a divalent group with the suffix-ene. For example, an arenetriyl substituted with —H is identical to an arylene group. Similarly, it is understood that if a group with the suffix-triyl is substituted at two positions with —H, then this group is identical to a monovalent group. For example, an arenetriyl substituted with two —H is identical to an aryl group.

It is understood that if a group, for example an alkyl group, contains a heteroatom, then this group is identical to a hetero-variant of this group. For example, if an alkyl group contains a heteroatom, this group is identical to a heteroalkyl group. Similarly, if an aryl group contains a heteroatom, this group is identical to a heteroaryl group. It is understood that "contain" and its conjugations mean herein that when a group contains a heteroatom, this heteroatom is part of the backbone of the group. For example, a $C_2$ alkylene containing an N refers to —NH—$CH_2$—$CH_2$—, —$CH_2$—NH—$CH_2$—, and —$CH_2$—$CH_2$—NH—.

Unless indicated otherwise, a group may contain a heteroatom at non-terminal positions or at one or more terminal positions. In this case, "terminal" refers to the terminal position within the group, and not necessarily to the terminal position of the entire compound. For example, if an ethylene group contains a nitrogen atom, this may refer to —NH—$CH_2$—$CH_2$—, —$CH_2$—NH—$CH_2$—, and —$CH_2$—$CH_2$—NH—. For example, if an ethyl group contains a nitrogen atom, this may refer to —NH—$CH_2$—$CH_3$, —$CH_2$—NH—$CH_3$, and —$CH_2$—$CH_2$—$NH_2$.

Herein, it is understood that cyclic compounds (i.e. aryl, cycloalkyl, cycloalkenyl, etc.) are understood to be monocyclic, polycyclic or branched. It is understood that the number of carbon atoms for cyclic compounds not only refers to the number of carbon atoms in one ring, but that the carbon atoms may be comprised in multiple rings. These rings may be fused to the main ring or substituted onto the main ring. For example, $C_{10}$ aryl optionally containing heteroatoms may refer to inter alia a naphthyl group (fused rings) or to e.g. a bipyridyl group (substituted rings, both containing an N atom).

Unless stated otherwise, (hetero)alkyl groups, (hetero) cycloalkyl groups, (hetero)alkenyl groups, (hetero)alkynyl groups, (hetero)cycloalkyl groups, (hetero)cycloalkenyl groups, (hetero)cycloalkynyl groups, (hetero)alkylcycloalkyl groups, (hetero)alkylcycloalkenyl groups, (hetero)alkylcycloalkynyl groups, (hetero)cycloalkylalkyl groups, (hetero)cycloalkenylalkyl groups, (hetero)cycloalkynylalkyl groups, (hetero)alkenylcycloalkyl groups, (hetero)alkenylcycloalkenyl groups, (hetero)alkenylcycloalkynyl groups, (hetero)cycloalkylalkenyl groups, (hetero)cycloalkenylalkenyl groups, (hetero)cycloalkynylalkenyl groups, (hetero) alkynylcycloalkyl groups, (hetero)alkynylcycloalkenyl groups, (hetero)alkynylcycloalkynyl groups, (hetero)cycloalkylalkynyl groups, (hetero)cycloalkenylalkynyl groups, (hetero)cycloalkynylalkynyl groups, (hetero)aryl groups, (hetero)arylalkyl groups, (hetero)arylalkenyl groups, (hetero)arylalkynyl groups, alkyl(hetero)aryl groups, alkenyl(hetero)aryl groups, alkynyl(hetero)aryl groups, cycloalkyl(hetero)aryl groups, cycloalkenyl(hetero) aryl groups, cycloalkynyl(hetero)aryl groups, (hetero)arylcycloalkyl groups, (hetero)arylcycloalkenyl groups, (hetero) arylcycloalkynyl groups, (hetero)alkylene groups, (hetero) alkenylene groups, (hetero)alkynylene groups, (hetero) cycloalkylene groups, (hetero)cycloalkenylene groups, (hetero)cycloalkynylene groups, (hetero)arylene groups, alkyl(hetero)arylene groups, (hetero)arylalkylene groups, (hetero)arylalkenylene groups, (hetero)arylalkynylene groups, alkenyl(hetero)arylene, alkynyl(hetero)arylene, (hetero)arenetriyl groups, (hetero)cycloalkanetriyl groups, (hetero)cycloalkenetriyl and (hetero)cycloalkynetriyl groups are optionally substituted with one or more substituents independently selected from the group consisting of —Cl, —F, —Br, —I, —OH, —$NH_2$, —$SO_3H$, —$PO_3H$, —$PO_4H_2$, —$NO_2$, —$CF_3$, =O, =$NR_5$, —$SR_5$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ alkyl(hetero)aryl groups, $C_3$-$C_{24}$ (hetero)arylalkyl groups, $C_4$-$C_{24}$ (hetero)arylalkenyl groups, $C_4$-$C_{24}$ (hetero)arylalkynyl groups, $C_4$-$C_{24}$ alkenyl (hetero)aryl groups, $C_4$-$C_{24}$ alkynyl(hetero)aryl groups, $C_4$-$C_{24}$ alkylcycloalkyl groups, $C_6$-$C_{24}$ alkylcycloalkenyl groups, $C_{13}$-$C_{24}$ alkylcycloalkynyl groups, $C_4$-$C_{24}$ cycloalkylalkyl groups, $C_6$-$C_{24}$ cycloalkenylalkyl groups, $C_{13}$-$C_{24}$ cycloalkynylalkyl groups, $C_5$-$C_{24}$ alkenylcycloalkyl groups, $C_7$-$C_{24}$ alkenylcycloalkenyl groups, $C_{14}$-$C_{24}$ alkenylcycloalkynyl groups, $C_5$-$C_{24}$ cycloalkylalkenyl groups, $C_7$-$C_{24}$ cycloalkenylalkenyl groups, $C_{14}$-$C_{24}$ cycloalkynylalkenyl groups, $C_5$-$C_{24}$ alkynylcycloalkyl groups, $C_7$-$C_{24}$ alkynylcycloalkenyl groups, $C_{14}$-$C_{24}$ alkynylcycloalkynyl groups, $C_5$-$C_{24}$ cycloalkylalkynyl groups, $C_7$-$C_{24}$ cycloalkenylalkynyl groups, $C_{14}$-$C_{24}$ cycloalkynylalkynyl groups, $C_5$-$C_{24}$ cycloalkyl(hetero)aryl groups, $C_7$-$C_{24}$ cycloalkenyl(hetero) aryl groups, $C_{14}$-$C_{24}$ cycloalkynyl(hetero)aryl groups, $C_5$-$C_{24}$ (hetero)arylcycloalkyl groups, $C_7$-$C_{24}$ (hetero)arylcycloalkenyl groups, and $C_{14}$-$C_{24}$ (hetero)arylcycloalkynyl groups. Unless stated otherwise, the substituents disclosed herein optionally contain one or more heteroatoms selected from the group consisting of O, S, $NR_5$, P, and Si, wherein the N, S, and P atoms are optionally oxidized, wherein the N atoms are optionally quaternized. Preferably, these substituents optionally contain one or more heteroatoms selected from the group consisting of O, S, and $NR_5$.

In some embodiments, the substituents are selected from the group consisting of —Cl, —F, —Br, —I, —OH, —$NH_2$, —$SO_3H$, —$PO_3H$, —$PO_4H_2$, —$NO_2$, —$CF_3$, =O, =NRs, —$SR_5$, $C_1$-$C_{12}$ alkyl groups, $C_2$-$C_{12}$ alkenyl groups, $C_2$-$C_{12}$ alkynyl groups, $C_6$-$C_{12}$ aryl groups, $C_2$-$C_{12}$ heteroaryl groups, $C_3$-$C_{12}$ cycloalkyl groups, $C_5$-$C_{12}$ cycloalkenyl groups, $C_{12}$ cycloalkynyl groups, $C_3$-$C_{12}$ alkyl(hetero)aryl groups, $C_3$-$C_{12}$ (hetero)arylalkyl groups, $C_4$-$C_{12}$ (hetero) arylalkenyl groups, $C_4$-$C_{12}$ (hetero)arylalkynyl groups, $C_4$-$C_{12}$ alkenyl(hetero)aryl groups, $C_4$-$C_{12}$ alkynyl(hetero)aryl groups, $C_4$-$C_{12}$ alkylcycloalkyl groups, $C_6$-$C_{12}$ alkylcycloalkenyl groups, $C_{13}$-$C_{16}$ alkylcycloalkynyl groups, $C_4$-$C_{12}$ cycloalkylalkyl groups, $C_6$-$C_{12}$ cycloalkenylalkyl groups, $C_{18}$-$C_{16}$ cycloalkynylalkyl groups, $C_5$-$C_{12}$ alkenylcycloalkyl groups, $C_7$-$C_{12}$ alkenylcycloalkenyl groups, $C_{14}$-$C_{16}$ alkenylcycloalkynyl groups, $C_5$-$C_{12}$ cycloalkylalkenyl groups, $C_7$-$C_{12}$ cycloalkenylalkenyl groups, $C_{14}$-$C_{16}$ cycloalkynylalkenyl groups, $C_5$-$C_{12}$ alkynylcycloalkyl groups, $C_7$-$C_{12}$ alkynylcycloalkenyl groups, $C_{14}$-$C_{16}$ alkynylcycloalkynyl groups, $C_5$-$C_{12}$ cycloalkylalkynyl groups, $C_7$-$C_{12}$ cycloalkenylalkynyl groups, $C_{14}$-$C_{16}$ cycloalkynylalkynyl groups, $C_5$-$C_{12}$ cycloalkyl(hetero)aryl groups, $C_7$-$C_{12}$ cycloalkenyl(hetero)aryl groups, $C_{14}$-$C_{16}$ cycloalkynyl(hetero)aryl groups, $C_5$-$C_{12}$ (hetero)arylcycloalkyl groups, $C_7$-$C_{12}$ (hetero)arylcycloalkenyl groups, and $C_{14}$-$C_{16}$ (hetero)arylcycloalkynyl groups.

In some embodiments, the substituents are selected from the group consisting of —Cl, —F, —Br, —I, —OH, —$NH_2$, —$SO_3H$, —$PO_3H$, —$PO_4H_2$, —$NO_2$, —$CF_3$, =O, =NRs, —$SR_5$, $C_1$-$C_7$ alkyl groups, $C_2$-$C_7$ alkenyl groups, $C_2$-$C_7$ alkynyl groups, $C_6$-$C_7$ aryl groups, $C_2$-$C_7$ heteroaryl groups, $C_3$-$C_7$ cycloalkyl groups, $C_5$-$C_7$ cycloalkenyl groups, $C_{12}$ cycloalkynyl groups, $C_3$-$C_7$ alkyl(hetero)aryl groups, $C_3$-$C_7$ (hetero)arylalkyl groups, $C_4$-$C_7$ (hetero)arylalkenyl groups, $C_4$-$C_7$ (hetero)arylalkynyl groups, $C_4$-$C_7$ alkenyl(hetero)aryl groups, $C_4$-$C_7$ alkynyl(hetero)aryl groups, $C_4$-$C_7$ alkylcycloalkyl groups, $C_6$-$C_7$ alkylcycloalkenyl groups, $C_{13}$-$C_{16}$ alkylcycloalkynyl groups, $C_4$-$C_7$ cycloalkylalkyl groups, $C_6$-$C_7$ cycloalkenylalkyl groups, $C_{13}$-$C_{16}$ cycloalkynylalkyl groups, $C_5$-$C_7$ alkenylcycloalkyl groups, $C_7$-$C_7$ alkenylcycloalkenyl groups, $C_{14}$-$C_{16}$ alkenylcycloalkynyl groups, $C_5$-$C_7$ cycloalkylalkenyl groups, $C_7$-$C_8$ cycloalkenylalkenyl groups, $C_{14}$-$C_{16}$ cycloalkynylalkenyl groups, $C_5$-$C_7$ alkynylcycloalkyl groups, $C_7$-$C_5$ alkynylcycloalkenyl groups, $C_{14}$-$C_{16}$ alkynylcycloalkynyl groups, $C_5$-$C_7$ cycloalkylalkynyl groups, $C_7$-$C_8$ cycloalkenylalkynyl groups, $C_{14}$-$C_{16}$ cycloalkynylalkynyl groups, $C_5$-$C_7$ cycloalkyl(hetero)aryl groups, $C_7$-$C_5$ cycloalkenyl(hetero)aryl groups, $C_{14}$-$C_{16}$ cycloalkynyl(hetero)aryl groups, $C_5$-$C_7$ (hetero)arylcycloalkyl groups, $C_7$-$C_8$ (hetero)arylcycloalkenyl groups, $C_{14}$-$C_{16}$ (hetero)arylcycloalkynyl groups, $C_4$-$C_8$ (hetero)arylalkenyl groups, $C_4$-$C_5$ (hetero)arylalkynyl groups, $C_4$-$C_8$ alkenyl (hetero)aryl groups, $C_4$-$C_5$ alkynyl(hetero)aryl groups $C_5$-$C_9$ cycloalkyl(hetero)aryl groups, $C_7$-$C_{11}$ cycloalkenyl(hetero) aryl groups, $C_{14}$-$C_{18}$ cycloalkynyl(hetero)aryl groups, $C_5$-$C_9$ (hetero)arylcycloalkyl groups, $C_7$-$C_{11}$ (hetero)arylcycloalkenyl groups, and $C_{14}$-$C_{18}$ (hetero)arylcycloalkynyl groups.

Unless stated otherwise, any group disclosed herein that is not cyclic is understood to be linear or branched. In particular, hetero)alkyl groups, (hetero)alkenyl groups, (hetero)alkynyl groups, (hetero)alkylene groups, (hetero)alkenylene groups, (hetero)alkynylene groups, and the like are linear or branched, unless stated otherwise.

The general term “sugar” is herein used to indicate a monosaccharide, for example glucose (Glc), galactose (Gal), mannose (Man) and fucose (Fuc). The term “sugar derivative” is herein used to indicate a derivative of a monosaccharide sugar, i.e. a monosaccharide sugar comprising substituents and/or functional groups. Examples of a sugar derivative include amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA).

A sugar may be without further substitution, and then it is understood to be a monosaccharide. A sugar may be further substituted with at one or more of its hydroxyl groups, and then it is understood to be a disaccharide or an oligosaccharide. A disaccharide contains two monosaccharide moieties linked together. An oligosaccharide chain may be linear or branched, and may contain from 3 to 10 monosaccharide moieties.

The term “protein” is herein used in its normal scientific meaning. Herein, polypeptides comprising about 10 or more amino acids are considered proteins. A protein may comprise natural, but also unnatural amino acids. The term “protein” herein is understood to comprise antibodies and antibody fragments.

The term “peptide” is herein used in its normal scientific meaning. Herein, peptides are considered to comprise a number of amino acids in a range of from 2 to 9.

The term “peptoids” is herein used in its normal scientific meaning.

An antibody is a protein generated by the immune system that is capable of recognizing and binding to a specific antigen. While antibodies or immunoglobulins derived from IgG antibodies are particularly well-suited for use in this invention, immunoglobulins from any of the classes or subclasses may be selected, e.g. IgG, IgA, IgM, IgD and IgE. Suitably, the immunoglobulin is of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, recombinant antibodies, anti-idiotype antibodies, multispecific antibodies, antibody fragments, such as, Fv, VHH, Fab, $F(ab)_2$, Fab', Fab'-SH, $F(ab')_2$, single chain variable fragment antibodies (scFv), tandem/bis-scFv, Fc, pFc', scFv-Fc, disulfide Fv (dsFv), bispecific antibodies (bc-scFv) such as BiTE antibodies, trispecific antibody derivatives such as tribodies, camelid antibodies, minibodies, nanobodies, resurfaced antibodies, humanized antibodies, fully human antibodies, single domain antibodies (sdAb, also known as Nanobody™), chimeric antibodies, chimeric antibodies comprising at least one human constant region, dual-affinity antibodies such as dual-affinity retargeting proteins (DART™), and multimers and derivatives thereof, such as divalent or multivalent single-chain variable fragments (e.g. di-scFvs, tri-scFvs) including but not limited to minibodies, diabodies, triabodies, tribodies, tetrabodies, and the like, and multivalent antibodies. Reference is made to [Trends in Biotechnology 2015, 33, 2, 65], [Trends Biotechnol. 2012, 30, 575-582], and [Canc. Gen. Prot. 2013 10, 1-18], and [BioDrugs 2014, 28, 331-343], the contents of which are hereby incorporated by reference. “Antibody fragment” refers to at least a portion of the variable region of the immunoglobulin that binds to its target, i.e. the antigen-binding region. Other embodiments use antibody mimetics as $T^T$, such as but not limited to Affimers, Anticalins, Avimers, Alphabodies, Affibodies, DARPins, and multimers and derivatives thereof; reference is made to [Trends in Biotechnology 2015, 33, 2, 65], the contents of which is hereby incorporated by reference. For the avoidance of doubt, in the context of this invention the term “antibody” is meant to encompass all of the antibody variations, fragments, derivatives, fusions, analogs and mimetics outlined in this paragraph, unless specified otherwise.

A linker is herein defined as a moiety that connects two or more elements of a compound. For example in a bioconjugate, a biomolecule and a targeting moiety are covalently connected to each other via a linker.

A biomolecule is herein defined as any molecule that can be isolated from nature or any molecule composed of smaller molecular building blocks that are the constituents of macromolecular structures derived from nature, in particular nucleic acids, proteins, glycans and lipids. Examples of a biomolecule include an enzyme, a (non-catalytic) protein, a polypeptide, a peptide, an amino acid, an oligonucleotide, a monosaccharide, an oligosaccharide, a polysaccharide, a glycan, a lipid and a hormone.

The term "salt thereof" means a compound formed when an acidic proton, typically a proton of an acid, is replaced by a cation, such as a metal cation or an organic cation and the like. The term "salt thereof" also means a compound formed when an amine is protonated. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt.

The term "pharmaceutically accepted" salt means a salt that is acceptable for administration to a patient, such as a mammal (salts with counter-ions having acceptable mammalian safety for a given dosage regime). Such salts may be derived from pharmaceutically acceptable inorganic or organic bases and from pharmaceutically acceptable inorganic or organic acids.

"Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc.

The logarithm of the partition-coefficient, i.e. Log P, is herein used as a measure of the hydrophobicity of a compound. Typically, the Log P is defined as $$\log\left(\frac{[\text{Solute}]^{un\text{-}ionized}_{octanol}}{[\text{Solute}]^{un\text{-}ionized}_{water}}\right)$$

The skilled person is aware of methods to determine the partition-coefficient of compounds without undue experimentation. Alternatively, the skilled person knows that software is available to reliably estimate the Log P value, for example as a function within ChemDraw® software or online available tools.

The unified atomic mass unit or Dalton is herein abbreviated to Da. The skilled person is aware that Dalton is a regular unit for molecular weight and that 1 Da is equivalent to 1 g/mol (grams per mole).

It will be understood that herein, the terms "moiety" and "group" are used interchangeably when referring to a part of a molecule.

It will be understood that when a heteroatom is denoted as-$X(R')_2$-, wherein X is the heteroatom and R' is a certain moiety, then this denotes that two moieties R' are attached to the heteroatom.

It will be understood that when a group is denoted as, for example, -$((R_{51})_2$-$R_{52})_2$- or a similar notation, in which $R_{51}$ and $R_{52}$ are certain moieties, then this denotes that first, it should be written as-$R_{51}$-$R_{51}$-$R_{52}$-$R_{51}$-$R_{51}$-$R_{52}$-before the individual $R_{51}$ and $R_{52}$ moieties are selected, rather than first selecting moieties $R_{51}$ and $R_{52}$ and then writing out the formula.

The Inverse Electron-Demand Diels-Alder reaction (IEDDA)

The established IEDDA conjugation chemistry generally involves a pair of reactants that comprise, as one reactant (i.e. one Bio-orthogonal Reactive Group), a suitable diene, such as a derivative of tetrazine (TZ), e.g. an electron-deficient tetrazine and, as the other reactant (i.e. the other Bio-orthogonal Reactive Group), a suitable dienophile, such as a trans-cyclooctene (TCO). The exceptionally fast reaction of (substituted) tetrazines, in particular electron-deficient tetrazines, with a TCO moiety results in an intermediate that rearranges to a dihydropyridazine Diels-Alder adduct by eliminating $N_2$ as the sole by-product. The initially formed 4,5-dihydropyridazine product may tautomerize to a 1,4- or a 2,5-dihydropyridazine product, especially in aqueous environments. Below a reaction scheme is given for a [4+2] IEDDA reaction between (3,6)-di-(2-pyridyl)-s-tetrazine diene and a trans-cyclooctene dienophile, followed by a retro Diels Alder reaction in which the product and dinitrogen is formed. Because the trans-cyclooctene derivative does not contain electron withdrawing groups as in the classical Diels Alder reaction, this type of Diels Alder reaction is distinguished from the classical one, and frequently referred to as an "inverse-electron-demand Diels Alder (IEDDA) reaction". In the following text the sequence of both reaction steps, i.e. the initial Diels-Alder cyclo-addition (typically an inverse electron-demand Diels Alder cyclo-addition) and the subsequent retro Diels Alder reaction will be referred to in shorthand as the "inverse electron-demand Diels Alder reaction" or "inverse electron-demand Diels Alder conjugation" or "IEDDA". The product of the reaction is then the IEDDA adduct or conjugate. This is illustrated in Scheme 1 below.

Scheme 1: the IEDDA conjugation reaction

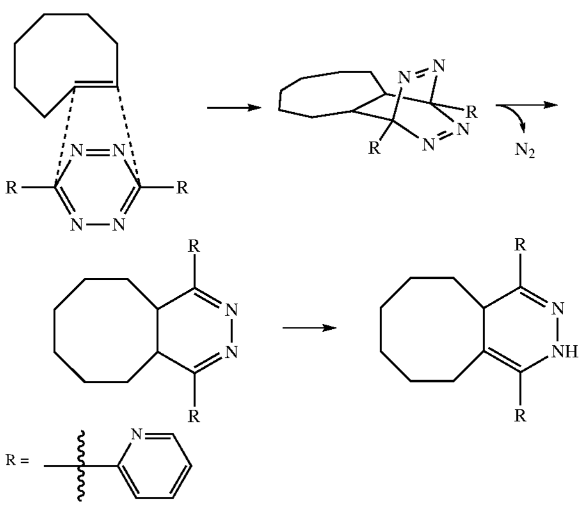

The two reactive species are abiotic and do not undergo fast metabolism or side reactions in vitro or in vivo. They are bio-orthogonal, e.g. they selectively react with each other in physiologic media. Thus, the compounds and the method of the invention can be used in a living organism. Moreover, the reactive groups are relatively small and can be introduced in biological samples or living organisms without significantly altering the size of biomolecules therein. References on the inverse electron demand Diels Alder reaction, and the behavior of the pair of reactive species include: [Thalhammer et al., Tetrahedron Lett., 1990, 31, 47, 6851-6854], [Wijnen et al., J. Org. Chem., 1996, 61, 2001-2005], [Blackman et al., J. Am. Chem. Soc., 2008, 130, 41, 13518-19], [Rossin et al., Angew. Chem. Int. Ed. 2010, 49, 3375], [Devaraj et al., Angew. Chem. Int. Ed. 2009, 48, 7013], [Devaraj et al., Angew. Chem. Int. Ed., 2009, 48, 1-5].

The IEDDA Pyridazine Elimination Reaction

Below, the dienophile, a TCO, that is comprised in kits of the invention may be referred to as a "Trigger". The dienophile is connected at the allylic position to a Construct-A. Moreover, tetrazines that are used in the IEDDA pyridazine elimination reaction may be referred to as "Activators". The term Construct-A in this invention is used to indicate any substance, carrier, biological or chemical group, of which it is desired to have it first in a bound (or masked) state, and being able to provoke release from that state.

The inventors previously demonstrated that the dihydropyridazine product derived from a tetrazine (the Activator) and a TCO containing a carbamate-linked drug (doxorubicin, the Construct-A) at the allylic position is prone to eliminate $CO_2$ and the amine-containing drug, eventually affording aromatic pyridazine.

Without wishing to be bound by theory, the inventors believe that the Activator provokes Construct-A release via a cascade mechanism within the IEDDA adduct, i.e. the dihydropyridazine. The cascade mechanism can be a simple one step reaction, or it can be comprised in multiple steps that involves one or more intermediate structures. These intermediates may be stable for some time or may immediately degrade to the thermodynamic end-product or to the next intermediate structure. In any case, whether it be a simple or a multistep process, the result of the cascade mechanism is that the Construct-A gets released from the IEDDA adduct. Without wishing to be bound by theory, the design of the diene is such that the distribution of electrons within the IEDDA adduct is unfavorable, so that a rearrangement of these electrons must occur. This situation initiates the cascade mechanism, and it therefore induces the release of the Construct-A. Specifically, and without wishing to be bound by theory, the inventors believe that the NH moiety comprised in the various dihydropyridazine tautomers, such as the 1,4-dihydropyridazine tautomer, of the IEDDA adduct can initiate an electron cascade reaction, a concerted or consecutive shift of electrons over several bonds, leading to release of the Construct-A. Occurrence of the cascade reaction in and/or Construct-A release from the Trigger is not efficient or cannot take place prior to the IEDDA reaction, as the Trigger-Construct-A conjugate itself is relatively stable as such. The cascade can only take place after the Activator and the Trigger-Construct conjugate have reacted and have been assembled in the IEDDA adduct.

With reference to Scheme 2 below, and without wishing to be bound by theory, the inventors believe that the pyridazine elimination occurs from the 1,4-dihydropyridazine tautomer 4. Upon formation of the 4,5-dihydropyridazine 3, tautomerization affords intermediates 4 and 7, of which the 2,5-dihydropyridazine 7 cannot eliminate the Construct-A ($C^A$). Instead it can slowly convert into aromatic 8, which also cannot eliminate $C^A$ or it can tautomerize back to intermediate 3. Upon formation of 4 the $C^A$ is eliminated near instantaenously, affording free $C^A$ 8 as an amine, and pyridazine elimination products 5 and 6. This elimination reaction has been shown to work equally well in the cleavage of carbonates, esters and ethers from the TCO trigger. The Trigger in Scheme 2 is also optionally bound to a Construct-B ($C^B$), which in this case cannot release from the Trigger. Thereby Construct A can be seperated from Construct B by means of the IEDDA pyridazine elimination.

Scheme 2. Proposed IEDDA pyridazine elimination mechanism.

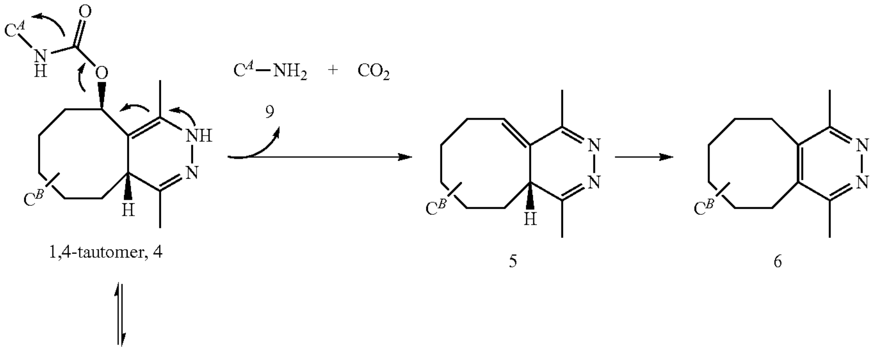

1,4-tautomer, 4

5

6

-continued

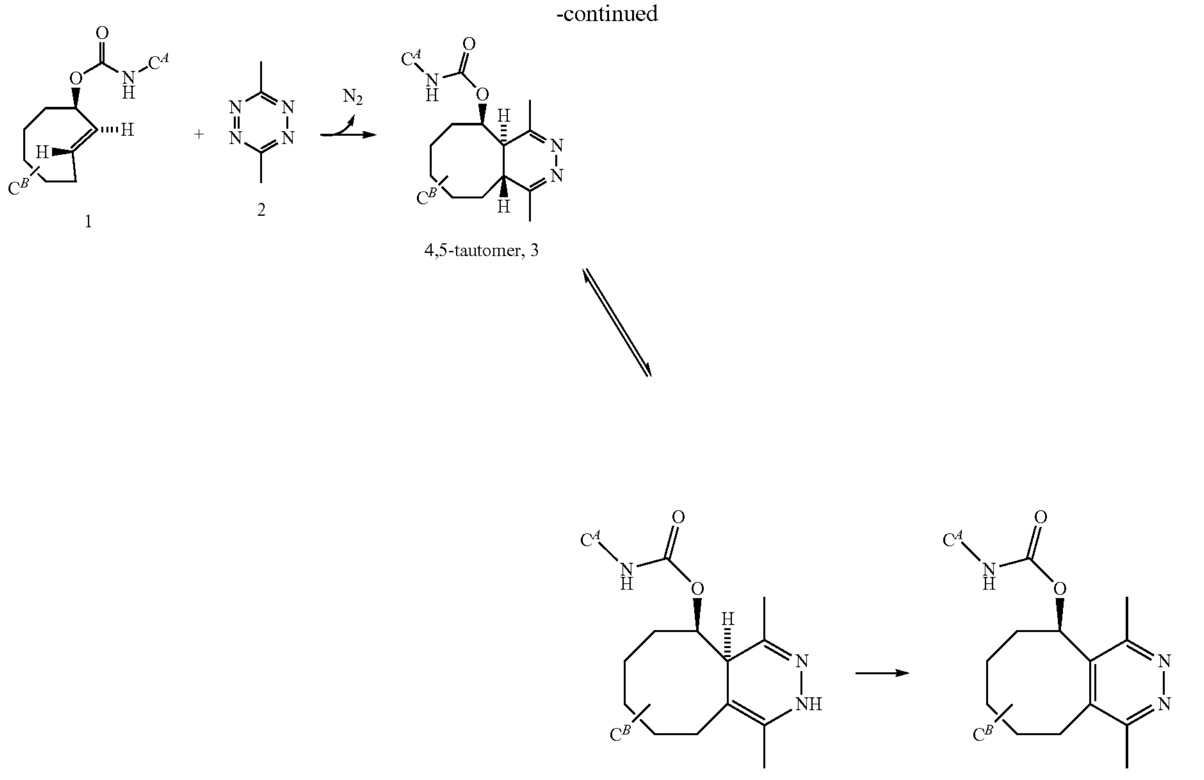

1 2 4,5-tautomer, 3

2,5-tautomer, 7 8

In some embodiments, the dienophile trigger moiety used in the present invention comprises a trans-cyclooctene ring. Herein, this eight-membered ring moiety will be defined as a trans-cyclooctene moiety, for the sake of legibility, or abbreviated as "TCO" moiety. It will be understood that the essence resides in the possibility of the eight-membered ring to act as a dienophile and to be released from its conjugated Construct-A upon reaction.

The tetrazines of the kits of the invention and dienophiles are capable of reacting in an inverse electron-demand Diels-Alder reaction (IEDDA). IEDDA reaction of the Trigger with the Activator leads to release of the Construct-A through an electron-cascade-based elimination, termed the "pyridazine elimination". When an Activator reacts with a Trigger capable of eliminating Construct-A, the combined process of reaction and Construct-A elimination is termed the "IEDDA pyridazine elimination".

This invention provides an Activator that reacts with a Construct-A-conjugated Trigger, resulting in the cleavage of the Trigger from the Construct-A and optionally the cleavage of one or more Construct-A from one or more Construct-B. In some embodiments, the Trigger is used as a reversible covalent bond between two molecular species.

Scheme 3 below is a general scheme of Construct release according to this invention, wherein the Construct being released is termed Construct-A ($C^A$), and wherein another Construct, Construct-B ($C^B$) can be bound to the dienophile, wherein Construct-B may or may not be able to be released from the dienophile. Typically, only Construct-A can be released from the dienenophile.

Scheme 3: General scheme of IEDDA pyridazine elimination reaction for the release of Construct-A according to this invention

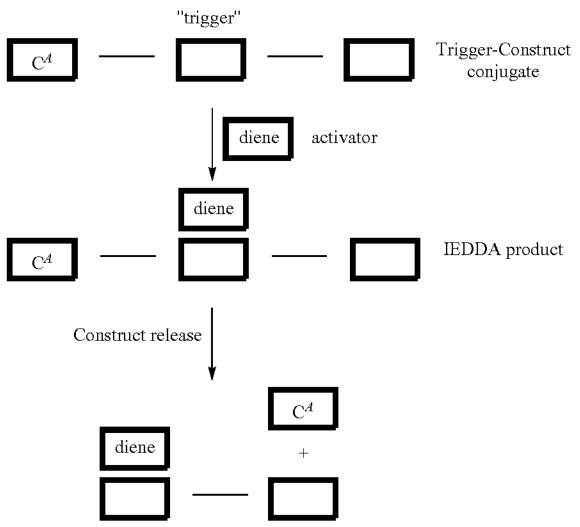

$C^A$ = Construct-A
$C^B$ = optional Construct B

The Construct release occurs through a powerful, abiotic, bio-orthogonal reaction of the dienenophile (Trigger) with the diene (Activator), viz, the aforementioned IEDDA. The masked or bound Construct is a Construct-dienenophile conjugate. Possibly the Construct-A is linked to one or more additional Constructs A linked via a self-immolative linker. It will be understood that in Scheme 3 in the IEDDA adduct as well as in the end product after release, the indicated dienophile group and the indicated diene group are the residues of, respectively, the dienophile and diene groups after these groups have been converted in the IEDDA reaction.

The invention provides, in one aspect, the use of a tetrazine as an Activator for the release, in a chemical, biological, or physiological environment, of a Construct linked to a TCO. In connection herewith, the invention also pertains to a tetrazine as an Activator for the release, in a chemical, biological, or physiological environment, of a substance linked to a TCO. The fact that the reaction is bio-orthogonal, and that many structural options exist for the reaction pairs, will be clear to the skilled person. E.g., the IEDDA reaction is known in the art of bioconjugation, diagnostics, pre-targeted medicine. Reference is made to, e.g., WO 2010/119382, WO 2010/119389, and WO 2010/051530. Whilst the invention presents an entirely different use of the reaction, it will be understood that the various structural possibilities available for the IEDDA reaction pairs as used in e.g. pre-targeting, are also available in the field of the present invention.

Other than is the case with e.g. medicinally active substances, where the in vitro or in vivo action is often changed with minor structural changes, the present invention first and foremost requires the right chemical reactivity combined with sufficient stability for the intended application. Thus, the possible structures extend to those of which the skilled person is familiar with that these are reactive as dienes or dienophiles.

The TCO Trigger:

The dienophile Trigger moiety used in the present invention comprises a trans-cyclooctene ring, and particularly refers to a structure satisfying Formula (1) and pharmaceutically acceptable salts thereof.

Formula (1)

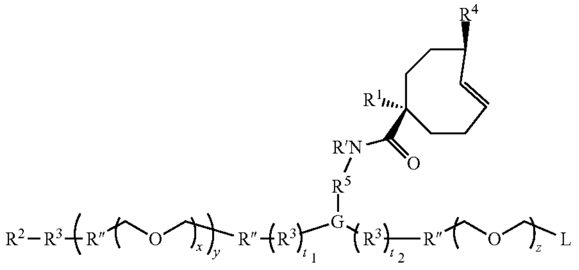

wherein $t_1$ is 0 or 1, wherein $t_2$ is 0 or 1, wherein x is an integer in a range of from 1 to 12, wherein y is 0 or 1, wherein z is an integer in a range of from 6 to 48, In another aspect, the invention pertains to Targeting Agents, preferably compounds selected from the group consisting of antibodies, proteins, peptoids and peptides, comprising at least one moiety M selected from the group consisting of —OH, —NHR', —$CO_2$H, —SH, —S—S—, —$N_3$, terminal alkynyl, terminal alkenyl, —C(O)R', $C_8$-$C_{12}$ (hetero)cycloalkynyl, nitrone, nitrile oxide, (imino)sydnone, isonitrile, (oxa)norbornene before modification with a compound according to Formula (1), wherein the compound selected from the group consisting of antibodies, proteins, peptoids and peptides satisfies Formula (2) after modification with at least one compound according to Formula (1):

Formula (2)

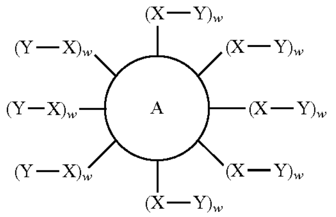

wherein moiety A is preferably selected from the group consisting of antibodies, proteins peptoids and peptides, wherein each individual w is 0 or 1, wherein at least one w is 1, wherein each moiety Y is independently selected from moieties according to Formula (3) and preferably including pharmaceutically accepted salts thereof, wherein at least one moiety Y satisfies said Formula (3):

Formula (3)

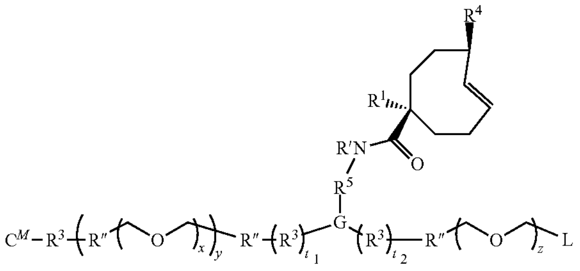

wherein moiety X is part of moiety A and was a moiety M before modification of moiety A, wherein moiety $C^M$ is part of moiety Y and was a moiety $R^2$ as defined herein for compounds according to Formula (1) before modification of moiety A, wherein when moiety X is —S—, then $C^M$ is selected from the group consisting of

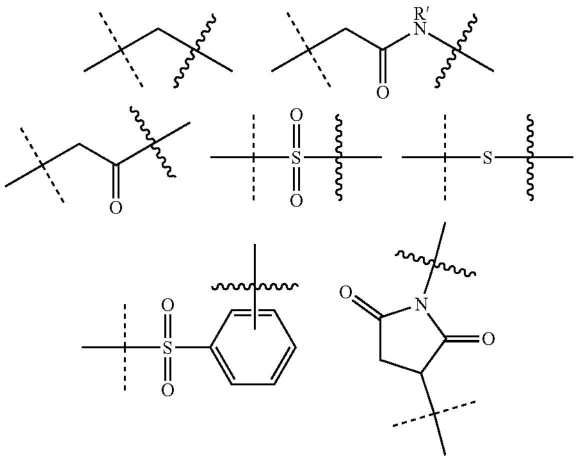

-continued

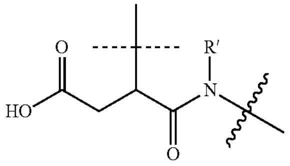

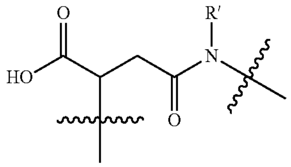

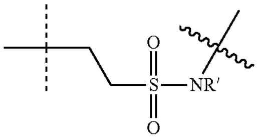

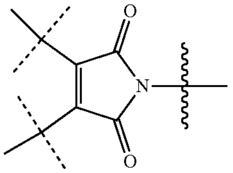

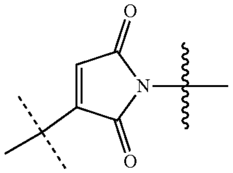

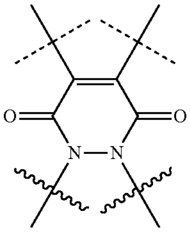

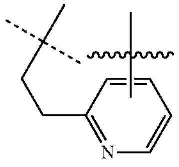

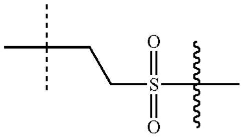

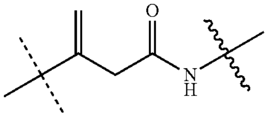

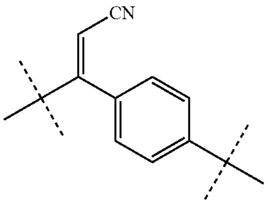

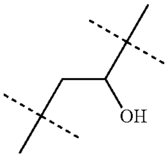

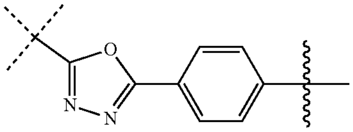

wherein the wiggly line denotes a bond to the remaining part of moiety Y, and wherein the dashed line denotes a bond to moiety X, wherein when moiety X is —NR'—, then $C^M$ is selected from the group consisting of

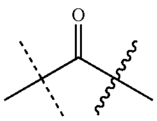

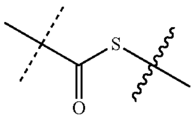

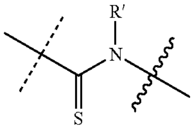

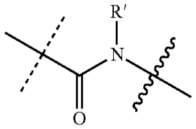

-continued

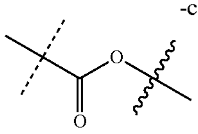

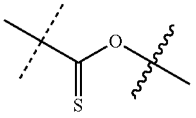

wherein the wiggly line denotes a bond to the remaining part of moiety Y, and wherein the dashed line denotes a bond to moiety X, wherein when moiety X is —C— derived from a moiety M that was —C(O)R' or —C(O)R'—, then $C^M$ is selected from the group consisting of

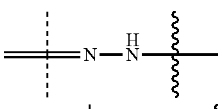

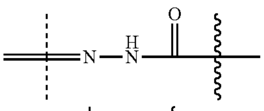

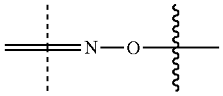

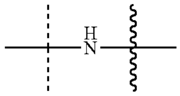

wherein the wiggly line denotes a bond to the remaining part of moiety Y, and wherein the dashed line denotes a bond to moiety X, wherein when moiety X is —C(O)— derived from a moiety M that was —C(O)OH, then $C^M$ is selected from the group consisting of

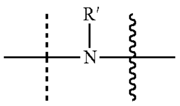

wherein the wiggly line denotes a bond to the remaining part of moiety Y, and wherein the dashed line denotes a bond to moiety X, wherein when moiety X is —O—, then $C^M$ is selected from the group consisting of

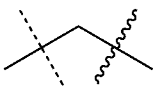

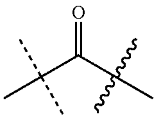

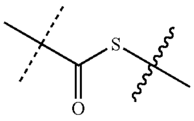

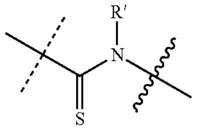

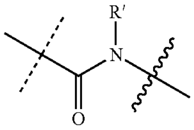

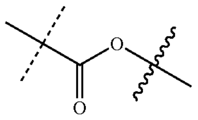

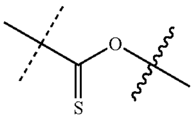

wherein the wiggly line denotes a bond to the remaining part of moiety Y, and wherein the dashed line denotes a bond to moiety X, wherein when moiety X is derived from a moiety M that was —$N_3$ and that was reacted with an $R^2$ that comprised an alkyne group, then X and $C^M$ together form a moiety $C^X$, wherein $C^A$ comprises a triazole ring, wherein, in some embodiments each $C^X$ is independently selected from the group consisting of

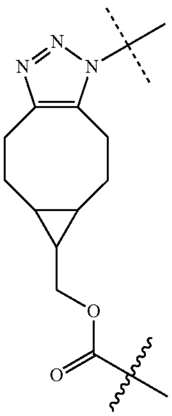

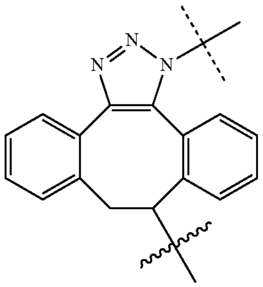

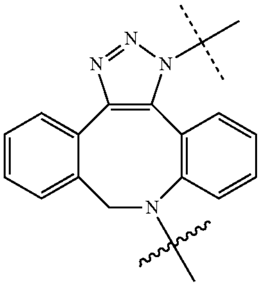

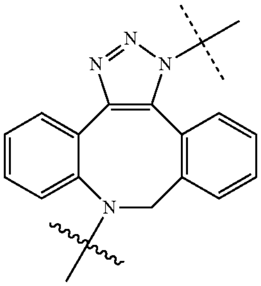

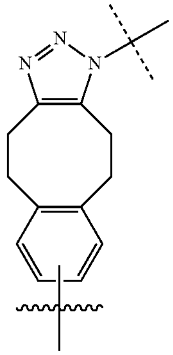

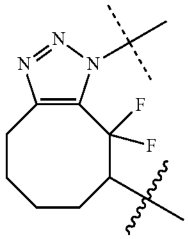

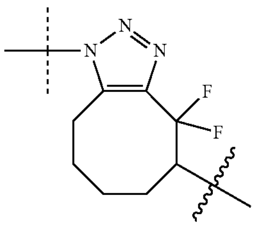

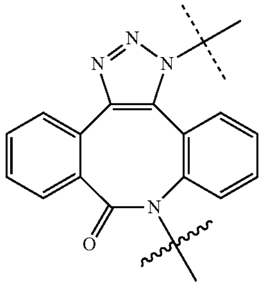

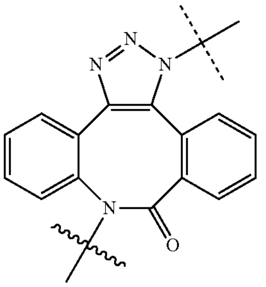

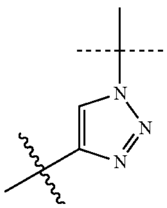

-continued

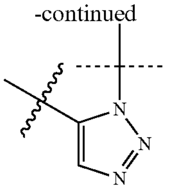

wherein the wiggly line denotes a bond to the remaining part of moiety Y, and wherein the dashed line denotes a bond to moiety X.

TCO moieties may consist of multiple isomers, also comprising the equatorial vs. axial positioning of substituents on the TCO. In this respect, reference is made to Whitham et al. *J. Chem. Soc.* (*C*), 1971, 883-896, describing the synthesis and characterization of the equatorial and axial isomers of trans-cyclo-oct-2-en-ol, identified as (1RS, 2RS) and (1SR, 2RS), respectively. In these isomers the OH substituent is either in the equatorial or axial position. Without wishing to be bound by theory, the inventors believe that the presence of an axial substituent increases the TCO ring strain resulting in higher reactivity in the IEDDA reaction. A background reference providing further guidance is WO 2012/049624.

Furthermore, in case of allylic substituents on the TCO in some embodiments it is preferred that these are positioned axially and not equatorially It should be noted that, depending on the choice of nomenclature, the TCO dienophile may also be denoted E-cyclooctene. With reference to the conventional nomenclature, it will be understood that, as a result of substitution on the cyclooctene ring, depending on the location and molecular weight of the substituent, the same cyclooctene isomer may formally become denoted as a Z-isomer. In the present invention, any substituted variants of the invention, whether or not formally "E" or "Z," or "cis" or "trans" isomers, will be considered derivatives of unsubstituted trans-cyclooctene, or unsubstituted E-cyclooctene. The terms "trans-cyclooctene" (TCO) as well as E-cyclooctene are used interchangeably and are maintained for all dienophiles according to the present invention, also in the event that substituents would formally require the opposite nomenclature. I.e., the invention relates to cyclooctene in which carbon atoms 1 and 6 as numbered below are in the E (entgegen) or trans position.

Formula (14)

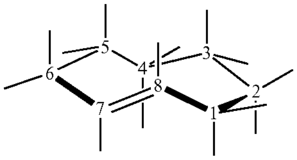

The dienophiles for use in the invention can be synthesized by the skilled person, on the basis of known synthesis routes to cyclooctenes and corresponding hetero atom(s)-containing rings. The skilled person further is aware of the wealth of cyclooctene derivatives that can be synthesized via the ring closing metathesis reaction using Grubbs catalysts. As mentioned above, the TCO possibly includes one or more heteroatoms in the ring. This is as such sufficiently accessible to the skilled person. Reference is made, e.g., to the presence of a thioether in TCO: [Cere et al. J. Org. Chem.

1980, 45, 261]. Also, e.g., an-O-SiR$_2$—O moiety in TCO: [Prevost et al. J. Am. Chem. Soc. 2009, 131, 14182]. Exemplary TCO structures and intermediates, indicating the wide chemical scope are shown below with literature references.

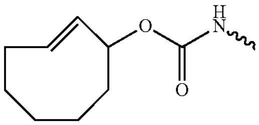

Angew. Chem. Int. Ed. 2013, 52, 14112

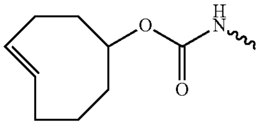

Angew. Chem. Int. Ed. 2010, 49, 3375

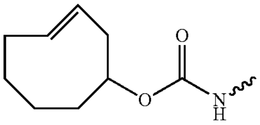

Angew. Chem. Int. Ed. 2014, 53, 2245

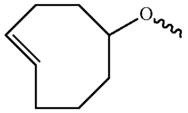

Bioconjug. Chem, 2013, 24, 7, 1210

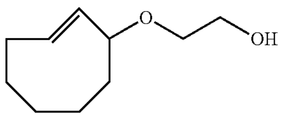

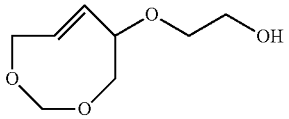

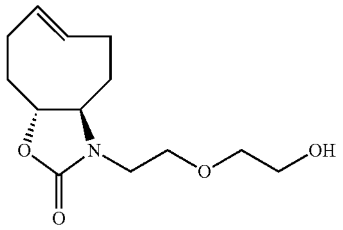

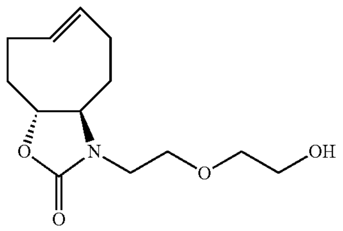

Varga, Thesis, 2014, University of Budapest

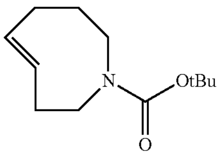

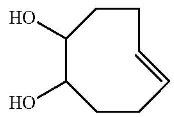

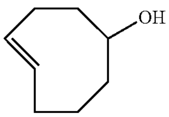

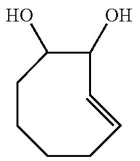

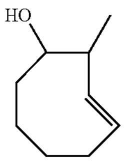

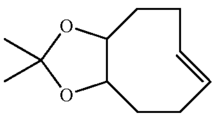

J. Am. Chem. Soc. 2008, 130, 3760

-continued

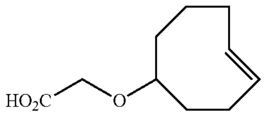

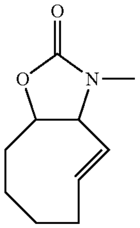

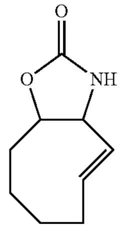

J. Am. Chem. Soc. 2008, 130, 3760

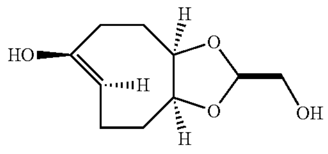

Chem Sci. 2014 Oct 1; 5(10):3770

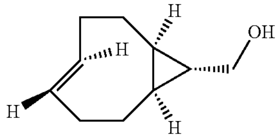

J. Am. Chem. Soc. 2011, 133, 9646

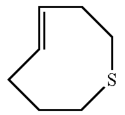

Journal of Organic Chemistry 1980, 45, 261

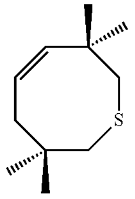

Chem. Ber. 1992, 125; 1431-1437

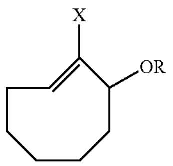

X = Cl, Br
R = H, Me
J. Chem. Soc. Perkin I 1975, 2422
J. Am. Chem. Soc. 1970, 92, 2566

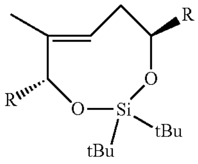

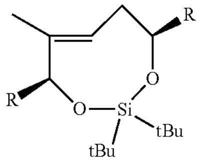

J. Am. Chem. Soc., 2009, 131, 14182
Dalton Trans 210, 9275

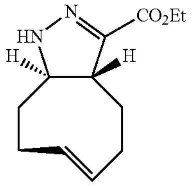

RSC Adv., 2014, 4, 52241

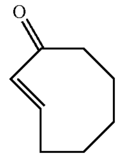

J. Am. Chem. Soc, 1964, 2087

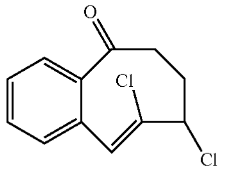

J. Chem. Soc. Chem Comm 1992, 1433

-continued

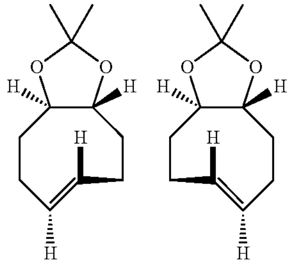

Tetrahedron: Asymmetry 15 (2004) 3123

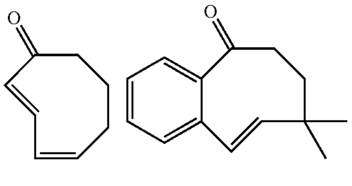

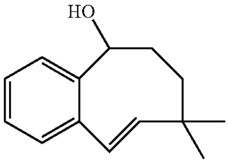

Tetrahedron Lett 1975, 49, 4327

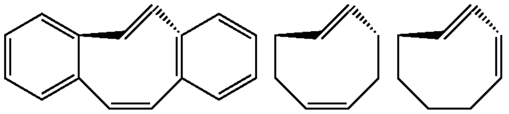

Angew. Chem. Int. Ed. 2008, 47, 2982

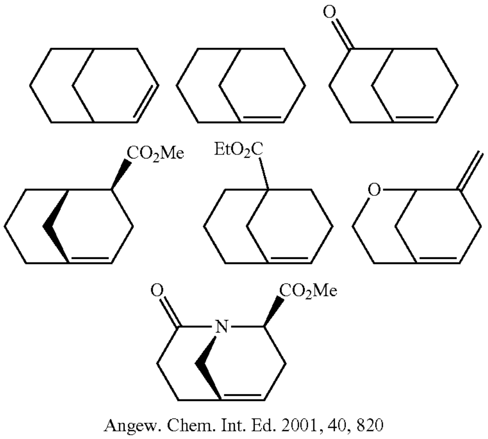

Angew. Chem. Int. Ed. 2001, 40, 820

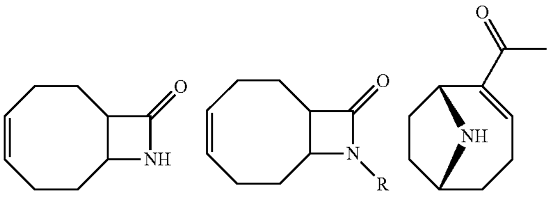

Zuniga, Thesis 2012, University of Salamanca

-continued

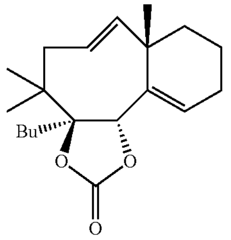

Molecules 2010, 15, 4242-4260

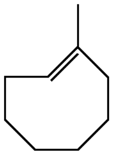

J. Am. Chem. Soc 1992, 114, 3044

= rest of molecule

Preferred TCO compounds according to this invention are the racemic and enantiomerically pure compounds listed below:

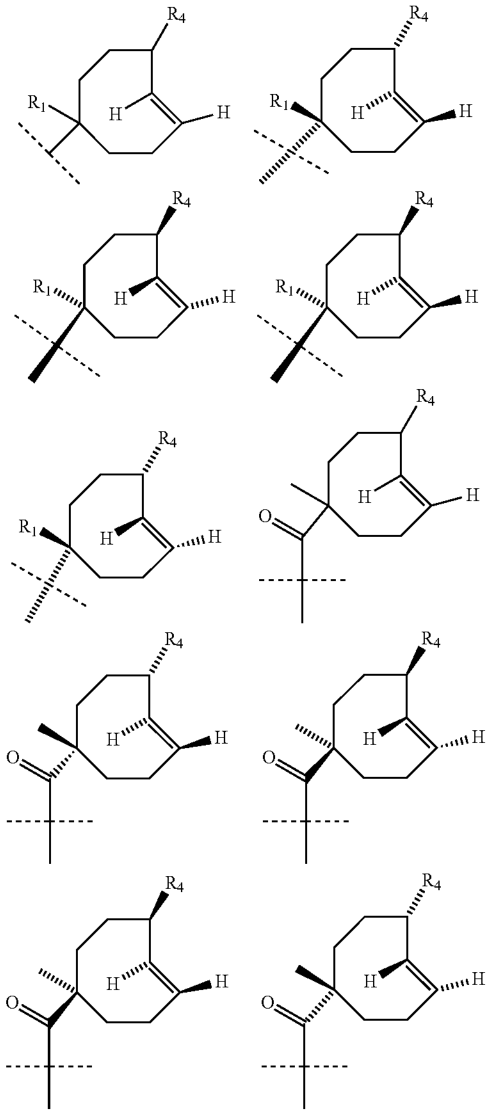

wherein the dashed line denotes a bond to the remainder of the molecule.

Especially preferred TCO compounds according to this invention are the enantiomerically pure compounds listed below:

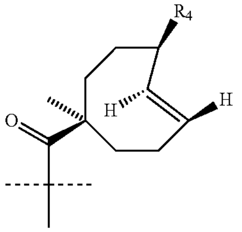

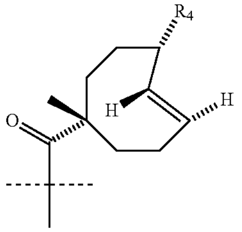

Preferred TCO intermediates to prepare the TCO prodrugs of the invention are listed below. Particularly preferred intermediates from the below are enantiomerically pure compounds A-F, in particular A, D, E, F. A person skilled in the art will understand that compounds E and F still need to be isomerized to E-cyclooctenes, after which the enantiomer with the axial OH can be separated from the enantiomer with the equatorial OH as described by Rossin et al Bioconj. Chem., 2016 27(7): 1697-1706.

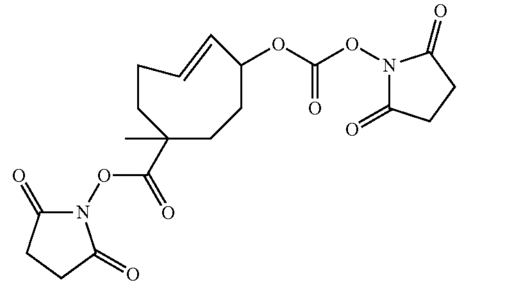

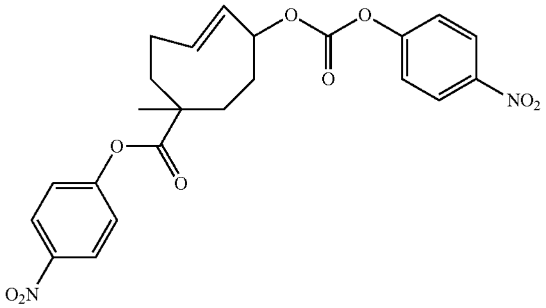

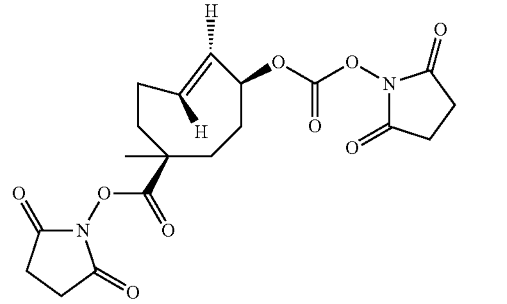

-continued

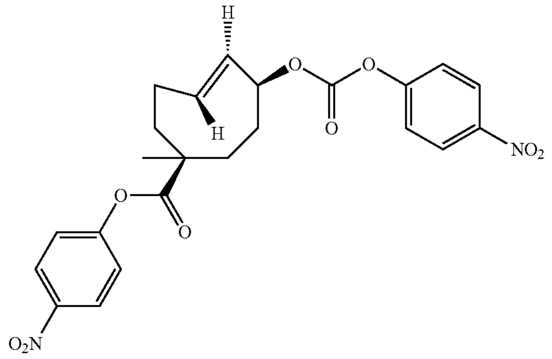

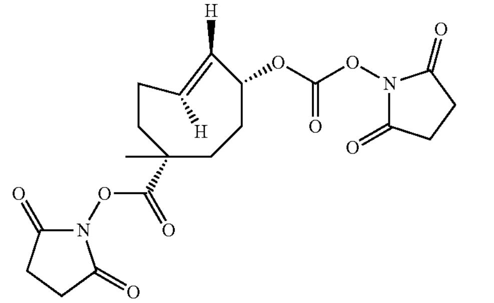

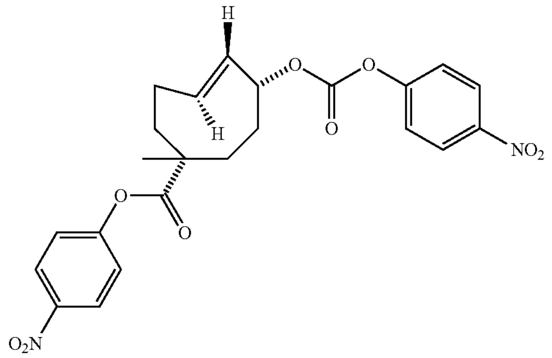

A

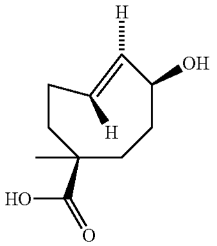

B

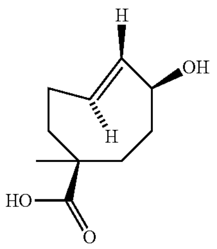

-continued

C

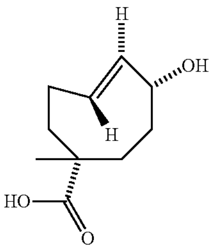

D

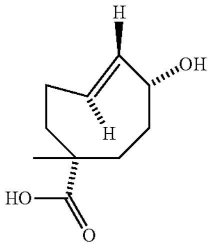

-continued

E

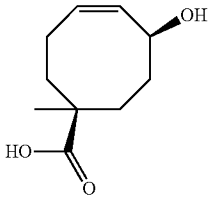

F

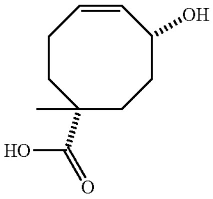

A general synthesis method of a preferred TCO trigger of this invention and its corresponding prodrugs is shows directly below. The synthesis method is as reported in Rossin et al Nature Communications 2018, 9, 1484 and Rossin et al Bioconj. Chem., 2016 27(7): 1697-1706 with the exception of the conversion of D to F, which now is conducted by mixing D with hydroxide solution in methanol, followed by evaporation and reaction with iodomethane. Please note that for sake of clarity only one of the two enantiomers of E-K is shown. A person skilled in the art will understand that the enantiomers can be separated at various stages in the synthesis using established chiral resolution methods to obtain enantiomerically pure B, E, F, H, for example, such as chiral salts.

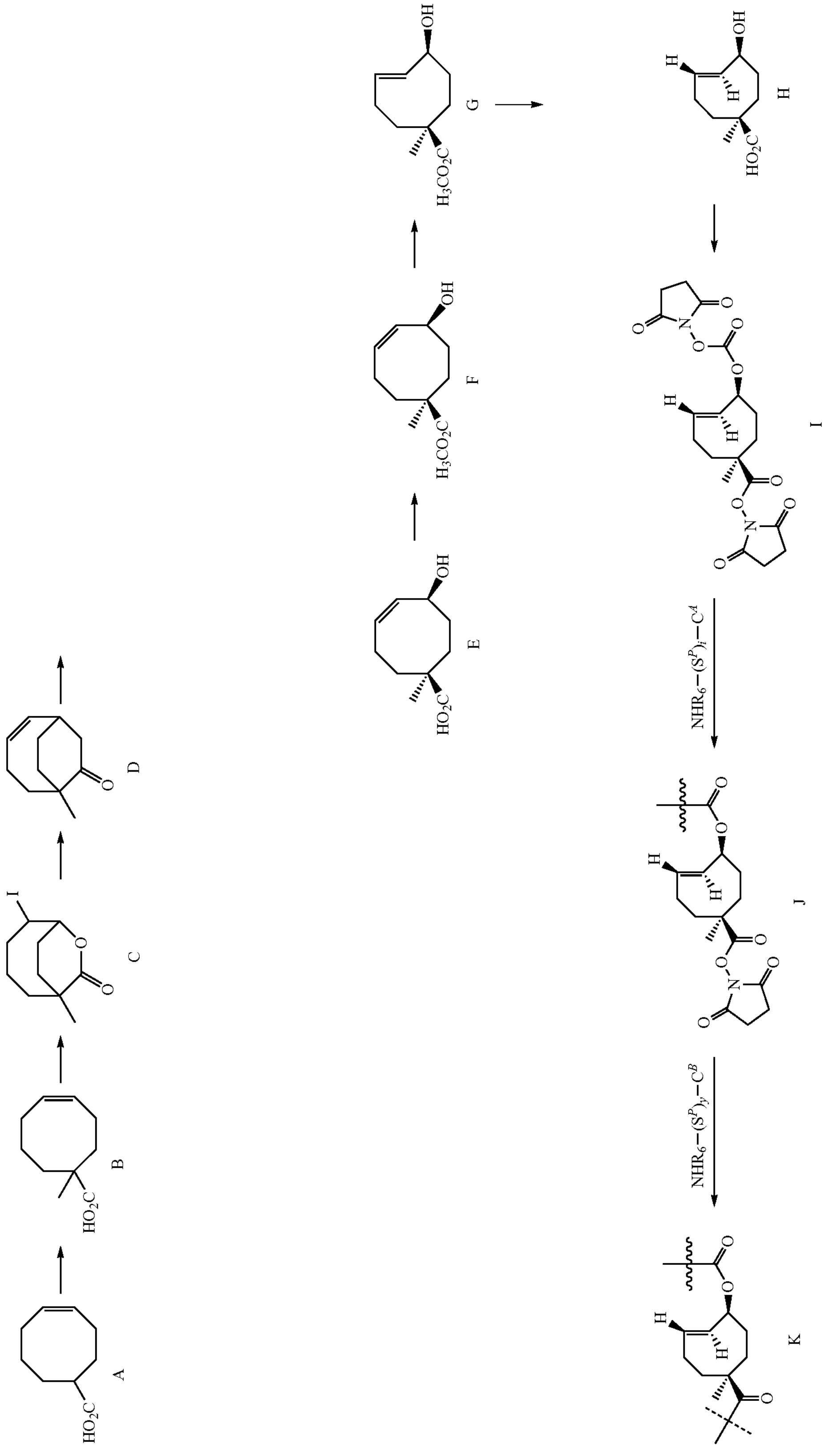
A
B
C
D
E
F
G
H
I
$NHR_6-(S^P)_i-C^A$
J
$NHR_6-(S^P)_y-C^B$
K wherein the wiggly line and the dashed line denote bonds to the respective remainders of the molecule.

Tetrazine

The compound comprising a tetrazine used to activate the dienophile is herein referred to as "Activator". The tetrazine reacts with the other Bio-orthogonal Reactive Group, that is a dienophile (vide supra). The diene of the Activator is selected so as to be capable of reacting with the dienophile, the TCO, by undergoing a Diels-Alder cycloaddition followed by a retro Diels-Alder reaction, giving the IEDDA adduct. This intermediate adduct then releases the Construct-A, where this release can be caused by various circumstances or conditions that relate to the specific molecular structure of the IEDDA adduct.

Synthesis routes to tetrazines in general are readily available to the skilled person, based on standard knowledge in the art. References to tetrazine synthesis routes include for example Lions et al, *J. Org. Chem.*, 1965, 30, 318-319; Horwitz et al, *J. Am. Chem. Soc.*, 1958, 80, 3155-3159; Hapiot et al, *New J. Chem.*, 2004, 28, 387-392, Kaim et al, *Z. Naturforsch.*, 1995, 50b, 123-127; Yang et al., *Angew. Chem.* 2012, 124, 5312-5315; Mao et al., *Angew. Chem. Int. Ed.* 2019, 58, 1106-1109; Qu et al. *Angew. Chem. Int. Ed.* 2018, 57, 12057-12061; Selvaraj et al., *Tetrahedron Lett.* 2014, 55, 4795-4797; Fan et al., *Angew. Chem. Int. Ed.* 2016, 55, 14046-14050.

Linker $L^C$ $L^C$ is an optional self-immolative linker, which may consist of multiple units arranged linearly and/or branched and may release one or more $C^A$ moieties. By way of further clarification, if n in $R_4$ is 0 the species $C^A$ directly constitutes the leaving group of the release reaction, and if n in $R_4$ is 1, the self-immolative linker $L^C$ constitutes the leaving group of the release reaction. The position and ways of attachment of linkers $L^C$ and constructs $C^A$ are known to the skilled person, see for example [Papot et al., Anticancer Agents Med. Chem., 2008, 8, 618-637]. Nevertheless, typical but non-limiting examples of self-immolative linkers $L^C$ are benzyl-derivatives, such as those drawn below. There are two main self-immolation mechanisms: electron cascade elimination and cyclization-mediated elimination. The example below on the left functions by means of the cascade mechanism, wherein the bond to the $Y^C$ between Trigger and $L^C$, here termed $Y^{C1}$, is cleaved, and an electron pair of $Y^{C1}$, for example an electron pair of $NR_6$, shifts into the benzyl moiety resulting in an electron cascade and the formation of 4-hydroxybenzyl alcohol, $CO_2$ and the liberated $C^A$ also comprising an YC, here termed $Y^{C2}$. The example in the middle functions by means of the cyclization mechanism, wherein cleavage of the bond to the amine of $Y^{C1}$ leads to nucleophilic attack of the amine on the carbonyl, forming a 5-ring 1,3-dimethylimidazolidin-2-one and liberating the $C^A$ including $Y^{C2}$. The example on the right combines both mechanisms, this linker will degrade not only into $CO_2$ and one unit of 4-hydroxybenzyl alcohol (when $Y^{C1}$ is O), but also into one 1,3-dimethylimidazolidin-2-one unit.

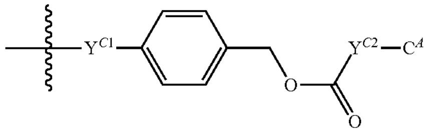

$Y^{C1}$ = O, S, $NR^6$ $Y^{C2}$ = O, S, secondary or tertiary amine; preferably secondary or tertiary amine indicates bond to Trigger -continued

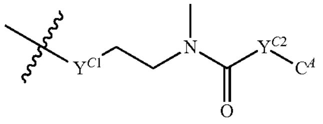

$Y^{C1}$ = $NR^6$; $R^6$ is preferably methyl $Y^{C2}$ = O, S indicates bond to Trigger

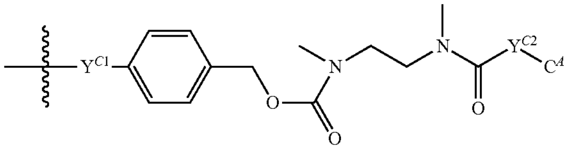

$Y^{C1}$ = O, S, $NR^6$ $Y^{C2}$ = O, S indicates bond to Trigger

By substituting the benzyl groups of aforementioned self-immolative linkers $L^C$, it is possible to tune the rate of release of the construct $C^A$, caused by either steric and/or electronic effects on the cyclization and/or cascade release. Synthetic procedures to prepare such substituted benzyl-derivatives are known to the skilled person (see for example [Greenwald et al, J. Med. Chem., 1999, 42, 3657-3667] and [Thornthwaite et al, Polym. Chem., 2011, 2, 773-790]. Some examples of substituted benzyl-derivatives with different release rates are drawn below.

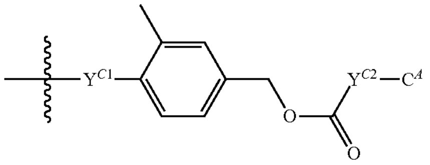

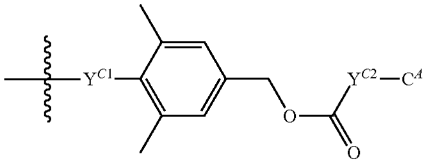

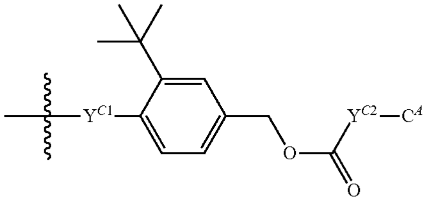

$Y^{C1}$ = O, S, $NR^6$ $Y^{C2}$ = O, S, secondary or tertiary amine; preferably secondary or tertiary amine indicates bond to Trigger In some exemplary embodiments the $L^C$ satisfies one of the following Formulae 15a-c Formula 15a

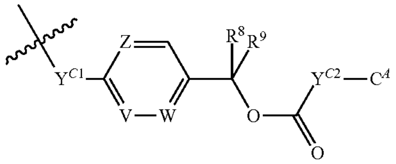

-continued

Formula 15b

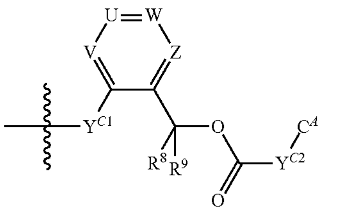

Formula 15c

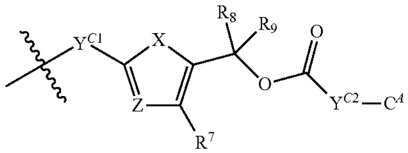

indicated bond to Trigger wherein $Y^{C1}$ is O, S or $NR_6$; V, U, W, Z are each independently $CR^7$ or N; $Y^{C2}$ is O, S, secondary amine or tertiary amine, wherein these $Y^{C2}$ moieties are part of CA; with $R^6$, $R^7$, $R^8$, $R^9$ as defined above. In some embodiments it is preferred that $R^6$ is H or methyl, $R^7$ is H, $R^8$ is H or methyl and $R^9$ is H. In some embodiments the $R^7$ comprised in Formula 15c is $CF_3$ and Z is N.

In other embodiments the $L^C$ satisfies the following Formula 15d

Formula 15d

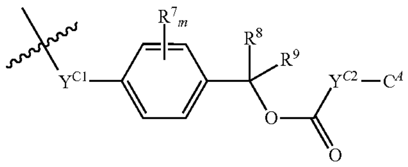

indicates bond to Trigger wherein $Y^{C1}$ is O, S or $NR_6$; $Y^{C2}$ is O, S, secondary amine or tertiary amine, wherein these $Y^{C2}$ moieties are part of CA; with $R^6$, $R^7$, $R^8$, $R^9$ as defined above; preferably $R^7$ is $C_1$-$C_8$alkyl, $C_6$-$C_{12}$ aryl, $C_1$-$C_5$ O-alkyl, $C_6$-$C_{12}$ O-aryl, $NO_2$, F, Cl, Br, I, CN, with m being an integer from 0 to 4; each $R^8$ and $R^9$ are independently H, $C_1$-$C_8$alkyl, $C_6$-$C_{12}$ aryl, $C_1$-$C_8$ O-alkyl, $C_6$-$C_{12}$ O-aryl, $NO_2$, F, Cl, Br, I, CN. Preferably $R^7$ is electron donating and preferably m is an integer between 0 and 2, more preferably m is 0. Preferably $R^8$ is H and $R^9$ is H or methyl.

Self-immolative linkers that undergo cyclization include but are not limited to substituted and unsubstituted aminobutyric acid amide, appropriately substituted bicyclo[2.2.1] and bicyclo[2.2.2] ring system, 2-aminophenylpropionic acid amides, and trimethyl lock-based linkers, see e.g. [Chem. Biol. 1995, 2, 223], [J. Am. Chem. Soc. 1972, 94, 5815], [J. Org. Chem. 1990, 55, 5867], the contents of which are hereby incorporated by reference.

In other embodiments such cyclization $L^C$ satisfies one of the following Formulae 16a-d.

Formula 16a

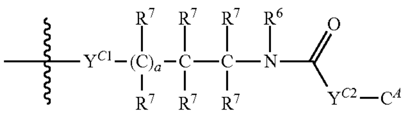

-continued

Formula 16b

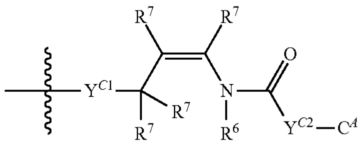

Formula 16c

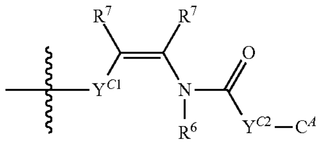

Formula 16d

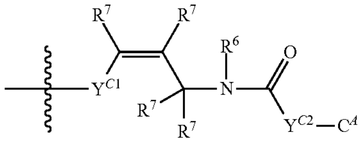

indicates bond to Trigger

Wherein $Y^{C1}$ is $NR_6$; $Y^{C2}$ is O or S, wherein these $Y^{C2}$ moieties are part of $C^A$; a is independently 0 or 1; $R^6$ and $R^7$ are as defined above. Preferably $R^6$ and $R^7$ are H, unsubstituted $C_1$-$C_8$alkyl, $C_6$ aryl, more preferably $R^6$ is H or methyl and $R^7$ is H.

Several non-limiting example structures of $L^C$ are shown below. In these examples $C^A$ is preferably bound to $L^C$ via an $Y^{C2}$ that is O or S, wherein O or Sis part of $C^A$. For the avoidance of doubt, in these examples $Y^{C1}$ is not denoted as such but is embodied by the relevant NH, $NR_6$, S, O groups.

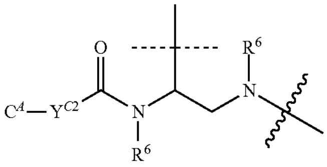

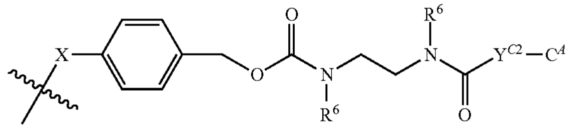

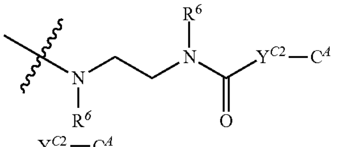

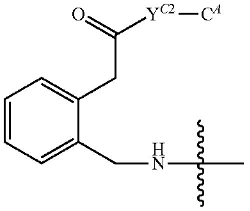

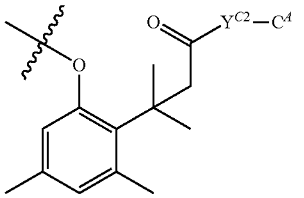

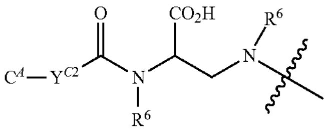

-continued

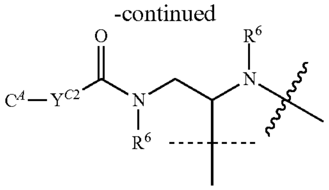

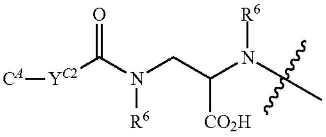

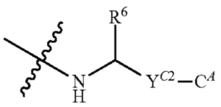

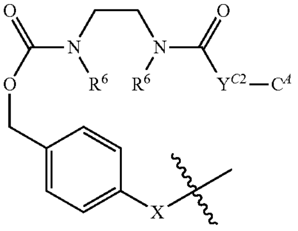

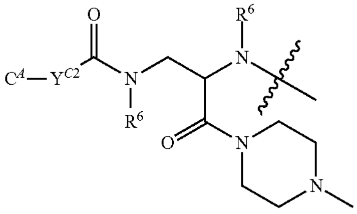

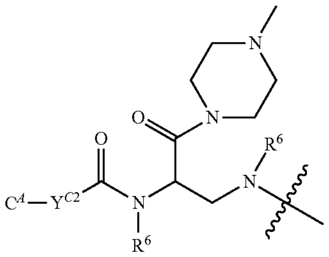

indicates bond to Trigger

----- indicates bond to $C^B$ or $S^P$—$C^B$ or $S^P$

Preferably $Y^{C2}$ is O or S

X = O, S, $NR^6$ $R^6$ is as defined for Formula 1

Several other non-limiting example structures of $L^C$ are shown below. In these examples $C^A$ is preferably bound to $L^C$ via an $Y^{C2}$ that is a secondary or primary amine, and wherein said $Y^{C2}$ is part of $C^A$. For the avoidance of doubt, in these examples $Y^{C1}$ is not denoted as such but is embodied by the relevant NH, $NR_6$, S, O groups

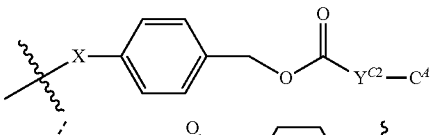

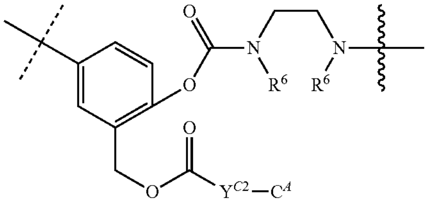

-continued

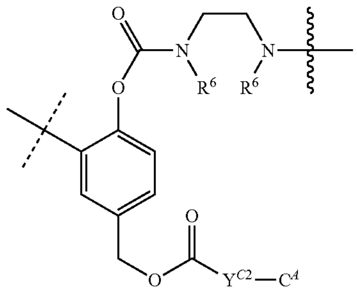

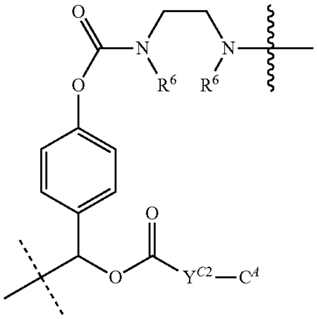

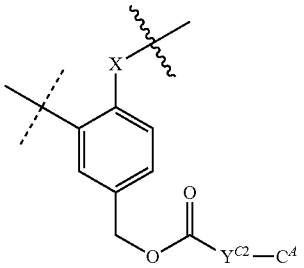

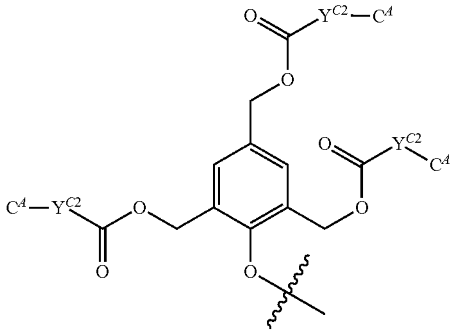

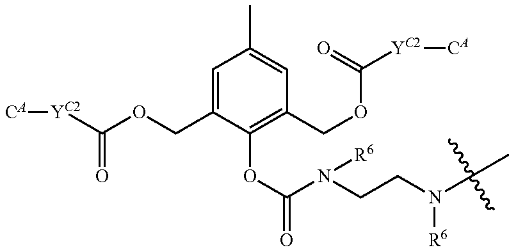

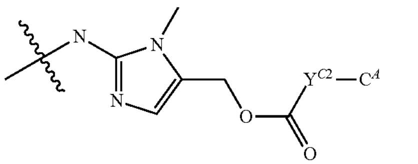

-continued

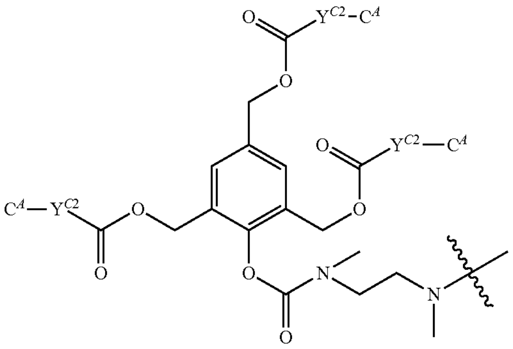

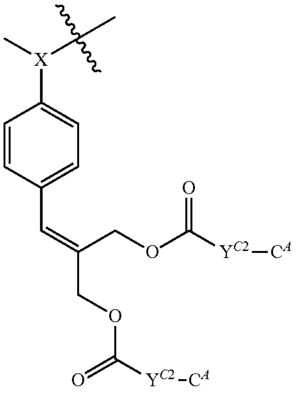

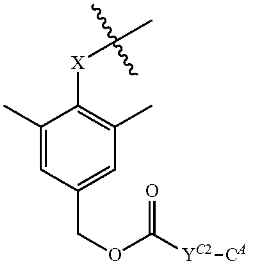

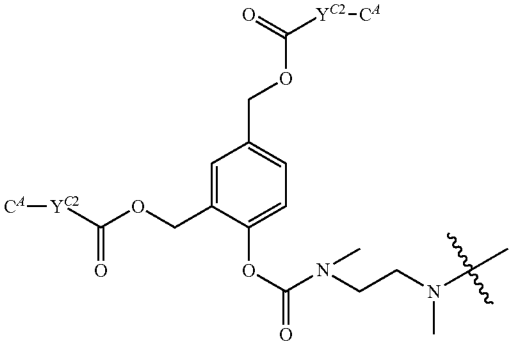

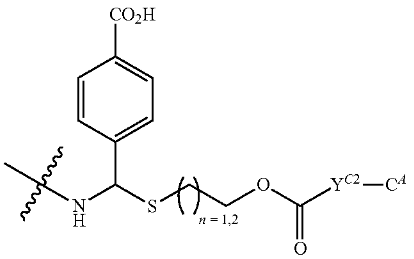

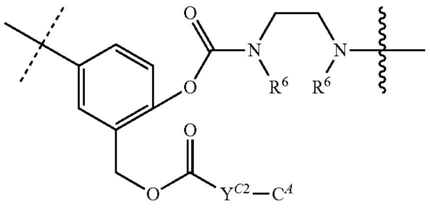

-continued

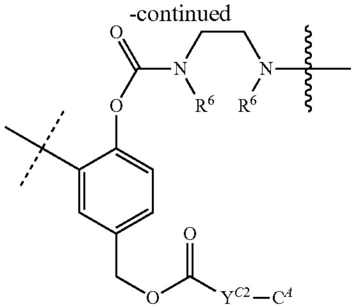

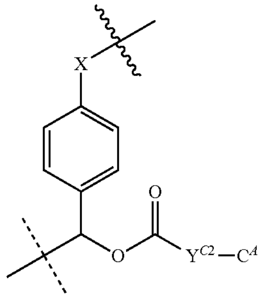

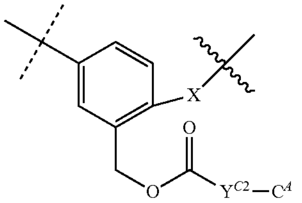

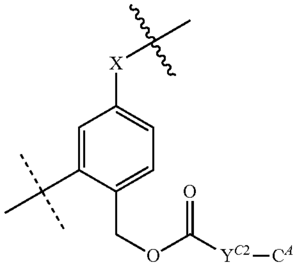

$\sim\sim$ indicates bond to Trigger

----- indicates bond to $C^B$ or $S^P$—$C^B$ or $S^P$

Preferably $Y^{C2}$ is seconary or tertiary amine

X = O, S, $NR^6$ $R^6$ is as defined for formula 1

Further non-limiting examples of $L^C$ can be found in WO2009017394 (A1), U.S. Pat. No. 7,375,078, WO2015038426A1, WO2004043493, Angew. Chem. Int. Ed. 2015, 54, 7492-7509, the contents of which are hereby incorporated by reference.

In some aspects of the invention the $L^C$ has a mass of no more than 1000 daltons, no more than 500 daltons, no more than 400 daltons, no more than 300 daltons, or from 10, 50 or 100 to 1000 daltons, from 10, 50, 100 to 400 daltons, from 10, 50, 100 to 300 daltons, from 10, 50, 100 to 200 daltons, e.g., 10-1000 daltons, such as 50-500 daltons, such as 100 to 400 daltons.

Construct A ($C^A$)

Construct-A in this invention is defined as a Drug or Drugs, bound to the Trigger, optionally via a self immolative linker $L^C$.

Construct B ($C^B$)

Construct-B in this invention is defined as a Targeting Agent, bound to the Trigger.

Prodrug

Figure 14:
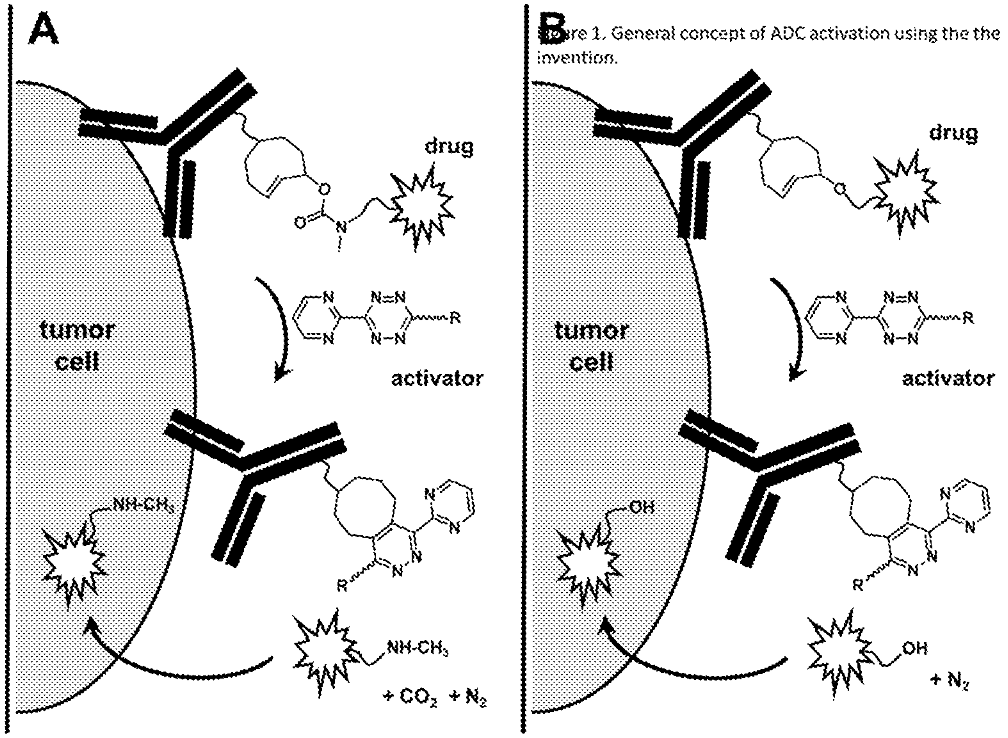
FIG. 14 depicts a preferred embodiment of this invention. In both panels an ADC is administered to a cancer patient, and is allowed to circulate and bind to a target on the cancer cell. After the freely circulating ADC has sufficiently cleared from circulation, for example after 2 days post injection, the Activator, is administered and distributes systemically, allowing the reaction with the Trigger of cancer-bound Prodrug or ADC, releasing the Drug, after which the Drug can penetrate and kill neighbouring cancer cells. Panel A depicts the cleavage of a carbamate-linked Drug and Panel B depicts the cleavage of an ether-linked Drug.

In a preferred embodiment Construct A is a Drug. A Prodrug is a conjugate of the Drug and the TCO and thus comprises a Drug that is capable of increased therapeutic action after its release from the TCO. Such a Prodrug may optionally have specificity for disease targets. In a preferred embodiment the targeted Prodrug is an Antibody-Drug Conjugate (ADC). Activation of the Prodrug by the IEDDA pyridazine elimination of the TCO with the Activator leads to release of the Drug (FIG. 14).

It is desirable to be able to activate targeted Prodrugs such as ADCs selectively and predictably at the target site without being dependent on homogenous penetration and targeting, and on endogenous activation parameters (e.g. pH, enzymes) which may vary en route to and within the target, and from indication to indication and from patient to patient. The use of a biocompatible chemical reaction that does not rely on endogenous activation mechanisms for selective Prodrug activation would represent a powerful new tool in cancer therapy. It would expand the scope to cancer-related receptors and extracellular matrix targets that do not afford efficient internalization of the ADC and therefore cannot be addressed with the current ADC approaches. In addition, extraneous and selective activation of Prodrugs when and where required leads to enhanced control over Prodrug activation, intracellularly and extracellularly. Finally this approach would maximize the bystander effect, allowing more efficient Drug permeation throughout the tumor tissue.

In order to avoid the drawbacks of current prodrug activation, this invention makes use of an abiotic, bio-orthogonal chemical reaction to provoke release of the Drug from the Prodrug, such as an ADC. In this type of ADC, the Drug is attached to the antibody (or another type of Targeting Agent) via a Trigger, and this Trigger is not activated endogeneously by e.g. an enzyme or a specific pH, but by a controlled administration of the Activator, i.e. a species that reacts with the Trigger moiety in the ADC, to induce release of the Drug from the Trigger (or vice versa, release of the Trigger from the Drug, however one may view this release process) (FIG. 14).

The present invention provides a kit for the administration and activation of a Prodrug, the kit comprising a Drug, denoted as $C^A$, linked directly, or indirectly through a linker $L^C$, to a Trigger moiety TR, wherein TR is bound to a Construct-B, that is Targeting Agent $T^T$, and an Activator for the Trigger moiety, wherein the Trigger moiety comprises a dienophile and the Activator comprises a diene, the dienophile satisfying Formula (1).

In yet another aspect, the invention provides a method of modifying a Drug compound into a Prodrug that can be triggered by an abiotic, bio-orthogonal reaction, the method comprising the steps of providing a Drug and chemically linking the Drug to a TCO moiety satisfying Formula (1).

In a still further aspect, the invention provides a method of treatment wherein a patient suffering from a disease that can be modulated by a Drug, is treated by administering, to said patient, a Prodrug comprising a Drug, a Trigger moiety and a Targeting agent after activation of which by administration of an Activator the Drug will be released, wherein the Trigger moiety comprises a structure satisfying Formula (1).

In a still further aspect, the invention is a compound comprising a TCO moiety, said moiety comprising a linkage to a Drug, for use in Prodrug therapy in an animal or a human being.

In another aspect, the invention is the use of a tetrazine as an Activator for the release, in a physiological environment, of a substance covalently linked to a compound satisfying Formula (1). In connection herewith, the invention also pertains to a tetrazine for use as an Activator for the release, in a physiological environment, of a substance linked to a compound satisfying Formula (1), and to a method for activating, in a physiological environment, the release of a substance linked to a compound satisfying Formula (1), wherein a tetrazine is used as an Activator.

A Prodrug is a conjugate of the Drug and the Trigger and thus comprises a Drug that is capable of increased therapeutic action after its release from the Trigger. In embodiments where the Prodrug is targeted to e.g. a Primary Target, as is the case with for example Antibody Drug Conjugates, the Prodrug comprises a Targeting agent, which is bound to the Trigger.

According to a further particular embodiment of the invention, the Prodrug is selected so as to target and or address a disease, such as cancer, an inflammation, an autoimmune disease, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme.

According to one embodiment, the Prodrug and/or the Activator can be multimeric compounds, comprising a plurality of Drugs and/or bioorthogonal reactive moieties. These multimeric compounds can be polymers, dendrimers, liposomes, polymer particles, or other polymeric constructs.

It is preferred that the optional $L^C$ comprised in the Prodrug is self-immolative, affording traceless release of the Drug.

Drugs that can be used in a Prodrug relevant to this invention are pharmaceutically active compounds, in particular low to medium molecular weight compounds (e.g. about 200 to about 2500 Da, preferably about 300 to about 1750 Da, more preferably about 300 to about 1000 Da).

In a preferred embodiment the pharmaceutically active compound is selected from the group consisting of cytotoxins, antiproliferative/antitumor agents, antiviral agents, antibiotics, anti-inflammatory agents, chemosensitizing agents, radiosensitizing agents, immunomodulators, immunosuppressants, immunostimulants, anti-angiogenic factors, and enzyme inhibitors.

In some embodiments these pharmaceutically active compounds are selected from the group consisting of antibodies, antibody derivatives, antibody fragments, proteins, aptamers, oligopeptides, oligonucleotides, oligosaccharides, carbohydrates, as well as peptides, peptoids, steroids, toxins, hormones, cytokines, chemokines In preferred embodiments these drugs are low to medium molecular weight compounds, preferably organic compounds (e.g. about 200 to about 2500 Da, preferably about 300 to about 1750 Da, more preferably about 300 to about 1000 Da).

Exemplary cytotoxic drug types for use as conjugates to the TCO and to be released upon IEDDA reaction with the Activator, for example for use in cancer therapy, include but are not limited to DNA damaging agents, DNA crosslinkers, DNA binders, DNA alkylators, DNA intercalators, DNA cleavers, microtubule stabilizing and destabilizing agents, topoisomerases inhibitors, radiation sensitizers, anti-metabolites, natural products and their analogs, peptides, oligonucleotides, enzyme inhibitors such as dihydrofolate reductase inhibitors and thymidylate synthase inhibitors.

Examples include but are not limited to colchinine, vinca alkaloids, anthracyclines (e.g. doxorubicin, epirubicin, idarubicin, daunorubicin), camptothecins, taxanes, taxols, vinblastine, vincristine, vindesine, calicheamycins, tubulysins, tubulysin M, cryptophycins, methotrexate, methopterin, aminopterin, dichloromethotrexate, irinotecans, enediynes, amanitins, deBouganin, dactinomycines, CC1065 and its analogs, duocarmycins, maytansines, maytansinoids, dolastatins, auristatins, pyrrolobenzodiazepines and dimers (PBDs), indolinobenzodiazepines and dimers, pyridinobenzodiazepines and dimers, mitomycins (e.g. mitomycin C, mitomycin A, caminomycin), melphalan, leurosine, leurosideine, actinomycin, tallysomycin, lexitropsins, bleomycins, podophyllotoxins, etoposide, etoposide phosphate, staurosporin, esperamicin, the pteridine family of drugs, SN-38 and its analogs, platinum-based drugs, cytotoxic nucleosides.

Other exemplary drug classes are angiogenesis inhibitors, cell cycle progression inhibitors, P13K/m-TOR/AKT pathway inhibitors, MAPK signaling pathway inhibitors, kinase inhibitors, protein chaperones inhibitors, HDAC inhibitors, PARP inhibitors, Wnt/Hedgehog signaling pathway inhibitors, and RNA polymerase inhibitors.

Examples of auristatins include dolastatin 10, monomethyl auristatin E (MMAE), auristatin F, monomethyl auristatin F (MMAF), auristatin F hydroxypropylamide (AF HPA), auristatin F phenylene diamine (AFP), monomethyl auristatin D (MMAD), auristatin PE, auristatin EB, auristatin EFP, auristatin TP and auristatin AQ. Suitable auristatins are also described in U.S. Publication Nos. 2003/0083263, 2011/0020343, and 2011/0070248; PCT Application Publication Nos. WO09/117531, WO2005/081711, WO04/010957; WO02/088172 and WO01/24763, and U.S. Pat. Nos. 7,498,298; 6,884,869; 6,323,315; 6,239,104; 6,124,431; 6,034,065; 5,780,588; 5,767,237; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,879,278; 4,816,444; and 4,486,414, the disclosures of which are incorporated herein by reference in their entirety.

Exemplary drugs include the dolastatins and analogues thereof including: dolastatin A (U.S. Pat. No. 4,486,414), dolastatin B (U.S. Pat. No. 4,486,414), dolastatin 10 (U.S. Pat. Nos. 4,486,444, 5,410,024, 5,504,191, 5,521,284, 5,530,097, 5,599,902, 5,635,483, 5,663,149, 5,665,860, 5,780,588, 6,034,065, 6,323,315), dolastatin 13 (U.S. Pat. No. 4,986,988), dolastatin 14 (U.S. Pat. No. 5,138,036), dolastatin 15 (U.S. Pat. No. 4,879,278), dolastatin 16 (U.S. Pat. No. 6,239,104), dolastatin 17 (U.S. Pat. No. 6,239,104), and dolastatin 18 (U.S. Pat. No. 6,239,104), each patent incorporated herein by reference in their entirety.

Exemplary maytansines, maytansinoids, such as DM-1 and DM-4, or maytansinoid analogs, including maytansinol and maytansinol analogs, are described in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 6,441,163; 6,716,821 and 7,276,497. Other examples include mertansine and ansamitocin.

Pyrrolobenzodiazepines (PBDs), which expressly include dimers and analogs, include but are not limited to those described in [Denny, Exp. Opin. Ther. Patents, 10(4): 459-474 (2000)], [Hartley et al., Expert Opin Investig Drugs. 2011, 20(6): 733-44], Antonow et al., Chem Rev. 2011, 111(4), 2815-64]. Exemplary indolinobenzodiazepines are described in literature. Exemplary pyridinobenzodiazepines are described in literature.

Calicheamicins include, e.g. enediynes, esperamicin, and those described in U.S. Pat. Nos. 5,714,586 and 5,739,116

Examples of duocarmycins and analogs include CC1065, duocarmycin SA, duocarmycin A, duocarmycin B1, duocarmycin B2, duocarmycin C1, duocarmycin C2, duocarmycin D, DU-86, KW-2189, adozelesin, bizelesin, carzelesin, seco-adozelesin, CPI, CBI. Other examples include those described in, for example, U.S. Pat. Nos. 5,070,092; 5,101,092; 5,187,186; 5,475,092; 5,595,499; 5,846,545; 6,534,660; 6,548,530; 6,586,618; 6,660,742; 6,756,397; 7,049,316; 7,553,816; 8,815,226; US20150104407; 61/988,011 filed May 2, 2014 and 62/010,972 filed Jun. 11, 2014; the disclosure of each of which is incorporated herein in its entirety.

Exemplary vinca alkaloids include vincristine, vinblastine, vindesine, and navelbine, and those disclosed in U.S. Publication Nos. 2002/0103136 and 2010/0305149, and in U.S. Pat. No. 7,303,749, the disclosures of which are incorporated herein by reference in their entirety.

Exemplary epothilone compounds include epothilone A, B, C, D, E, and F, and derivatives thereof. Suitable epothilone compounds and derivatives thereof are described, for example, in U.S. Pat. Nos. 6,956,036; 6,989,450; 6,121,029; 6,117,659; 6,096,757; 6,043,372; 5,969,145; and 5,886,026; and WO97/19086; WO98/08849; WO98/22461; WO98/25929; WO98/38192; WO99/01124; WO99/02514; WO99/03848; WO99/07692; WO99/27890; and WO99/28324; the disclosures of which are incorporated herein by reference in their entirety.

Exemplary cryptophycin compounds are described in U.S. Pat. Nos. 6,680,311 and 6,747,021; the disclosures of which are incorporated herein by reference in their entirety.

Exemplary platinum compounds include cisplatin, carboplatin, oxaliplatin, iproplatin, ormaplatin, tetraplatin.

Exemplary DNA binding or alkylating drugs include CC-1065 and its analogs, anthracyclines, calicheamicins, dactinomycines, mitromycines, pyrrolobenzodiazepines, indolinobenzodiazepines, pyridinobenzodiazepines and the like.

Exemplary microtubule stabilizing and destabilizing agents include taxane compounds, such as paclitaxel, docetaxel, tesetaxel, and carbazitaxel; maytansinoids, auristatins and analogs thereof, vinca alkaloid derivatives, epothilones and cryptophycins.

Exemplary topoisomerase inhibitors include camptothecin and camptothecin derivatives, camptothecin analogs and non-natural camptothecins, such as, for example, CPT-11, SN-38, topotecan, 9-aminocamptothecin, rubitecan, gimatecan, karenitecin, silatecan, lurtotecan, exatecan, diflometotecan, belotecan, lurtotecan and S39625. Other camptothecin compounds that can be used in the present invention include those described in, for example, J. Med. Chem., 29:2358-2363 (1986); J. Med. Chem., 23:554 (1980); J. Med Chem., 30:1774 (1987).

Angiogenesis inhibitors include, but are not limited to, MetAP2 inhibitors, VEGF inhibitors, PIGF inhibitors, VGFR inhibitors, PDGFR inhibitors, MetAP2 inhibitors. Exemplary VGFR and PDGFR inhibitors include sorafenib, sunitinib and vatalanib. Exemplary MetAP2 inhibitors include fumagillol analogs, meaning compounds that include the fumagillin core structure.

Exemplary cell cycle progression inhibitors include CDK inhibitors such as, for example, BMS-387032 and PD0332991; Rho-kinase inhibitors such as, for example, AZD7762; aurora kinase inhibitors such as, for example, AZD1152, MLN8054 and MLN8237; PLK inhibitors such as, for example, BI 2536, BI6727, GSK461364, ON-01910; and KSP inhibitors such as, for example, SB 743921, SB 715992, MK-0731, AZD8477, AZ3146 and ARRY-520.

Exemplary P13K/m-TOR/AKT signalling pathway inhibitors include phosphoinositide 3-kinase (P13K) inhibitors, GSK-3 inhibitors, ATM inhibitors, DNA-PK inhibitors and PDK-1 inhibitors.

Exemplary P13 kinases are disclosed in U.S. Pat. No. 6,608,053, and include BEZ235, BGT226, BKM120, CAL263, demethoxyviridin, GDC-0941, GSK615, IC87114, LY294002, Palomid 529, perifosine, PF-04691502, PX-866, SAR245408, SAR245409, SF1126, Wortmannin, XL147 and XL765.

Exemplary AKT inhibitors include, but are not limited to AT7867.

Exemplary MAPK signaling pathway inhibitors include MEK, Ras, JNK, B-Raf and p38 MAPK inhibitors.

Exemplary MEK inhibitors are disclosed in U.S. Pat. No. 7,517,944 and include GDC-0973, GSK1120212, MSC1936369B, AS703026, RO5126766 and RO4987655, PD0325901, AZD6244, AZD8330 and GDC-0973.

Exemplary B-raf inhibitors include CDC-0879, PLX-4032, and SB590885.

Exemplary B p38 MAPK inhibitors include BIRB 796, LY2228820 and SB 202190.

Exemplary receptor tyrosine kinases inhibitors include but are not limited to AEE788 (NVP-AEE 788), BIBW2992 (Afatinib), Lapatinib, Erlotinib (Tarceva), Gefitinib (Iressa), AP24534 (Ponatinib), ABT-869 (linifanib), AZD2171, CHR-258 (Dovitinib), Sunitinib (Sutent), Sorafenib (Nexavar), and Vatalinib.

Exemplary protein chaperon inhibitors include HSP90 inhibitors. Exemplary inhibitors include 17AAG derivatives, BIIB021, BIIB028, SNX-5422, NVP-AUY-922 and KW-2478.

Exemplary HDAC inhibitors include Belinostat (PXD101), CUDC-101, Droxinostat, ITF2357 (Givinostat, Gavinostat), JNJ-26481585, LAQ824 (NVP-LAQ824, Dacinostat), LBH-589 (Panobinostat), MC1568, MGCD0103 (Mocetinostat), MS-275 (Entinostat), PCI-24781, Pyroxamide (NSC 696085), SB939, Trichostatin A and Vorinostat (SAHA).

Exemplary PARP inhibitors include iniparib (BSI 201), olaparib (AZD-2281), ABT-888 (Veliparib), AG014699, CEP9722, MK 4827, KU-0059436 (AZD2281), LT-673, 3-aminobenzamide, A-966492, and AZD2461.

Exemplary Wnt/Hedgehog signalling pathway inhibitors include vismodegib, cyclopamine and XAV-939.

Exemplary RNA polymerase inhibitors include amatoxins. Exemplary amatoxins include alpha-amanitins, beta amanitins, gamma amanitins, eta amanitins, amanullin, amanullic acid, amanisamide, amanon, and proamanullin.

Exemplary immunemodulators are APRIL, cytokines, including IL-2, IL-7, IL-10, IL-12, IL-15, IL-21, TNF, interferon gamma, GMCSF, NDV-GMCSF, and agonists and antagonists of STING, agonists and antagonists of TLRs including TLR1/2, TLR3, TLR4, TLR7/8, TLR9, TLR12, agonists and antagonists of GITR, CD3, CD28, CD40, CD74, CTLA4, OX40, PD1, PDL1, RIG, MDA-5, NLRP1, NLRP3, AIM2, IDO, MEK, cGAS, and CD25, NKG2A.

Exemplary cytokines include IL-2, IL-7, IL-10, IL-12, IL-15, IL-21, TNF.

Other exemplary drugs include puromycins, topetecan, rhizoxin, echinomycin, combretastatin, netropsin, estramustine, cemadotin, discodermolide, eleutherobin, mitoxantrone, pyrrolobenzimidazoles (PBI), gamma-interferon, Thialanostatin (A) and analogs, CDK11, immunotoxins, comprising e.g. ricin A, diphtheria toxin, cholera toxin.

In exemplary embodiments of the invention, the drug moiety is a mytomycin compound, a vinca alkaloid compound, taxol or an analogue, an anthracycline compound, a calicheamicin compound, a maytansinoid compound, an auristatin compound, a duocarmycin compound, SN38 or an analogue, a pyrrolobenzodiazepine compound, a indolinobenzodiazepine compound, a pyridinobenzodiazepine compound, a tubulysin compound, a non-natural camptothecin compound, a DNA binding drug, a kinase inhibitor, a MEK inhibitor, a KSP inhibitor, a P13 kinase inhibitor, a topoisomerase inhibitor, or analogues thereof.

In one preferred embodiment the drug is a non-natural camptothecin compound, vinca alkaloid, kinase inhibitor, (e.g. P13 kinase inhibitor: GDC-0941 and PI-103), MEK inhibitor, KSP inhibitor, RNA polymerase inhibitor, PARP inhibitor, docetaxel, paclitaxel, doxorubicin, dolastatin, calicheamicins, SN38, pyrrolobenzodiazepines, pyridinobenzodiazepines, indolinobenzodiazepines, DNA binding drugs, maytansinoids DM1 and DM4, auristatin MMAE, CC1065 and its analogs, camptothecin and its analogs, SN-38 and its analogs.

In another preferred embodiment the drug is selected from DNA binding drugs and microtubule agents, including pyrrolobenzodiazepines, indolinobenzodiazepines, pyridinobenzodiazepines, maytansinoids, maytansines, auristatins, tubulysins, duocarmycins, anthracyclines, taxanes.

In another preferred embodiment the drug is selected from colchinine, vinca alkaloids, tubulysins, irinotecans, an inhibitory peptide, amanitin and deBouganin.

In another embodiment, a combination of two or more different drugs are used.

In other embodiments the released Drug is itself a prodrug designed to release a further drug.

Drugs optionally include a membrane translocation moiety (e.g. adamantine, poly-lysine/arginine, TAT, human lactoferrin) and/or a targeting agent (against e.g. a tumor cell receptor) optionally linked through a stable or labile linker. Exemplary references include: Trends in Biochemical Sciences, 2015, 40, 12, 749; J. Am. Chem. Soc. 2015, 137, 12153-12160; Pharmaceutical Research, 2007, 24, 11, 1977.

It will further be understood that, in addition to the CB, being a targeting agent attached to the Trigger, another CB, being a targeting agent, may optionally be attached to the Drug.

Alternatively, it will be further understood that the targeting agent $C^B$ may comprise one or more additional Drugs which are bound to the targeting agent by other types of linkers, e.g. cleavable by proteases, pH, thiols, or by catabolism The invention further contemplates that when the targeting agent $C^B$ is a suitably chosen antibody or antibody derivative that the targeting agent $C^B$ can induce antibody-dependent cellular toxicity (ADCC) or complement dependent cytotoxicity (CDC).

Several drugs may be replaced by an imageable label to measure drug targeting and release.

It will be understood that chemical modifications may also be made to the desired compound in order to make reactions of that compound more convenient for purposes of preparing conjugates of the invention.

Drugs containing an amine functional group for coupling to the TCO include mitomycin-C, mitomycin-A, daunorubicin, doxorubicin, aminopterin, actinomycin, bleomycin, 9-amino camptothecin, N8-acetyl spermidine, 1-(2 chloroethyl) 1,2-dimethanesulfonyl hydrazide, tallysomycin, cytarabine, dolastatins (including auristatins) and derivatives thereof.

Drugs containing a hydroxyl function group for coupling to the TCO include etoposide, camptothecin, taxol, esperamicin, 1,8-dihydroxy-bicyclo[7.3.1]trideca-4-9-diene-2,6-diyne-13-one (U.S. Pat. No. 5,198,560), podophyllotoxin, anguidine, vincristine, vinblastine, morpholine-doxorubicin, n-(5,5-diacetoxy-pentyl) doxorubicin, and derivatives thereof.

Drugs containing a sulfhydryl functional group for coupling to the TCO include esperamicin and 6-mecaptopurine, and derivatives thereof.

It will be understood that the drugs can optionally be attached to the TCO derivative through a self-immolative linker $L^C$, or a combination thereof, and which may consist of multiple (self-immolative, or non immolative) units.

Several drugs may be replaced by an imageable label to measure drug targeting and release.

According to a further particular embodiment of the invention, the Prodrug is selected so as to target and or address a disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme.

In the Prodrug, the Drug and the TCO derivative can be directly linked to each other. They can also be bound to each other via a linker or a self-immolative linker $L^C$. It will be understood that the invention encompasses any conceivable manner in which the dienophile TCO is attached to the Drug.

Methods of affecting conjugation to these drugs, e.g. through reactive amino acids such as lysine or cysteine in the case of proteins, are known to the skilled person.

It will be understood that the drug moiety is linked to the TCO in such a way that the drug is eventually capable of being released after formation of the IEDDA adduct. Generally, this means that the bond between the drug and the TCO, or in the event of a linker, the bond between the TCO and the linker $L^C$, or in the event of a self-immolative linker $L^C$, the bond between the linker and the TCO and between the drug and the linker, should be cleavable. Predominantly, the drug and the optional linker is linked via a hetero-atom, preferably via O, N, NH, or S. The cleavable bond is preferably selected from the group consisting of carbamate, thiocarbamate, carbonate, ether, ester, amine, amide, thioether, thioester, sulfoxide, and sulfonamide bonds.

Targeting

The kits and method of the invention are very suitable for use in targeted delivery of drugs.

A "primary target" as used in the present invention relates to a target for a targeting agent for therapy. For example, a primary target can be any molecule, which is present in an organism, tissue or cell. Targets include cell surface targets, e.g. receptors, glycoproteins; structural proteins, e.g. amyloid plaques; abundant extracellular targets such as stroma, tumor microenvironment targets, extracellular matrix targets such as growth factors, and proteases; intracellular targets, e.g. surfaces of Golgi bodies, surfaces of mitochondria, RNA, DNA, enzymes, components of cell signaling pathways; and/or foreign bodies, e.g. pathogens such as viruses, bacteria, fungi, yeast or parts thereof. Examples of primary targets include compounds such as proteins of which the presence or expression level is correlated with a certain tissue or cell type or of which the expression level is up regulated or down-regulated in a certain disorder. According to a particular embodiment of the present invention, the primary target is a protein such as a (internalizing or non-internalizing) receptor.

According to the present invention, the primary target can be selected from any suitable targets within the human or animal body or on a pathogen or parasite, e.g. a group comprising cells such as cell membranes and cell walls, receptors such as cell membrane receptors, intracellular structures such as Golgi bodies or mitochondria, enzymes, receptors, DNA, RNA, viruses or viral particles, antibodies, proteins, carbohydrates, monosaccharides, polysaccharides, cytokines, hormones, steroids, somatostatin receptor, monoamine oxidase, muscarinic receptors, myocardial sympatic nerve system, leukotriene receptors, e.g. on leukocytes, urokinase plasminogen activator receptor (uPAR), folate receptor, apoptosis marker, (anti-)angiogenesis marker, gastrin receptor, dopaminergic system, serotonergic system, GABAergic system, adrenergic system, cholinergic system, opioid receptors, GPIIb/IIIa receptor and other thrombus related receptors, fibrin, calcitonin receptor, tuftsin receptor, integrin receptor, fibronectin, VEGF/EGF and VEGF/EGF receptors, TAG72, CEA, CD19, CD20, CD22, CD40, CD45, CD74, CD79, CD105, CD138, CD174, CD227, CD326, CD340, MUC1, MUC16, GPNMB, PSMA, Cripto, Tenascin C, Melanocortin-1 receptor, CD44v6, G250, HLA DR, ED-B, TMEFF2, EphB2, EphA2, FAP, Mesothelin, GD2, CAIX, 5T4, matrix metalloproteinase (MMP), P/E/L-selectin receptor, LDL receptor, P-glycoprotein, neurotensin receptors, neuropeptide receptors, substance P receptors, NK receptor, CCK receptors, sigma receptors, interleukin receptors, herpes simplex virus tyrosine kinase, human tyrosine kinase, MSR1, FAP, CXCR, tumor endothelial marker (TEM), cMET, IGFR, FGFR, GPA33, and hCG.

In order to allow specific targeting of the above-listed primary targets, the targeting agent $T^T$ can comprise compounds including but not limited to antibodies, antibody fragments, e.g. Fab2, Fab, scFV, diabodies, triabodies, VHH, antibody (fragment) fusions (e.g. bi-specific and trispecific mAb fragments), proteins, peptides, e.g. octreotide and derivatives, VIP, MSH, LHRH, chemotactic peptides, cell penetrating peptide, membrane translocation moiety, bombesin, elastin, peptide mimetics, organic compounds, inorganic compounds, carbohydrates, monosaccharides, oligosaccharides, polysaccharides, whole cells, drugs, polymers, liposomes, chemotherapeutic agents, receptor agonists and antagonists, cytokines, hormones, and steroids.

Examples of organic compounds envisaged within the context of the present invention are, or are derived from, estrogens, e.g. estradiol, androgens, progestins, corticosteroids, methotrexate, folic acid, and cholesterol.

In a preferred embodiment, the targeting agent $T^T$ is an antibody.

According to a particular embodiment of the present invention, the primary target is a receptor and a targeting agent is employed, which is capable of specific binding to the primary target. Suitable targeting agents include but are not limited to, the ligand of such a receptor or a part thereof which still binds to the receptor, e.g. a receptor binding peptide in the case of receptor binding protein ligands. Other examples of targeting agents of protein nature include interferons, e.g. alpha, beta, and gamma interferon, interleukins, and protein growth factor, such as tumor growth factor, e.g. alpha, beta tumor growth factor, platelet-derived growth factor (PDGF), uPAR targeting protein, apolipoprotein, LDL, annexin V, endostatin, and angiostatin. Alternative examples of targeting agents include DNA, RNA, PNA and LNA which are e.g. complementary to the primary target.

According to a further particular embodiment of the invention, the primary target and targeting agent are selected so as to result in the specific or increased targeting of a tissue or disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme. This can be achieved by selecting primary targets with tissue-, cell- or disease-specific expression. For example, membrane folic acid receptors mediate intracellular accumulation of folate and its analogs, such as methotrexate. Expression is limited in normal tissues, but receptors are overexpressed in various tumor cell types.

In a preferred embodiment the $T^T$ is selected from antibodies and antibody derivatives such as antibody fragments, fragment fusions, proteins, peptides, peptide mimetics, organic molecules, dyes, fluorescent molecules, enzyme substrates.

In a preferred embodiment the $T^T$ being an organic molecule has a molecular weight of less than 2000 Da, more preferably less than 1500 Da, more preferably less than 1000 Da, even more preferably less than 500 Da.

In another preferred embodiment the $T^T$ is selected from antibody fragments, fragment fusions, and other antibody derivatives that do not contain a Fc domain.

In one embodiment the Targeting Agent specifically binds or complexes with a cell surface molecule, such as a cell surface receptor or antigen, for a given cell population. Following specific binding or complexing of the $T^T$ with the receptor, the cell is permissive for uptake of the Prodrug, which then internalizes into the cell. The subsequently administered Activator will then enter the cell and activate the Prodrug, releasing the Drug inside the cell. In another embodiment the Targeting Agent specifically binds or complexes with a cell surface molecule, such as a cell surface receptor or antigen, for a given cell population. Following specific binding or complexing of the $T^T$ with the receptor, the cell is not permissive for uptake of the Prodrug. The subsequently administered Activator will then activate the Prodrug on the outside of the cell, after which the released Drug will enter the cell.

As used herein, a $T^T$ that "specifically binds or complexes with" or "targets" a cell surface molecule, an extracellular matrix target, or another target, preferentially associates with the target via intermolecular forces. For example, the ligand can preferentially associate with the target with a dissociation constant ($K_d$ or $K_D$) of less than about 50 nM, less than about 5 nM, or less than about 500 μM.

In another embodiment the targeting agent $T^T$ localizes in the target tissue by means of the EPR effect. An exemplary $T^T$ for use in with the EPR effect is a polymer.

Administration

When administering the Prodrug and the Activator to a living system, such as an animal or human, in preferred embodiments the Prodrug is administered first, and it will take a certain time period before the Prodrug has reached the Primary Target. This time period may differ from one application to the other and may be minutes, days or weeks. After the time period of choice has elapsed, the Activator is administered, will find and react with the Prodrug and will thus activate the Prodrug and/or afford Drug release at the Primary Target. In some preferred embodiments, the time interval between the administration of the Prodrug and the Activator is between 10 minutes and 4 weeks. In some preferred embodiments, the time interval between the administration of the Prodrug and the Activator is between 1 hour and 2 weeks, preferably between 1 and 168 hours, more preferably between 1 and 120 hours, even more preferably between 1 and 96 hours, most preferably between 3 and 72 hours.

The compositions of the invention can be administered via different routes including but not limited to intravenous or subcutaneous injection, intraperitoneal, local injection, oral administration, rectal administration and inhalation. Formulations suitable for these different types of administrations are known to the skilled person. Prodrugs or Activators according to the invention can be administered together with a pharmaceutically acceptable carrier. A suitable pharmaceutical carrier as used herein relates to a carrier suitable for medical or veterinary purposes, not being toxic or otherwise unacceptable. Such carriers are well known in the art and include for example saline, buffered saline, dextrose, water, glycerol, ethanol, and combinations thereof. The formulation should suit the mode of administration.

It will be understood that the chemical entities administered, viz. the Prodrug and the Activator, can be in a modified form that does not alter the chemical functionality of said chemical entity, such as salts, hydrates, or solvates thereof.

After administration of the Prodrug, and before the administration of the Activator, it is preferred to remove excess Prodrug by means of a Clearing Agent in cases when Prodrug activation in circulation is undesired and when natural Prodrug clearance is insufficient. A Clearing Agent is an agent, compound, or moiety that is administered to a subject for the purpose of binding to, or complexing with, an administered agent (in this case the Prodrug) of which excess is to be removed from circulation. The Clearing Agent is capable of being directed to removal from circulation. The latter is generally achieved through liver receptor-based mechanisms, although other ways of secretion from circulation exist, as are known to the skilled person. In the invention, the Clearing Agent for removing circulating Prodrug, preferably comprises a dienophile moiety, e.g. as discussed above, capable of reacting to the tetrazine moiety of the Prodrug.

In other embodiments the Activator is administered first, followed by the Prodrug, wherein the time interval between the administration of the two components ranges from 1 minute to 1 week, preferably from 10 minutes to 3 days.

In other embodiments, the Prodrug and Activator are administered at the same time. either as two separate administrations or as a co-administration.

In yet another embodiment, the Prodrug and Activator are reacted with one another prior to administration and the resulting reaction mixture is then administered, wherein the time interval between start of the reaction and the administration varies from 1 minute to 3 days, preferably 1 minute to 1 day, more preferably from 1 minute to 3 hours.

Embodiments

In preferred embodiments of the invention, the amide moiety between the trans-cyclooctene ring and a moiety according to $R^5$ and $R^4$ are substituted axially onto the trans-cyclooctene ring.

Formula (1) Embodiments

In some embodiments of the invention, the compounds pertaining to Formula (1) can be further specified by any one of the Formulae (la), (1b), (1c), (1d), (1e), (1f), (1g), (1h), (1i), (1j), (1k), (11), and (1m) depicted below:

Formula (1a)
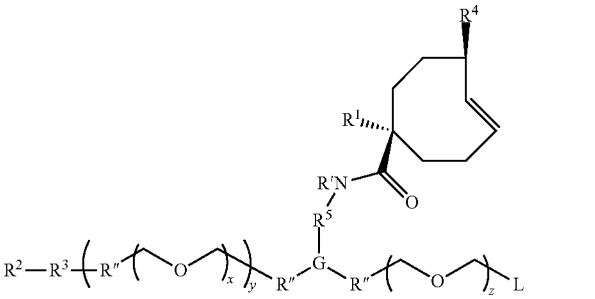
Formula (1b)
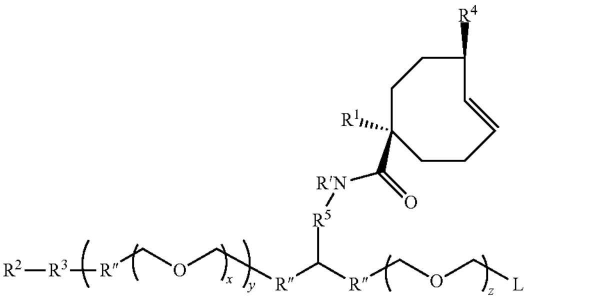
Formula (1c)
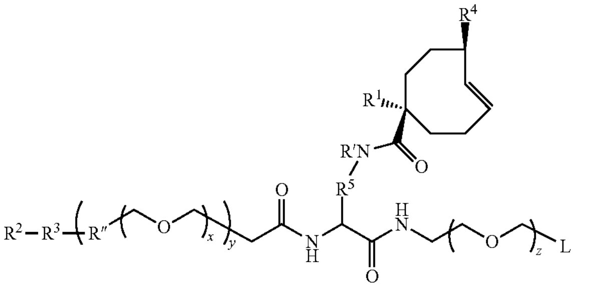
Formula (1d)
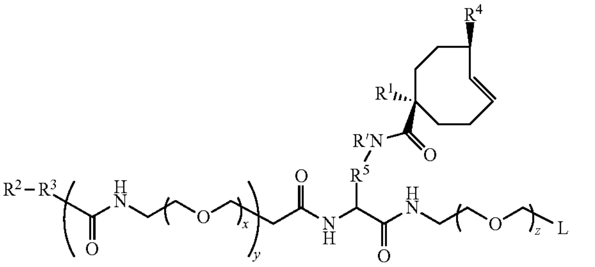
Formula (1e)
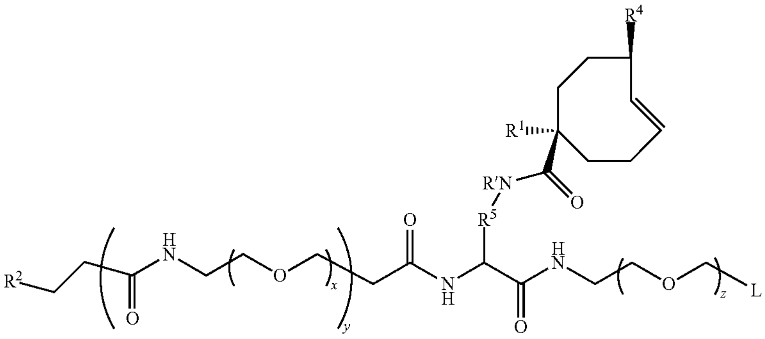
Formula (1f)
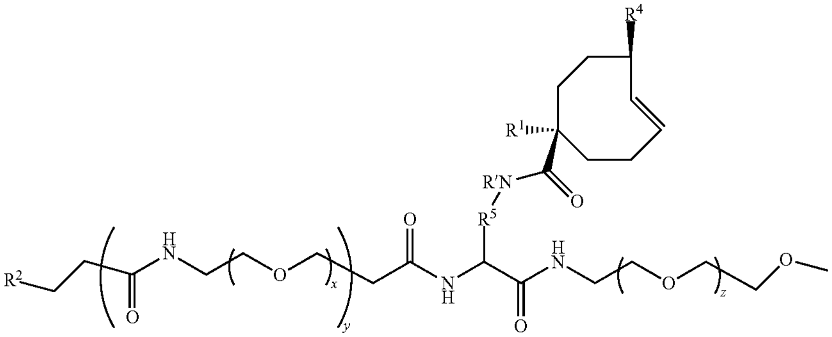

-continued
Formula (1g)
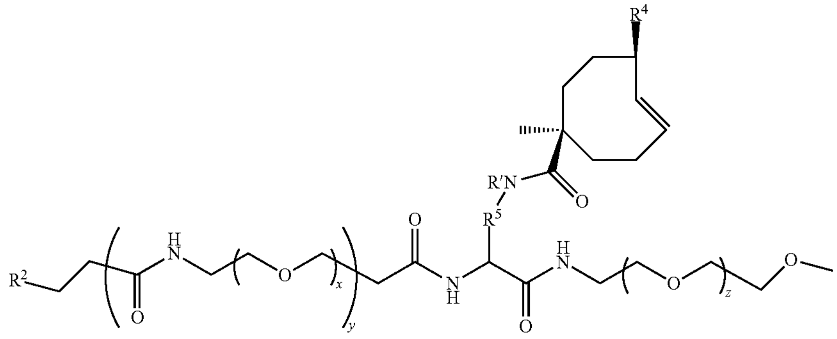
Formula (1h)
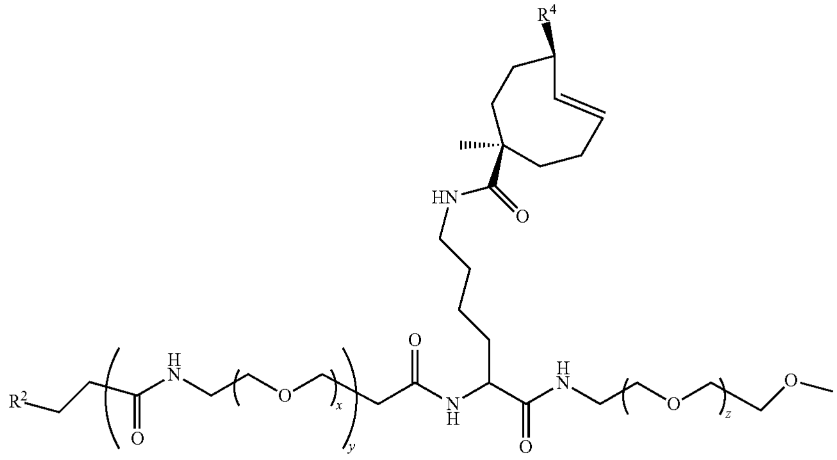
Formula (1i)
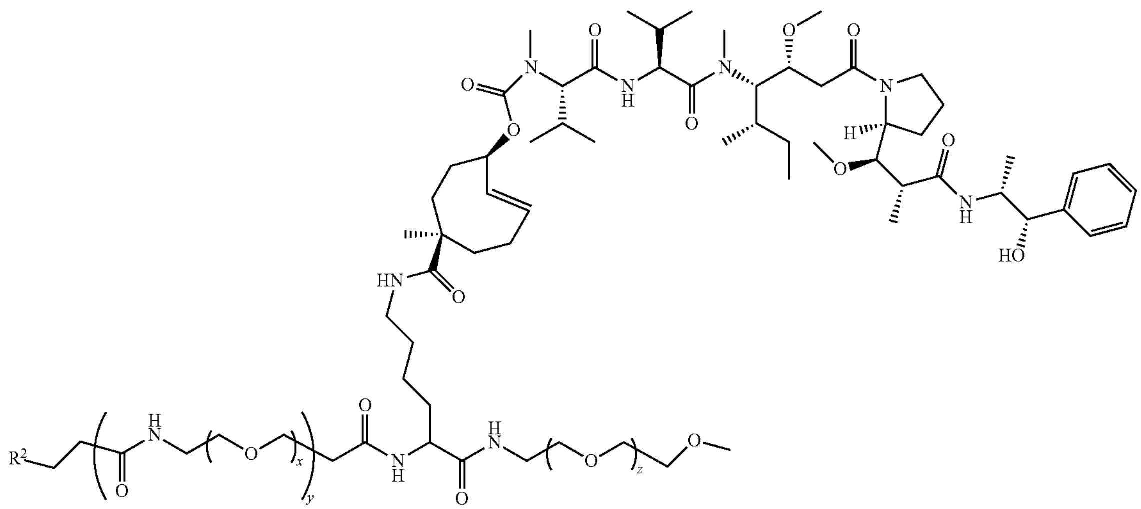

-continued
Formula (1j)
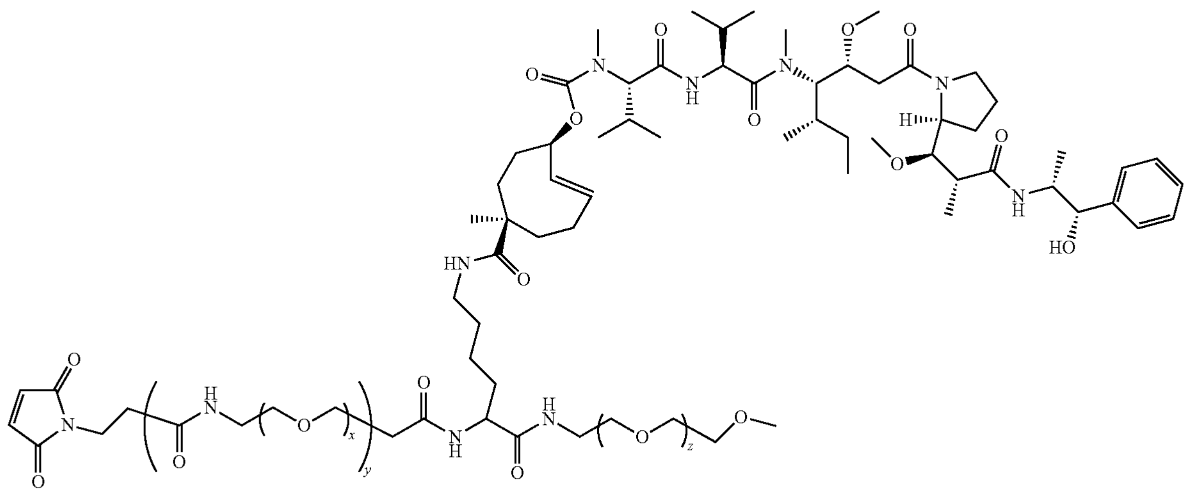
Formula (1k)
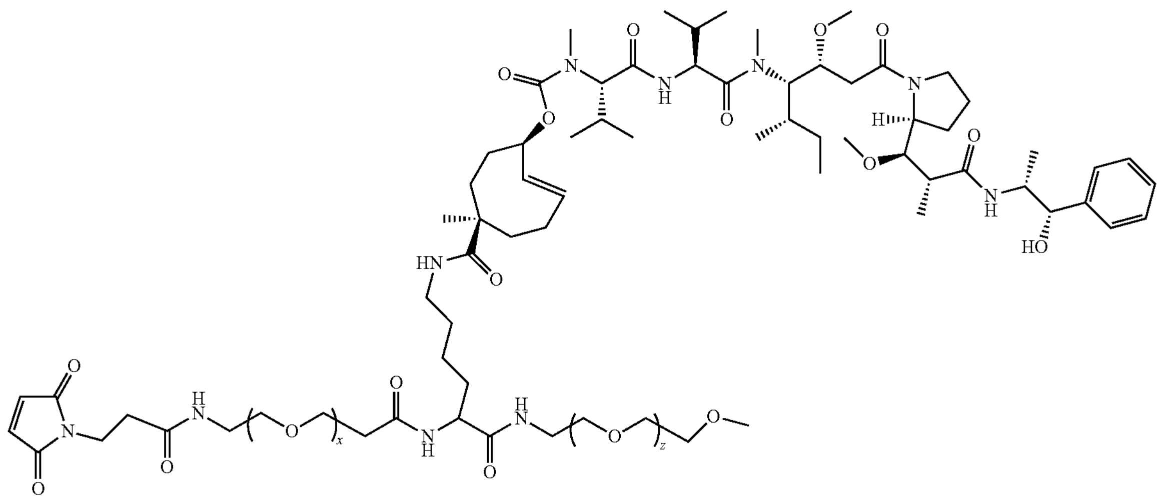
Formula (1l)
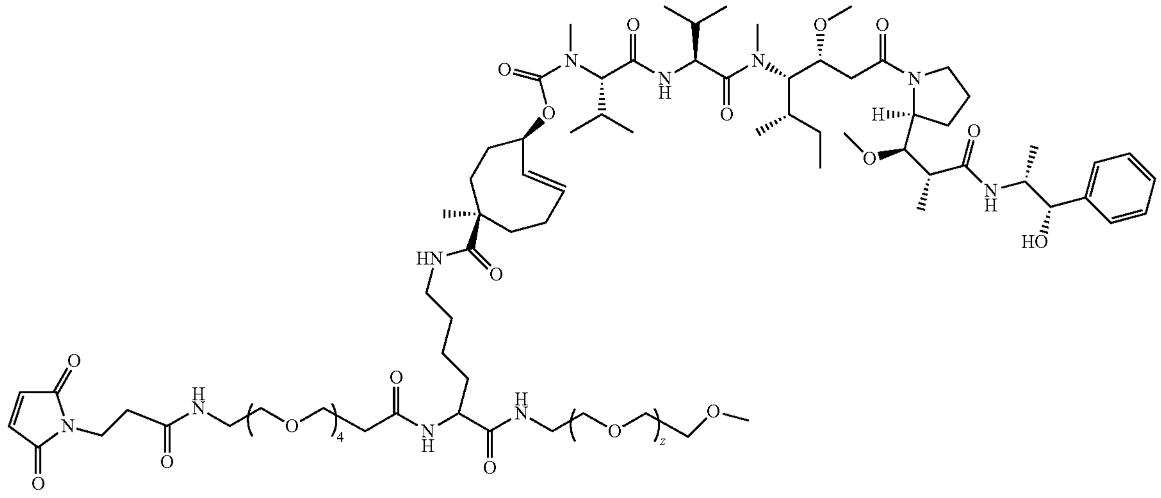

-continued
Formula (1m)
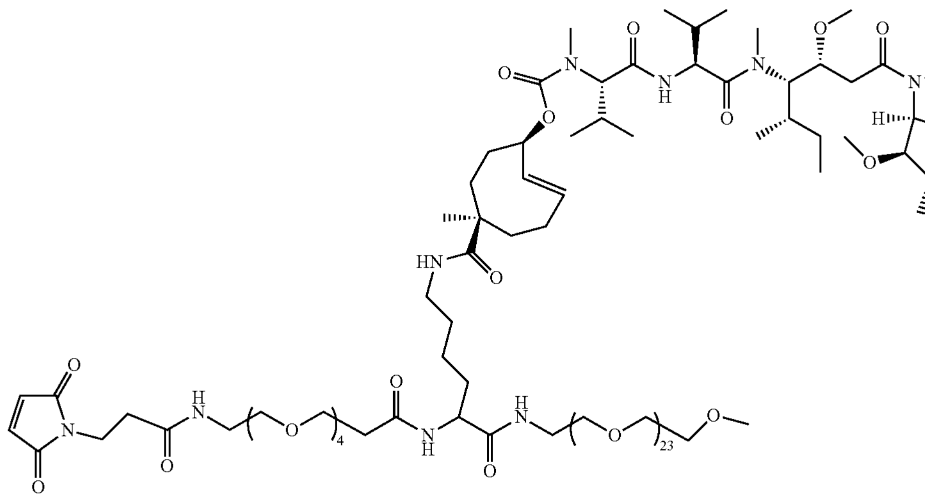
In Formulae (1a), (1b), (1c), (1d), (1e), (1f), (1g), (1h), (1i), (1j), (1k), and (11), $R^1$, $R^2$, $R^3$, $R^4$, $R^5$, R', R", G, L, x, y, and z are as defined in this document for Formula (1).
Other particularly favourable embodiments according to Formula (1) are:
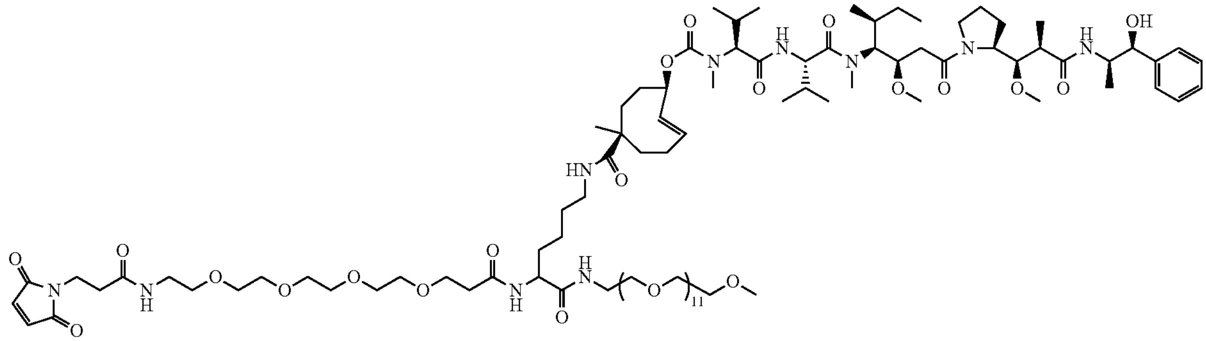
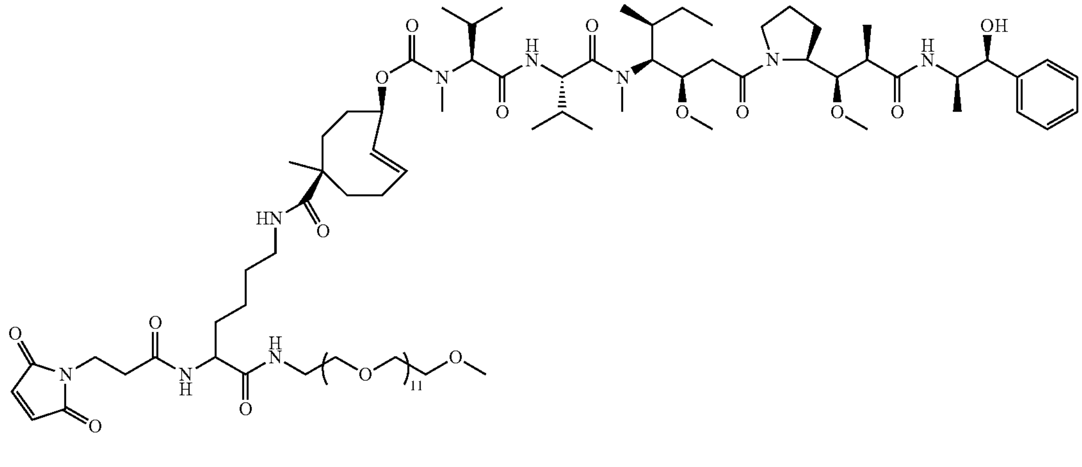

-continued
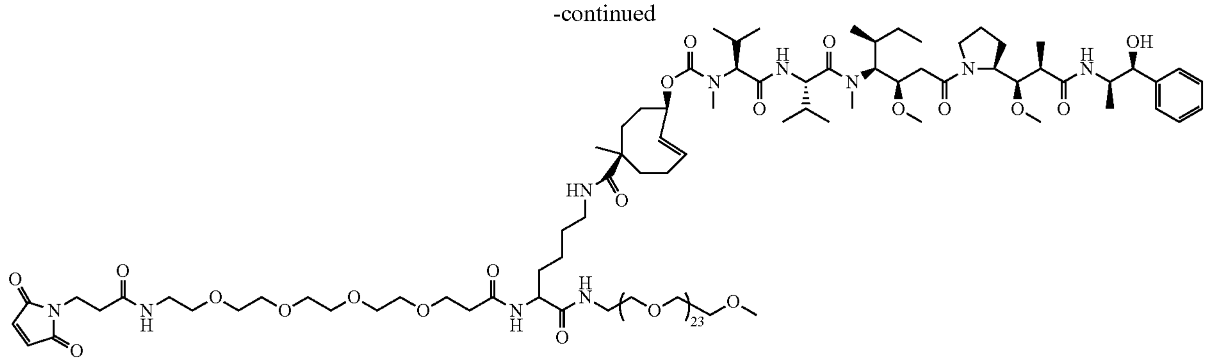
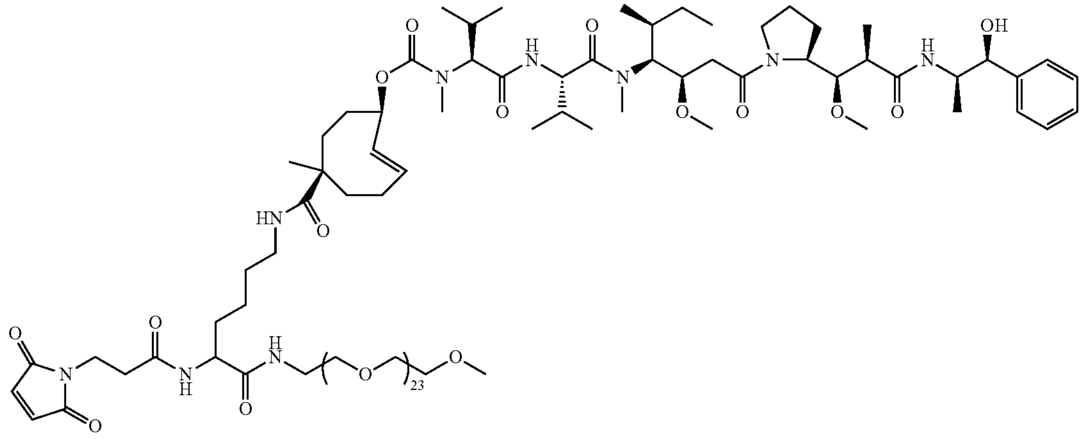
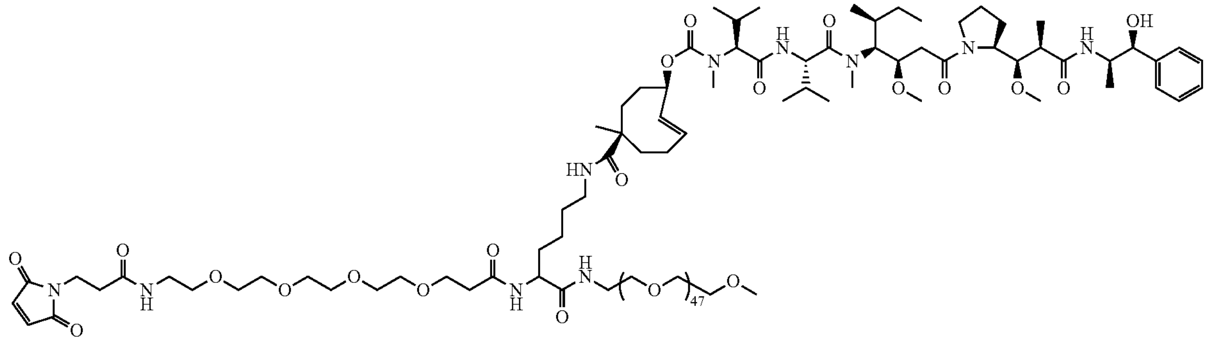
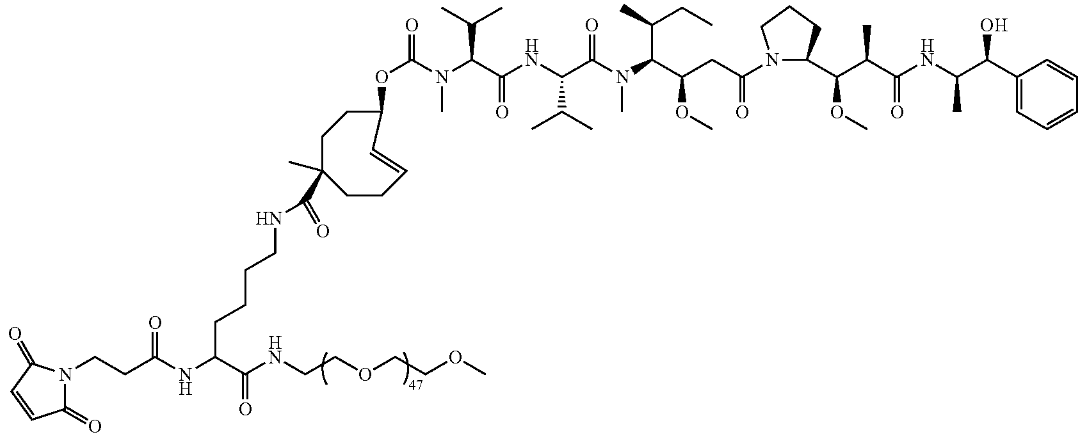

-continued
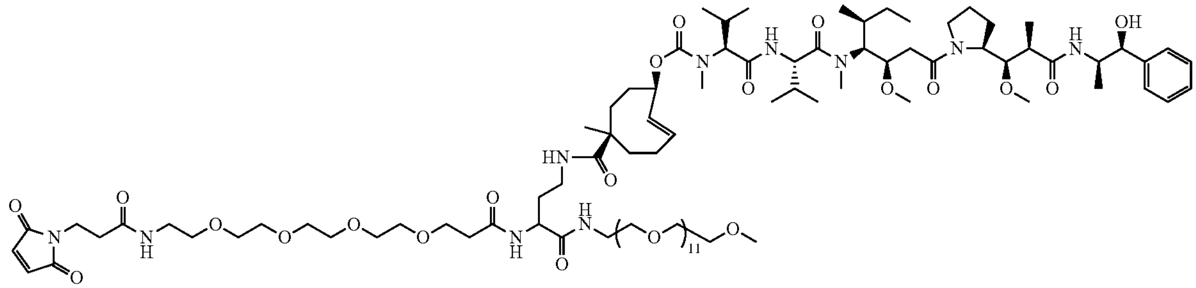
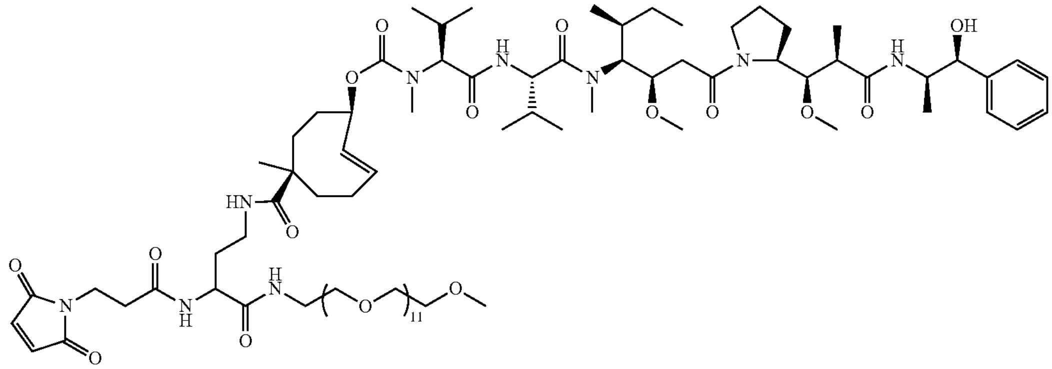
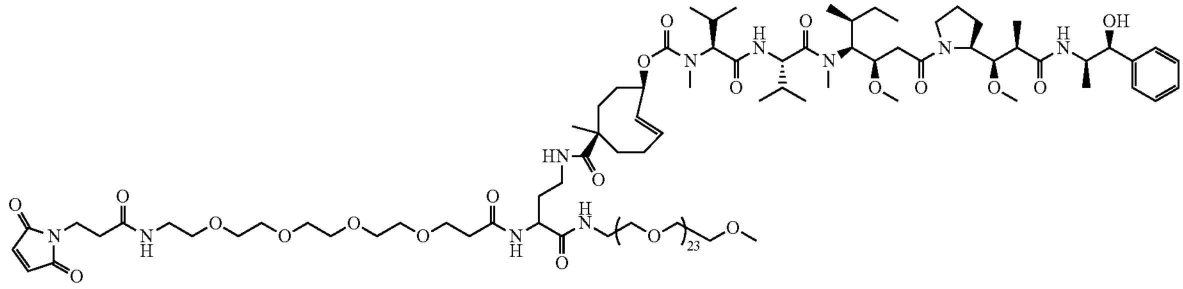
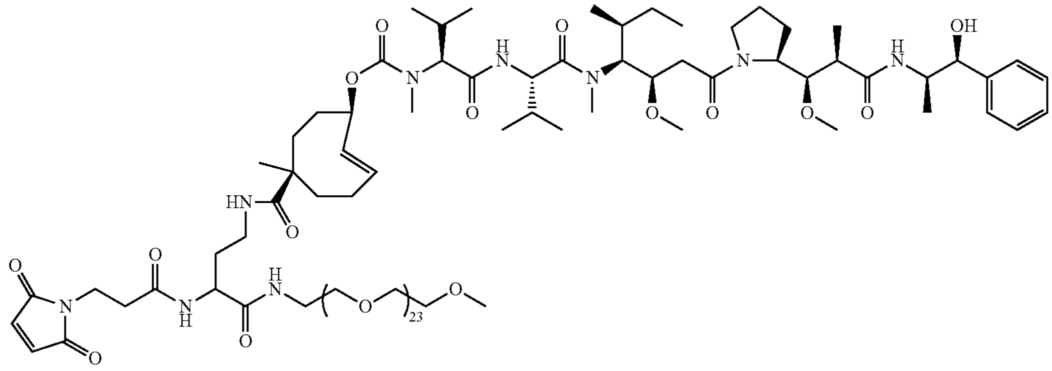
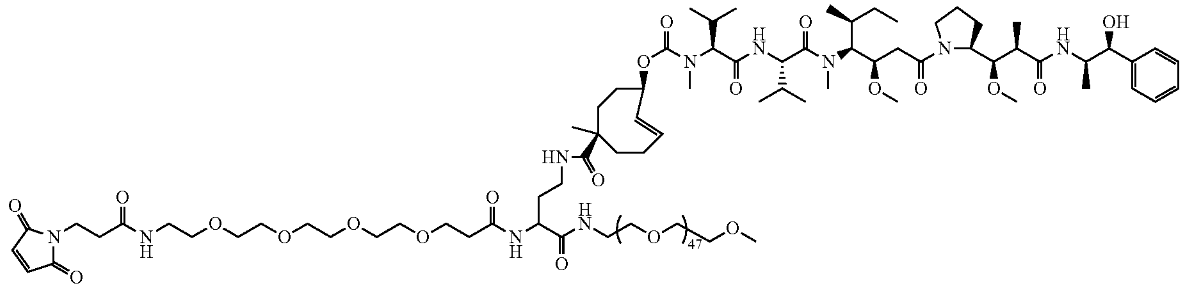

-continued
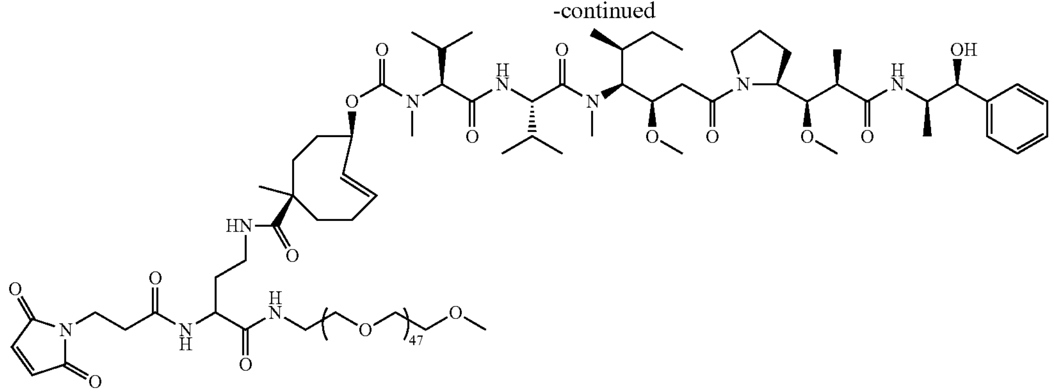
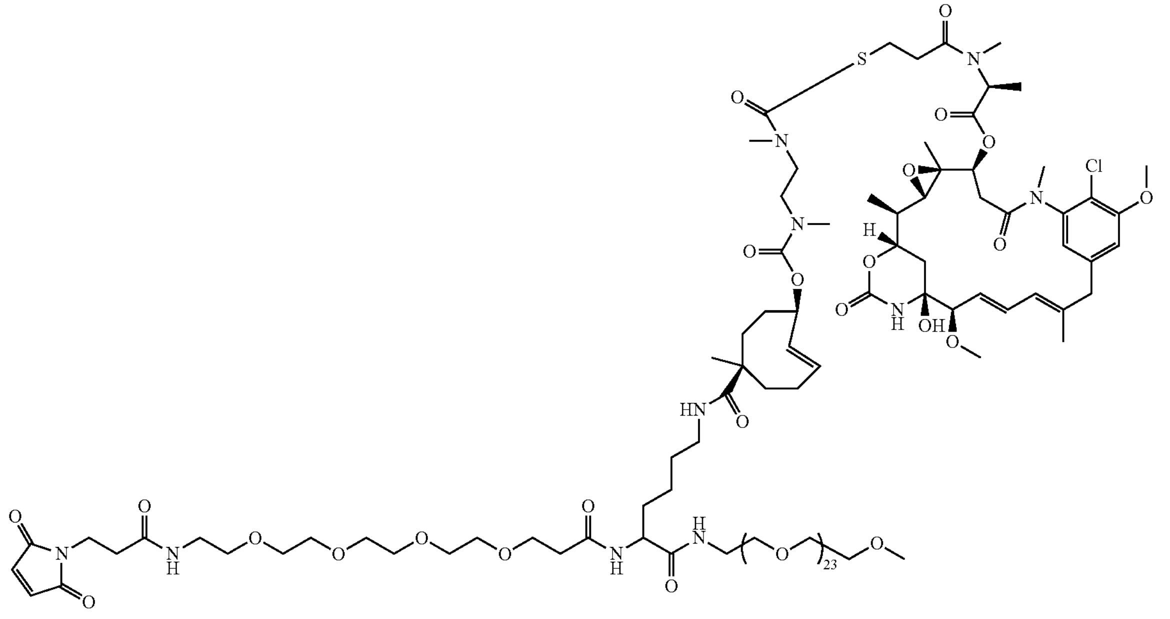

-continued
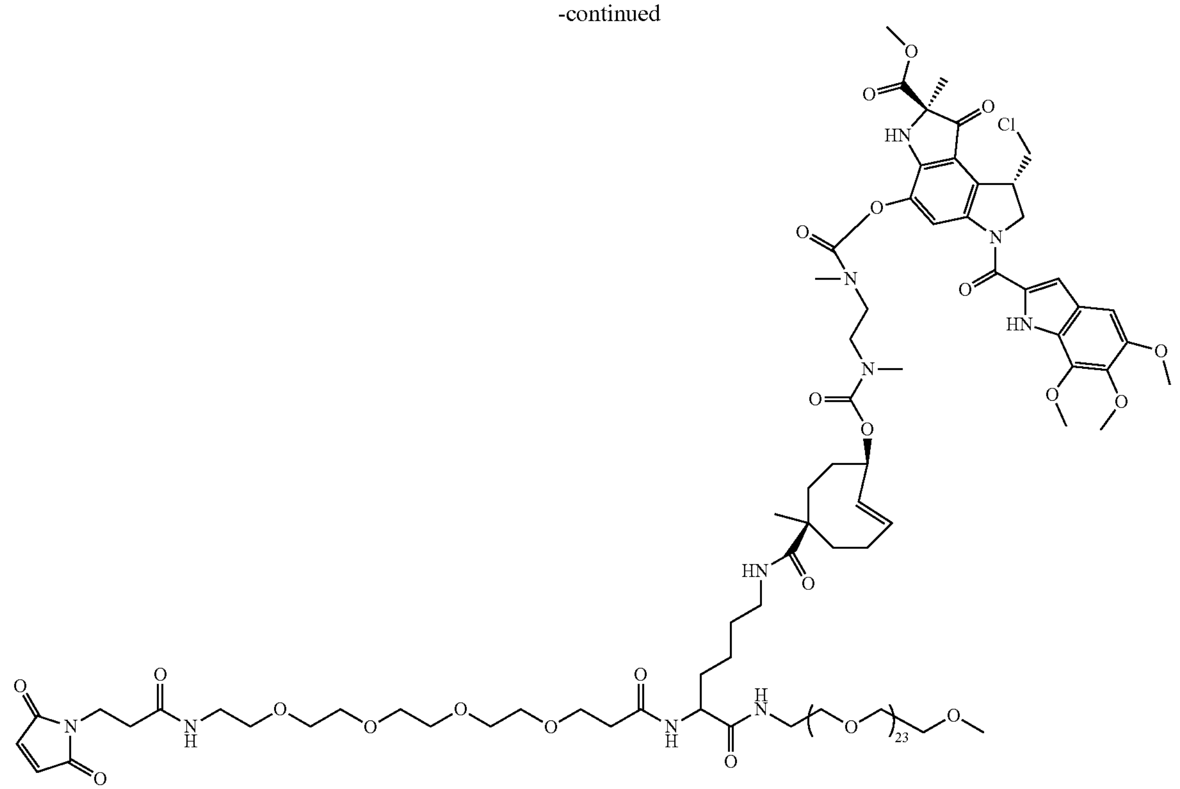
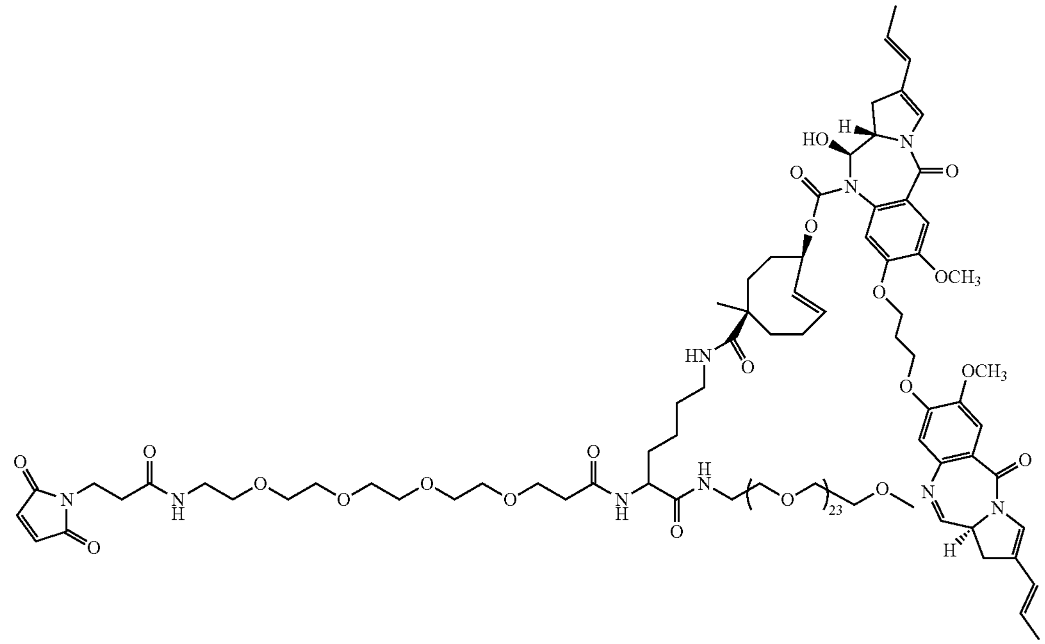

-continued

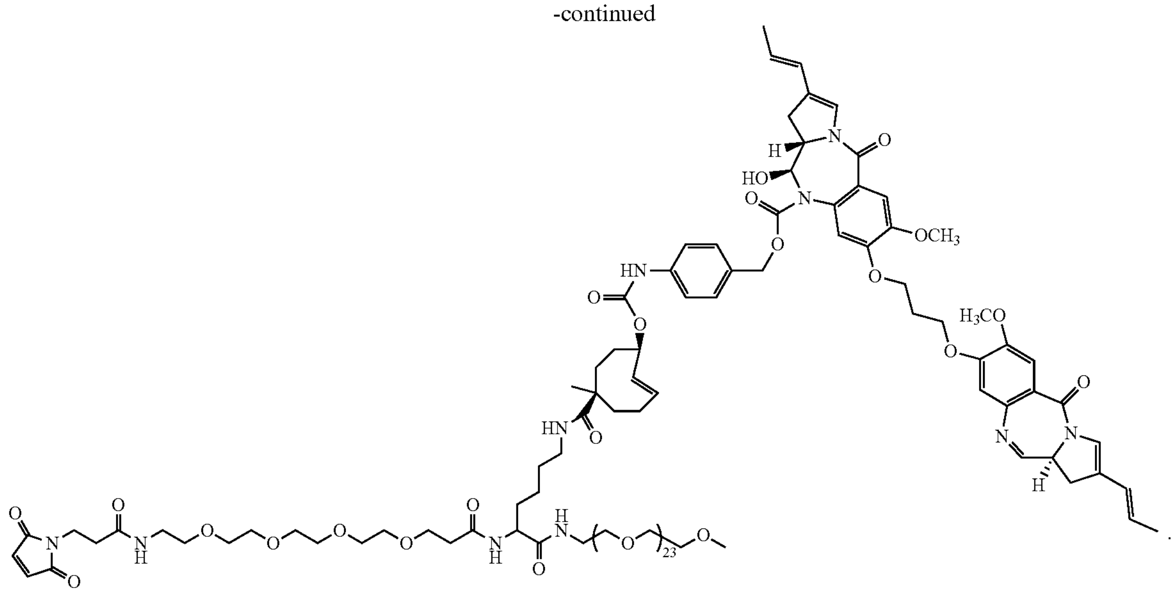

Formula (2)

In preferred embodiments, moiety A is selected from the group consisting of antibodies, proteins, peptoids and peptides.

In some embodiments, moiety A can be modified with a group according to any one of Formulae (3a), (3b), (3c), (3d), (3e), (3f), (3g), (3h), (31), (3j), (3k), (31), and (3m) as disclosed herein.

Preferably, moiety A is modified at 1 to 8 positions, more preferably from 1 to 6 positions, even more preferably at 1 to 4 positions.

In particularly favourable embodiments, moiety A is a diabody according to the sequence listed below in Table 1 as SEQ ID NO:1.

TABLE 1

| Diabody | Diabody sequence (SEQ ID NO:1) |
|---|---|
| TAG72-binding | SVQLQQSDAELVKPGASVKISCKASGYTFTD<br>HAIHWVKQNPEQGLEWIGYFSPGNDDFKY |

TABLE 1-continued

| Diabody | Diabody sequence (SEQ ID NO:1) |
|---|---|
| diabody<br>derived<br>from<br>the CC49<br>antibody | NERFKGKATLTADKSSSTAYLQLNSLTSEDS<br>AVYFCTRSLNMAYWGQGTSVTVSSGGGGSD<br>IVMTQSCSSCPVSVGEKVTLSCKSSQSLLYS<br>GNQKNYLAWYQQKPGQSPKLLIYWASTRES<br>GVPDRFTGSGSGTDFTLSISSVETEDLAVYY<br>CQQYYSYPLTFGAGTKLVLKR |

Formula (3)

In some embodiments of the invention, the compounds pertaining to Formula (3) can be further specified by any one of the Formulae (3a), (3b), (3c), (3d), (3e), (3f), 5 (3g), (3h), (3i), (3j), (3k), (31), and (3m) depicted below:

Formula (3a)

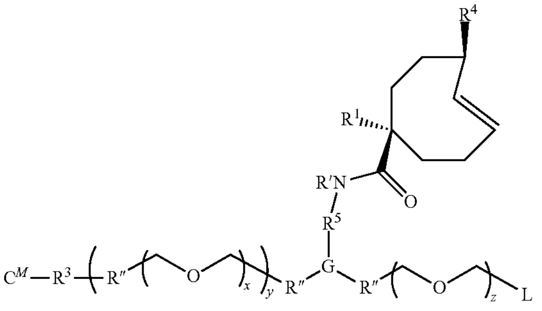

Formula (3b)

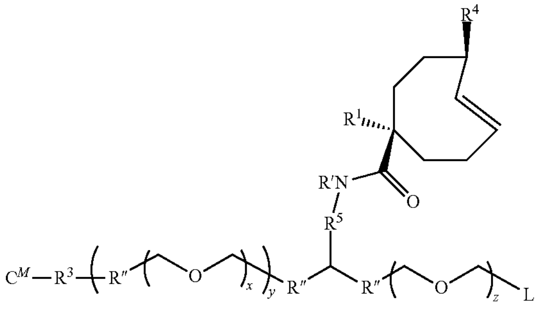

-continued
Formula (3c)
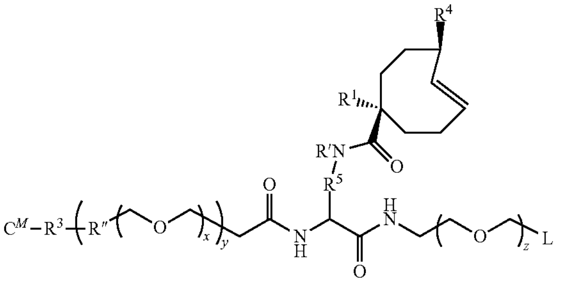
Formula (3d)
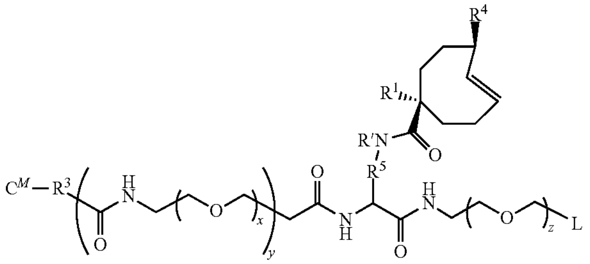
Formula (3e)
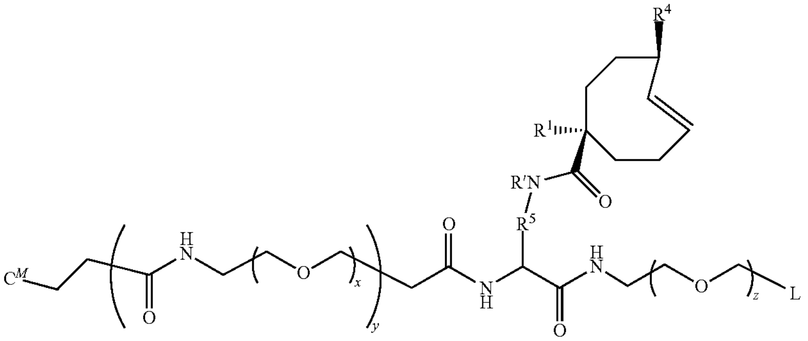
Formula (3f)
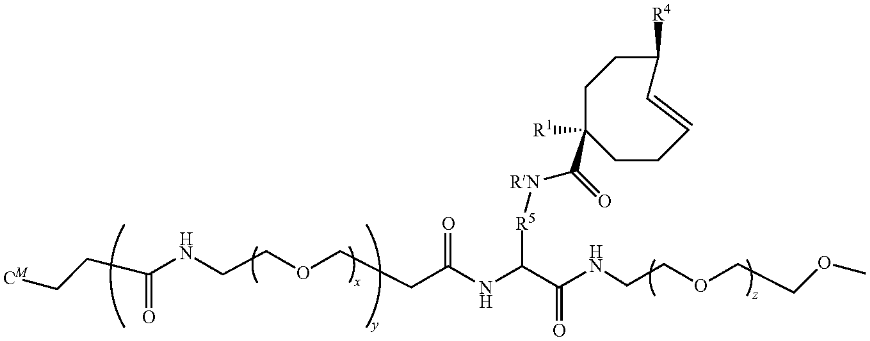
Formula (3g)
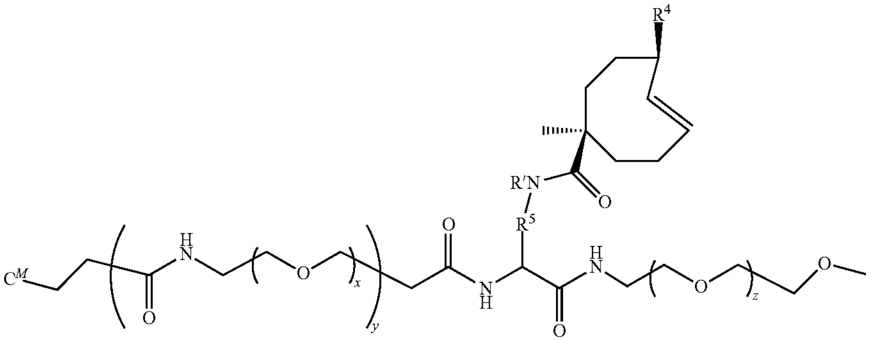

-continued
Fomula (3h)
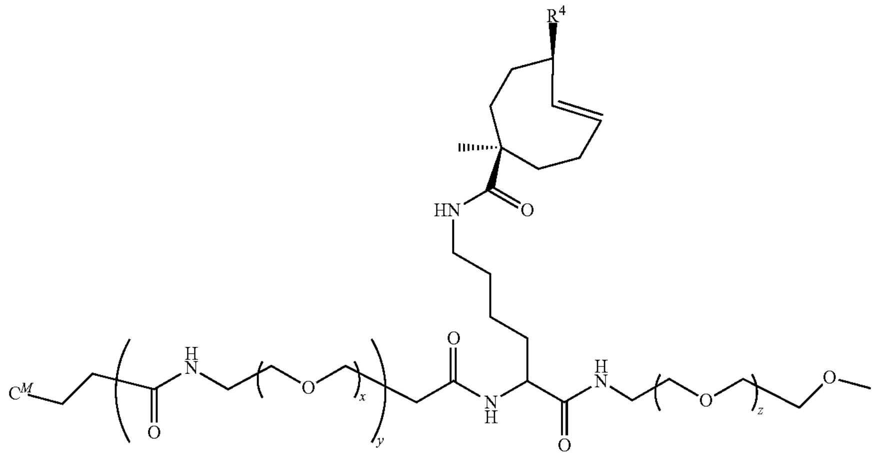
Formula (3i)
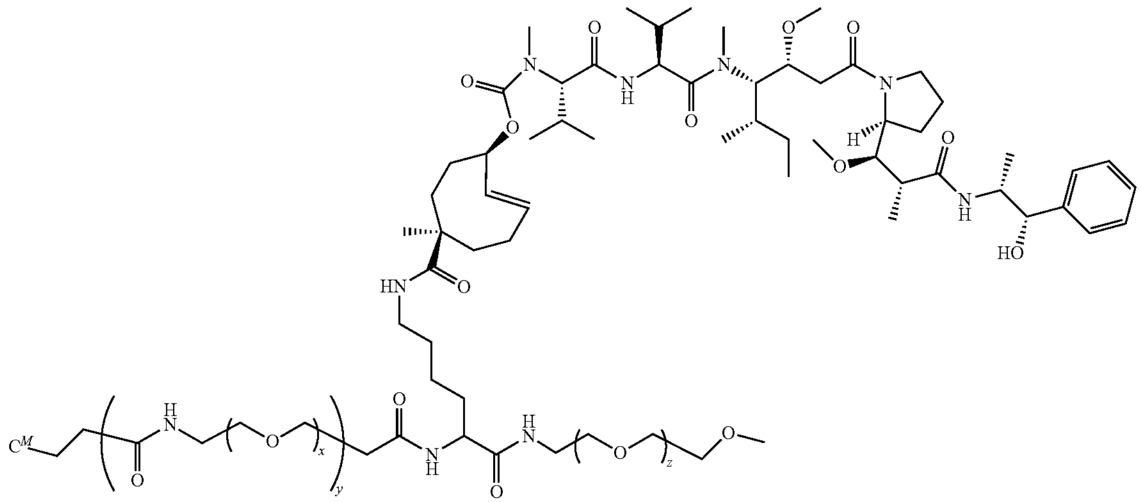
Formula (3j)
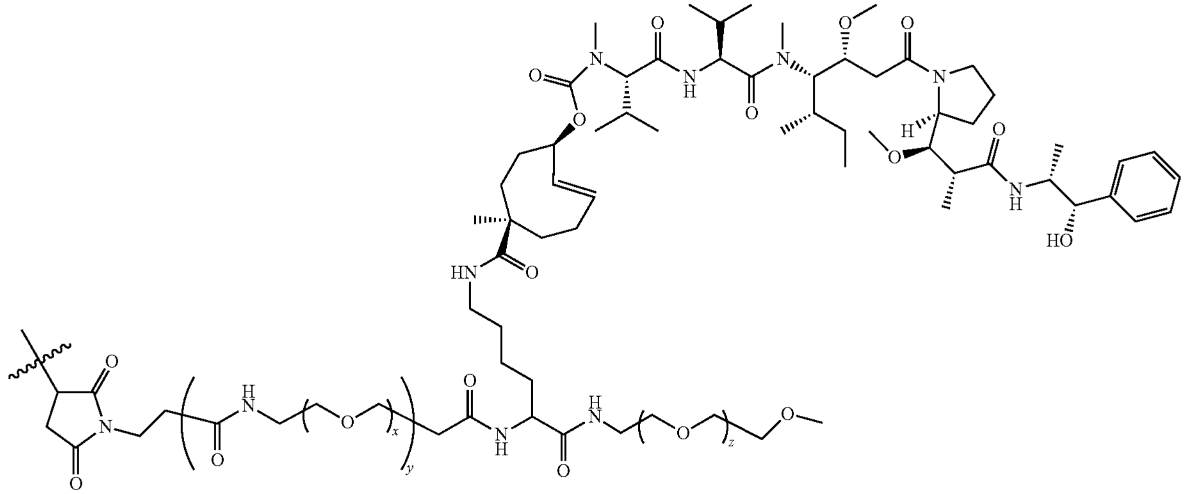

-continued
Formula (3k)
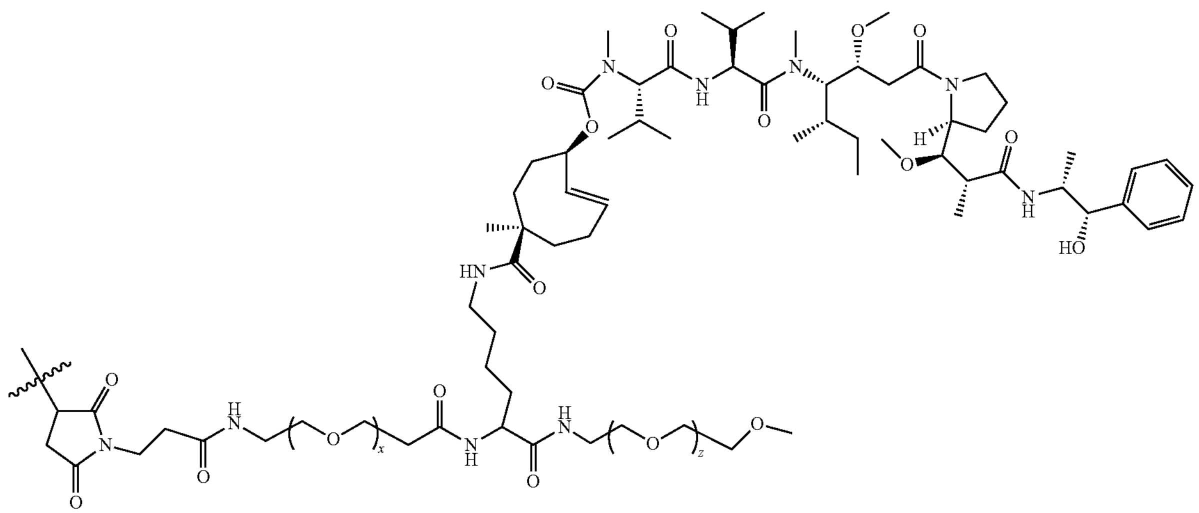
Formula (3l)
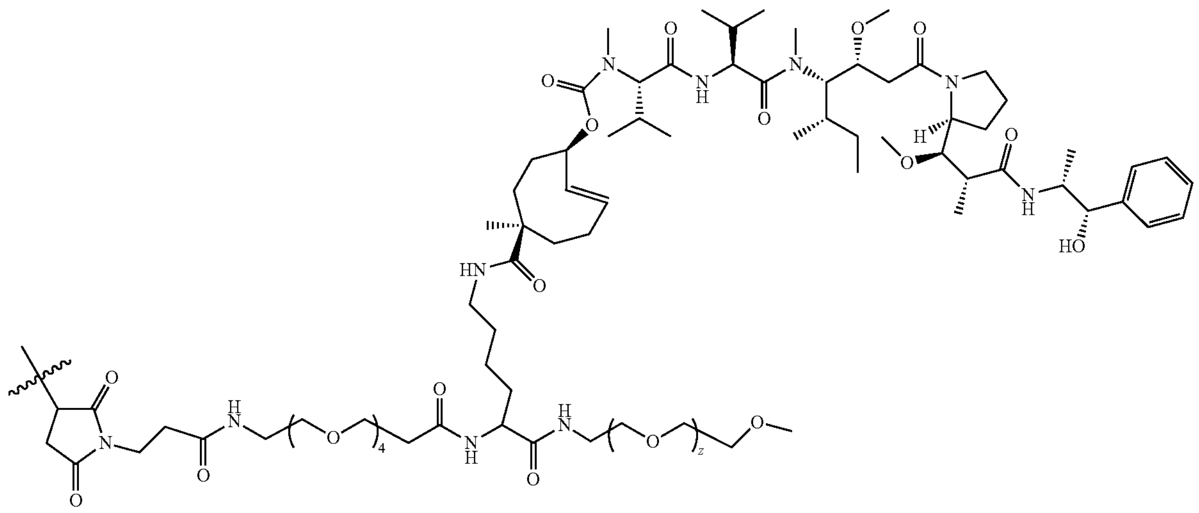
Formula (3m)
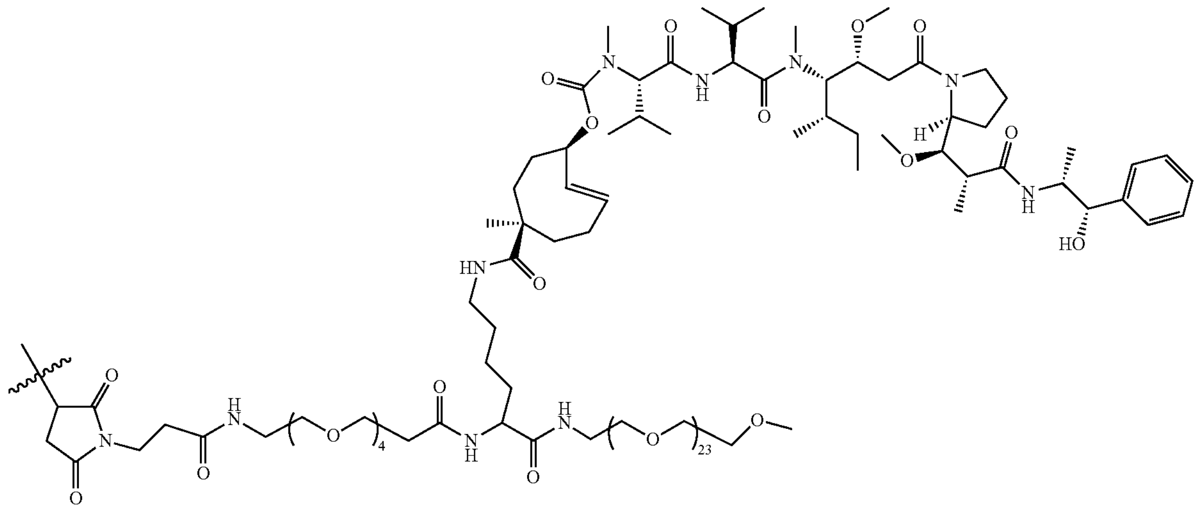

In Formulae (3a), (3b), (3c), (3d), (3e), (3f), (3g), (3h), (3i), (3j), (3k), and (3l), $R^1$, $R^2$, $R^8$, $R^4$, $R^5$, R', R", G, L, x, y, and z are as defined in this document for Formula (3).

In Formulae (3j), (3k), (3l), and (3m) the wiggly line indicates a bond to moiety X in Formula (2).

It will be understood that the imide moiety (3j), (3k), (3l), and (3m) may hydrolyze in aqueous environments. The hydrolysis products of these compounds, which comprise regioisomers, are understood to be disclosed herein as well.

In a particularly favourable embodiment, in Formula (2) moiety A is a diabody according to SEQ ID NO:1 as disclosed herein, and Y is the compound according to any one of the Formulae (3a), (3b), (3c), (3d), (3e), (3f), (3g), (3h), (3i), (3j), (3k), (3l), and (3m).

Preferably, in Formula (2) moiety A is a diabody according to SEQ ID NO: 1 as disclosed herein, and Y is the compound according to the Formula (3m).

More preferably, in Formula (2) moiety A is a diabody according to SEQ ID NO: 1 as disclosed herein, and Y is the compound according to the Formula (3m), and in four moieties —(X—Y)$_w$ of Formula (2) w is 1, i.e. the diabody according to SEQ ID NO: 1 is modified at four positions.

Even more preferably, in Formula (2) moiety A is a diabody according to SEQ ID NO: 1 as disclosed herein, and Y is the compound according to the Formula (3m), and in four moieties —(X—Y)$_w$ of Formula (2) w is 1, and X in these four moieties —(X—Y)$_w$ is a sulphur atom, i.e. S, that is part of a cysteine that is part of the diabody according to SEQ ID NO:1.

$R^1$

In some embodiments, $R^1$ is selected from the group consisting of hydrogen, $C_1$-$C_6$ alkyl groups, $C_6$ aryl groups, $C_4$-$C_5$ heteroaryl groups, $C_3$-$C_6$ cycloalkyl groups, $C_5$-$C_{12}$ alkyl(hetero)aryl groups, $C_5$-$C_{12}$ (hetero)arylalkyl groups, $C_4$-$C_{12}$ alkylcycloalkyl groups, —N(R')$_2$, —OR', —SR', —$SO_3H$, —C(O)OR', and Si(R')$_3$, wherein for $R^1$ the alkyl groups, (hetero)aryl groups, cycloalkyl groups, alkyl(hetero) aryl groups, (hetero)arylalkyl groups, alkylcycloalkyl groups are optionally substituted with a moiety selected from the group consisting of —Cl, —F, —Br, —I, $NO_2$, $SO_3H$, $PO_3H$, —$PO_4H_2$, —OR', —N(R')$_2$, —$CF_3$, =O, =NR', —SR', and optionally contain one or more heteroatoms selected from the group consisting of —O—, —S—, —NR'—, —P—, and —Si—, wherein the N, S, and P atoms are optionally oxidized, wherein the N atoms are optionally quaternized, In preferred embodiments, $R^1$ is hydrogen. In other preferred embodiments, $R^1$ is —$CH_3$.

$R^2$

In some embodiments, $R^2$ is a moiety that allows conjugation to a protein comprising natural and/or non-natural amino acids. Moieties suitable for conjugation are known to the skilled person. Conjugation strategies are for example found in [O. Boutureira, G. J. L. Bernardes, Chem. Rev., 2015, 115, 2174-2195].

In particularly favourable embodiments, $R^2$ is selected from the group consisting of N-maleimidyl groups, halogenated N-alkylamido groups, sulfonyloxy N-alkylamido groups, vinyl sulfone groups, activated carboxylic acids, benzenesulfonyl halides, ester groups, carbonate groups, sulfonyl halide groups, thiol groups or derivatives thereof, $C_{2-6}$ alkenyl groups, $C_{2-6}$ alkynyl groups, $C_{7-18}$ cycloalkynyl groups, $C_{5-18}$ heterocycloalkynyl groups, bicyclo[6.1.0]non-4-yn-9-yl] groups, $C_{4-12}$ cycloalkenyl groups, azido groups, phosphine groups, nitrile oxide groups, nitrone groups, nitrile imine groups, isonitrile groups, diazo groups, ketone groups, (O-alkyl) hydroxylamino groups, hydrazine groups, halogenated N-maleimidyl groups, aryloxymaleimides, dithiophenolmaleimides, bromo- and dibromopyridazinediones, 2,5-dibromohexanediamide groups, alkynone groups, 3-arylpropiolonitrile groups, 1,1-bis(sulfonylmethyl)-methylcarbonyl groups or elimination derivatives thereof, carbonyl halide groups, allenamide groups, 1,2-quinone groups, isothiocyanate groups, aldehyde groups, triazine groups, squaric acids, 2-imino-2-methoxyethyl groups, (oxa)norbornene groups, (imino)sydnones, methylsulfonyl phenyloxadiazole groups, aminooxy groups, 2-amino benzamidoxime groups, groups reactive in the Pictet-Spengler ligation and hydrazino-Pictet-Spengler (HIPS) ligation.

In preferred embodiments, $R^2$ is an N-maleimidyl group connected to the remaining part of the compound according to Formula (1) via the N atom of the N-maleimidyl group.

$R^3$

In some embodiments, each individual $R^3$ is selected from the group consisting of $C_1$-$C_{12}$ alkylene groups, $C_2$-$C_{12}$ alkenylene groups, $C_2$-$C_{12}$ alkynylene groups, $C_6$ arylene groups, $C_4$-$C_5$ heteroarylene groups, $C_3$-$C_8$ cycloalkylene groups, $C_5$-$C_8$ cycloalkenylene groups, $C_5$-$C_{12}$ alkyl(hetero) arylene groups, $C_5$-$C_{12}$ (hetero)arylalkylene groups, $C_4$-$C_{12}$ alkylcycloalkylene groups, $C_4$-$C_{12}$ cycloalkylalkylene groups, wherein the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups, are optionally substituted with a moiety selected from the group consisting of —Cl, —F, —Br, —I, —OR', —N(R')$_2$, =O, —NR', —SR', —$SO_3H$, —$PO_3H$, —$PO_4H_2$, —$NO_2$ and —Si(R')$_3$, and optionally contain one or more heteroatoms selected from the group consisting of —O—, —S—, —NR'—, —P—, and —Si—, wherein the N, S, and P atoms are optionally oxidized, wherein the N atoms are optionally quaternized.

In particularly favourable embodiments, each individual $R^3$ is selected from the group consisting of $C_1$-$C_6$ alkylene groups, $C_2$-$C_6$ alkenylene groups, and $C_2$-$C_6$ alkynylene groups, more preferably from the group consisting of $C_1$-$C_8$alkylene groups, $C_2$-$C_3$ alkenylene groups, and $C_2$-$C_3$ alkynylene groups.

$R^4$

In some embodiments, each individual $R^4$ is selected from the group consisting of —OH, —OC(O)Cl, —OC(O)O—N-succinimidyl, —OC(O)O-4-nitrophenyl, —OC(O)O-tetrafluorophenyl, —OC(O)O-pentafluorophenyl, —OC(O)—$C^A$, —OC(S)—$C^A$, —O-($L^C$($C^A$), ($C^A$)$_s$)$_n$-$C^A$, and —$C^A$, wherein preferably n is an integer in range of from 0 to 2, wherein each s is independently 0 or 1.

It is preferred that $R^4$ is an axial substituent on the TCO ring.

$R^5$

In some embodiments, each individual $R^5$ is selected from the group consisting of $C_1$-$C_8$alkylene groups, $C_2$-$C_5$ alkenylene groups, $C_2$-$C_5$ alkynylene groups, $C_6$ arylene groups, $C_4$-$C_5$ heteroarylene groups, $C_3$-$C_6$ cycloalkylene groups, $C_5$-$C_8$ cycloalkenylene groups, $C_5$-$C_{12}$ alkyl(hetero) arylene groups, $C_5$-$C_{12}$ (hetero)arylalkylene groups, $C_4$-$C_{12}$ alkylcycloalkylene groups, $C_4$-$C_{12}$ cycloalkylalkylene groups, wherein for the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups, are optionally substituted with a moiety selected from the group consisting of —Cl, —F, —Br, —I, —OR', —N(R')$_2$, =O, =NR', —SR', —$SO_3H$, —$PO_3H$, —$PO_4H_2$, —$NO_2$ and —$Si(R')_3$, and optionally contain one or more heteroatoms selected from the group consisting of —O—, —S—, —NR'—, —P—, and —Si—, wherein the N, S, and P atoms are optionally oxidized, wherein the N atoms are optionally quaternized.

In some embodiments, each individual $R^5$ is selected from the group consisting of $C_1$-$C_4$ alkylene groups, $C_2$-$C_4$ alkenylene groups, $C_2$-$C_4$ alkynylene groups, $C_6$ arylene groups, $C_4$-$C_5$ heteroarylene groups, $C_3$-$C_6$ cycloalkylene groups, wherein the alkylene groups, alkenylene groups, alkynylene groups, (hetero)arylene groups, and cycloalkylene groups, are optionally substituted with a moiety selected from the group consisting of —Cl, —F, —Br, —I, —OR', —$N(R')_2$, —O, =NR', —SR', —$SO_3H$, —$PO_3H$, —$PO_4H_2$, —$NO_2$ and —$Si(R')_3$, and optionally contain one or more heteroatoms selected from the group consisting of —O—, —S—, —NR'—, —P—, and —Si—, wherein the N, S, and P atoms are optionally oxidized, wherein the N atoms are optionally quaternized.

$R^6$

In some embodiments, $R^6$ is selected from the group consisting of hydrogen, $C_1$-$C_4$ alkyl groups, $C_2$-$C_4$ alkenyl groups, and $C_{4-6}$ (hetero)aryl groups, wherein for $R^6$ the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$ and —$NO_2$ and optionally contain at most two heteroatoms selected from the group consisting of —O—, —S—, —NH—, —P—, and —Si—, wherein the N, S, and P atoms are optionally oxidized.

In some embodiments, $R^6$ is selected from the group consisting of hydrogen, $C_1$-$C_3$ alkyl groups, $C_2$-$C_5$ alkenyl groups, and $C_{4-6}$ (hetero)aryl groups, wherein for $R^6$ the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$ and —$NO_2$ and optionally contain at most two heteroatoms selected from the group consisting of —O—, —S—, —NH—, —P—, and —Si—, wherein the N, S, and P atoms are optionally oxidized.

$R^7$

In some embodiments, each $R^7$ is independently selected from the group consisting of hydrogen and $C_1$-$C_3$ alkyl groups, $C_2$-$C_3$ alkenyl groups, and $C_{4-6}$ (hetero)aryl groups, wherein the alkyl groups, alkenyl groups, and (hetero)aryl groups are optionally substituted with a moiety selected from the group consisting of —Cl, —F, —Br, —I, —OH, —$NH_2$, =O, =NH, —$N(CH_3)_2$, —$S(O)_2CH_3$, and —SH, and are optionally interrupted by at most one heteroatom selected from the group consisting of —O—, —S—, —NH—, —P—, and —Si—, wherein the N, S, and P atoms are optionally oxidized, wherein the N atoms are optionally quaternized.

In preferred embodiments, $R^7$ is preferably selected from the group consisting of hydrogen, methyl, —$CH_2$—$CH_2$—$N(CH_3)_2$, and —$CH_2$—$CH_2$—$S(O)_2$—$CH_3$, $R^8$ and $R^9$ $R^8$ and $R^9$ are as defined for $R^6$. In some embodiments, at least one or all $R^8$ are-H. In some embodiments, at least one or all $R^8$ are-$CH_3$. In some embodiments, at least one or all $R^9$ are-H. In some embodiments, at least one or all $R^9$ are-$CH_3$.

R'

In some embodiments, each R' is independently selected from the group consisting of hydrogen, $C_1$-$C_6$ alkylene groups, $C_2$-$C_6$ alkenylene groups, $C_2$-$C_6$ alkynylene groups, $C_6$ arylene, $C_4$-$C_5$ heteroarylene, $C_3$-$C_6$ cycloalkylene groups, $C_5$-$C_8$cycloalkenylene groups, $C_5$-$C_{12}$ alkyl(hetero)arylene groups, $C_5$-$C_{12}$ (hetero)arylalkylene groups, $C_4$-$C_{12}$ alkylcycloalkylene groups, and $C_4$-$C_{12}$ cycloalkylalkylene groups.

In some embodiments, each R' is independently selected from the group consisting of hydrogen, $C_1$-$C_4$ alkylene groups, $C_2$-$C_4$ alkenylene groups, $C_2$-$C_4$ alkynylene groups, $C_6$ arylene, $C_4$-$C_5$ heteroarylene, $C_3$-$C_6$ cycloalkylene groups, $C_5$-$C_8$cycloalkenylene groups, $C_5$-$C_5$ alkyl(hetero)arylene groups, $C_5$-$C_8$ (hetero)arylalkylene groups, $C_4$-$C_{12}$ alkylcycloalkylene groups, and $C_4$-$C_8$ cycloalkylalkylene groups.

Unless stated otherwise, for R' the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups are optionally substituted with a moiety selected from the group consisting of —Cl, —F, —Br, —I, —OH, —$NH_2$, =O, —SH, —$SO_3H$, —$PO_3H$, —$PO_4H_2$, —$NO_2$, and optionally contain one or more heteroatoms selected from the group consisting of —O—, —S—, —NH—, —P—, and —Si, wherein the N, S, and P atoms are optionally oxidized.

R"

In some embodiments, each R" is independently selected from the group consisting of

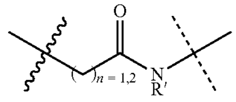
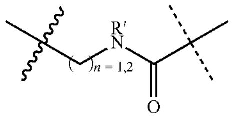
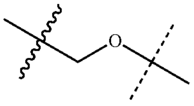
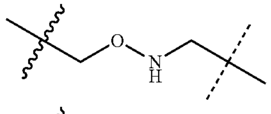
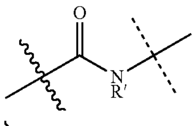
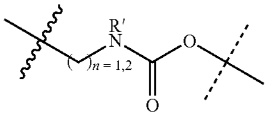
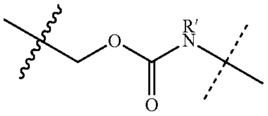
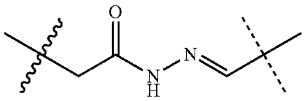
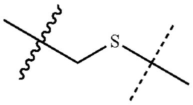
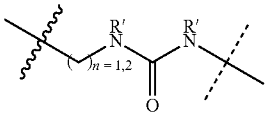
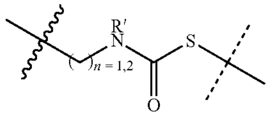
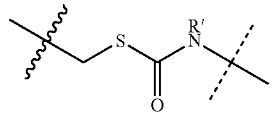
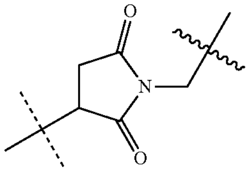
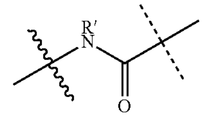
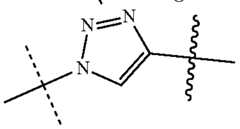
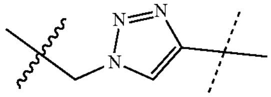

-continued

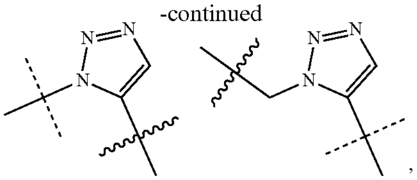

wherein the wiggly line depicts a bond to an ethylene glycol group or optionally to the $R^3$ adjacent to $R^2$ when y is 0, and the dashed line depicts a bond to $R^3$ or G.

In preferred embodiments, R" is —$CH_2$—C(O)NR'— or —$CH_2$—NR'C(O)—.

G

In some embodiments, G is selected from the group consisting of CR', N, $C_5$-$C_6$ arenetriyl, $C_4$-$C_5$ heteroarenetriyl, $C_3$-$C_6$ cycloalkanetriyl, and $C_4$-$C_6$ cycloalkenetriyl, wherein the arenetriyl, heteroarenetriyl, cycloalkanetriyl, and cycloalkenetriyl are optionally further substituted with groups selected from the group consisting of —Cl, —F, —Br, —I, —OR', —$N(R')_2$, —SR', —$SO_3H$, —$PO_3H$, —$PO_4H_2$, —$NO_2$, —$CF_3$ and —$R^1$, and optionally contain one or more heteroatoms selected from the group consisting of —O—, —S—, —NR'—, —P—, and —Si—, wherein the N, S, and P atoms are optionally oxidized, wherein the N atoms are optionally quaternized. Preferably, G is CR'.

L

In some embodiments, L is selected from the group consisting of —$CH_2$—$OCH_3$, —$CH_2$—OH, —$CH_2$—C(O)OH, —C(O)OH. In some embodiments, L is preferably-$CH_2$—$OCH_3$, Moieties M and X It is understood that when moiety M is modified with a compound according to Formula (1), and M is —OH, —NHR', or —SH, that it will lose a proton and will become a moiety X that is —O—, —NR'— or —S—, respectively. It is understood that when moiety M is —C(O)OH, that it will lose an-OH upon modification with a compound according to Formula (1), and that the resulting moiety X is —C(O)—. It is understood that when moiety M is —C(O)R' or —C(O)R'— it will become a moiety X that is —C-upon modification with a compound according to Formula (1).

It is understood that a moiety M that is a-COOH may be derived from the C-terminus of the peptide, protein or peptoid, or from an acidic amino acid residue such as aspartic acid or glutamic acid.

It is understood that moiety M may be derived from non-natural amino acid residues containing —OH, —NHR', —$CO_2H$, —SH, —$N_3$, terminal alkynyl, terminal alkenyl, —C(O)R', —C(O)R'—, $C_8$-$C_{12}$ (hetero)cycloalkynyl, nitrone, nitrile oxide, (imino)sydnone, isonitrile, or a (oxa) norbornene.

It is understood that when moiety M is —OH it may be derived from an amino acid residue such as serine, threonine and tyrosine.

It is understood that when moiety M is —SH it may be derived from an amino acid residue such as cysteine.

It is understood that when moiety M is —NHR' it may be derived from an amino acid residue such as lysine, homolysine, or ornithine.

x, y, z, $t_1$, $t_2$

In some embodiments, $t_1$ is 0. In other embodiments, $t_1$ is 1.

In some embodiments, $t_2$ is 0. In other embodiments, $t_2$ is 1.

In some embodiments, x is an integer in a range of from 0 to 12. Preferably, x is an integer in a range of from 1 to 10, more preferably in a range of from 2 to 8. In particularly favourable embodiments, x is 4 and y is 1.

In some embodiments, y is 0. In other embodiments, y is 1.

In some embodiments, z is an integer in a range of from 12 to 48, preferably from 15 to 40, more preferably from 17 to 35, even more preferably from 20 to 30, most preferably from 22 to 28. In particularly preferred embodiments, z is 23.

Diene

Dienes suitable for reacting with TCOs are known to the skilled person.

In some embodiments of the invention, the diene comprised in a kit with TCOs of the invention is a tetrazine. In some embodiments of the invention, the tetrazine is in accordance with Formula (4), and preferably including pharmaceutically accepted salts thereof:

Formula (4)

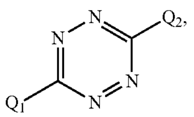

wherein each moiety $Q_1$ and $Q_2$ is independently selected from the group consisting of hydrogen and moieties according to Formula (5):

Formula (5)

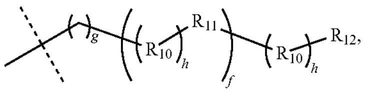

wherein the dashed line indicates a bond to the tetrazine group of Formula (4), wherein preferably each f is an integer independently selected from a range of from 0 to 24, wherein preferably g is an integer in a range of from 0 to 12, wherein preferably each h is independently 0 or 1, wherein preferably the moiety according to Formula (5) is optionally substituted with another independently selected moiety according to Formula (5).

It is preferred that at least one of moieties $Q_1$ and $Q_2$ in Formula (4) is not hydrogen.

In some embodiments, $Q_1$ in Formula (4) is selected from the group consisting of $C_6$-$C_{24}$ aryl, and $C_2$-$C_{24}$ heteroaryl, and is optionally further substituted with a moiety according to Formula (5), preferably not more than one moiety according to Formula (5).

In some embodiments, $Q_1$ in Formula (4) is selected from the group consisting of $C_6$ aryl, and $C_3$-$C_5$ heteroaryl, and is optionally further substituted with at least one moiety according to Formula (5), preferably not more than one moiety according to Formula (5). Herein, preferred heteroaryls are 2-pyridyl, 3-pyridyl, 4-pyridyl, 2,6-pyrimidyl, 3,5-pyrimidyl, 2,5-pyrimidyl, 2,4-pyrimidyl, 2,4 imidazyl, 2,5 imidazyl, phenyl, 2,3-pyrazyl, 3,4-pyrazyl, oxazol, isoxazol, thiazol, oxazoline, 2-pyrryl, 3-pyrryl, 2-thiophene, and 3-thiophene.

In some embodiments, $Q_1$ in Formula (4) is $C_3$-$C_5$ heteroaryl, and is optionally further substituted with at least one moiety according to Formula (5), preferably not more than one moiety according to Formula (5), and $Q_2$ is $C_3$-$C_5$ heteroaryl, and is optionally further substituted with a moiety according to Formula (5), preferably not more than one moiety according to Formula (5). Herein, preferred heteroaryls are 2-pyridyl, 3-pyridyl, 4-pyridyl, 2,6-pyrimidyl, 3,5-pyrimidyl, 2,5-pyrimidyl, 2,4-pyrimidyl, 2,4 imidazyl, 2,5 imidazyl, phenyl, 2,3-pyrazyl, 3,4-pyrazyl, oxazol, isoxazol, thiazol, oxazoline, 2-pyrryl, 3-pyrryl, 2-thiophene, and 3-thiophene.

In some embodiments, $Q_1$ in Formula (4) is a phenyl ring, and is optionally further substituted with at least one moiety according to Formula (5), preferably not more than one moiety according to Formula (5), and $Q_2$ is —H.

In some embodiments, $Q_1$ in Formula (4) is a phenyl ring, and is optionally further substituted with at least one moiety according to Formula (5), preferably not more than one moiety according to Formula (5), and $Q_2$ is a phenyl ring, and is optionally further substituted with at least one moiety according to Formula (5), preferably not more than one moiety according to Formula (5).

In some embodiments, $Q_1$ in Formula (4) is a phenyl ring, and is optionally further substituted with at least one moiety according to Formula (5), preferably not more than one moiety according to Formula (5), and $Q_2$ is selected from the group consisting of $C_6$ aryl, and $C_{3-5}$ heteroaryl, and is optionally further substituted with at least one moiety according to Formula (5), preferably not more than one moiety according to Formula (5).

In some embodiments, $Q_1$ in Formula (4) is $C_1$-$C_{12}$ alkyl, and is optionally further substituted with at least one moiety according to Formula (5), preferably not more than one moiety according to Formula (5), and $Q_2$ selected from the group consisting of $C_6$ aryl, and $C_{3-5}$ heteroaryl, and is optionally further substituted with at least one moiety according to Formula (5), preferably not more than one moiety according to Formula (5).

In some embodiments of the invention the tetrazine is in accordance with any one of the Formulae (6), (7), (8), (9), (10), (11), (12), or (13):

Formula (6)

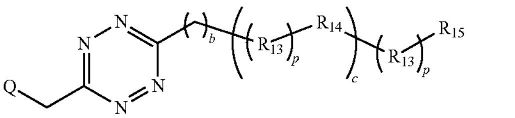

Formula (7)

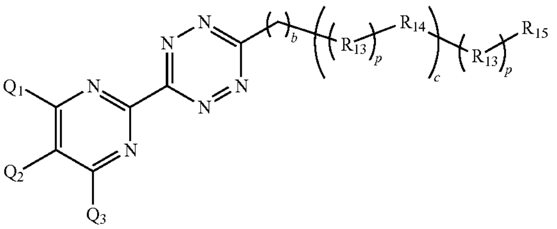

Formula (8)

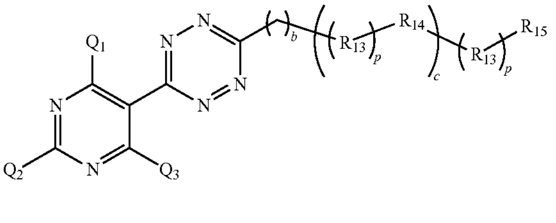

-continued

Formula (9)

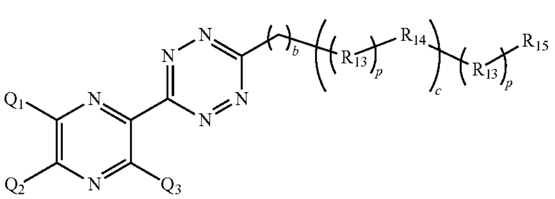

Formula (10)

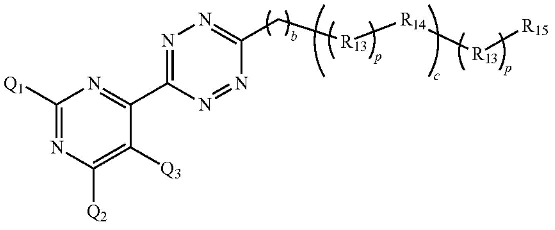

Formula (11)

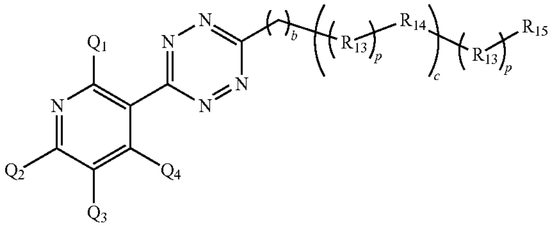

Formula (12)

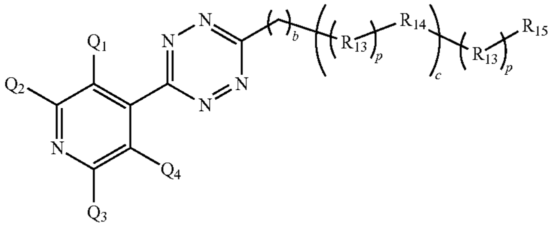

Formula (13)

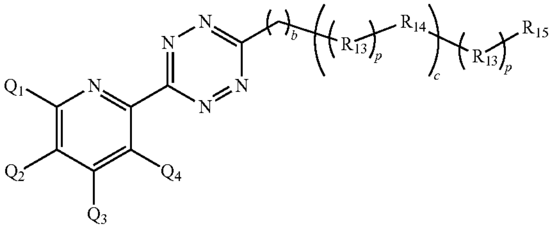

wherein each moiety Q, $Q_1$, $Q_2$, $Q_3$, and $Q_4$ is independently selected from the group consisting of hydrogen and moieties according to Formula (5) as defined above.

In some embodiments, in the tetrazines according to any one of Formulae (6), (7), (8), (9), (10), (11), (12), and (13), at most one moiety selected from the group consisting of Q, $Q_1$, $Q_2$, $Q_3$, and $Q_4$ is hydrogen.

In other embodiments, in the tetrazines according to any one of Formulae (7), (8), (9), (10), (11), (12), and (13), at most two moieties selected from the group consisting of Q, $Q_1$, $Q_2$, $Q_3$, and $Q_4$ are hydrogen.

In other embodiments, in the tetrazines according to any one of Formulae (7), (8), (9), (10), (11), (12), and (13), at most three moieties selected from the group consisting of Q, $Q_1$, $Q_2$, $Q_3$, and $Q_4$ are hydrogen.

In yet other embodiments, in the tetrazines according to any one of Formulae (7), (8), (9), (10), (11), (12), and (13), all moieties selected from the group consisting of Q, $Q_1$, $Q_2$, $Q_3$, and $Q_4$ are hydrogen.

In other embodiments, in the tetrazines according to any one of Formulae (7), (8), (9), (10), (11), (12), and (13), at most one moiety selected from the group consisting of Q, $Q_1$, $Q_2$, $Q_3$, and $Q_4$ is not hydrogen.

In other embodiments, in the tetrazines according to any one of Formulae (7), (8), (9), (10), (11), (12), and (13), at most two moieties selected from the group consisting of Q, $Q_1$, $Q_2$, $Q_3$, and $Q_4$ is not hydrogen.

According to one embodiment, the Activator can be a multimeric compound, comprising a plurality of dienes. These multimeric compounds include but are not limited to polymers, dendrimers, liposomes, polymer particles, or other polymeric constructs.

According to one embodiment, the dienes of this invention can be bound to a Targeteing Agent $T^T$.

According to one embodiment, the dienes of this invention can be bound to a Pharmacokinetics-Modulating ($P^K$) Moiety. It will be understood that a $P^K$ Moiety in relation to the invention is a moiety that modulates the pharmacokinetics of a diene according to any one of Formulae (4), (6)-(13). The functions of the $P^K$ Moiety include, but are not limited to, one or more of delaying clearance of said compound, affecting the volume of distribution of said compound (e.g. reducing or increasing the volume of distribution), affecting (more particularly avoiding) the metabolism of said compound, and/or affecting (more particularly avoiding) the (undesired) sticking or (undesired) uptake of said compound to tissues. The skilled person is well aware of such groups, and how to synthesize these.

In a preferred embodiment, each $P^K$ Moiety is individually selected from the group consisting of polymer, peptide, peptoid, dendrimer, protein, carbohydrate, oligonucleotide, oligosaccharide, lipid, albumin, albumin-binding moiety, dye moiety, fluorescent moiety, imaging probe, and a Targeting Agent (TT). Typically, a suitable polymer as a $P^K$ Moiety is polyethyleneglycol (PEG). Such suitable PEG includes PEG with a number of repeating units in a range of from 2 to 4000, and PEG with a molecular weight in a range of from 200 Da to 100,000 Da.

Log P

In some embodiments, compounds disclosed herein comprising a tetrazine group have a Log P value of 3.0 or lower, preferably 2.0 or lower, more preferably 1.0 or lower, most preferably 0.0 or lower.

In another preferred embodiment the Log P of compounds disclosed herein comprising a tetrazine group have a value in a range of from 2.0 and −2.0, more preferably in a range of from 1.0 and −1.0.

Molecular Weight

For all compounds disclosed herein comprising a group Q, $Q_1$, $Q_2$, $Q_3$, $Q_4$ or $(CH_2)_y$-$((R_{13})p$-$R_{14})_n$-$(R_{13})_p$-$R_{15}$, at least one of these groups has a molecular weight in a range of from 100 Da to 3000 Da. Preferably, at least one of these groups has a molecular weight in a range of from 100 Da to 2000 Da. More preferably, at least one of these groups has a molecular weight in a range of from 100 Da to 1500 Da, even more preferably in a range of from 150 Da to 1500 Da. Even more preferably still, at least one of these groups has a molecular weight in a range of from 150 Da to 1000 Da, most preferably in a range of from 200 Da to 1000 Da.

For all compounds disclosed herein comprising a group Q, Q1, Q2, Q3, Q4 or -$(CH_2)_b$—$((R_{13})_p$-$R_{14})_c$-$(R_{13})_p$-$R_{15}$, none of these groups has a molecular weight of more than 3000 Da.

Group-$(CH_2)_b$—$((R_{13})_p$-$R_{14})_c$-$(R_{13})_p$-$R_{15}$

In some embodiments, b is an integer in a range of from 1 to 12, preferably from 1 to 10, more preferably from 1 to 8, even more preferably from 2 to 6, most preferably from 2 to 4. In some embodiments, b is at least 2, preferably b is at least 3.

In some embodiments, p is 0 or 1, wherein each p is independently selected.

In some embodiments, each c is an integer independently selected from a range of from 0 to 24, preferably from 1 to 12, more preferably from 1 to 6, even more preferably from 1 to 3, most preferably c is 0 or 1. In other embodiments c is preferably an integer from 12 to 24.

In some embodiments, the entire group-$((R_{13})_p$-$R_{14})_c$-$(R_{13})_p$-$R_{15}$ has a molecular weight in a range of from 100 Da to 3000 Da. Preferably, the entire group —$(CH_2)_b$—$((R_{13})_p$ -$R_{14})_c$-$(R_{13})_p$-$R_{15}$ has a molecular weight in a range of from 100 Da to 2000 Da. More preferably, the entire group —$(CH_2)_h$-$((R_{13})_p$-$R_{14})_c$-$(R_{13})_p$-R is has a molecular weight in a range of from 100 Da to 1500 Da, even more preferably in a range of from 150 Da to 1500 Da. Even more preferably still, the entire group —$(CH_2)_b$—$((R_{13})_p$-$R_{14})_c$-$(R_{13})_p$-$R_{15}$ has a molecular weight in a range of from 150 Da to 1000 Da, most preferably in a range of from 200 Da to 1000 Da.

In some embodiments, the entire group —$(CH_2)_b$—$((R_{13})_p$ -$R_{14})_c$-$(R_{13})_p$-$R_{15}$ satisfies molecules from Group RM shown below:

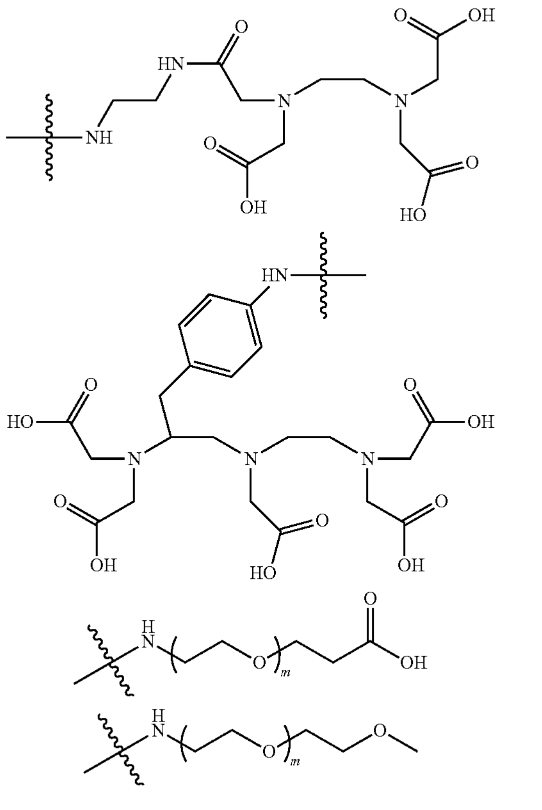

-continued
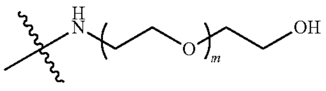
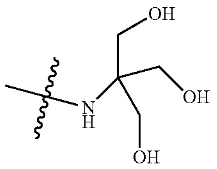
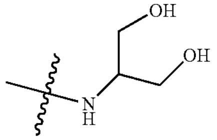
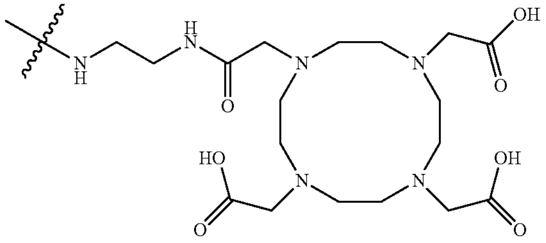
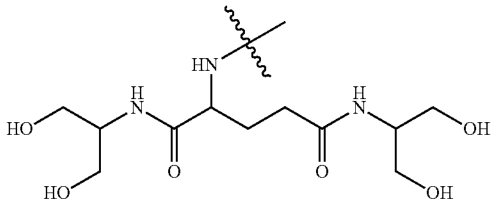
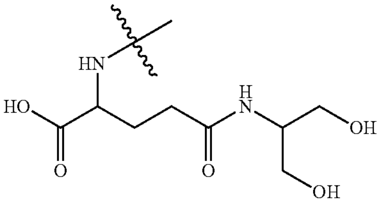
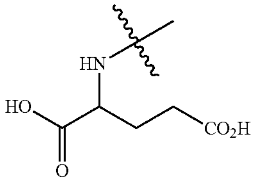
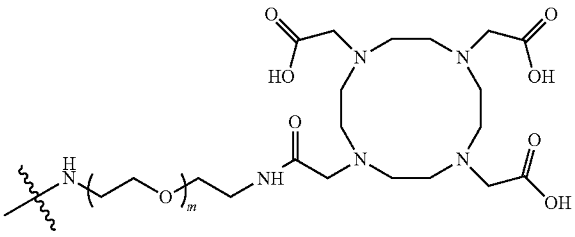
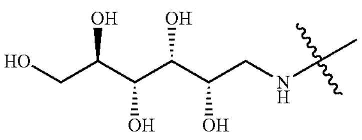
-continued
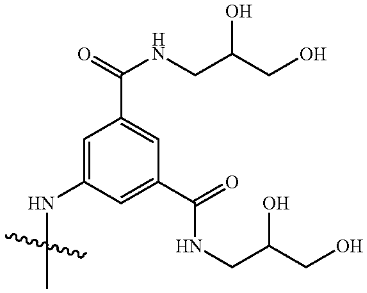
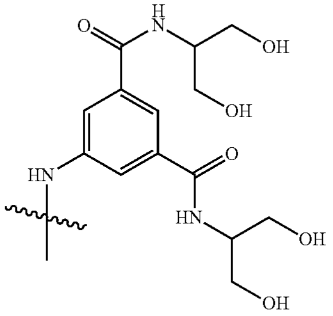
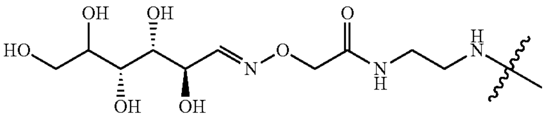
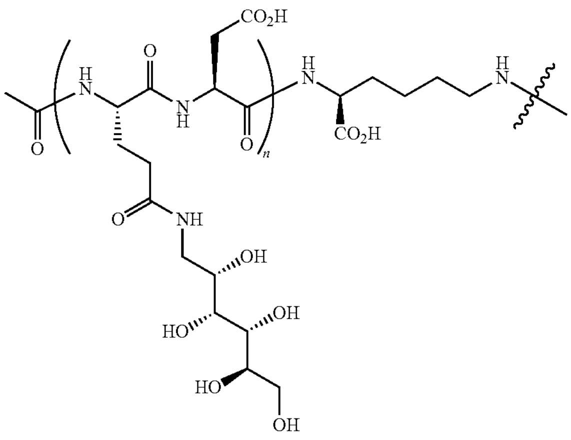
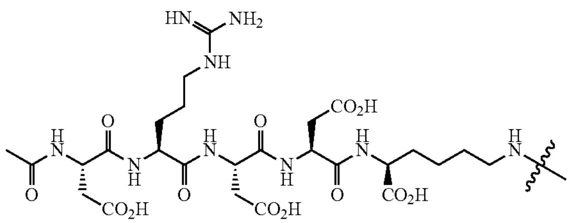
m = 1-24, pref max 12
n = 1-8, pref max 4
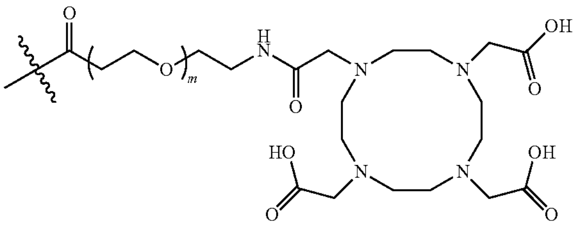

-continued
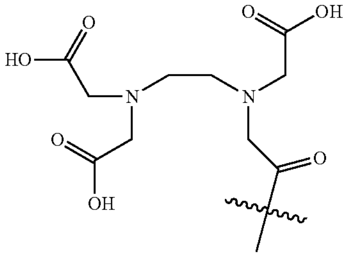
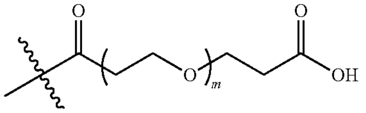
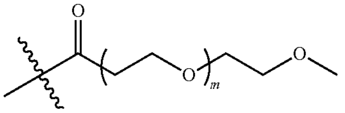
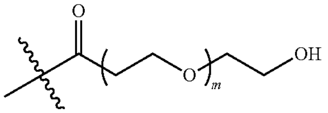
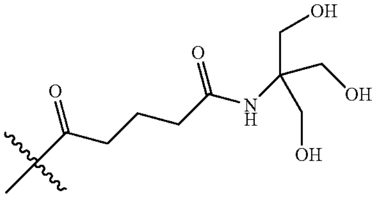
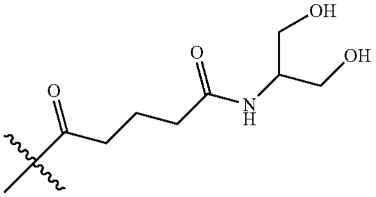
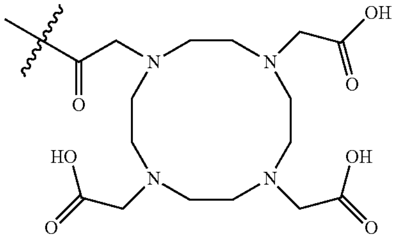
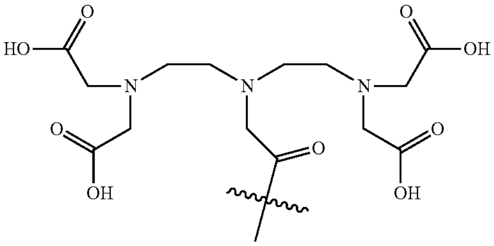
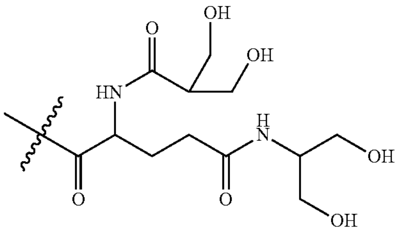
-continued
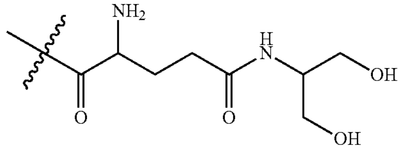
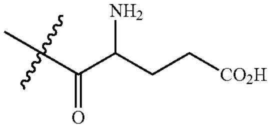
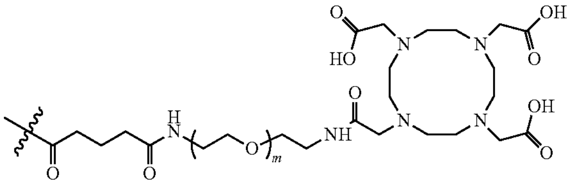
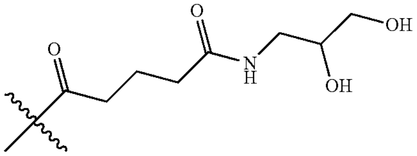
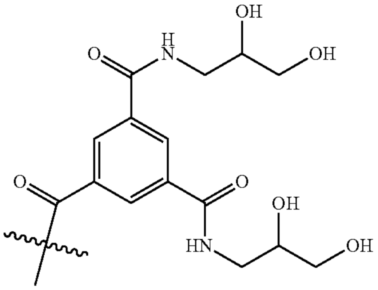
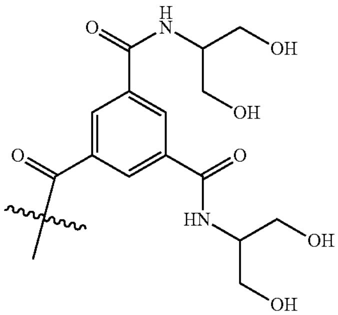
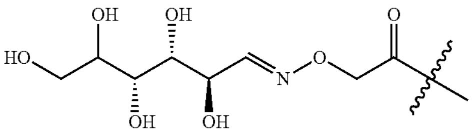
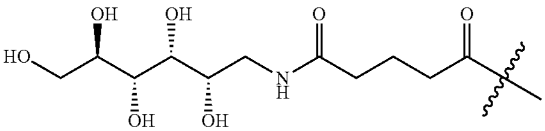

-continued

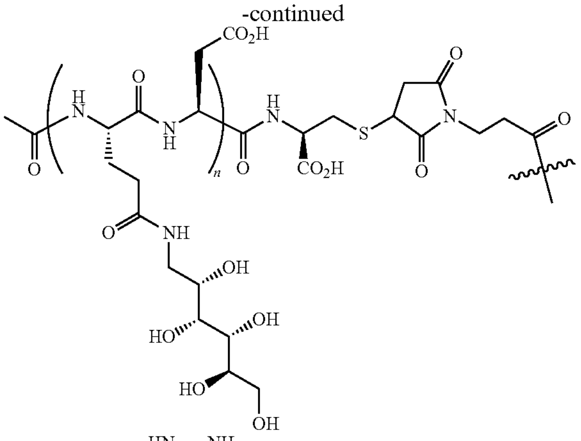

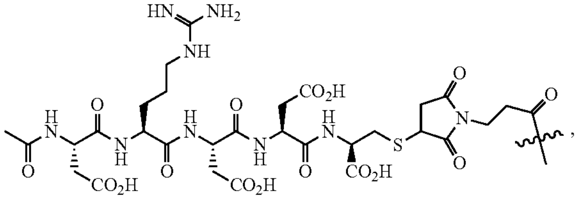

m = 1-24, pref max 12 n = 1-8, pref max 4 wherein the wiggly line denotes a bond to a tetrazine group as disclosed herein or to a group $R_{11}$ or $R_{14}$.

In some embodiments, the group $—(CH_2)_b—((R_{13})_p-R_{14})_c-(R_{13})_p-R_{15}$ or $-(CH_2)_g-((R_{10})_h-R_{11})_f-(R_{10})_h-R_{12}$ satisfies molecules from Group $R^M$, wherein it is understood that for example when f or c is more than 1, $-(CH_2)_b—((R_{13})_p-R_{14})_c-(R_{13})_p-R_{15}$ may be preceded by a group$-((R_{13})_p-R_{14})-$ so as to form a group$-((R_{13})_p-R_{14})-((R_{13})_p-R_{14})_c-1-(R_{13})_p-R_{15}$. It is understood that this follows from the definition of how to write out the repeating units, i.e. $-((R_{13})_p-R_{14})_2—$ would first be written as $—(R_{13})_p-R_{14}-(R_{13})_p-R_{14}—$ before $R_{13}$, p, and $R_{14}$ are independently selected. It will be understood that$-(CH_2)_g-((R_{10})_n-R_{11})_f-(R_{10})_h-R_{12}$ is to be written in the same way.

$R_{10}$

In some embodiments, each $R_{10}$ is independently selected from the group consisting of —O—, —S—, —SS—, $—NR_{16}—$, —N≡N—, —C(O)—, $—C(O)NR_{16}—$, —OC(O)—, —C(O)O—, —OC(O)O—, $—OC(O)NR_{16}—$, $—NR_{16}C(O)—$, $—NR_{16}C(O)O—$, $—NR_{16}C(O)NR_{16}—$, —SC(O)—, —C(O)S—, —SC(O)O—, —OC(O)S—, $—SC(O)NR_{16}—$, $—NR_{16}C(O)S—$, —S(O)—, $—S(O)_2—$, $—OS(O)_2—$, $—S(O_2)O—$, $—OS(O)_2O—$, $—OS(O)_2NR_{16}—$, $—NR_{16}S(O)_2O—$, $—C(O)NR_{16}S(O)_2NR_{16}—$, $—OC(O)NR_{16}S(O)_2NR_{16}—$, —OS(O)—, —OS(O)O—, $—OS(O)NR_{16}—$, $—ONR_{16}C(O)—$, $—ONR_{16}C(O)O—$, $—ONR_{16}C(O)NR_{16}—$, $—NR_{16}OC(O)—$, $—NR_{16}OC(O)O—$, $—NR_{16}OC(O)NR_{16}—$, $—ONR_{16}C(S)—$, $—ONR_{16}C(S)O—$, $—ONR_{16}C(S) NR_{16}—$, $—NR_{16}OC(S)—$, $—NR_{16}OC(S)O—$, $—NR_{16}OC(S) NR_{16}—$, —OC(S)—, —C(S)O—, —OC(S)O—, $—OC(S) NR_{16}—$, $—NR_{16}C(S)—$, $—NR_{16}C(S)O—$, $—SS(O)_2—$, $—S(O)_2S—$, $—OS(O_2)S—$, $—SS(O)_2 O—$, $—NR_{16}OS(O)—$, $—NR_{16}OS(O)O—$, $—NR_{16}OS(O)NR_{16}—$, $—NR_{16}OS(O)_2—$, $—NR_{16}OS(O)_2O—$, $—NR_{16}OS(O)_2NR_{16}—$, $—ONR_{16}S(O)—$, $—ONR_{16}S(O)O—$, $—ONR_{16}S(O)NR_{16}—$, $—ONR_{16}S(O)_2O—$, $—ONR_{16}S(O)_2NR_{16}—$, $—ONR_{16}S(O)_2—$, $—OP(O)(R_{16})_2—$, $—SP(O)(R_{16})_2—$, $—NR_{16}P(O)(R_{16})_2—$, and combinations thereof, wherein $R_{16}$ is defined as described herein.

$R_{11}$

In some embodiments, each $R_{11}$ is independently selected from the group consisting of $C_1$-$C_{24}$ alkylene groups, $C_2$-$C_{24}$ alkenylene groups, $C_2$-$C_{24}$ alkynylene groups, $C_6$-$C_{24}$ arylene, $C_2$-$C_{24}$ heteroarylene, $C_3$-$C_{24}$ cycloalkylene groups, $C_5$-$C_{24}$ cycloalkenylene groups, and $C_{12}$-$C_{24}$ cycloalkynylene groups, which are optionally further substituted with one or more substituents selected from the group consisting of —Cl, —F, —Br, —I, —OH, $—NH_2$, $—SO_3H$, $—PO_3H$, $—PO_4H_2$, $—NO_2$, $—CF_3$, —O, $=NR_{17}$, $—SR_{17}$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ alkyl(hetero)aryl groups, $C_3$-$C_{24}$ (hetero)arylalkyl groups, $C_4$-$C_{24}$ (hetero)arylalkenyl groups, $C_4$-$C_{24}$ (hetero)arylalkynyl groups, $C_4$-$C_{24}$ alkenyl (hetero)aryl groups, $C_4$-$C_{24}$ alkynyl(hetero)aryl groups, $C_4$-$C_{24}$ alkylcycloalkyl groups, $C_4$-$C_{24}$ alkylcycloalkenyl groups, $C_{13}$-$C_{24}$ alkylcycloalkynyl groups, $C_4$-$C_{24}$ cycloalkylalkyl groups, $C_6$-$C_{24}$ cycloalkenylalkyl groups, $C_{13}$-$C_{24}$ cycloalkynylalkyl groups, $C_5$-$C_{24}$ alkenylcycloalkyl groups, $C_7$-$C_{24}$ alkenylcycloalkenyl groups, $C_{14}$-$C_{24}$ alkenylcycloalkynyl groups, $C_5$-$C_{24}$ cycloalkylalkenyl groups, $C_7$-$C_{24}$ cycloalkenylalkenyl groups, $C_{14}$-$C_{24}$ cycloalkynylalkenyl groups, $C_5$-$C_{24}$ alkynylcycloalkyl groups, $C_7$-$C_{24}$ alkynylcycloalkenyl groups, $C_{14}$-$C_{24}$ alkynylcycloalkynyl groups, $C_5$-$C_{24}$ cycloalkylalkynyl groups, $C_7$-$C_{24}$ cycloalkenylalkynyl groups, $C_{14}$-$C_{24}$ cycloalkynylalkynyl groups, $C_5$-$C_{24}$ cycloalkyl(hetero)aryl groups, $C_7$-$C_{24}$ cycloalkenyl(hetero) aryl groups, $C_{14}$-$C_{24}$ cycloalkynyl(hetero)aryl groups, $C_5$-$C_{24}$ (hetero)arylcycloalkyl groups, $C_7$-$C_{24}$ (hetero)arylcycloalkenyl groups, and $C_{14}$-$C_{24}$ (hetero)arylcycloalkynyl groups, wherein the substituents optionally contain one or more heteroatoms selected from the group consisting of O, S, $NR_{17}$, P, and Si, wherein the N, S, and P atoms are optionally oxidized, wherein the N atoms are optionally quaternized; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{17}$, P, and Si, wherein the N, S, and P atoms are optionally oxidized, wherein the N atoms are optionally quaternized.

In some embodiments, each $R_{11}$ is independently selected from the group consisting of $C_1$-$C_{12}$ alkylene groups, $C_2$-$C_{12}$ alkenylene groups, $C_2$-$C_{12}$ alkynylene groups, $C_6$-$C_{12}$ arylene, $C_2$-$C_{12}$ heteroarylene, $C_3$-$C_{12}$ cycloalkylene groups, $C_5$-$C_{12}$ cycloalkenylene groups, and $C_{12}$ cycloalkynylene groups; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{17}$, P, and Si, wherein the N, S, and P atoms are optionally oxidized, wherein the N atoms are optionally quaternized.

In some embodiments, each $R_{11}$ is independently selected from the group consisting of $C_1$-$C_6$ alkylene groups, $C_2$-$C_6$ alkenylene groups, $C_2$-$C_6$ alkynylene groups, $C_6$-$C_6$ arylene, $C_2$-$C_6$ heteroarylene, $C_3$-$C_6$ cycloalkylene groups, and $C_5$-$C_6$ cycloalkenylene groups; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{17}$, P, and Si, wherein the N, S, and P atoms are optionally oxidized, wherein the N atoms are optionally quaternized.

In some embodiments, the $R_{11}$ groups are optionally further substituted with one or more substituents selected from the group consisting of —Cl, —F, —Br, —I, —OH, $—NH_2$, $—SO_3H$, $—PO_3H$, $—PO_4H_2$, $—NO_2$, $—CF_3$, =O, $=NR_{17}$, $—SR_{17}$, $C_1$-$C_{12}$ alkyl groups, $C_2$-$C_{12}$ alkenyl groups, $C_2$-$C_{12}$ alkynyl groups, $C_6$-$C_{12}$ aryl groups, $C_2$-$C_{12}$ heteroaryl groups, $C_3$-$C_{12}$ cycloalkyl groups, $C_5$-$C_{12}$ cycloalkenyl groups, $C_{12}$ cycloalkynyl groups, $C_3$-$C_{12}$ alkyl (hetero)aryl groups, $C_3$-$C_{12}$ (hetero)arylalkyl groups, $C_4$-$C_{12}$ (hetero)arylalkenyl groups, $C_4$-$C_{12}$ (hetero)arylalkynyl groups, $C_4$-$C_{12}$ alkenyl(hetero)aryl groups, $C_4$-$C_{12}$ alkynyl (hetero)aryl groups, $C_4$-$C_{12}$ alkylcycloalkyl groups, $C_3$-$C_{12}$ alkylcycloalkenyl groups, $C_{13}$-$C_{18}$ alkylcycloalkynyl groups, $C_4$-$C_{12}$ cycloalkylalkyl groups, $C_6$-$C_{12}$ cycloalkenylalkyl groups, $C_{13}$-$C_{18}$ cycloalkynylalkyl groups, $C_5$-$C_{12}$ alkenylcycloalkyl groups, $C_7$-$C_{12}$ alkenylcycloalkenyl groups, $C_{14}$-$C_{16}$ alkenylcycloalkynyl groups, $C_5$-$C_{12}$ cycloalkylalkenyl groups, $C_7$-$C_{12}$ cycloalkenylalkenyl groups, $C_{14}$-$C_{16}$ cycloalkynylalkenyl groups, $C_5$-$C_{12}$ alkynylcycloalkyl groups, $C_7$-$C_{12}$ alkynylcycloalkenyl groups, $C_{14}$-$C_{16}$ alkynylcycloalkynyl groups, $C_5$-$C_{12}$ cycloalkylalkynyl groups, $C_7$-$C_{12}$ cycloalkenylalkynyl groups, $C_{14}$-$C_{16}$ cycloalkynylalkynyl groups, $C_5$-$C_{12}$ cycloalkyl(hetero)aryl groups, $C_7$-$C_{12}$ cycloalkenyl(hetero)aryl groups, $C_{14}$-$C_{16}$ cycloalkynyl(hetero)aryl groups, $C_5$-$C_{12}$ (hetero)arylcycloalkyl groups, $C_7$-$C_{12}$ (hetero)arylcycloalkenyl groups, and $C_{14}$-$C_{16}$ (hetero)arylcycloalkynyl groups, wherein the substituents optionally contain one or more heteroatoms selected from the group consisting of O, S, $NR_{17}$, P, and Si, wherein the N, S, and P atoms are optionally oxidized, wherein the N atoms are optionally quaternized.

In some embodiments, the $R_{11}$ groups are optionally further substituted with one or more substituents selected from the group consisting of —Cl, —F, —Br, —I, —OH, $—NH_2$, $—SO_3H$, $—PO_3H—PO_4H_2$, $—NO_2$, $—CF_3$, =O, $=NR_{17}$, $—SR_{17}$, $C_1$-$C_6$ alkyl groups, $C_2$-$C_6$ alkenyl groups, $C_2$-$C_6$ alkynyl groups, $C_6$ aryl groups, $C_2$-$C_6$ heteroaryl groups, $C_3$-$C_6$ cycloalkyl groups, $C_5$-$C_6$ cycloalkenyl groups, $C_3$-$C_6$ alkyl(hetero)aryl groups, $C_3$-$C_6$ (hetero)arylalkyl groups, $C_4$-$C_6$ (hetero)arylalkenyl groups, $C_4$-$C_6$ (hetero)arylalkynyl groups, $C_4$-$C_6$ alkenyl(hetero)aryl groups, $C_4$-$C_6$ alkynyl(hetero)aryl groups, $C_4$-$C_6$ alkylcycloalkyl groups, $C_6$ alkylcycloalkenyl groups, $C_4$-$C_6$ cycloalkylalkyl groups, $C_6$ cycloalkenylalkyl groups, $C_5$-$C_6$ alkenylcycloalkyl groups, $C_7$ alkenylcycloalkenyl groups, $C_5$-$C_6$ cycloalkylalkenyl groups, $C_7$ cycloalkenylalkenyl groups, $C_5$-$C_6$ alkynylcycloalkyl groups, $C_7$ alkynylcycloalkenyl groups, $C_5$-$C_6$ cycloalkylalkynyl groups, $C_5$-$C_6$ cycloalkyl(hetero) aryl groups, and $C_5$-$C_6$ (hetero)arylcycloalkyl groups, wherein the substituents optionally contain one or more heteroatoms selected from the group consisting of O, S, $NR_{17}$, P, and Si, wherein the N, S, and P atoms are optionally oxidized, wherein the N atoms are optionally quaternized.

$R_{12}$ $R_{12}$ is selected from the group consisting of —H, —OH, $—NH_2$, $—N_3$, —Cl, —Br, —F, —I, and a chelating moiety.

Non-limiting examples of chelating moieties for use in $R_{12}$ are DTPA (diethylenetriaminepentaacetic acid), DOTA (1,4,7,10-tetraazacyclododecane-N,N',N",N"-tetraacetic acid), NOTA (1,4, 7-triazacyclononane-N,N',N"-triacetic acid), TETA (1,4,8,11-tetraazacyclotetradecane-N,N',N",N'-tetraacetic acid), OTTA (N1-(p-isothiocyanatobenzyl)-diethylenetriamine-$N_1$,$N_2$,$N_3$,$N_9$-tetraacetic acid), deferoxamine or DFA (N'-[5-[[4-[[5-(acetylhydroxyamino)pentyl]amino]-1,4-dioxobutyl]hydroxyamino]pentyl]-N-(5-aminopentyl)-N-hydroxybutanediamide) or HYNIC (hydrazinonicotinamide).

Other examples of chelating moieties for use in $R_{12}$ are

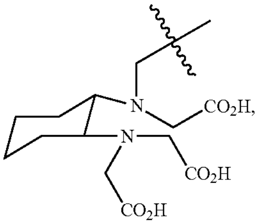

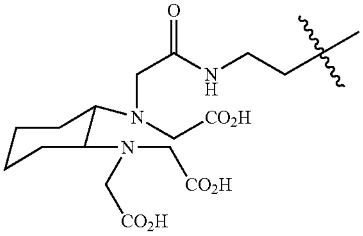

,

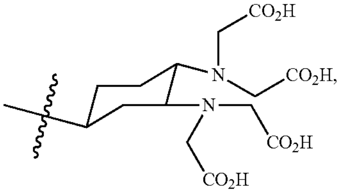

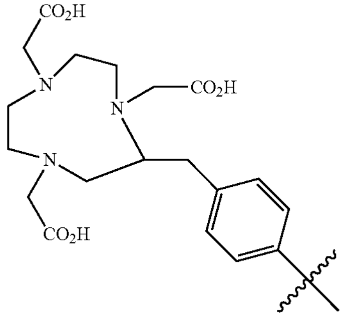

,

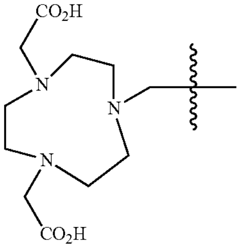

,

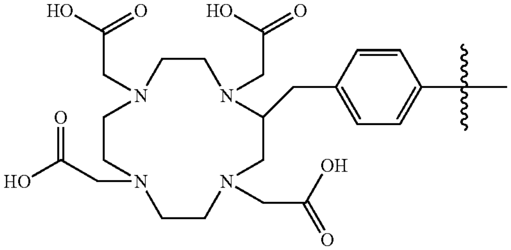

,

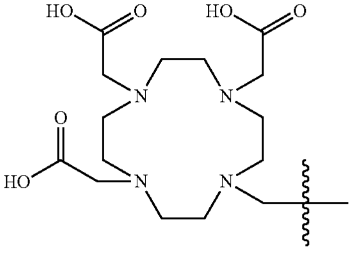

,

-continued
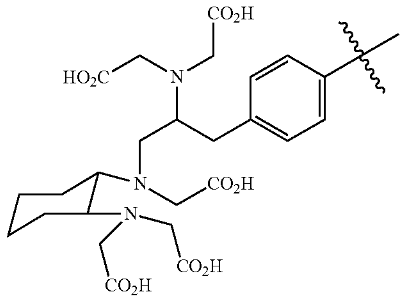
,
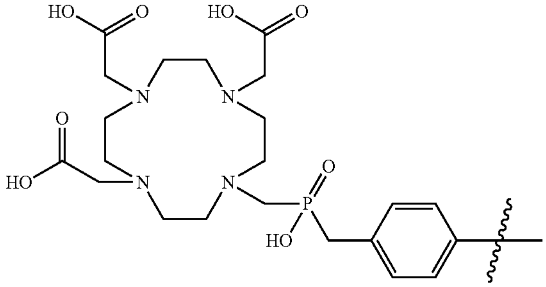
,
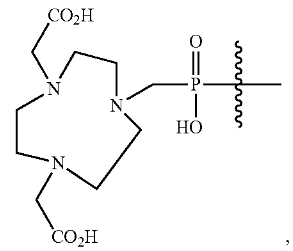
,
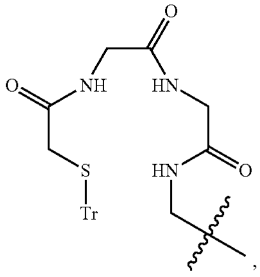
,
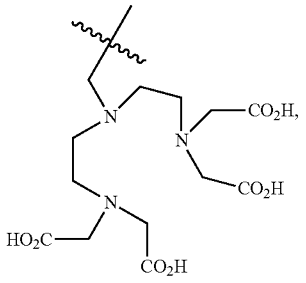
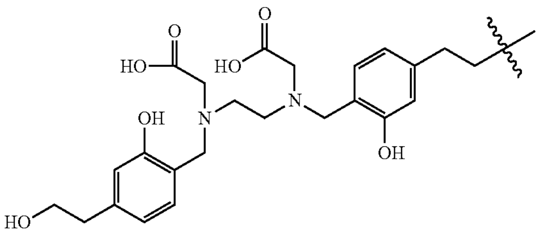
,
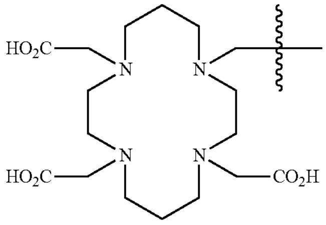
,
-continued
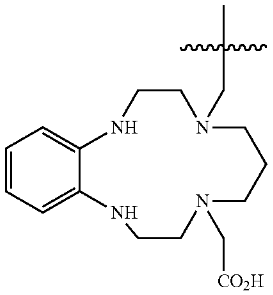
,
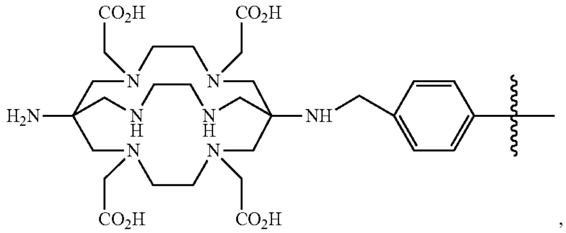
,
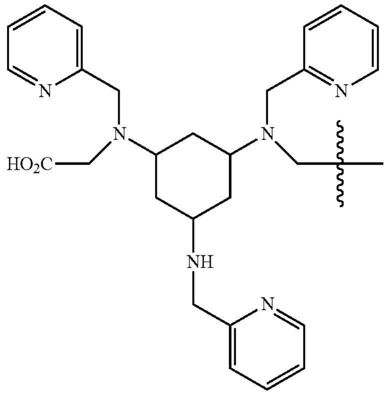
,
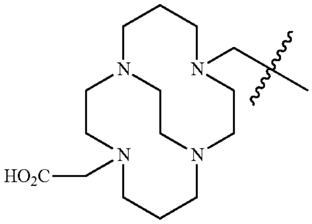
,
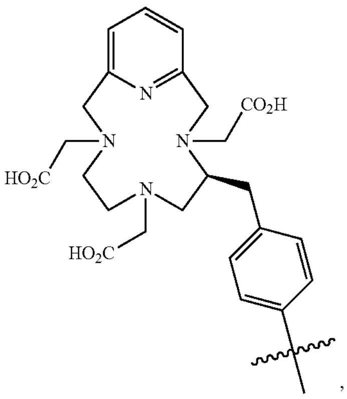
, and -continued

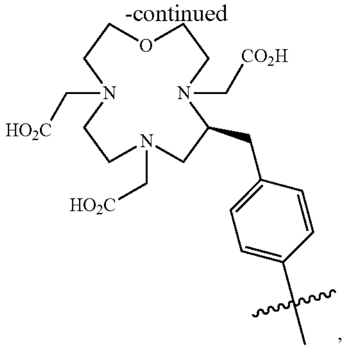

, wherein the wiggly line denotes a bond to the remaining part of the molecule, optionally bound via-C(O) NH—, wherein the chelator moieties according to said group optionally chelate a metal ion.

In some embodiments the chelator moiety chelates an isotope selected from the group consisting of $^{62}Cu$, $^{64}Cu$, $^{66}Ga$, $^{67}Ga$, $^{67}Cu$, $^{68}Ga$, $^{86}Y$, $^{89}Zr$, $^{90}Y$, $^{99m}Tc$, $^{111}In$, $^{166}Ho$, $^{177}Lu$, $^{186}Re$, $^{188}Re$, $^{211}Bi$, $^{212}Bi$, $^{212}Pb$, $^{213}Bi$, $^{214}Bi$, and $^{225}Ac$.

$R_{13}$

In some embodiments, each $R_{13}$ is independently selected from the group consisting of —O—, —S—, —SS—, —$NR_{16}$—, —N═N—, —C(O)—, —C(O)$NR_{16}$—, —OC(O)—, —C(O)O—, —OC(O)O—, —OC(O)$NR_{16}$—, —$NR_{16}$C(O)—, —$NR_{16}$C(O)O—, —$NR_{16}$C(O)$NR_{16}$—, —SC(O)—, —C(O)S—, —SC(O)O—, —OC(O)S—, —SC(O)$NR_{16}$—, —$NR_{16}$C(O)S—, —S(O)—, —$S(O)_2$—, —$OS(O)_2$—, —$S(O_2)O$—,
- —$OS(O)_2O$—, —$OS(O)_2NR_{16}$—, —$NR_{16}S(O)_2O$—, —C(O)$NR_{16}S(O)_2NR_{16}$—, —OC(O)NR 16$S(O)_2$ $NR_{16}$—, —OS(O)—, —OS(O)O—, —OS(O)$NR_{16}$—, —$ONR_{16}$C(O)—, —$ONR_{16}$C(O)O—, —$ONR_{16}$C(O)$NR_{16}$—,
- —$NR_{16}$OC(O)—, —$NR_{16}$OC(O)O—, —$NR_{16}$OC(O)$NR_{16}$—, —$ONR_{16}$C(S)—, —$ONR_{16}$C(S)O—, —$ONR_{16}$C(S) $NR_{16}$—, —$NR_{16}$OC(S)—, —$NR_{16}$OC(S)O—, —$NR_{16}$OC(S) $NR_{16}$—, —OC(S)—, —C(S)O—,
- —OC(S)O—, —OC(S) $NR_{16}$—, —$NR_{16}$C(S)—, —$NR_{16}$C(S)O—, —$SS(O)_2$—, —$S(O)_2S$—, —$OS(O_2)S$—, —$SS(O)_2O$—, —$NR_{16}$OS(O)—, —$NR_{16}$OS(O)O—, —$NR_{16}$OS(O)$NR_{16}$—, —$NR_{16}OS(O)_2$—, —$NR_{16}OS(O)_2O$—, —$NR_{16}OS(O)_2NR_{16}$—, —$ONR_{16}$S(O)—, —$ONR_{16}$S(O)O—, —$ONR_{16}$S(O)$NR_{16}$—,
- —$ONR_{16}S(O)_2O$—, —$ONR_{16}S(O)_2NR_{16}$—, —$ONR_{16}S(O)_2$—, —$OP(O)(R_{16})_2$—, —$SP(O)(R_{16})_2$—, —$NR_{16}P(O)(R_{16})_2$—, and combinations thereof, wherein $R_{16}$ is defined as described herein.

$R_{14}$

In some embodiments, each $R_{14}$ is independently selected from the group consisting of $C_1$-$C_{24}$ alkylene groups, $C_2$-$C_{24}$ alkenylene groups, $C_2$-$C_{24}$ alkynylene groups, $C_6$-$C_{24}$ arylene, $C_2$-$C_{24}$ heteroarylene, $C_3$-$C_{24}$ cycloalkylene groups, $C_5$-$C_{24}$ cycloalkenylene groups, and $C_{12}$-$C_{24}$ cycloalkynylene groups, which are optionally further substituted with one or more substituents selected from the group consisting of —Cl, —F, —Br, —I, —OH, —$NH_2$, —$SO_3H$, —$PO_3H$, —$PO_4H_2$, —$NO_2$, —$CF_3$, ═O, ═$NR_{17}$, —$SR_{17}$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ alkyl(hetero)aryl groups, $C_3$-$C_{24}$ (hetero)arylalkyl groups, $C_4$-$C_{24}$ (hetero)arylalkenyl groups, $C_4$-$C_{24}$ (hetero)arylalkynyl groups, $C_4$-$C_{24}$ alkenyl (hetero)aryl groups, $C_4$-$C_{24}$ alkynyl(hetero)aryl groups, $C_4$-$C_{24}$ alkylcycloalkyl groups, $C_6$-$C_{24}$ alkylcycloalkenyl groups, $C_{13}$-$C_{24}$ alkylcycloalkynyl groups, $C_4$-$C_{24}$ cycloalkylalkyl groups, $C_6$-$C_{24}$ cycloalkenylalkyl groups, $C_{18}$-$C_{24}$ cycloalkynylalkyl groups, $C_5$-$C_{24}$ alkenylcycloalkyl groups, $C_7$-$C_{24}$ alkenylcycloalkenyl groups, $C_{14}$-$C_{24}$ alkenylcycloalkynyl groups, $C_5$-$C_{24}$ cycloalkylalkenyl groups, $C_7$-$C_{24}$ cycloalkenylalkenyl groups, $C_{14}$-$C_{24}$ cycloalkynylalkenyl groups, $C_5$-$C_{24}$ alkynylcycloalkyl groups, $C_7$-$C_{24}$ alkynylcycloalkenyl groups, $C_{14}$-$C_{24}$ alkynylcycloalkynyl groups, $C_5$-$C_{24}$ cycloalkylalkynyl groups, $C_7$-$C_{24}$ cycloalkenylalkynyl groups, $C_{14}$-$C_{24}$ cycloalkynylalkynyl groups, $C_5$-$C_{24}$ cycloalkyl(hetero)aryl groups, $C_7$-$C_{24}$ cycloalkenyl(hetero) aryl groups, $C_{14}$-$C_{24}$ cycloalkynyl(hetero)aryl groups, $C_5$-$C_{24}$ (hetero)arylcycloalkyl groups, $C_7$-$C_{24}$ (hetero)arylcycloalkenyl groups, and $C_{14}$-$C_{24}$ (hetero)arylcycloalkynyl groups, wherein the substituents optionally contain one or more heteroatoms selected from the group consisting of O, S, $NR_{17}$, P, and Si, wherein the N, S, and P atoms are optionally oxidized, wherein the N atoms are optionally quaternized; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{17}$, P, and Si, wherein the N, S, and P atoms are optionally oxidized, wherein the N atoms are optionally quaternized.

In some embodiments, each $R_{14}$ is independently selected from the group consisting of $C_1$-$C_{12}$ alkylene groups, $C_2$-$C_{12}$ alkenylene groups, $C_2$-$C_{12}$ alkynylene groups, $C_6$-$C_{12}$ arylene, $C_2$-$C_{12}$ heteroarylene, $C_3$-$C_{12}$ cycloalkylene groups, $C_5$-$C_{12}$ cycloalkenylene groups, and $C_{12}$ cycloalkynylene groups; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{17}$, P, and Si, wherein the N, S, and P atoms are optionally oxidized, wherein the N atoms are optionally quaternized.

In some embodiments, each $R_{14}$ is independently selected from the group consisting of $C_1$-$C_6$ alkylene groups, $C_2$-$C_6$ alkenylene groups, $C_2$-$C_6$ alkynylene groups, $C_6$-$C_6$ arylene, $C_2$-$C_6$ heteroarylene, $C_3$-$C_6$ cycloalkylene groups, and $C_5$-$C_6$ cycloalkenylene groups; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{17}$, P, and Si, wherein the N, S, and P atoms are optionally oxidized, wherein the N atoms are optionally quaternized.

In some embodiments, the $R_{14}$ groups are optionally further substituted with one or more substituents selected from the group consisting of —Cl, —F, —Br, —I, —OH, —$NH_2$, —$SO_3H$, —$PO_3H$—$PO_4H_2$, —$NO_2$, —$CF_3$, ═O, ═$NR_{17}$, —$SR_{17}$, $C_1$-$C_{12}$ alkyl groups, $C_2$-$C_{12}$ alkenyl groups, $C_2$-$C_{12}$ alkynyl groups, $C_6$-$C_{12}$ aryl groups, $C_2$-$C_{12}$ heteroaryl groups, $C_3$-$C_{12}$ cycloalkyl groups, $C_5$-$C_{12}$ cycloalkenyl groups, $C_{12}$ cycloalkynyl groups, $C_3$-$C_{12}$ alkyl (hetero)aryl groups, $C_3$-$C_{12}$ (hetero)arylalkyl groups, $C_4$-$C_{12}$ (hetero)arylalkenyl groups, $C_4$-$C_{12}$ (hetero)arylalkynyl groups, $C_4$-$C_{12}$ alkenyl(hetero)aryl groups, $C_4$-$C_{12}$ alkynyl (hetero)aryl groups, $C_4$-$C_{12}$ alkylcycloalkyl groups, $C_6$-$C_{12}$ alkylcycloalkenyl groups, $C_{13}$-$C_{18}$ alkylcycloalkynyl groups, $C_4$-$C_{12}$ cycloalkylalkyl groups, $C_6$-$C_{12}$ cycloalkenylalkyl groups, $C_{13}$-$C_{18}$ cycloalkynylalkyl groups, $C_5$-$C_{12}$ alkenylcycloalkyl groups, $C_7$-$C_{12}$ alkenylcycloalkenyl groups, $C_{14}$-$C_{16}$ alkenylcycloalkynyl groups, $C_5$-$C_{12}$ cycloalkylalkenyl groups, $C_7$-$C_{12}$ cycloalkenylalkenyl groups, $C_{14}$-$C_{16}$ cycloalkynylalkenyl groups, $C_5$-$C_{12}$ alkynylcycloalkyl groups, $C_7$-$C_{12}$ alkynylcycloalkenyl groups, $C_{14}$-$C_{16}$ alkynylcycloalkynyl groups, $C_5$-$C_{12}$ cycloalkylalkynyl groups, $C_7$-$C_{12}$ cycloalkenylalkynyl groups, $C_{14}$-$C_{16}$ cycloalkynylalkynyl groups, $C_5$-$C_{12}$ cycloalkyl(hetero)aryl groups, $C_7$-$C_{12}$ cycloalkenyl(hetero)aryl groups, $C_{14}$-$C_{16}$ cycloalkynyl(hetero)aryl groups, $C_5$-$C_{12}$ (hetero)arylcycloalkyl groups, $C_7$-$C_{12}$ (hetero)arylcycloalkenyl groups, and $C_{14}$-$C_{16}$ (hetero)arylcycloalkynyl groups, wherein the substituents optionally contain one or more heteroatoms selected from the group consisting of O, S, $NR_{17}$, P, and Si, wherein the N, S, and P atoms are optionally oxidized, wherein the N atoms are optionally quaternized.

In some embodiments, the $R_{14}$ groups are optionally further substituted with one or more substituents selected from the group consisting of —Cl, —F, —Br, —I, —OH, —$NH_2$, —$SO_3H$, —$PO_3H$, —$PO_4H_2$, —$NO_2$, —$CF_3$, ═O, ═$NR_{17}$, —$SR_{17}$, $C_1$-$C_6$ alkyl groups, $C_2$-$C_6$ alkenyl groups, $C_2$-$C_6$ alkynyl groups, $C_6$ aryl groups, $C_2$-$C_6$ heteroaryl groups, $C_3$-$C_6$ cycloalkyl groups, $C_5$-$C_6$ cycloalkenyl groups, $C_3$-$C_6$ alkyl(hetero)aryl groups, $C_3$-$C_6$ (hetero)arylalkyl groups, $C_4$-$C_6$ (hetero)arylalkenyl groups, $C_4$-$C_6$ (hetero)arylalkynyl groups, $C_4$-$C_6$ alkenyl(hetero)aryl groups, $C_4$-$C_6$ alkynyl(hetero)aryl groups, $C_4$-$C_6$ alkylcycloalkyl groups, $C_6$ alkylcycloalkenyl groups, $C_4$-$C_6$ cycloalkylalkyl groups, $C_6$ cycloalkenylalkyl groups, $C_5$-$C_6$ alkenylcycloalkyl groups, $C_7$ alkenylcycloalkenyl groups, $C_5$-$C_6$ cycloalkylalkenyl groups, $C_7$ cycloalkenylalkenyl groups, $C_5$-$C_6$ alkynylcycloalkyl groups, $C_7$ alkynylcycloalkenyl groups, $C_5$-$C_6$ cycloalkylalkynyl groups, $C_5$-$C_6$ cycloalkyl(hetero) aryl groups, and $C_5$-$C_6$ (hetero)arylcycloalkyl groups, wherein the substituents optionally contain one or more heteroatoms selected from the group consisting of O, S, $NR_{17}$, P, and Si, wherein the N, S, and P atoms are optionally oxidized, wherein the N atoms are optionally quaternized.

$R_{15}$ $R_{15}$ is selected from the group consisting of —H, —OH, —$NH_2$, —$N_3$, —Cl, —Br, —F, —I, and a chelating moiety.

Non-limiting examples of chelating moieties for use in $R_{15}$ are DTPA (diethylenetriaminepentaacetic acid), DOTA (1,4,7,10-tetraazacyclododecane-N,N',N",N"-tetraacetic acid), NOTA (1,4,7-triazacyclononane-N,N',N"-triacetic acid), TETA (1,4,8, 11-tetraazacyclotetradecane-N,N',N", N'-tetraacetic acid), OTTA ($N_1$-(p-isothiocyanatobenzyl)-diethylenetriamine-$N_1$,$N_2$,$N_3$,$N_3$-tetraacetic acid), deferoxamine or DFA (N'-[5-[4-[5-(acetylhydroxyamino)pentyl] amino]-1,4-dioxobutyl]hydroxyamino]pentyl]-N-(5-aminopentyl)-N-hydroxybutanediamide) or HYNIC (hydrazinonicotinamide).

Other examples of chelating moieties for use in $R_{15}$ are

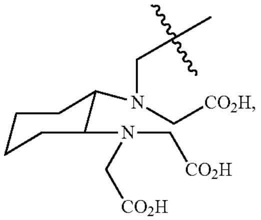

-continued

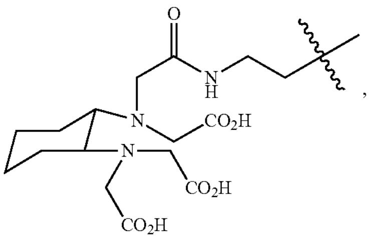

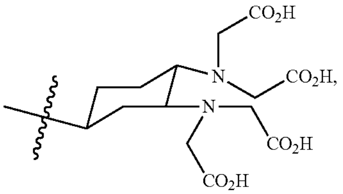

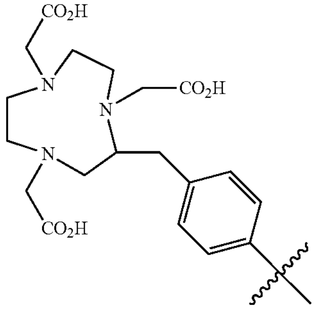

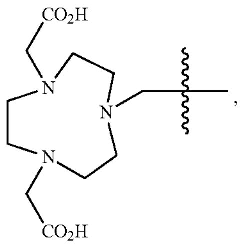

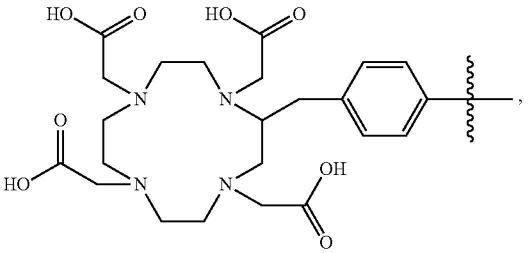

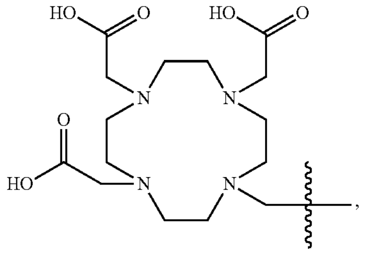

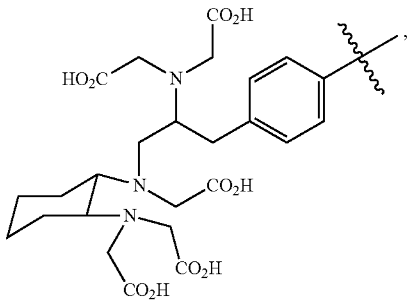

-continued
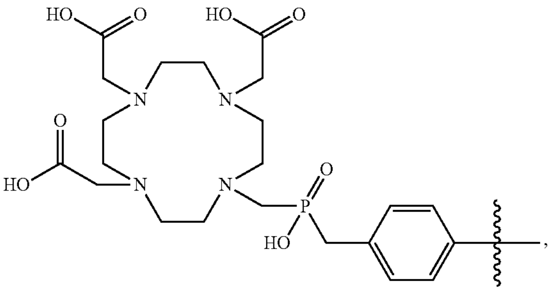,
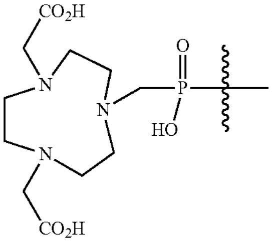,
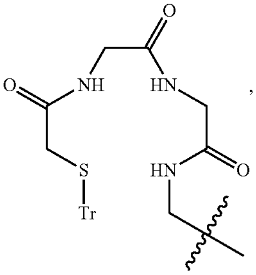,
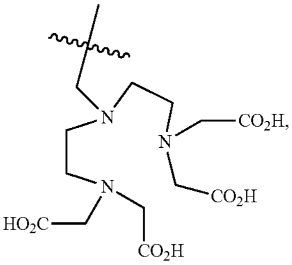
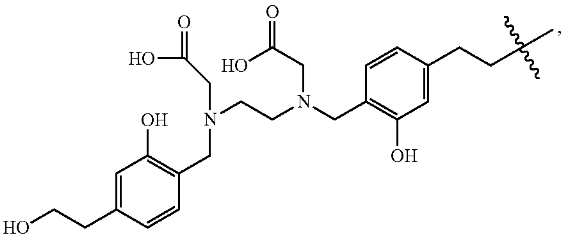,
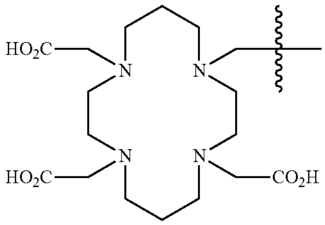,
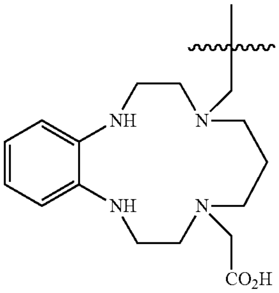,
-continued
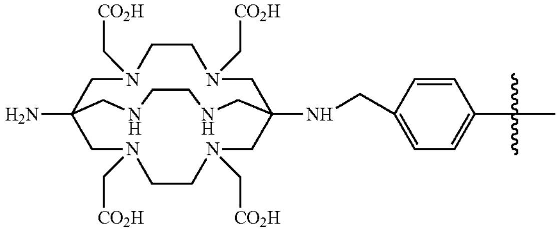,
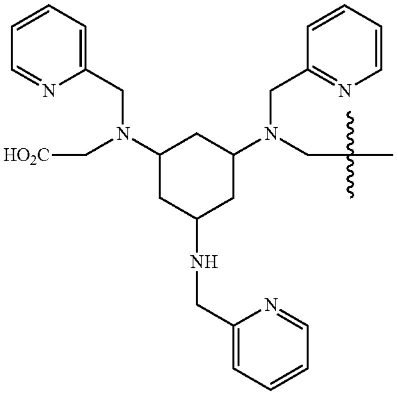,
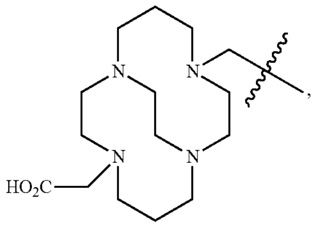,
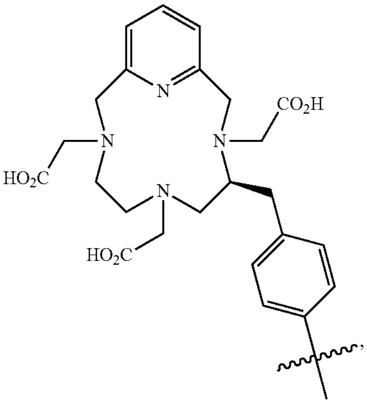, and
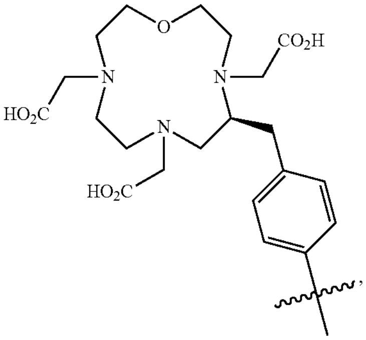,
wherein the wiggly line denotes a bond to the remaining part of the molecule, optionally bound via-C(O) NH—, wherein the chelator moieties according to said group optionally chelate a metal ion.

In some embodiments the chelator moiety chelates an isotope selected from the group consisting of $^{62}Cu$, $^{64}Cu$, $^{66}Ga$, $^{67}Ga$, $^{67}Cu$, $^{68}Ga$, $^{86}Y$, $^{89}Zr$, $^{90}Y$, $^{99m}Tc$, $^{111}In$, $^{166}Ho$, $^{177}Lu$, $^{186}Re$, $^{188}Re$, $^{211}Bi$, $^{212}Bi$, $^{212}Pb$, $^{213}Bi$, $^{214}Bi$, and $^{225}Ac$.

$R_{16}$ $R_{16}$ is independently selected from the group consisting of hydrogen, $C_1$-$C_{24}$ alkyl groups, $C_2$-$C_{24}$ alkenyl groups, $C_2$-$C_{24}$ alkynyl groups, $C_6$-$C_{24}$ aryl, $C_2$-$C_{24}$ heteroaryl, $C_3$-$C_{24}$ cycloalkyl groups, $C_5$-$C_{24}$ cycloalkenyl groups, $C_{12}$-$C_{24}$ cycloalkynyl groups.

In some embodiments $R_{16}$ is independently selected from the group consisting of hydrogen, $C_1$-$C_{12}$ alkyl groups, $C_2$-$C_{12}$ alkenyl groups, $C_2$-$C_{12}$ alkynyl groups, $C_6$-$C_{12}$ aryl, $C_2$-$C_{12}$ heteroaryl, $C_3$-$C_{12}$ cycloalkyl groups, $C_5$-$C_{12}$ cycloalkenyl groups, $C_{12}$ cycloalkynyl groups.

In some embodiments $R_{16}$ is independently selected from the group consisting of hydrogen, $C_1$-$C_6$ alkyl groups, $C_5$-$C_6$ alkenyl groups, $C_2$-$C_6$ alkynyl groups, $C_6$ aryl, $C_2$-$C_6$ heteroaryl, $C_3$-$C_6$ cycloalkyl groups, $C_5$-$C_6$ cycloalkenyl groups.

The $R_{16}$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, —NH, and —SH, and optionally contain one or more heteroatoms selected from the group consisting of O, S, NH, P, and Si, wherein the N, S, and P atoms are optionally oxidized, wherein the N atoms are optionally quaternized.

$R_{17}$ $R_{17}$ is independently selected from the group consisting of hydrogen, $C_1$-$C_8$alkyl groups, $C_2$-$C_5$ alkenyl groups, $C_2$-$C_5$ alkynyl groups, $C_6$-$C_{12}$ aryl, $C_2$-$C_{12}$ heteroaryl, $C_3$-$C_8$ cycloalkyl groups, $C_5$-$C_8$cycloalkenyl groups, $C_3$-$C_{12}$ alkyl (hetero)aryl groups, $C_3$-$C_{12}$ (hetero)arylalkyl groups, $C_4$-$C_{12}$ alkylcycloalkyl groups, $C_4$-$C_{12}$ cycloalkylalkyl groups, $C_5$-$C_{12}$ cycloalkyl(hetero)aryl groups and $C_5$-$C_{12}$ (hetero) arylcycloalkyl groups, wherein the $R_{17}$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized.

Moieties Q. $Q_1$, $Q_2$, $Q_8$, $Q_4$

In some embodiments, g is an integer in a range of from 0 to 12, preferably from 0 to 10, more preferably from 0 to 8, even more preferably from 1 to 6, most preferably from 2 to 4. In other preferred embodiments g is 0. In case more than one moiety selected from the group consisting of Q, $Q_1$, $Q_2$, $Q_3$, and $Q_4$ within one compound satisfies Formula (5), each g is independently selected.

In some embodiments, h is 0 or 1. In case more than one moiety selected from the group consisting of Q, $Q_1$, $Q_2$, $Q_3$, and $Q_4$ within one compound satisfies Formula (5), each h is independently selected.

In some embodiments, each f belonging to a moiety Q, $Q_1$, $Q_2$, $Q_3$, or $Q_4$ is an integer independently selected from a range of from 0 to 24, preferably from 1 to 12, more preferably from 1 to 6, even more preferably from 1 to 3, most preferably f is 0 or 1. In other embodiments f is preferably an integer from 12 to 24.

In some embodiments, the group-$((R_{10})_h$-$R_{11})_h$-$(R_{10})_h$-$R_{12}$ satisfies molecules from Group RM shown above.

In some embodiments, the group-$((R_{10})_h$-$R_{11})_f$-$(R_{10})_h$-$R_{12}$ satisfies molecules from Group $R^M$, wherein it is understood that when f is more than 1, —$((R_{10})_h$-$R_{11})_f$-$(R_{10})_h$-$R_{12}$ may be preceded by a group —$(R_{10})_h$-$R_{11}$-so as to form a group —$(R_{10})_h$-$R_{11}$-$((R_{10})_h$-$R_{11})_f$-$(R_{10})_h$-$R_{12}$. It is understood that this follows from the definition of how to write out the repeating units, i.e. -$((R_{10})_h$-$R_{11})_2$— would first be written as —$(R_{10})_h$-$R_{11}$-$(R_{10})_h$-$R_{11}$— before $R_{10}$, h, and $R_{11}$ are independently selected.

EXAMPLES

Example 1: Materials and Methods

All reagents, chemicals, materials and solvents were obtained from commercial sources, and were used as received. All solvents were of AR quality. O-(2-Aminoethyl)-O'-[2-(Boc-amino)ethyl]decaethylene glycol was obtained from Polypure. Monomethyl auristatin E (MMAE) was purchased from Selleck Chemicals.

$^1H$ NMR and $^{13}C$ NMR spectra were recorded on a Bruker 400 Ultrashield NMR spectrometer (400 MHz for $^1H$ NMR and 100 MHz for $^{13}C$ NMR). Chemical shifts are reported in ppm downfield from TMS at 25° C. Abbreviations used for splitting patterns are s=singlet, t-triplet, q=quartet, m=multiplet and br=broad. Reverse phase (RP) medium pressure liquid column chromatograpy was performed on a Biotage Isolera One MPLC system using a GracePure $C_{18}$ RP column (40 gram), and acetonitrile/water mixtures (containing 0.1 v/v % formic acid) as the eluent. HPLC-MS/PDA was performed using a Shimadzu LC-10 AD VP series HPLC coupled to a diode array detector (Finnigan Surveyor PDA Plus detector, Thermo Electron Corporation) and an Ion-Trap (LCQ Fleet, Thermo Scientific) MS-detector, employing an Alltech Alltima HP $C_{18}$ 3μ column using an injection volume of 1-4 μL, a flow rate of 0.2 mL/min and typically a gradient (5% to 100% in 10 min, held at 100% for 3 min) of acetonitrile in $H_2O$ (both containing 0.1 v/v % formic acid) at 35° C. Preparative RP-HPLC (acetonitrile/$H_2O$ with 0.1 v/v % formic acid) was performed using a Shimadzu SCL-10A VP coupled to two Shimadzu LC-8A pumps and a Shimadzu SPD-10AV VP UV-vis detector on a Phenomenex Gemini 5μ $C_{18}$ 110A column. Size exclusion chromatography (SEC) was performed on an Akta system equipped with a Superdex 200 column. HPLC-QTOF-MS analysis was performed on a Waters Acquity UPLC system equipped with a Sample Manager and a Xevo G2 Quadrupole Time of Flight (QTOF) detector, applying Zspray lockspray ionisation. Mass Lynx v4.1 software was used. SDS polyacrylamide gel electrophoresis (SDS-PAGE) was performed on a Mini-PROTEAN Tetra Cell system using 4-15% precast Mini-PROTEAN TGX gels and Precision Plus Protein All Blue Prestained protein standards (Bio-Rad). The radioactivity distribution on TLC plates and SDS-PAGE gels was monitored with a Typhoon FLA 7000 phosphor imager (GE Healthcare Life Science) using the AIDA software.

TCO-containing ADCs used in the examples include the anti-TAG72 diabody conjugate AVP0458-TCO-MMAE (tc-ADC; DAR=4), and the anti-PSMA diabody conjugate AVP06-TCO-MMAE (nb-ADC; DAR=4) and their synthesis and evaluation, including that of a protease-cleavable control (vc-ADC) have been reported in Rossin et al., *Nature Communications* 2018, 9, 1484. The bispyridyl-tetrazine-PEG-DOTA (BisPy-TZ) used in various assays to measure reactive TCO is shown below and has been reported in Rossin et al. *Angew. Chem.* 2010, 49, 3375-3378.

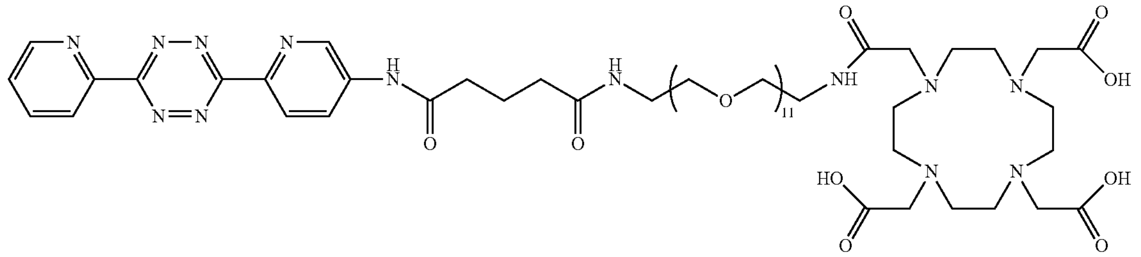

BisPy-TZ

General Procedure A—Tetrazine (TZ) Synthesis

The nitrile (or combination of two different nitriles) and zinc triflate (0.05 eq to the total nitrile content) were combined. When this did not yield a clear solution this was achieved by shortly heating the mixture at 60° C. or by the addition of a minimum amount of EtOH. When a clear solution was obtained hydrazine monohydrate (2 eq to the total nitrile content) was added at once and the mixture was stirred at 60° C. for typically 16 h, after which the volatiles were removed in vacuo.

A1. Oxidation of dihydrotetrazine precursor ([2H]-TZ) having NHBoc functionality: The crude mixture containing [2H]-TZ was divided between $CHCl_3$ and $H_2O$ and the aqueous layer was extracted with $CHCl_3$ (3×). The organic layer was dried with $Na_2SO_4$, filtrated and the volatiles were removed in vacuo. The crude [2H]-TZ was dissolved in $CH_2Cl_2$ and $PhI(OAc)_2$ (1.5 eq) was added. The mixture was stirred at room temperature until HPLC-PDA/MS indicated full conversion of [2H]-TZ to TZ (typically 2 to 4 h).

A2. Oxidation of [2H]-TZ lacking NHBoc functionality: The crude mixture containing [2H]-TZ was re-dissolved in THF/AcOH (1:1) and this solution was cooled on an ice-bath. $NaNO_2$ (5 eq to the total nitrile content) in $H_2O$ (5 to 10 mL per gram $NaNO_2$) was added dropwise (CAUTION: toxic fumes!). After stirring at room temperature for 10 min, $H_2O$ was added and the solution was extracted with $CHCl_3$ until an aqueous layer was obtained that lacked the typical TZ pink (sometimes red or purple) coloration. The organic layer was dried with $Na_2SO_4$, filtrated and the volatiles were removed in vacuo. Traces of AcOH were removed by flushing with $CHCl_3$, or by performing an additional sat. $NaHCO_3$wash.

A3. Alternative oxidation of [2H]-TZ lacking NHBoc functionality: To the crude mixture containing [2H]-TZ was added $NaNO_2$ (5 eq to the total nitrile content) in $H_2O$ (5 to 10 mL per gram $NaNO_2$). On an ice-bath, 1 M HCl was added dropwise (CAUTION: toxic fumes!) until pH=3. $H_2O$ was added and the solution was extracted with $CHCl_3$ until an aqueous layer was obtained that lacked the typical TZ pink (sometimes red or purple) coloration. The organic layer was dried with $Na_2SO_4$, filtrated and the volatiles were removed in vacuo.

General Procedure B—N-t-Boc Deprotection tBoc-protected TZ was dissolved in $CHCl_3$/TFA (1:1) and the mixture was stirred at room temperature for 30 min to 1 h. After removal of the volatiles in vacuo the product was flushed with $CHCl_3$ (3×).

General Procedure C—Coupling of TZ-Amine (TFA-Salt) to PEG-Acid

TZ amine (TFA-salt), PEG-acid and PyBOP (1.1 eq) were combined in $CH_2Cl_2$. Upon dropwise addition of N,N-diisopropylethylamine (3 eq) the solution cleared and was further stirred at room temperature until HPLC-PDA/MS indicated full conversion (typically 1 h). $CHCl_3$ was added and the organic layer was sequentially washed with 0.1 M HCl (2×), sat. $NaHCO_3$ and brine, dried with $Na_2SO_4$, filtrated and the filtrate was concentrated in vacuo.

General Procedure D—Coupling of Tz-Amine to Glutaric Acid

A solution of TZ-amine and N,N-diisopropylethylamine (4 eq) in $CH_2Cl_2$ was added to solid glutaric anhydride (1 eq). The solution was stirred at room temperature for 30 min and the solvent was removed in vacuo.

General Procedure E—Coupling of Tz-Glut-COOH to Mono-Boc-Protected PEG Diamine

TZ-glut-COOH, mono-boc-protected PEG diamine (1 eq) and N,N-diisopropylethylamine (3 eq) were combined in DMF. PyBOP (1 eq) was added as a solid and the solution was stirred at room temperature until HPLC-PDA/MS indicated full conversion (typically 1 h). DMF was removed in vacuo at 40° C. using an oil pump. $CHCl_3$ was added and the organic layer was sequentially washed with 0.1 M HCl, sat. $NaHCO_3$ and $H_2O$, dried with $Na_2SO_4$, filtrated and the filtrate was concentrated in vacuo.

General Procedure F—Coupling of TZ-PEG-Amine (TFA-Salt) to DOTA

TZ-PEG-amine (TFA-salt) was dissolved in DMF with N,N-diisopropylethylamine (10 eq). As a solid, 1,4,7,10-tetraazacyclododecane-1,4,7,10-tetraacetic acid p-nitrophenyl ester (Mier et al., Bioconjugate Chem. 2005, 16, 237-240) (1.1 eq) was added and the solution was stirred at room temperature until HPLC-PDA/MS indicated full conversion (typically 30 min). Precipitation was performed by directly adding the reaction mixture to a stirring solution of diethyl ether and followed by centrifugation and decantation. The solid was washed once with diethyl ether after which centrifugation and decantation were repeated. The resulting solid was dried in vacuo.

Example 2: Synthesis of 3,6-bisalkyl TZ Precursors and Activators

The synthesis of 3,6-dimethyl-1,2,4,5-tetrazine (2.1) was reported in Versteegen et al., Angew. Chem. Int. Ed., 2013, 52, 14112-14116. The syntheses of 3,6-dimethyl-1,2,4,5-tetrazine functional dextran (2.2) and 5-(((6-methyl-1,2,4,5-tetrazin-3-yl)methyl)amin o)-5-oxopentanoic acid (2.5) were reported in Rossin et al., Bioconjug. Chem., 2016, 27, 1697-1706.

Synthesis (2.9), (2.10) and (2.11)
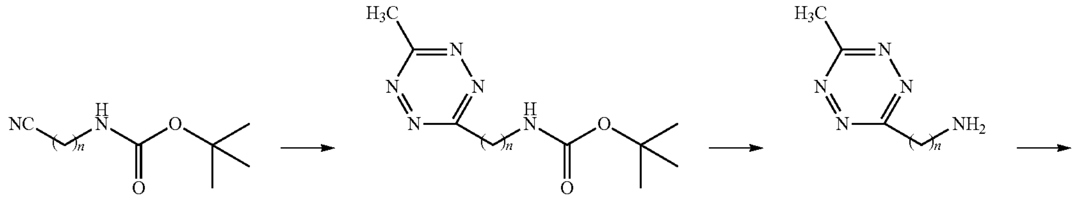
2.3-2.4
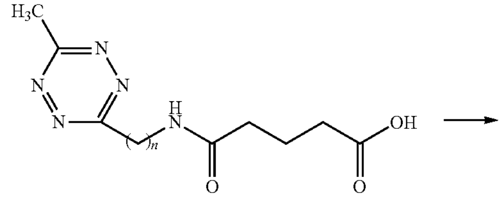
2.5-2.6
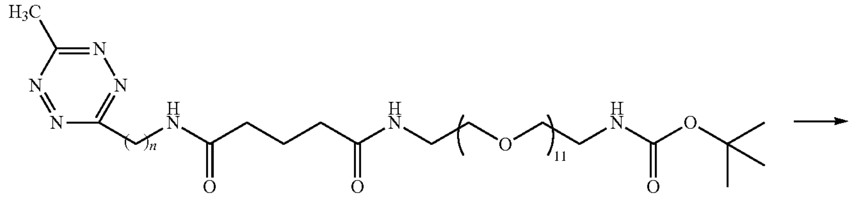
2.7-2.8
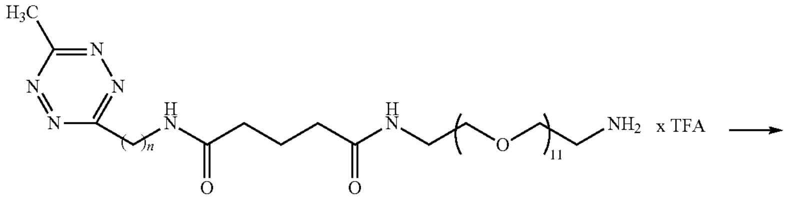
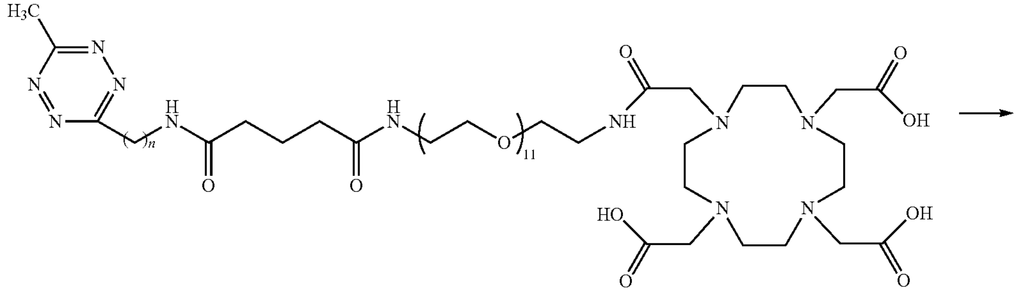
2.9-2.10
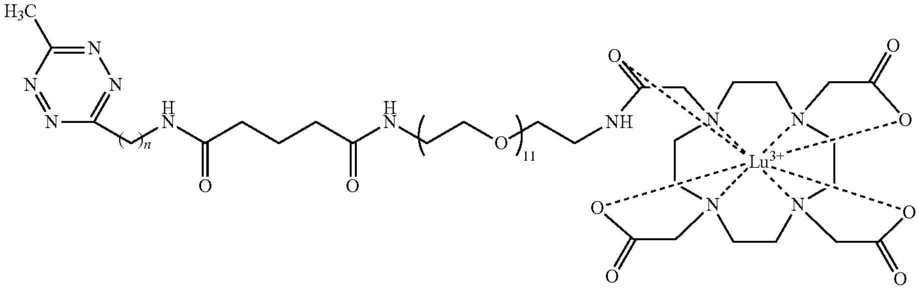
2.11-2.12

| Code | n |
|---|---|
| 2.3, 2.5, 2.7, 2.9, 2.11 | 1 |
| 2.4, 2.6, 2.8, 2.10, 2.12 | 3 |

Compound 2.4 has been prepared according to general procedure A.

This compound was prepared from 3-cyano-N-Boc-propylamine (Houssin et al., Synthesis, 1988, 1988, 259-261) and acetonitrile that were reacted in a 1:5 molar ratio. Oxidation was performed according to general procedure A2. Column chromatography (flash $SiO_2$) using 1:3 ethyl acetate/heptane and recrystallization from diisopropyl ether at −20° C. yielded pure 2.4. $^1H$ NMR ($CDCl_3$): δ=4.69 (br s, 1H), 3.35 (t, J=7.6 Hz, 2H), 3.28 (q, J=6.5 Hz, 2H), 2.15 (m, 2H), 1.44 (s, 9H) ppm. $^{13}C$ NMR ($CDCl_3$): δ=169.50, 167.45, 155.88, 79.36, 39.71, 31.96, 28.39, 28.34, 21.10 ppm. HPLC-MS/PDA (5% to 100% in 10 min): $t_r$=5.33 min (m/z=+137.08, +154.08, +198.00, +253.92 $[M+H]^+$; calcd 254.16 for $C_{11}H_{20}N_5O_2$; $\lambda_{max}$=277, 524 nm).

Compound 2.6 has been prepared according to general procedure D.

Compound 2.4 was deprotected and the reaction intermediate was reacted with glutaric anhydride in a 1:1 molar ratio. After trituration with cold diethyl ether, compound 2.6 was obtained as a pink powder. $^1H$ NMR ($CDCl_3$): δ=6.11 (br s, 1H), 3.41 (q, J=6.5 Hz, 2H), 3.35 (t, J=7.6 Hz, 2H), 3.05 (s, 3H), 2.43 (t, J=7.0 Hz, 2H), 2.31 (t, J=7.3 Hz, 2H), 2.18 (m, 2H), 1.98 (m, 2H) ppm. $^{13}C$ NMR ($CDCl_3$): δ=176.83, 173.31, 169.24, 167.46, 38.68, 35.19, 33.04, 31.88, 27.57, 21.00, 20.79 ppm. HPLC-MS/PDA (5% to 100% in 10 min): $t_r$=2.72 min (m/z=+268.17 Da $[M+H]^+$; calcd 268.14 for $C_{11}H_{18}N_5O_3$; $\lambda_{max}$=278, 518 nm).

The following compounds 2.7-2.8 have been prepared according to procedure E. 2.7

This compound was prepared from 2.5 and 37-amino-5,8,11,14,17,20,23,26,29,32,35-undecaoxa-2-azaheptatriacontanoic acid t-butyl ester that were reacted in a 1:1 molar ratio. Column chromatography (flash $SiO_2$) using an elution gradient of 0% to 8% MeOH in $CH_2Cl_2$ yielded pure 2.7 (2.46 g, 2.84 mmol, 95%) as a purple oil. $^1H$-NMR ($CDCl_3$): δ=7.72 (t, 1H, NH), 7.33 (t, 1H, NH), 5.08 (d, 2H, $TZCH_2$), 3.74-3.39 (m, 46H, $OCH_2$, $NHCH_2$), 3.31 (q, 2H, $CH_2NHBoc$), 3.07 (s, 3H, $TZCH_3$), 2.36 (t, 2H, NHC(O)$CH_2$), 2.24 (t, 2H, NHC(O)$CH_2$), 2.03 (m, 2H, $CH_2CH_2CH_2$), 1.44 (s, 9H, C $(CH_3)_3$). $^{13}C$-NMR ($CDCl_3$): δ=173.3, 173.0, 168.3, 166.8, 156.0, 79.0, 70.5, 70.2, 69.6, 42.2, 40.3, 39.3, 34.7, 34.0, 28.4, 21.8, 21.1. ESI-MS: m/z Calc, for $C_{38}H_{71}N_7O_{15}$ 865.50; Obs. $[M+H]^+$ 866.50, $[M+Na]^+$ 888.58.

2.8

Compound 2.6 was reacted with mono-Boc-protected PEG diamine in a 1:1 molar ratio. Compound 2.8 was obtained as a pink solid, containing a trace amount of tri(pyrrolidin-1-yl) phosphine oxide.

$^1H$ NMR ($CDCl_3$): δ=6.39 (s, 1H), 6.37 (s, 1H), 5.05 (br s, 1H), 3.85-3.59 (m, 40H), 3.59-3.49 (m, 4H), 3.44 (d, J=5.5 Hz, 2H), 3.41-3.23 (m, 6H), 3.04 (s, 3H), 2.27 (td, J=7.1, 2.0 Hz, 4H), 2.17 (m, 2H), 1.96 (m, 2H), 1.44 (s, 9H) ppm. $^{13}C$ NMR ($CDCl_3$): δ=172.73, 172.66, 169.35, 167.48, 155.96, 70.54 (m), 70.21, 70.19, 69.67, 46.28, 46.24, 40.35, 39.21, 38.41, 35.19, 35.12, 31.97, 28.41, 27.88, 26.44, 26.36, 21.84, 21.08 ppm. HPLC-MS/PDA (5% to 100% in 10 min): $t_r$=5.05 min (m/z=+894.33 Da $[M+H]^+$; calcd 894.54 for $C_{40}H_{76}N—O_{15}$; $\lambda_{max}$=277, 523 nm).

The following compounds 2.9-2.10 have been prepared according to general procedures B and F.

2.9

Compound 2.7 was deprotected and the reaction was monitored with HPLC-MS/PDA. ESI-MS: m/z Calc, for $C_{33}H_{63}N_7O_{13}$ 765.45; Obs. $[M+H]^+$ 766.67, $[M+Na]^+$ 788.50, $[M+2H]^{2+}$ 384.00. The intermediate was then reacted with the mono(4-nitrophenyl) ester derivative of DOTA in a 1:1.1 molar ratio. Precipitation (10 mL MeCN→200 mL diethyl ether) was followed by decantation and drying of the solid in vacuo. Purification with preparative RP-MPLC using an elution gradient of 10% to 40% MeCN in $H_2O$ (both containing 0.1% formic acid) followed by lyophilization yielded pure 2.9 (1.15 g, 1.00 mmol, 72% over two steps) as a red sticky solid. ESI-MS: m/z Calc, for $C_{49}H_{89}N_{11}O_{20}$ 1151.63; Obs. $[M+2H]^{2+}$ 577.17, $[M+H]^+$ 1152.75.

2.10

Compound 2.8 was deprotected and the reaction was monitored with MS. HPLC-MS/PDA (5% to 100% in 10 min): $t_r$=3.80 min (m/z=+794.50 Da $[M+H]^+$; calcd 794.49 for $C_{35}H_{68}N_7O_{13}$; $\lambda_{max}$=278, 521 nm).

The intermediate was then reacted with the mono(4-nitrophenyl) ester derivative of DOTA in a 1:1.1 molar ratio. The product was purified by column chromatography (RP silica gel, acetonitrile/0.1 v/v % aqueous formic acid=15:85), and isolated by lyophilization, to yield product 2.10 as a pink solid. 1H NMR ($D_2O$): δ=4.04-3.47 (m, 54H), 3.38 (m, 14H), 3.12 (m, 8H), 3.01 (s, 3H), 2.26 (m, 4H), 2.13 (m, 2H), 1.85 (m, 2H) ppm. HPLC-MS/PDA (5% to 100% in 10 min): $t_r$=3.82 min (m/z=+1180.83 Da $[M+H]^+$; calcd 1180.67 for $C_{51}H_{94}N_{11}O_{20}$; $\lambda_{max}$=276, 519 nm).

2.11

To a solution of compound 2.9 (0.159 g, 0.138 mmol) in 0.1 M aqueous sodium acetate buffer (5.5 mL, pH=5.5) was added lutetium (III) chloride hexahydrate (80.3 mg, 0.206 mmol). The solution was stirred at 20° C. for 1 h, and then the product was purified by column chromatography (RP silica gel, acetonitrile/0.1 v/v % aqueous formic acid=30:70), and isolated by lyophilization, to yield product 2.11 as a pink solid (0.170 g, 93%). $^1H$ NMR ($D_2O$): 8=5.00 (s, 2H), 3.90-3.10 (m, 60H), 3.05 (s, 3H), 2.90-2.45 (m, 12H), 2.41 (t, 2H), 2.31 (t, 2H), 1.92 (m, 2H) ppm. HPLC-MS/PDA (5% to 100% in 10 min): $t_r$=4.2 min (m/z=+663.25 $[M+2H]^{2+}$, +1324.75 $[M+H]^+$, −1323.33 $[M-H]^-$, −1367.83 $[M+HCOO]^-$ Da; calcd 1324.55 for $C_{49}H_{87}N_{11}O_{20}Lu$ $[M+H]^+$).

2.12

To a solution of compound 2.10 (1.94 g, 1.64 mmol) in 0.2 M aqueous sodium acetate buffer (60 mL, pH=5.5) was added lutetium (III) chloride hexahydrate (1.28 g, 3.28 mmol). The solution was stirred at 4° C. for 16 h, and then the product was purified by column chromatography (RP silica gel, acetonitrile/0.1 v/v % aqueous formic acid=20:80), and isolated by lyophilization, to yield product 2.11 as a pink solid (1.70 g, 77%). $^1H$ NMR ($D_2O$): δ=3.83-3.15 (m, 64H), 3.03 (s, 3H), 2.81 (m, 8H), 2.53 (m, 4H), 2.28 (m, 4H), 2.16 (m, 2H), 1.87 (m, 2H) ppm. $^{13}C$ NMR ($D_2O$): 8=180.78, 175.99, 175.85, 175.74, 169.18, 167.52, 69.57, 69.37, 68.80, 68.55, 65.71, 55.81, 55.29, 39.67, 38.89, 38.35, 34.86, 34.82, 31.28, 26.61, 21.75, 20.05 ppm. HPLC-MS/PDA (5% to 100% in 10 min): $t_r$=3.62 min (m/z=+677.17 $[M+2H]^{2+}$, +1352.83 $[M+H]^+$, −1351.17 $[M-H]^-$, −1396.00 $[M+HCOO]^-$ Da; calcd 1352.58 for $C_{51}H_{91}N_{11020}Lu$ $[M+H]^+$).

Example 3: Synthesis of 3-alkyl-6-pyridyl TZ Precursors and Activators

The synthesis of 3-(2-pyridyl)-6-methyl-1,2,4,5-tetrazine (3.1) was reported in Versteegen et al., Angew. Chem. Int. Ed., 2013, 52, 14112-14116.

The syntheses of 5-((6-(6-methyl-1,2,4,5-tetrazin-3-yl) pyridin-3-yl)amino)-5-oxopentanoic acid and 3-(pyridin-2-yl)-6-methyl-1,2,4,5-tetrazine functional dextran (3.2) were reported in Rossin et al., Bioconjug. Chem., 2016, 27, 1697-1706.

Synthesis of 2,2',2''-(10-(44-((6-(6-methyl-1,2,4,5-tetrazin-3-yl)pyridin-3-yl)amino)-2,40,44-trioxo-6,9,12, 15,18,21,24,27,30,33,36-undecaoxa-3,39-diaza-tetratetracontyl)-1,4,7,10-tetraazacyclododecane-1,4,7-triyl)triacetic acid (3.4)

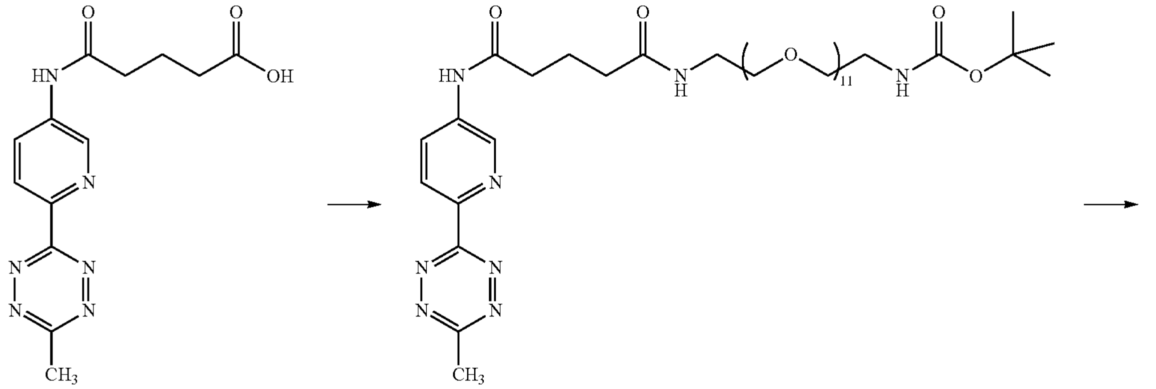

3.3

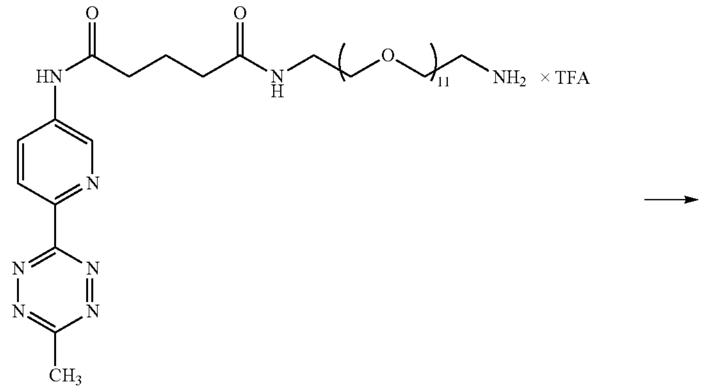

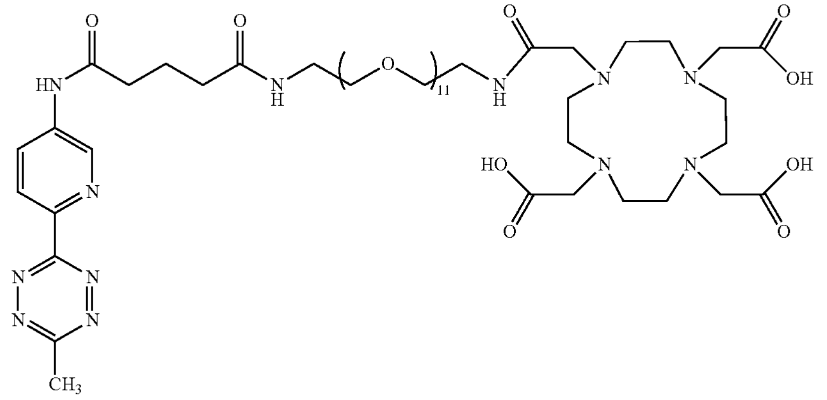

3.4

Compound 3.3 has been prepared according to general procedure E.

3.3

This compound was prepared from previously reported 5-((6-(6-methyl-1,2,4,5-tetrazin-3-yl)pyridin-3-yl)amino)-5-oxopentanoic acid (Rossin et al., Bioconjug. Chem., 2016, 27, 1697-1706) and 37-amino-5,8,11,14,17,20,23,26,29,32,35-undecaoxa-2-azaheptatriacontanoic acid t-butyl ester that were reacted in a 1:1 molar ratio. Column chromatography (flash $SiO_2$) using an elution gradient of 1% to 8% MeOH in $CHCl_3$ yielded pure 3.3 (2.60 g, 2.80 mmol, 79%) as a purple oil. $^1$H-NMR ($CDCl_3$): δ=9.63 (s, 1H, NH), 8.95 (t, 1H, ArH), 8.61 (d, 2H, ArH), 6.81 (br, 1H, NH), 5.08 (br, 1H, NH), 3.71-3.44 (m, 46H, $OCH_2$, $NHCH_2$), 3.30 (q, 2H, $CH_2NHBoc$), 3.13 (s, 3H, $TZCH_3$), 2.56 (t, 2H, NHC(O)$CH_2$), 2.37 (t, 2H, NHC(O)$CH_2$), 2.09 (qn, 2H, $CH_2CH_2CH_2$), 1.44 (s, 9H, C $(CH_3)_3$). $^{13}$C-NMR ($CDCl_3$): δ=172.9, 172.5, 167.6, 163.1, 156.0, 144.1, 141.8, 138.4, 126.5, 124.3, 79.1, 70.5, 70.1, 69.6, 40.3, 39.3, 36.0, 35.0, 28.4, 21.3, 21.2. ESI-MS: m/z Calc. for $C_{42}H_{72}N_8O_{15}$ 928.51; Obs. $[M+H]^+$ 929.58, $[M+Na]^+$ 951.58.

Compound 3.4 has been prepared according to general procedures B and F.

3.4

Compound 3.3 was deprotected and the reaction was monitored with HPLC-MS/PDA. ESI-MS: m/z Calc, for $C_{37}H_{64}N_8O_{13}$ 828.46; Obs. $[M+H]^+$ 829.67, $[M+2H]^{2+}$ 415.50. The intermediate was then reacted with the mono (4-nitrophenyl) ester derivative of DOTA in a 1:1.1 molar ratio. Precipitation (7 mL MeCN→150 mL diethyl ether) was followed by decantation and drying of the solid in vacuo. Purification with preparative RP-MPLC using an elution gradient of 10% to 30% MeCN in $H_2O$ (both containing 0.1% formic acid) followed by lyophilization yielded pure 3.4 (0.57 g, 0.47 mmol, 62% over two steps) as a red sticky solid. ESI-MS: m/z Calc, for $C_{53}H_{90}N_{12}O_{20}$ 1214.64; Obs. $[M+3H]^{3+}$ 406.08, $[M+2H]^{2+}$ 608.67, $[M+H]^+$ 1215.75, $[M+Na]^+$ 1237.67.

Example 4: Synthesis of alkyl-pyrimidyl TZ Building Blocks and Activators

The synthesis of 3-methyl-6-(pyrimidin-2-yl)-1,2,4,5-tetrazine (4.1) was reported in Fan et al., *Angew. Chem. Int. Ed.* 2016, 55, 14046-14050.

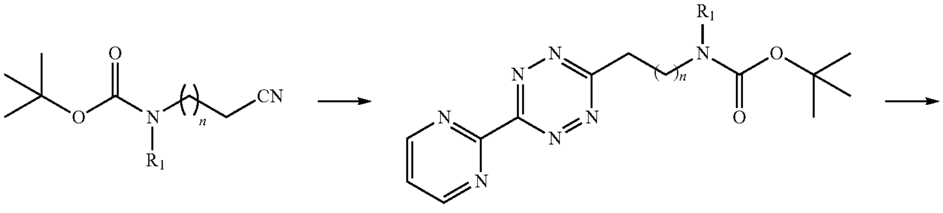

4.2-4.4

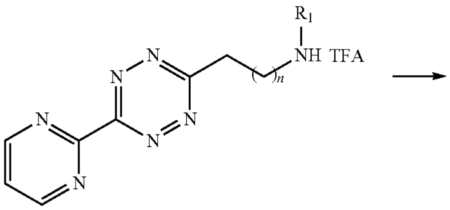

4.5-4.6

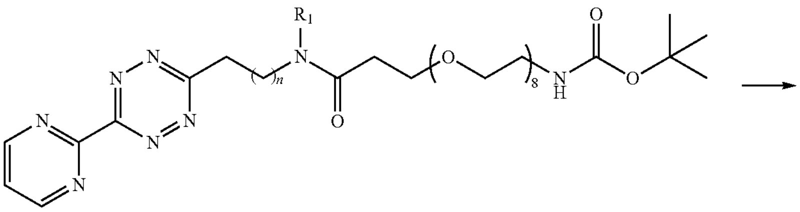

4.7-4.8

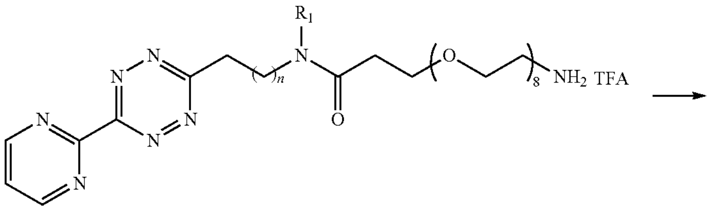

4.9-4.10

-continued

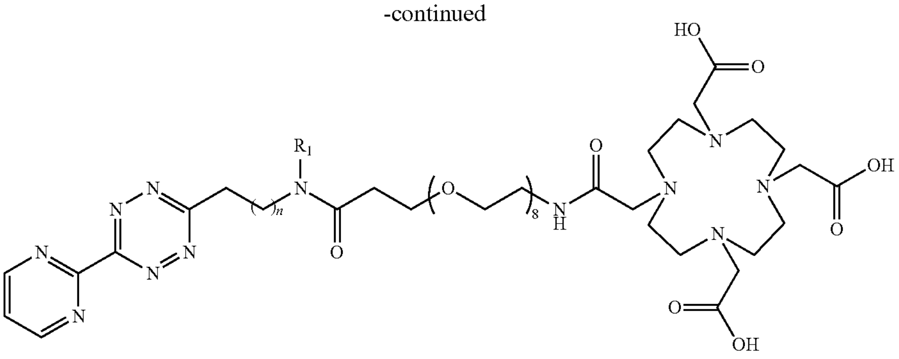

4.11-4.12

| Code | n | $R_1$ |
|---|---|---|
| 4.2 | 1 | H |
| 4.3, 4.5, 4.7, 4.9, 4.11 | 1 | Me |
| 4.4, 4.6, 4.8, 4.10, 4.12 | 2 | H |

The following compounds 4.2-4.4 have been prepared according to general procedure A.

4.2

This compound was prepared from 2-pyrimidinecarbonitrile and t-butyl N-(2-cyanoethyl) carbamate that were reacted in a 3:2 molar ratio. Oxidation was performed according to general procedure A1. Column chromatography (flash $SiO_2$) using an elution gradient of 20% to 60% EtOAc in $CHCl_3$ and, in a second chromatography step (normal $SiO_2$), elution with 55% acetone in heptane yielded pure 4.2 (113 mg, 0.37 mmol, 22%) as a red solid. $^1$H-NMR ($CDCl_3$): δ=9.13 (d, 2H, ArH), 7.60 (t, 1H, ArH), 5.18 (br, 1H, NH), 3.84 (q, 2H, $CH_2N$), 3.70 (t, 2H, $TZCH_2$), 1.39 (s, 9H, $CH_3$). $^{13}$C-NMR ($CDCl_3$): δ=169.4, 163.3, 159.4, 158.4, 155.8, 122.6, 79.4, 38.4, 35.6, 28.3. ESI-MS: m/z Calc, for $C_{13}H_{17}N_7O_2$ 303.14; Obs. $[M-tboc+H]^+$ 204.17, $[M-tbutyl+2H]^+$ 248.08, $[M+Na]^+$ 326.08.

4.3

This compound was prepared from 2-pyrimidinecarbonitrile and t-butyl N-(2-cyanoethyl)-N-methylcarbamate that were reacted in a 1:1 molar ratio. Oxidation was performed according to general procedure A2. Column chromatography (flash $SiO_2$) using an elution gradient of 20% to 50% EtOAc in $CHCl_3$ and, in a second chromatography step (normal $SiO_2$), elution with 40% acetone in heptane yielded pure 4.3 (56 mg, 0.18 mmol, 16%) as a red solid. $^1$H-NMR ($CDCl_3$): δ=9.12 (d, 2H, ArH), 7.59 (t, 1H, ArH), 3.86 (br, 2H, $CH_2N$), 3.70 (t, 2H, $TZCH_2$), 2.94 (s, 3H, $NCH_3$), 1.34 (s, 9H, $C(CH_3)_3$). ESI-MS: m/z Calc, for $C_{14}H_{19}N_7O_2$ 317.16; Obs. $[M-tboc+H]^+$ 218.00, $[M-tbutyl+2H]^+$ 261.92, $[M+Na]^+$ 340.08.

4.4

This compound was prepared from 2-pyrimidinecarbonitrile and t-butyl N-(3-cyanopropyl) carbamate that were reacted in a 3:2 molar ratio. Oxidation was performed according to general procedure A1. Column chromatography (flash $SiO_2$) using an elution gradient of 20% to 60% EtOAc in $CHCl_3$ and, in a second chromatography step (normal $SiO_2$), elution with 50% acetone in heptane yielded pure 4.4 (55 mg, 0.17 mmol, 20%) as a red oil. $^1$H-NMR ($CDCl_3$): δ=9.13 (d, 2H, ArH), 7.60 (t, 1H, ArH), 4.76 (br, 1H, NH), 3.53 (t, 2H, $TZCH_2$), 3.34 (q, 2H, $CH_2N$), 2.24 (qn, 2H, $CH_2CH_2N$), 1.44 (s, 9H, $CH_3$). $^{13}$C-NMR ($CDCl_3$): δ=171.0, 163.4, 159.6, 158.4, 155.9, 122.6, 79.4, 39.7, 32.4, 28.4 (2×). ESI-MS: m/z Calc. for $C_{14}H_{19}N_7O_2$ 317.16; Obs. $[M-tboc+H]^+$ 218.00, $[M-tbutyl+2H]^+$ 261.92, $[M+Na]^+$ 340.08.

The following compounds 4.5 and 4.6 have been prepared according to general procedure B.

4.5

This compound was prepared from 4.3. Pure 4.5 was obtained as a red oil (10.4 mg, 31 μmol, 100%). $^1$H-NMR ($CD_3OD$): δ=9.15 (d, 2H, ArH), 7.80 (t, 1H, ArH), 3.91 (t, 2H, $CH_2$), 3.78 (t, 2H, $CH_2$), 2.86 (s, 3H, $NCH_3$).

4.6

This compound was prepared from 4.4. Pure 4.6 was obtained as a red oil (109 mg, 0.33 mmol, 100%). $^1$H-NMR (CD: OD): 8=9.14 (d, 2H, ArH), 7.79 (t, 1H, ArH), 3.60 (t, 2H, $CH_2$), 3.22 (t, 2H, $CH_2$), 2.44 (qn, 2H, $CH_2CH_2N$). $^{13}$C-NMR ($CD_3OD$): δ=171.5, 164.0, 161.1 (q), 160.0, 159.7, 124.6, 117.1 (q), 40.1, 32.7, 26.0. $^{19}$F-NMR ($CD_3OD$): δ=−77.5. ESI-MS: m/z Calc, for $C_{11}H_{12}F_3N_7O_2$ 331.10; Obs. $[M-TFA+H]^+$ 218.00. Note that 4.6 is highly unstable in its free base form due to intramolecular nucleophilic attack by the amine functionality.

The following compounds 4.7 and 4.8 have been prepared according to general procedure C.

4.7

This compound was prepared from 4.5 and 5,8,11, 14, 17,20,23,26-octaoxa-2-azanonacosanedioic acid 1-t-butyl ester that were reacted in a 1:1 molar ratio. Title compound 4.7 was obtained as a purple oil and used without further purification. The NMR spectrum indicates the presence of two carbamate rotamers. $^1$H-NMR ($CDCl_3$): δ=9.13 (2d, 2H, ArH), 7.62 and 7.59 (2t, 1H, ArH), 5.10 (br, 1H, NH), 4.13-3.51 (m, 36H, $OCH_2$, $TZCH_2CH_2$), 3.31 (q, 2H, $CH_2NH$), 3.11 and 3.02 (2s, 3H, $NCH_3$), 2.73 and 2.57 (2t, 2H, $C(O)CH_2$), 1.44 (s, 9H, $C(CH_3)_3$). ESI-MS: m/z Calc, for $C_{33}H_{56}N_8O_{11}$ 740.41; Obs. $[M-tboc+H]^+$ 641.33, $[M+H]^+$ 741.00, $[M+Na]^+$ 763.17.

4.8

This compound was prepared from 4.6 and 5,811,14,17, 20,23,26-octaoxa-2-azanonacosanedioic acid 1-t-butyl ester that were reacted in a 1:1 molar ratio. Column chromatography (flash $SiO_2$) using an elution gradient of 1% to 6% MeOH in $CHCl_3$ yielded pure 4.8 (198 mg, 0.27 mmol, 81%) as a purple oil. 1H-NMR ($CDCl_3$): δ=9.13 (d, 2H, ArH), 7.61 (t, 1H, ArH), 6.89 (br t, 1H, NH), 5.09 (br, 1H, NH), 3.76-3.43 (m, 36H, $OCH_2$, $CH_2CH_2CH_2$), 3.31 (q, 2H, $OCH_2CH_2NH$), 2.49 (t, 2H, $C(O)CH_2$), 2.26 (qn, 2H, $CH_2CH_2CH_2$), 1.44 (s, 9H, $CH_3$). ESI-MS: m/z Calc, for $C_{33}H_{56}N_8O_{11}$ 740.41; Obs. $[M-tboc+H]^+$ 641.42, $[M+Na]^+$ 763.33.

The following compounds 4.9 and 4.10 have been prepared according to general procedure B.

4.9

This compound was prepared from 4.7. Precipitation (0.5 mL $CHCl_3$→25 mL diethyl ether) followed by centrifugation, decantation and drying of the solid in vacuo yielded pure 4.9 (55 mg, 0.17 mmol, 80%) as a red oil. The NMR spectrum indicates the presence of two carbamate rotamers. $^1$H-NMR ($CDCl_3$): δ=9.14 and 9.12 (2d, 2H, ArH), 7.62 and 7.60 (2t, 1H, ArH), 4.12-3.52 (m, 36H, $OCH_2$, $TZCH_2CH_2$), 3.18 (m, 2H, $CH_2NH_2$), 3.11 and 3.01 (2s, 3H, $NCH_3$), 2.73 and 2.56 (2t, 2H, $C(O)CH_2$). ESI-MS: m/z Calc, for $C_{30}H_{49}F_3N_8O_{11}$ 754.35; Obs. $[M-TFA+H]^+$ 641.33.

4.10

This compound was prepared from 4.8. Pure 4.10 was obtained as a red oil (202 mg, 0.27 mmol, 100%). $^1$H-NMR ($CDCl_3$): δ=9.19 (d, 2H, ArH), 7.70 (t, 1H, ArH), 3.81-3.46 (m, 36H, $OCH_2$, $CH_2CH_2CH_2$), 3.15 (m, 2H, $CH_2NH_2$), 2.63 (t, 2H, $C(O)CH_2$), 2.29 (qn, 2H, $CH_2CH_2CH_2$). 19F-NMR ($CDCl_3$): δ=−76.0. ESI-MS: m/z Calc, for $C_{30}H_{49}F_3N_8O_{11}$ 754.35; Obs. $[M-TFA+H]^+$ 641.50.

The following compounds 4.11 and 4.12 have been prepared according to general procedure F.

4.11

This compound was prepared from 4.9. Purification with preparative RP-HPLC using an elution gradient of 15% to 17% MeCN in $H_2O$ (both containing 0.1% formic acid) followed by lyophilization yielded pure 4.11 (35 mg, 34 μmol, 38%) as a red solid. ESI-MS: m/z Calc, for $C_{44}H_{74}N_{12}O_{16}$ 1026.53; Obs. $[M+2H]^{2+}$ 514.42, $[M+H]^+$ 1027.42.

4.12

This compound was prepared from 4.10. Purification with preparative RP-HPLC using an elution gradient of 14% to 18% MeCN in $H_2O$ (both containing 0.1% formic acid) followed by lyophilization yielded pure 4.12 (148 mg, 0.14 mmol, 54%) as a red solid. ESI-MS: m/z Calc, for $C_{44}H_{74}N_{12}O_{16}$ 1026.53; Obs. $[M+2H]^{2+}$ 514.50, $[M+H]^+$ 1027.67.

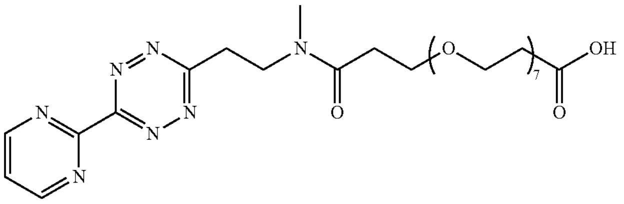

4.13

4.5

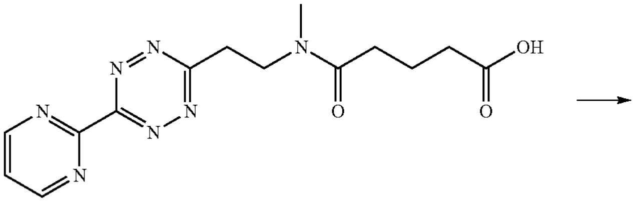

4.14

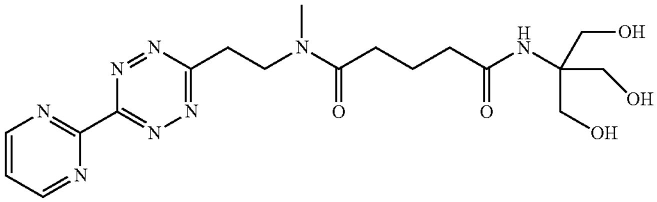

4.15

4.13

This compound has been prepared according to general procedure C from 4.5 and 4,7,10,13, 16, 19,22-heptaoxa-pentacosanedioic acid that were reacted in a 1:6 molar ratio. PyBOP was added to a mixture of TZ amine (TFA-salt), PEG-acid and N, N-diisopropylethylamine (16 eq) in $CH_2Cl_2$. During work-up, the sat. $NaHCO_3$wash was omitted. Precipitation (0.5 mL $CHCl_3$→20 mL diethyl ether) was promoted at −20° C. for 40 h followed by centrifugation, decantation and drying of the solid in vacuo. Purification with preparative RP-HPLC using an elution gradient of 20% to 25% MeCN in $H_2O$ (both containing 0.1% formic acid) followed by lyophilization yielded pure 4.13 (10.4 mg, 17 μmol, 30%) as a red oil. The NMR spectrum indicates the presence of two carbamate rotamers. $^1$H-NMR ($CDCl_3$): δ=9.14 (2d, 2H, ArH), 7.62 and 7.59 (2t, 1H, ArH), 4.13-3.55 (m, 32H, $OCH_2$, $TZCH_2CH_2$), 3.12 and 3.03 (2s, 3H, $NCH_3$), 2.74 and 2.59 and 2.57 (3t, 4H, $C(O)CH_2$). ESI-MS: m/z Calc, for $C_{27}H_{43}N_7O_{10}$ 625.31; Obs. $[M+H]^+$ 626.33, $[M+Na]^+$ 648.17.

4.14

To a 5 mL test tube containing glutaric anhydride (6.1 mg, 54 μmol, 1 eq), a solution of 4.5 (17.7 mg, 53 μmol) and N,N-diisopropylethylamine (37 μL, 0.21 mmol, 4 eq) in $CH_2Cl_2$ (1 mL) was added. The solution was stirred at room temperature for 30 min and the solvent was removed in vacuo. Column chromatography (flash $SiO_2$) using an elution gradient of 4% to 16% MeOH in $CHCl_3$ yielded the N,N-diisopropylethylamine salt of 4.14 (24 mg, 52 μmol, 97%) as a pink oil. The NMR spectrum indicates the presence of two carbamate rotamers. $^1$H-NMR ($CD_3OD$): δ=9.12 (2d, 2H, ArH), 7.78 and 7.77 (2t, 1H, ArH), 4.13 and 3.95 (2t, 2H, $CH_2$), 3.80-3.64 (m, 4H, $CH_2$, dipea-CH), 3.23 (q, 2H, dipea-$CH_2$), 3.19 and 3.02 (2s, 3H, $NCH_3$), 2.48 and 2.34 (2t, 2H, $C(O)CH_2$), 2.31 and 2.23 (2t, 2H, $C(O)CH_2$), 1.86 and 1.69 (2qn, 2H, $CH_2CH_2CH_2$), 1.37 (m, 15H, dipea-$CH_3$). ESI-MS: m/z Calc, for $C_{14}H_{17}N_7O_3$ 331.14; Obs. $[M+H]^+$ 332.08, $[2M+Na]^+$ 684.92.

4.15

The N,N-diisopropylethylamine salt of 4.14 (24 mg, 52 μmol), 2-amino-2-(hydroxymethyl) propane-1,3-diol (6.9 mg, 57 μmol, 1.1 eq) and N,N-diisopropylethylamine (29 μL, 0.16 mmol, 3 eq) were combined in DMF (800 μL). PyBOP (29 mg, 56 μmol, 1.1 eq) was added and the mixture was stirred at room temperature for 30 min. After removal of the solvent in vacuo, precipitation (1 mL DMF→25 mL diethyl ether) was followed by centrifugation and decantation. Purification with preparative RP-HPLC using an elution gradient of 12% to 14% MeCN in $H_2O$ (both containing 0.1% formic acid) followed by lyophilization yielded pure 4.15 (7.8 mg, 18 μmol, 34%) as a pink fluffy solid. The NMR spectrum indicates the presence of two carbamate rotamers. $^1$H-NMR ($CD_3CN$+2 drops $D_2O$): δ=9.08 (d, 2H, ArH), 7.70 (t, 1H, ArH), 6.91 and 6.77 (2br, 1H, NH), 4.00 and 3.85 (2t, 2H, $CH_2$), 3.72-3.55 (m, 8H, $CH_2$, $CH_2OH$), 3.07 and 2.93 (2s, 3H, $NCH_3$), 2.38 and 2.23 (2t, 2H, $C(O)CH_2$), 2.21 and 2.07 (2t, 2H, $C(O)CH_2$), 1.79 and 1.61 (2qn, 2H, $CH_2CH_2CH_2$). ESI-MS: m/z Calc, for $C_{18}H_{26}N_8O_5$ 434.20; Obs. $[M+H]^+$ 435.17, $[M+Na]^+$ 457.17.

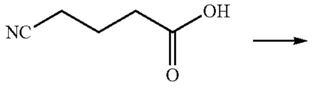

-continued

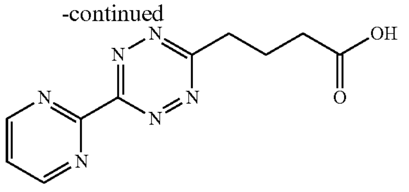

4.16

The following compound 4.16 has been prepared according to general procedure A.

4.16

This compound was prepared from 2-pyrimidinecarbonitrile and 4-cyanobutanoic acid that were reacted in a 1:1 molar ratio. Oxidation was performed according to general procedure A2. Column chromatography (flash $SiO_2$) using an elution gradient of 1% to 3% MeOH in $CHCl_3$ and, in a second chromatography step (normal $SiO_2$), elution with 50% acetone in heptane yielded pure 4.16 (38 mg, 0.15 mmol, 7%) as a red solid. $^1$H-NMR ($CDCl_3$): δ=9.13 (d, 2H, ArH), 7.62 (t, 1H, ArH), 3.57 (t, 2H, $TZCH_2$), 2.55 (t, 2H, $CH_2C(O)$), 2.37 (qn, 2H, $CH_2CH_2CH_2$).

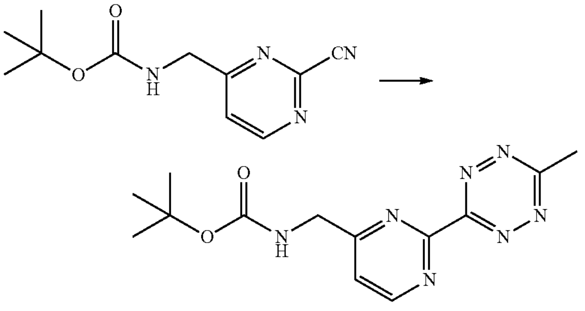

4.17

The following compound 4.17 has been prepared according to general procedure A.

4.17

This compound was prepared from t-butyl N-((2-cyano-4-pyrimidinyl)methyl) carbamate (Sweeney et al., *ACS Med. Chem. Lett.* 2014, 5, 937-941) and acetonitrile that were reacted in a 1:6 molar ratio. Oxidation was performed according to general procedure A1. Column chromatography (flash $SiO_2$) using an elution gradient of 0% to 70% EtOAc in $CHCl_3$ and, in a second chromatography step (normal $SiO_2$), elution with 40% acetone in heptane yielded pure 4.17 (33 mg, 0.11 mmol, 19%) as a purple solid. $^1$H-NMR ($CDCl_3$): δ=9.04 (d, 1H, ArH), 7.59 (d, 1H, ArH), 5.54 (br, 1H, NH), 4.64 (d, 2H, $CH_2NH$), 3.21 (s, 3H, $TZCH_3$), 1.48 (s, 9H, C $(CH_3)_3$). ESI-MS: m/z Calc, for $C_{13}H_{17}N_7O_2$ 303.14; Obs. $[M-tboc+H]^+$ 204.17, $[M-tbutyl+2H]^+$ 248.08, $[M+Na]^+$ 326.17.

The following compounds 4.18, 4.19 and 4.20 have been prepared according to general procedure A.

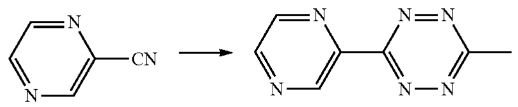

4.18

Compound 4.18 was prepared from pyrazine-2-carbonitrile and acetonitrile that were reacted in a 2:3 molar ratio. Oxidation was performed according to general procedure A3. Column chromatography (flash $SiO_2$) using an elution gradient of 10% to 40% EtOAc in $CHCl_3$ and, in a second chromatography step (normal $SiO_2$), elution with 40% acetone in heptane yielded pure 4.18 (70 mg, 0.40 mmol, 12%) as a pink solid. $^1$H-NMR ($CDCl_3$): δ=9.85 (d, 1H, ArH), 8.91 (m, 1H, ArH), 8.87 (d, 1H, ArH), 3.21 (s, 3H, $CH_3$). $^{13}$C-NMR ($CDCl_3$): δ=168.6, 162.8, 147.3, 146.0, 145.1, 145.0, 21.5. ESI-MS: m/z Calc, for $C_7H_6N_6$ 174.07; Obs. $[M+H]^+$ 175.08.

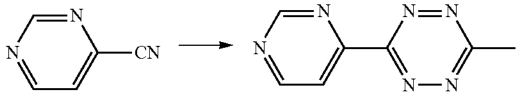

4.19

Compound 4.19 was prepared from pyrimidine-4-carbonitrile and acetonitrile that were reacted in a 2:3 molar ratio. Oxidation was performed according to general procedure A2. Column chromatography (flash $SiO_2$) using an elution gradient of 10% to 40% EtOAc in $CHCl_3$ and, in a second chromatography step (normal $SiO_2$), elution with 40% acetone in heptane yielded pure 4.19 (28 mg, 0.16 mmol, 6%) as a pink solid. $^1$H-NMR ($CDCl_3$): δ=9.58 (d, 1H, ArH), 9.11 (d, 1H, ArH), 8.59 (dd, 1H, ArH), 3.22 (s, 3H, $CH_3$). $^{13}$C-NMR ($CDCl_3$): δ=169.2, 162.9, 159.9, 159.2, 157.4, 119.8, 21.6. ESI-MS: m/z Calc, for $C_7H_6N_6$ 174.07; Obs. $[M+H]^+$ 175.08.

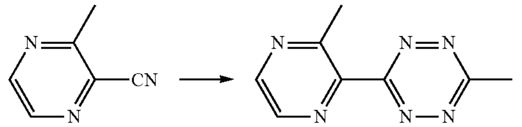

4.20

Compound 4.20 was prepared from 3-methylpyrazine-2-carbonitrile and acetonitrile that were reacted in a 2:3 molar ratio. Oxidation was performed according to general procedure A2. Column chromatography (flash $SiO_2$) using an elution gradient of 10% to 20% EtOAc in $CHCl_3$ and, in a second chromatography step (normal $SiO_2$), elution with 38% acetone in heptane yielded pure 4.20 (33 mg, 0.18 mmol, 9%) as a pink oil. $^1$H-NMR ($CDCl_3$): δ=8.72 (2d, 2H, ArH), 3.20 (s, 3H, $CH_3$), 2.88 (s, 3H, $CH_3$). $^{13}$C-NMR ($CDCl_3$): δ=167.7, 165.3, 154.7, 145.7, 145.5, 142.4, 23.2, 21.5. ESI-MS: m/z Calc, for $C_8H_8N_6$ 188.08; Obs. $[M+H]^+$ 189.08.

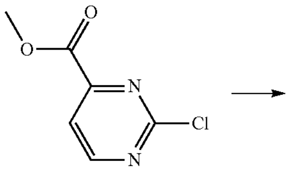

-continued

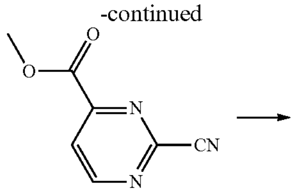

4.21

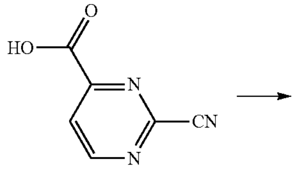

4.22

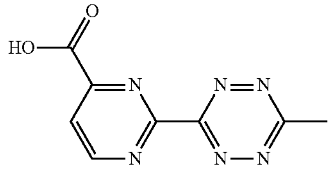

4.23

4.21:

Methyl 2-chloropyrimidine-4-carboxylate (0.80 g, 4.5 mmol), $Zn(CN)_2$ (0.56 g, 4.7 mmol, 1.04 eq) and Pd $(PPh_3)_4$ (0.52 g, 0.44 mmol, 0.1 eq) were combined in DMF (4 mL) and the mixture was stirred at 100° C. for 2 h. After cooling to room temperature, the solvent was removed in vacuo (oil pump, 44° C.) and the resulting purple paste was triturated with $CHCl_3$ (18 mL). The suspension was filtrated, the solid was washed with $CHCl_3$ (2×4 mL) and the filtrate was evaporated to dryness yielding a purple oil. The oil was purified with column chromatography (flash $SiO_2$) using an elution gradient of pentane/$CHCl_3$ 1:2 to $CHCl_3$ to 15% EtOAc in $CHCl_3$. Finally, precipitation (2 mL $CHCl_3$→60 mL pentane), filtration and drying the solid in vacuo yielded pure 4.21 (0.64 g, 3.9 mmol, 87%) as a white solid. $^1$H-NMR ($CDCl_3$): δ=9.11 (d, 1H, ArH), 8.20 (d, 1H, ArH), 4.08 (s, 3H, $CH_3$).

4.22:

4.21 (0.40 g, 2.5 mmol) was dissolved in 1,2-dichloroethane (14 mL). $Me_3SnOH$ (1.36 g, 7.4 mmol, 3 eq) was added as a solid and the mixture was stirred at 70° C. for 1½ h. The volatiles were removed in vacuo and the mixture was redissolved in EtOAc (100 mL). The organic layer was washed with 1 M HCl (30 mL), dried using $Na_2SO_4$ and the solvent was removed in vacuo. Trituration in hot $CHCl_3$ (10 mL), filtration and drying the solid in vacuo yielded pure 4.22 (0.27 g, 1.8 mmol, 73%) as a white solid. $^1$H-NMR (MeOD): δ=9.16 (d, 1H, ArH), 8.26 (d, 1H, ArH). ESI-MS: m/z Calc, for $C_6H_3N_3O_2$ 149.02; Obs. $[M-H]^-$ 148.08.

Compound 4.23 was prepared according to general procedure A from 4.22 and acetonitrile that were reacted in a 1:3 molar ratio. Water was added as a co-solvent during the [2H]-TZ synthesis. Oxidation was performed according to general procedure A3 except that 1 M HCl was added up to pH=1. Column chromatography (flash $SiO_2$) using an elution gradient of 20% to 80% EtOAc in $CHCl_3$ followed by 4% to 8% MeOH in $CHCl_3$ yielded 4.23 as a red solid. 1H-NMR (MeOD): δ=9.33 (d, 1H, ArH), 8.31 (d, 1H, ArH), 3.16 (s, 3H, $CH_3$). ESI-MS: m/z Calc, for $C_8H_6N_6O_2$ 218.06; Obs. $[M+H]^+$ 219.17.

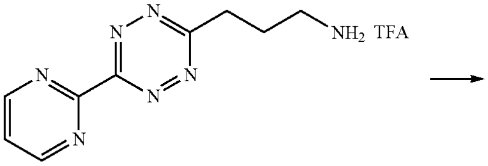

4.6

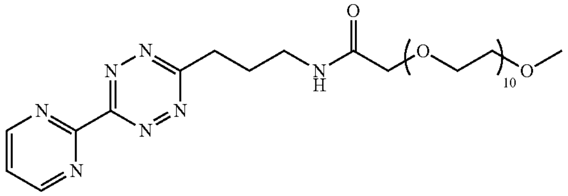

4.24

Compound 4.22 was prepared according to general procedure C from 4.6 and 3,6, 9,12,15, 18,21,24,27,30,33-undecaoxatetratriacontanoic acid that were reacted in a 1:1 molar ratio. Column chromatography (flash $SiO_2$) using an elution gradient of 3% to 5% MeOH in $CHCl_3$ yielded pure 4.24 (32 mg, 44 μmol, 58%) as a pink oil. $^1$H-NMR ($CDCl_3$): δ=9.13 (d, 2H, ArH), 7.60 (t, 1H, ArH), 7.26 (br t, 1H, NH), 4.00 (s, 2H, $C(O)CH_2$), 3.71-3.49 (m, 44H, $OCH_2$, $CH_2CH_2CH_2$), 3.38 (s, 3H, $OCH_3$), 2.29 (qn, 2H, $CH_2CH_2CH_2$). ESI-MS: m/z Calc, for $C_{32}H_{55}N_7O_{12}$ 729.39; Obs. $[M+H]^+$ 730.50, $[M+Na]^+$ 752.42.

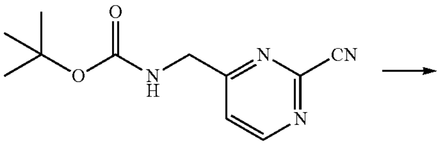

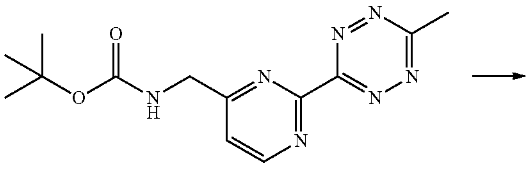

4.17

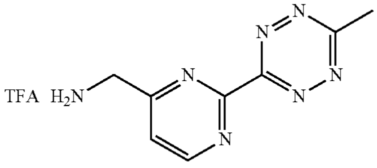

4.25

Compound 4.25 was prepared according to general procedure B from 4.17. Pure 4.25 was obtained as a pink oil (35 mg, 0.11 mmol, 100%). $^1$H-NMR ($CD_3OD$): δ=9.13 (d, 1H, ArH), 7.81 (d, 1H, ArH), 4.54 (s, 2H, $CH_2$), 3.18 (s, 3H, $CH_3$). $^{13}$C-NMR ($CD_3OD$): δ=170.6, 164.7, 163.7, 161.4 (q), 160.11, 160.08, 122.4, 117.3 (q), 43.5, 21.5. $^{19}$F-NMR ($CD_3OD$): δ=−77.4. ESI-MS: m/z Calc, for $C_{10}H_{10}F_3N_7O_2$ 317.08; Obs. $[M-TFA+H]^+$ 204.17.

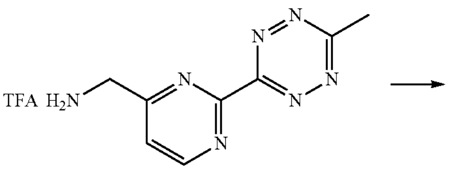

4.25

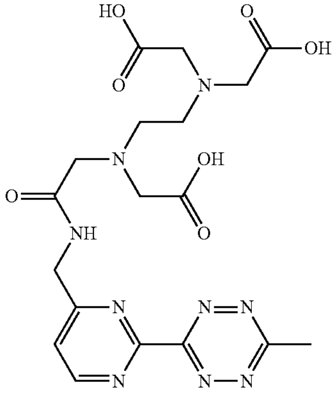

4.26

4.26

A solution of 4.25 (35 mg, 0.11 mmol) in dry DMSO (2 mL) was added to a solution of ethylenediaminetetraacetic dianhydride (341 mg, 1.30 mmol, 12 eq) in dry DMSO (3 mL) under Ar. N,N-diisopropylethylamine (230 μL, 1.30 mmol, 12 eq) was added dropwise over 5 min and the resulting mixture was stirred at room temperature for 1 h. Precipitation was induced by the addition of $CHCl_3$ (5 mL) and diisopropylether (ca. 30 mL) yielding a red solid that was filtrated, washed with diisopropylether and dried in vacuo. Purification was achieved with repeated RP-MPLC using an elution gradient of 2% to 12% MeCN in $H_2O$ (both containing 0.1 v/v % formic acid). Lyophilization yielded pure 4.26 as a pink, fluffy solid (14.5 mg, 30 μmol, 28%). $^1$H-NMR ($D_2O$): δ=9.04 (d, 1H, ArH), 7.79 (d, 1H, ArH), 3.93 (s, 4H, $CH_2COOH$), 3.83 (s, 2H, $NCH_2$), 3.76 (s, 2H, $NCH_2$), 3.51 (t, 2H, $CH_2CH_2$), 3.32 (t, 2H, $CH_2CH_2$), 3.19 (s, 3H, $CH_3$). The $TZCH_2$ signal is not observed since it overlaps with the residual $H_2O$ peak at δ=4.79. $^{18}$C-NMR ($D_2O$): δ=173.2, 171.7, 170.5, 169.1, 168.4, 162.1, 158.6, 157.8, 120.7, 57.0, 56.0, 55.5, 52.3, 50.2, 43.9, 20.5. ESI-MS: m/z Calc, for $C_{18}H_{23}N_9O_7$ 477.17; Obs. $[M+H]^+$ 478.25.

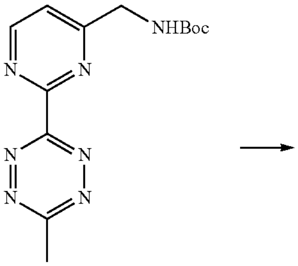

4.17

-continued

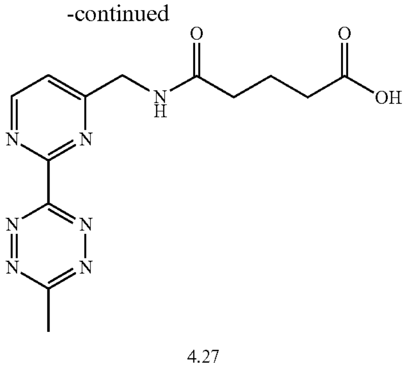

4.27

-continued

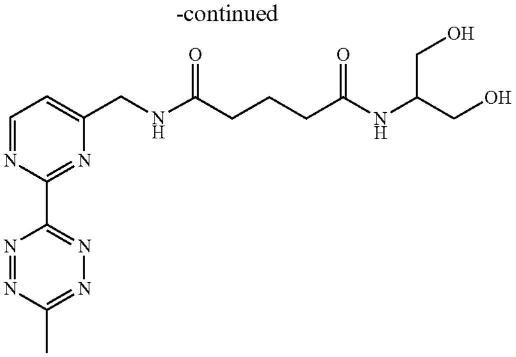

4.28

Compound 4.27 was prepared from 4.17 according to general procedure B followed by general procedure D. Preparative RP-HPLC purification using an elution gradient of 5% to 40% MeCN in $H_2O$ (both containing 0.1% TFA) followed by lyophilization yielded pure 4.27 (60 mg, 189 μmol, 26%) as a pink fluffy solid. $^1H$ NMR (400 MHz, CD OD): 8 9.04 (d, 1H, ArH), 7.70 (d, 1H, ArH) 4.68 (d, 2H, CH 2NH), 3.17 (s, 3H, $TZCH_3$), 2.44 (t, 2H, $CH_2C(O)OH$), 2.38 (t, 2H, $NHC(O)CH_2$), 1.97 (qn, 2H,$CH_2CH_2CH_2$) ppm. ESI-MS: m/z Calc, for $C_{13}H_{15}N_7O_3$ 317.12; Obs. $[M-H]^-$ 316.08, $[2M-H]^-$ 632.72, $[M+H]^+$ 317.84, $[2M+H]^+$ 634.36.

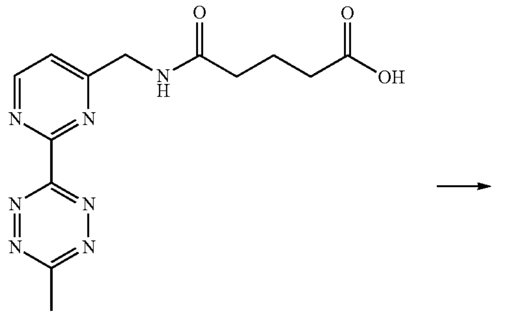

4.27

4.28:

4.27 (10 mg, 31.5 μmol), serinol (4.3 mg, 47.3 μmol), PyBOP (24.6 mg, 47.3 mmol) and DiPEA (22 μL, 126.1 μmol) were stirred in DMF (0.5 mL) for 45 minutes at room temperature. The reaction mixture was diluted with $H_2O$/formic acid (99:1) followed by preparative RP-HPLC purification using an elution gradient of 5% to 40% MeCN in $H_2O$ (both containing 0.1% TFA). Lyophilization yielded pure 4.28 (6.0 mg, 15.4 μmol, 49%) as a pink solid. $^1H$ NMR (400 MHz, $CD_3OD$): δ 9.04 (d, 1H, ArH), 7.72 (d, 1H, ArH) 4.69 (d, 2H, $CH_2NH$), 3.55-3.64 (m, 4H, CH $(CH_2OH)$ 2), 3.25 (qn, 1H, $NHCH(CH_2OH)_2$), 3.17 (s, 3H, $TZCH_3$), 2.41 (t, 2H, $CH_2C(O)$ NH), 2.38 (t, 2H, $NHC(O)CH_2$), 2.00 (qn, 2H, $CH_2CH_2CH_2$) ppm. ESI-MS: m/z Calc, for $C_{16}H_{22}N_8O_4$ 390.18; Obs. $[M+H]^+$ 390.76, $[2M+H]^+$ 780.16.

Example 5: Synthesis of TCOs and TCO-Drug Constructs

Maleimide-TCO($PEG_{24}$)-MMAE (5.5)

The synthesis of rel-(1R,4E,6R,pS)-2,5-dioxopyrrolidin-1-yl-6-((((2,5-dioxopyrrolidin-1-yl)oxy) carbonyl)oxy)-1-methylcyclooct-4-ene-1-carboxylate (axial isomer) (5.1) was reported in Rossin et al. *Bioconjug. Chem.* 2016, 27, 1697-1706.

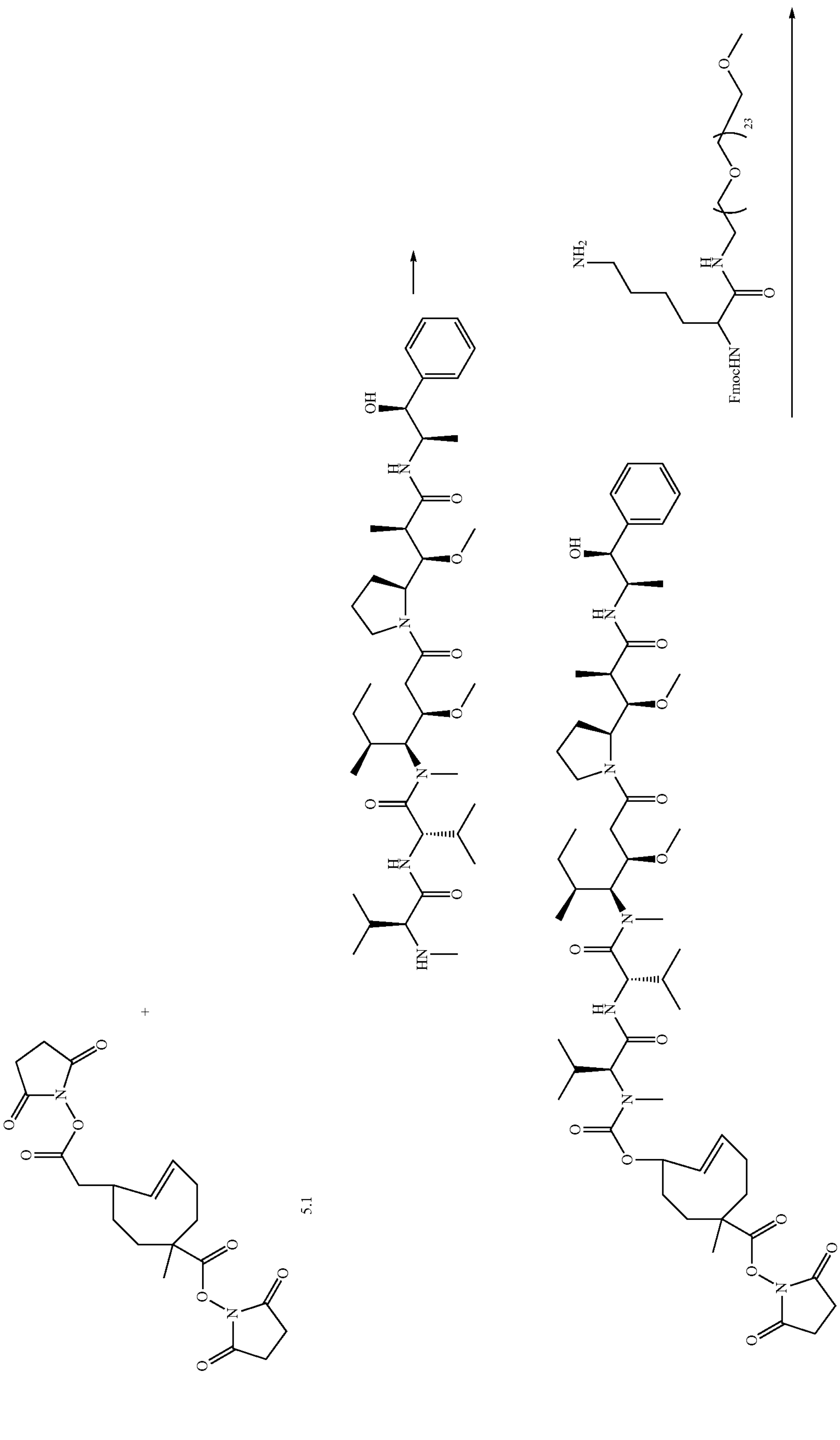
5.1
5.2

-continued
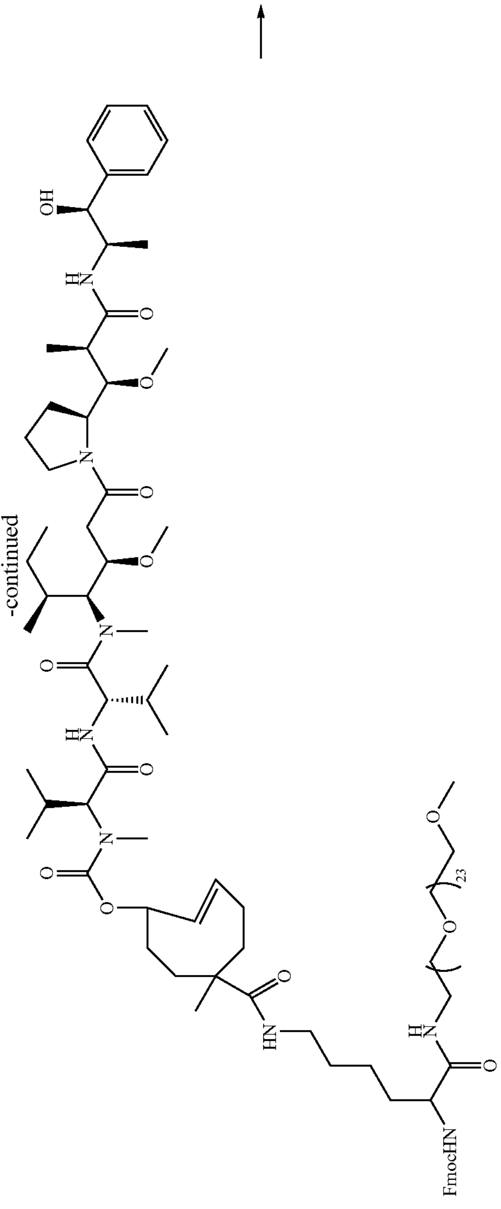
5.3
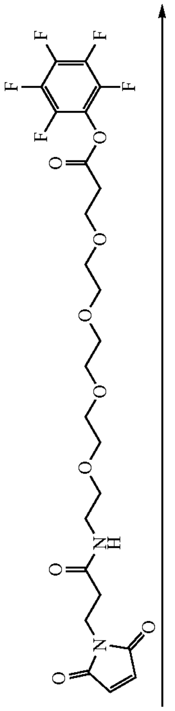
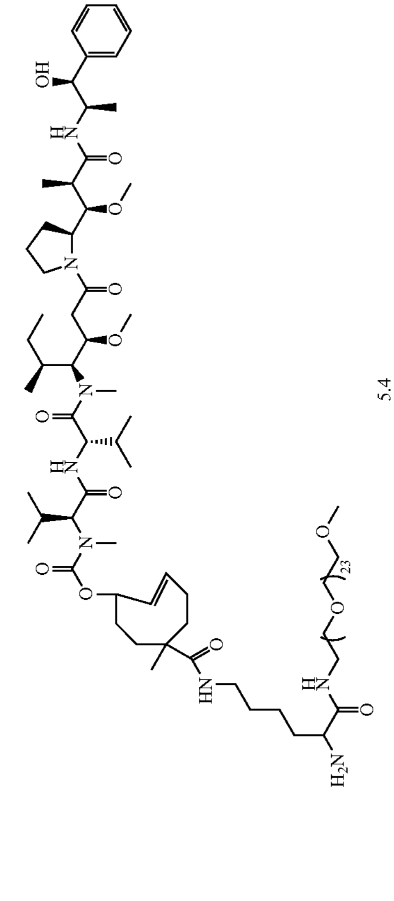
5.4

-continued
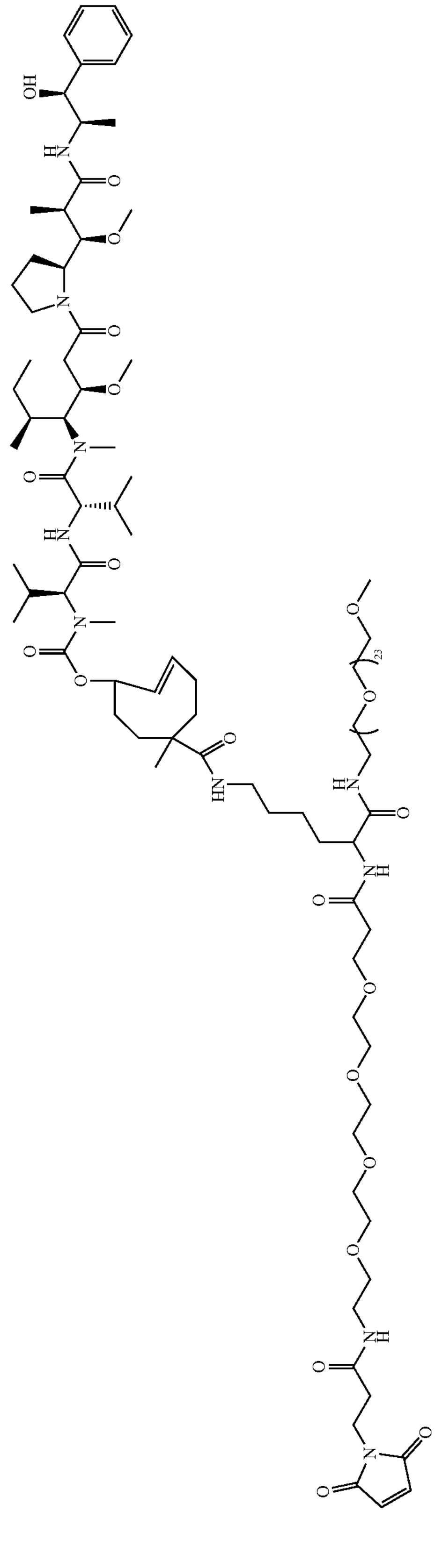
5.5

To a solution MMAE (112 mg as mono TFA salt, 135 μmol, Levena Biopharma) in 2 mL of anhydrous DMF was added 5.1 (57 mg, 135 μmol) and DIEA (70 μL, 405 μmol). The mixture was stirred at RT in the dark for 3 days, at which point LC-MS analysis indicated >94% conversion to intermediate 5.2. Fmoc-Lys-$PEG_{24}$ (as mono TFA salt, 251 mg, 162 μmol, Levena Biopharma) and DIEA (28 μL, 161 μmol) were then added and the reaction mixture was stirred at RT in the dark for 3 days, at which point LC-MS analysis showed complete formation of intermediate 5.3. Piperidine (150 μL, 1.52 mmol) was added to the mixture and the stirring was continued for 20 min, at which point LC-MS analysis indicated complete formation of compound 5.4. The product was purified by preparative HPLC (20 min run, 10 to 70% acetonitrile at 50 mL/min). The collected fractions were analyzed by HPLC/LC-MS. The pure fractions were lyophilized in the dark to give 5.4 as acetate salt as a viscous colorless gum (275 mg, 93%). $^1$H NMR ($CDCl_3$): δ=7.97 (br s, 1H), 7.36 (m, 2H), 7.31 (m, 2H), 7.24 (m, 1H), 6.53-6.59 (br m, 1H), 5.77-5.91 (br m, 1H), 5.57-5.62 (br m, 1H), 4.66-4.72 (br m, 1H), 4.25 (br m, 1H), 4.13 (br m, 1H), 3.9-4.1 (br m, 10H), 3.85 (m, 1H), 3.77 (m, 1H), 3.63 (br s, 92H), 3.48-3.54 (m, 7H), 3.38-3.41 (m, 6H), 3.36 (s, 3H), 3.29-3.32 (m, 3H), 3.15-3.22 (m, 2H), 2.97-3.03 (m, 2H), 2.94 (m, 2H), 2.89 (m, 1H), 2.43 (m, 1H), 2.35 (m, 1H), 2.17-2.30 (br m, 3H), 1.95-2.10 (m, 8H), 1.73-1.87 (br m, 6H), 1.55-1.67 (br m, 2H), 1.45-1.53 (m, 2H), 1.30-1.41 (br m, 3H), 1.23 (d, J=6.5 Hz, 3H), 1.11 (s, 3H), 0.95-1.05 (m, 7H), 0.78-0.94 (m, 15H) ppm. $^{13}$C NMR ($CDCl_3$): δ=180.62, 174.82, 173.73, 170.79, 170.17, 161.81, 161.54, 156.62, 141.44, 131.77, 131.41, 128.45, 128.22, 127.43, 126.54, 82.20, 78.75, 75.97, 73.33, 72.11, 71.21, 70.69, 70.59 (br), 70.45, 70.31, 70.04, 65.20, 64.99, 61.11, 60.28, 59.18, 58.51, 58.16, 54.75, 54.22, 51.74, 51.36, 48.00, 46.86, 45.77, 45.17, 44.88, 44.61, 44.44, 39.32, 39.24, 37.92, 36.12, 33.71, 33.64, 31.89, 31.63, 31.52, 31.35, 31.20, 29.73, 29.23, 26.29, 25.93, 25.17, 25.09, 23.58, 22.87, 21.61, 19.56, 19.48, 18.77, 18.16, 17.98, 16.17, 14.58, 14.16, 11.10 ppm. HPLC-MS/PDA: m/z 1064.4 Da [M+2H]2+; calcd 1063.68 for $C_{105}H_{194}N_8O_{35}$.

To a solution of 5.4 (275 mg, 126 μmol) in 3 mL of anhydrous DMF was added Mal-NH-$PEG_4$-$CH_2CH_2COOPFP$ (75 mg, 129 μmol, Levena Biopharma) and DIEA (44 μL, 253 μmol). The mixture was stirred at RT for 10 min in the dark, at which point LC-MS analysis indicated complete conversion to compound 5.5. The reaction was purified by preparative HPLC (20 min run, from 10 to 80% acetonitrile at 50 mL/min). The collected fractions were analyzed by HPLC/LC-MS and the pure fractions were lyophilized in a dark to give 5.5 as viscous gum (181 mg, 57%). $^1$H NMR ($CDCl_3$): δ=7.36 (m, 2H), 7.31 (m, 2H), 7.23 (m, 1H), 6.85-7.16 (br m, 2H), 6.67-6.73 (br m, 2H), 6.45-6.65 (br m, 1H), 5.55-5.90 (m, 3H), 4.55-5.25 (m, 4H), 4.35 (m, 1H), 4.23 (m, 1H), 4.00-4.18 (br m, 3H), 3.81 (m, 3H), 3.67-3.77 (br m, 3H), 3.55-3.67 (br m, 104H), 3.45-3.55 (m, 8H), 3.34-3.43 (m, 11H), 3.28-3.31 (m, 3H), 3.07-3.20 (br m, 3H), 2.85-3.05 (m, 5H), 2.58 (br m, 1H), 2.49 (m, 5H), 2.42 (m, 1H), 2.35 (m, 1H), 2.23 (m, 4H), 1.90-2.10 (br m, 6H), 1.82 (m, 6H), 1.59 (m, 2H), 1.47 (m, 2H), 1.31 (m, 2H), 1.22 (d, J=7.0 Hz, 3H), 1.09 (m, 3H), 0.93-1.04 (m, 7H), 0.78-0.93 (m, 15H) ppm. $^{13}$C NMR ($CDCl_3$): δ=180.51, 174.70, 173.84, 171.96, 171,67, 170.71, 170.09, 156.56, 141.50, 134.41, 131.43, 128.20, 127.40, 126.50, 82.19, 75.98, 73.26, 72.13, 70.75 (br.), 70.62, 70.53, 70.49, 70.43, 70.32, 69.96, 69.83, 67.49, 65.50, 65.03, 61.05, 60.25, 59.18, 58.14, 54.11, 53.12, 51.77, 47.94, 45.86, 45.07, 44.42, 39.47, 39.43, 37.95, 37.09, 36.13, 34.68, 34.56, 33.66, 32.00, 31.54, 31.29, 31.17, 29.71, 29.25, 26.27, 25.93, 25.16, 25.10, 22.97, 19.86, 19.55, 18.75, 18.19, 16.17, 14.53, 14.08, 11.11 ppm. HPLC-MS/PDA: m/z 1263.0 Da $[M+2H]^{2+}$; calcd 1262.77 for $C_{129}H_{220}N_{10}O_{43}$.

Dox-TCO-PEG4-Mal (5.8)

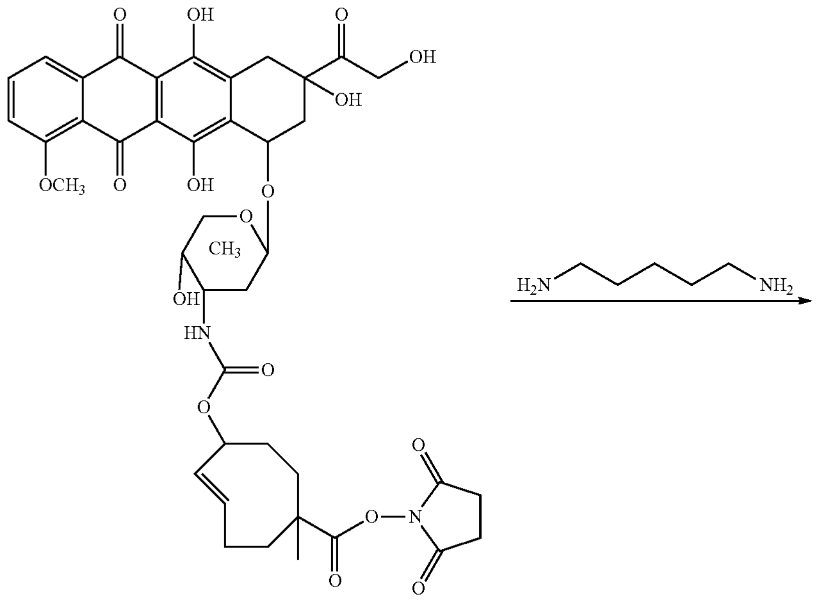

5.6

-continued

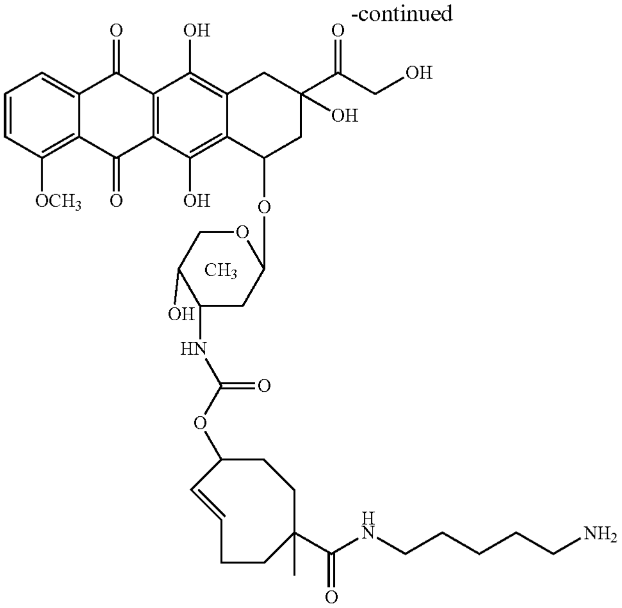

5.7

5.7 +

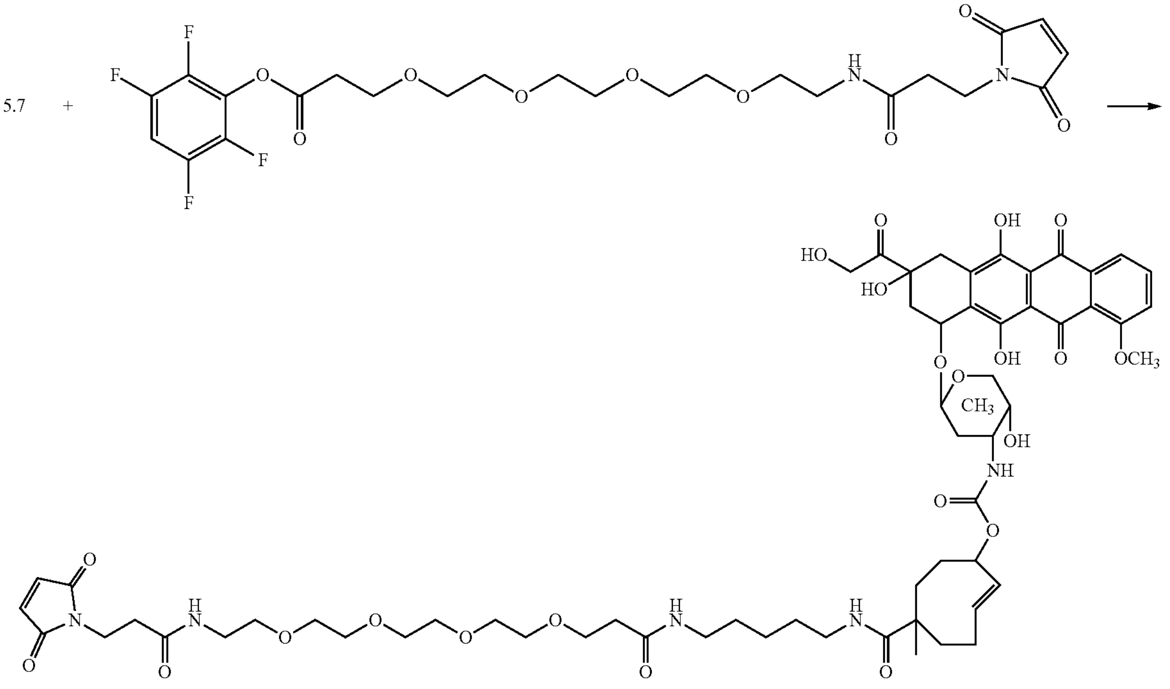

5.8

The synthesis of Dox-TCO-NHS 5.6 was reported in Rossin et al. *Bioconjug. Chem.* 2016, 27, 1697-1706. Dox-TCO-NHS 2.7 (66.8 mg; $7.85*10^{-5}$ mol) was dissolved in DMF (8 mL), and subsequently DIPEA (20 mg; $1.57*10^{-4}$ mol) and 1,5-diaminopentane (40 mg; $3.93*10^{-4}$ mol) were added. The mixture was stirred at 20° C. After 15 min, subsequently acetonitrile (15 mL), formic acid (0.15 mL), and water (50 mL) were added, and the clear, orange solution was filtered and purified by preparative RP-HPLC (25 v % acetonitrile in water, containing 0.1 v % formic acid). The product 5.7 was isolated by lyophilization to yield 33 mg of an orange powder (50%). $^{1}H$ NMR (10 v % MeOD in $CDCl_3$): δ=δ 8.46 (br.s, 1H), 8.00 (s, 1H), 7.76 (s, 1H), 7.37 (d, J=8.3 Hz, 1H), 6.49 (br.s, 1H), 5.80 (m, 1H), 5.46 (m, 2H), 5.26 (s, 1H), 5.05 (s, 1H), 4.72 (s, 2H), 4.10 (s, 1H), 4.04 (s, 3H), 3.81 (m, 1H), 3.60 (s, 1H), 3.35 (s, 2H), 3.3-2.7 (m+$H_2O$), 2.32 (d, J=14.5 Hz, 1H), 2.17 (m, 3H), 2.01 (m, 2H), 1.85 (m, 3H), 1.71 (m, 3H), 1.60 (m, 2H), 1.46 (m, 3H), 1.26 (m, 6H), 1.02 (m, 3H) ppm. LC-MS: m/z=+838.33 $[M+Na]^+$, −836.50 $[M-H]^-$ (calcd 837.37 for $C_{43}H_{55}N_3O_{14}$).

Dox-TCO-$C_5$-amine 5.7 (10.1 mg; $1.21*10^{-5}$ mol) was dissolved in DMF (1.5 mL), and DIPEA (3.6 mg; $2.8*10^{-5}$ mol) was added. Maleimide-dPEG4-TFP ester (7.5 mg; $1.33*10^{-5}$ mol) was added to the mixture, that was stirred at 20° C. for 1 h. Subsequently, formic acid (10 μL) and water (4.5 mL) were added, and the clear, orange solution was filtered and purified by preparative RP-HPLC (30 v % acetonitrile in water, containing 0.1 v % formic acid). The product 5.8 was isolated by lyophilization to yield 6.0 mg of an orange powder (40%). $^{1}$H-NMR ($CDCl_3$): δ=13.98 (s, 1H), 13.26 (s, 1H), 8.04 (d, J=8.0 Hz, 1H), 7.78 (t, J=8.1 Hz, 1H), 7.39 (d, J=8.5 Hz, 1H), 6.70 (d, 2H), 6.66 (m, 1H), 5.82 (m, 1H), 5.71 (m, 1H), 5.52 (m, 3H), 5.31 (s, 1H), 5.13 (m, 1H), 4.76 (s, 2H), 4.60 (s, 1H), 4.12 (m, 1H), 4.08 (s, 3H), 3.84 (t, J=7.2 Hz, 2H), 3.8-3.5 (m, 14H), 3.42 (q, J=5.3 Hz, 2H), 3.35-3.11 (m, 5H), 3.03 (m, 2H), 2.54 (t, J=7.3, 2H), 2.48 (t, J=5.7, 2H), 2.41-2.04 (m, 5H), 1.77 (m, J=40.5, 27.0 Hz, 8H), 1.64-1.41 (m, 7H), 1.41-1.13 (m, 12H), 1.07 (m, 5H), 0.83 (d, J=2.3 Hz, 7H) ppm. LC-MS: m/z=+1235.92 $[M+H]^+$, −1234.83 $[M-H]^-$ (calcd 1235.54 for $C_{61}H_{81}N_5O_{22}$).

Dox-TCO-PEG24-Mal (5.9)

5.7 +

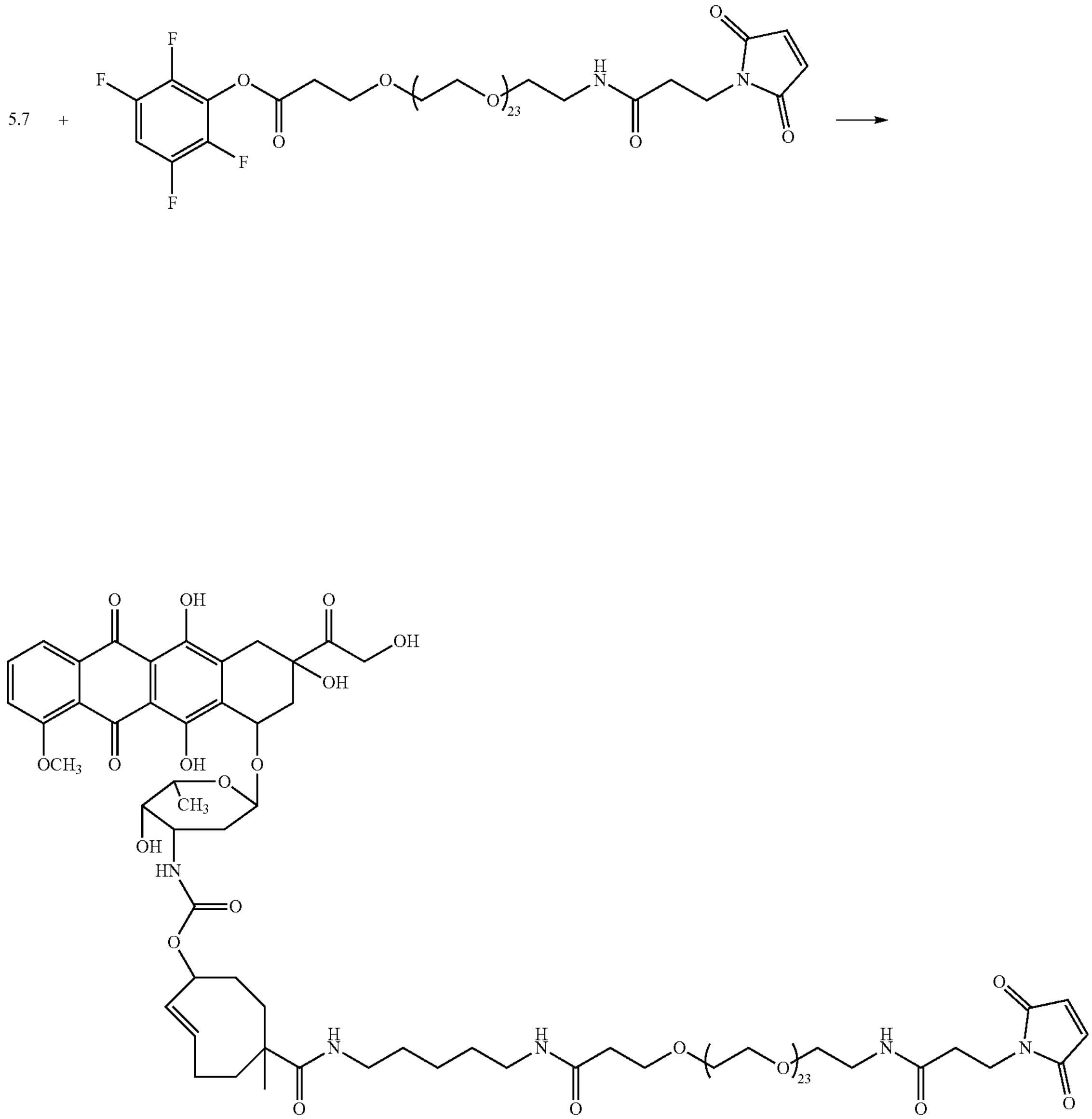

5.9

Dox-TCO-$C_5$-amine 5.7 (10.1 mg; $1.21*10^{-5}$ mol) was dissolved in DMF (1.5 mL), and DIPEA (3.6 mg; $2.8*10^{-5}$ mol) was added. Maleimide-dPEG24-TFP ester (19.2 mg; $1.33*10^{-5}$ mol) was added to the mixture, that was stirred at 20° C. for 1 h. Subsequently, formic acid (80 μL) and water (6 mL) were added, and the clear, orange solution was filtered and purified by preparative RP-HPLC (40 v % acetonitrile in water, containing 0.1 v % formic acid). The product 5.9 was isolated by lyophilization to yield 5.0 mg of an orange powder (20%).

$^1$H-NMR ($CDCl_3$): δ=13.99 (s, 1H), 13.28 (s, 1H), 8.05 (d, J=7.9 Hz, 1H), 7.79 (t, J=8.1 Hz, 1H), 7.40 (d, J=8.8 Hz, 1H), 6.70 (s, 2H), 6.66 (m, 1H), 6.31 (s, 1H), 5.84 (m, 1H), 5.54 (m, 3H), 5.31 (s, 2H), 5.13 (m, 1H), 4.75 (m, 2H), 4.59 (s, 1H), 4.12 (m, 1H), 4.08 (s, 3H), 3.84 (p, J=8.1 Hz, 2H), 3.64 (m, 68H), 3.50-3.35 (m, 2H), 3.25 (m, 5H), 3.11-2.88 (m, 2H), 2.50 (m, 3H), 2.41-1.73 (m, 11H), 1.67 (m, 5H), 1.51 (m, 5H), 1.29 (m, 6H), 1.01 (m, 3H) ppm. LC-MS: m/z=+1059.08 $[M+2H]^{2+}$ (calcd 2116.06 for $C_{101}H_{161}N_5O_{42}$).

Dox-TCO-Mal-PEG24 (5.10)

5.6 +

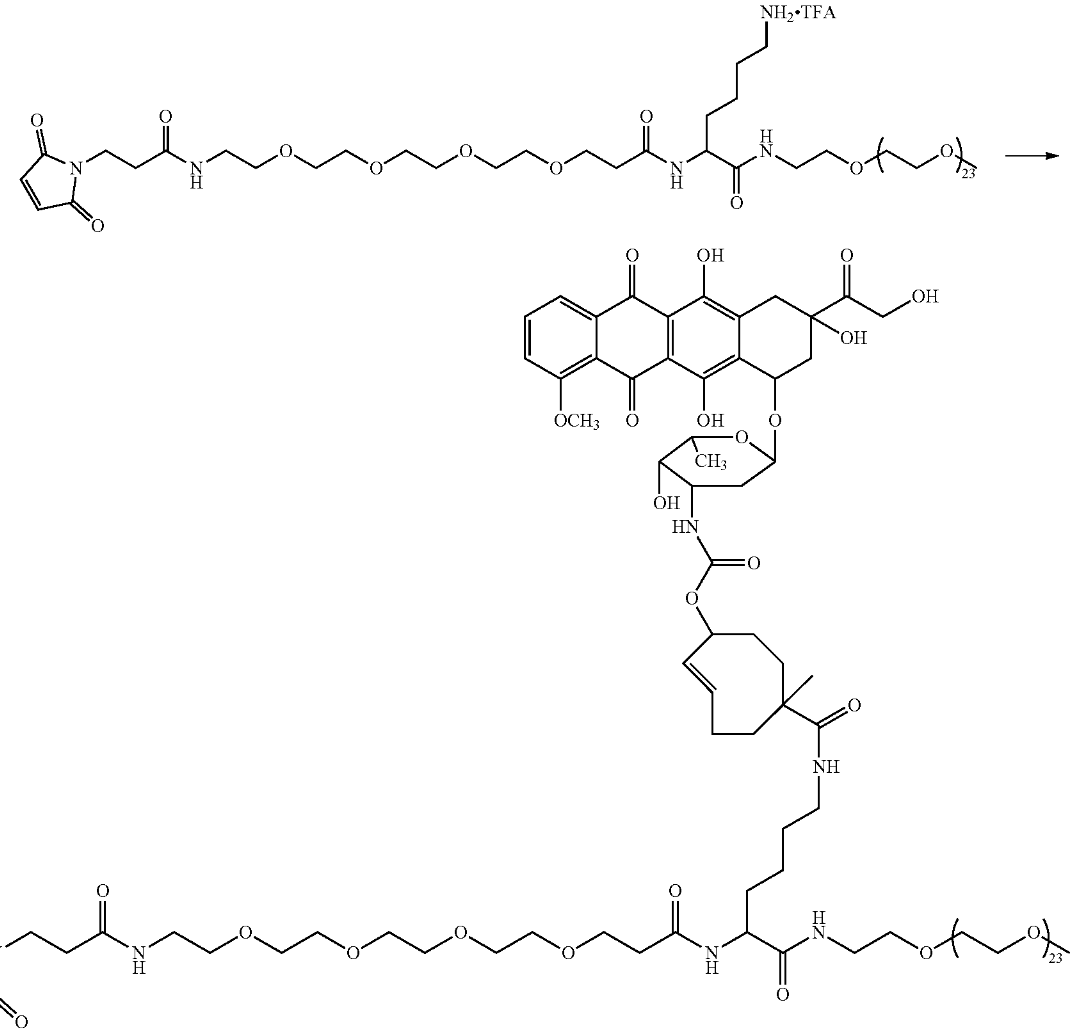

5.10

Dox-TCO-NHS 5.6 (2.09 mg; 2.45*$10^{-6}$ mol) was dissolved in DMF (0.1 mL), and DIPEA (1.58 mg; 1.23*$10^{-5}$ mol) was added. Next, a solution of branched PEG24 linker (4.24 mg; 2.45*$10^{-6}$ mol) in DMF (0.1 mL) was added, and the mixture was stirred at 20° C. After 3 h, acetonitrile (0.2 mL), formic acid (0.01 mL), and water (0.8 mL) were added, and the clear, orange solution was filtered and purified by preparative RP-HPLC (35 v % acetonitrile in water, containing 0.1 v % formic acid). The product was isolated by lyophilization to yield 1.18 mg of an orange powder (20%). LC-MS: m/z=−2349.91 $[M-H]^-$ (calcd 2349.19 for $C_{111}H_{180}N_6O_{47}$).

Synthesis of Alternative TCO Trigger Comprising an Ethyl Instead of a Methyl Moiety: bis-NHS TCO Compound 5.17

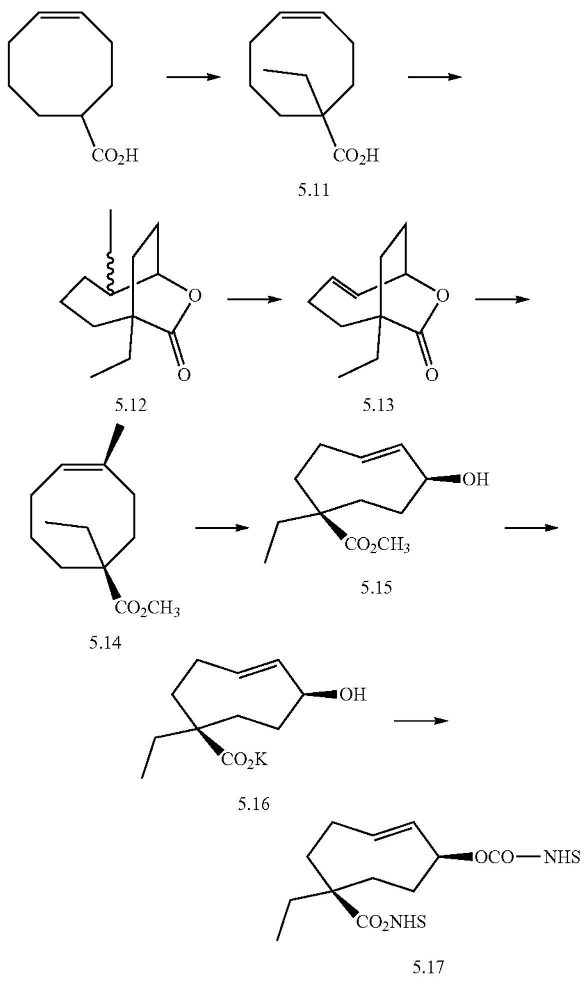

5.11 5.12 5.13 5.14 5.15 5.16 5.17

(Z)-1-ethylcyclooct-4-ene-1-carboxylic acid (5.11)

A mixture of DIPEA (57.13 g, 0.566 mol) and 260 mL THF was cooled below-200° C. n-Butyllithium in hexanes (2.5 N, 205 mL, 0.512 mol) was slowly added. The solution was stirred for 15 min, then cooled to −50° C. (Z)-cyclooct-4-ene-1-carboxylic acid (33.4 g, 0.217 mol), dissolved in 90 mL THF, was added over a 30 min period and stirred for an additional 40 minutes, allowing the temperature to rise to −5° C. The mixture was subsequently heated for 3½ h at 50° C., then cooled to −50° C. Iodoethane (131.5 g, 0.843 mol) was added over a 15 min period. The mixture was stirred at RT for 48h, followed by rotary evaporation. Toluene (250 mL) and 100 mL water were added to the residue, followed by 100 mL 37% hydrochloric acid. The layers were separated, and the organic layer was washed with 50 mL water. The successive aqueous layers were extracted with 250 mL toluene. The organic layers were dried and rotary evaporated. The residue was purified by Kugelrohr distillation to yield 38.01 g of the ethylated acid (0.208 mol, 96%). $^1$H-NMR ($CDCl_3$, product signals): 8 5.65 (m, 1H), 5.45 (m, 1H), 2.1-2.4 (m, 4H), 1.4-1.9 (m, 8H), 0.85 (t, 3H). MS: 180.9 (M−1).

(1R,6R,E)-1-ethyl-7-oxabicyclo[4.2.2]dec-4-en-8-one (5.12)

To a mixture of the ethylated acid (37.51 g, 0.206 mol), 300 mL dichloromethane, and 150 mL water was added sodium bicarbonate (56.0 g, 0.667 mol). The mixture was stirred for 1 h, then it was cooled in ice. A mixture of potassium iodide (40.1 g, 0.241 mol) and iodine (56.0 g, 0.220 mol) was added over a 1½ h period followed by stirring for 1½ h. 50 mL water was added, the layers were separated, and the aqueous layer was extracted with 200 mL dichloromethane. The successive organic layers were washed with 100 mL water, then dried and rotary evaporated to give the desired iodolactone 5.12. $^1$H-NMR ($CDCl_3$, product signals): 8 5.0 (m, 1H), 4.6 (m, 1H), 1.4-2.6 (m, 12H), 0.85 (t, 3H).

Bicyclic Olefin 5.13

The iodolactone was dissolved in 200 mL toluene, and DBU (39.8 g, 0.261 mol) was added. The mixture was heated for 8 h at 75-100° C. After cooling, the reaction mixture was washed with 2×50 mL water. The successive aqueous layers were extracted with 100 mL toluene. The organic layers were dried and rotary evaporated. The residue was purified by Kugelrohr distillation to yield 32.30 g of the bicyclic olefin 5.13 (0.179 mol, 87%). $^1$H-NMR ($CDCl_3$): δ 5.95 (m, 1H), 5.45 (m, 1H), 5.1 (m, 1H), 1.4-2.6 (m, 10H), 0.95 (t, 3H). MS: 181.0 (M+1).

Methyl (Z)-1-ethyl-6-hydroxycyclooct-4-ene-1-carboxylate (5.14)

The bicyclic olefin obtained above (31.28 g, 173.5 mmol), 150 mL methanol and potassium hydroxide (16.0 g, 242.9 mmol) were heated under reflux for 5 h, and then stirred at 300° C. overnight. 20 mL ethyl acetate was added, the mixture was heated for 30 min and then rotary evaporated, toluene (100 mL) was added and the mixture was rotary evaporated again. DMF (100 mL) was added, the mixture was rotary evaporated at 60° C. in order to remove traces of low-boiling materials. The remaining suspension was cooled in ice-water and iodomethane (44.6 g, 0.314 mol) was added over a 15 min period. The mixture was stirred overnight and the thin suspension was poured into a mixture of 230 mL water and 200 mL TBME. The layers were separated and the upper layer was washed with 3×50 mL water. The successive aqueous layers were extracted with 2×150 mL TBME. The combined organic layers were dried and rotary evaporated to give the product 5.14 (24.7 g, 116.4 mmol, 67%) which was used as such in the next step. $^1$H-NMR ($CDCl_3$): δ 5.6 (m, 1H), 5.35 (m, 1H), 5.0 (m, 1H), 3.65 (s, 3H), 1.4-2.4 (m, 10H), 0.8 (t, 3H). MS: 195.0 (M+1, $-H_2O$).

Methyl (E)-1-ethyl-6-hydroxycyclooct-4-ene-1-carboxylate (5.15)

The hydroxy ester obtained above (23.7 g, 111.6 mmol) was mixed with 26.0 g methyl benzoate and heptane/ethyl acetate (ca. 4/1). The solution was irradiated, the irradiated solution being continuously flushed through a silver nitrate impregnated silica column (190 g, containing ca. 112 mmol silver nitrate). The irradiation and flushing were stopped after 78 h and the silica column was successively eluted with 500 mL TBME, 500 mL TBME/5% methanol, and 600 mL TBME/20% methanol. The successive eluates were washed with 250 mL 15% ammonia, then dried and rotary evaporated (the same ammonia layer was used for all eluates). The third eluate contained the minor isomer 5.15 (7.06 g). The residual column material was stirred with TBME, 100 mL water and the ammonia layer of above. Filtration, layer separation, drying and rotary evaporation gave 8.35 g of major isomer 5.15.

$^1$H-NMR of the minor isomer (axially positioned allylic OH) ($CDCl_3$): δ 6.1 (m, 1H), 5.6 (m, 1H), 4.5 (m, 1H), 3.6 (s, 3H), 1.5-2.4 (m, 10H), 0.8 (t, 3H). $^1$H-NMR of the major isomer (equatorially positioned allylic OH) ($CDCl_3$): δ 5.8 (m, 1H), 5.35 (dd, 1H), 4.2 (m, 1H), 3.75 (s, 3H), 2.7 (m, 1H), 1.2-2.4 (m, 9H), 0.8 (t, 3H).

Potassium (E)-1-ethyl-6-hydroxycyclooct-4-ene-1-carboxylate (5.16)

A solution of potassium hydroxide (4.95 g, 75.1 mmol) in 30 mL water was added to a solution of the minor trans cyclooctene ester 5.15 (6.56 g, 30.9 mmol; containing a small amount of the major isomer) in 50 mL methanol, cooled with a water-bath. The solution was stirred for 7 d at 53° C. Most of the methanol was removed by rotary evaporation, and 30 mL water was added to the residue. The mixture was extracted with 3×50 mL TBME, and the successive organic layers were washed with 30 mL water. The combined aqueous layers were mixed with 20 mL ethyl acetate and so much methanol that a solution was obtained. The solution was rotary evaporated at 55° C., toluene was added to the residue and the mixture was again rotary evaporated. The residue was chromatographed on 106 g silica, using dichloromethane containing increasing amounts of methanol as the eluent. The product, as its potassium salt, eluted with dichloromethane containing 10-20% methanol. A total amount of 3.84 g of 5.16 was obtained (16.3 mmol, 53%).

$^1$H-NMR ($CDCl_3$): δ 6.1 (m, 1H), 5.6 (m, 1H), 4.5 (m, 1H), 1.5-2.4 (m, 10H), 0.85 (t, 3H). MS: 180.9 (M+1, free acid-$H_2O$), 196.9 (M−1, free acid). 2,5-dioxopyrrolidin-1-yl (E)-5-(((2,5-dioxopyrrolidin-1-yl)oxy) carbonyl)oxy)-1-ethylcyclooct-3-ene-1-carboxylate (5.17)

DIPEA (5.60 g, 43.4 mmol) was added to a solution of the acid 5.16 (1.98 g, 8.38 mmol) in 20 mL acetonitrile. Di-NHS-carbonate (7.50 g, 29.27 mmol) was added and the mixture was stirred at rt for 48h. It was rotary evaporated at 55° C., and the residue was stirred with 40 mL toluene and 30 g ice for 2 h in a cold water-bath. The layers were separated, and the organic layer was washed with 20 mL water. The successive aqueous layers were extracted with 30 mL toluene. Drying and rotary evaporation of the organic layers gave a residue, which was stirred for 5 h with 20 mL heptane, 20 mL toluene and 30 g ice. The liquids were decanted from the sticky material, and this wet sticky material was stirred with toluene, containing 20% dichloromethane, and anhydrous sodium sulfate. Filtration and rotary evaporation gave a residue, which was stirred for 2 days with 30 mL TBME. Filtration and washing with TBME gave 1.11 g colourless solid 5.17 (1.11 g, 2.54 mmol, 30%). $^1$H-NMR ($CDCl_3$): δ 6.1 (m, 1H), 5.6 (d, 1H), 5.25 (m, 1H), 2.8 (s, 8H), 2.5-1.5 (m, 10H), 1.0 (t, 3H).

Example 6: Conjugation of TCO-Drug Constructs to Diabody

Maleimide-TCO($PEG_{24}$)-MMAE Conjugation to Diabody AVP0458

A ca. 2 mg/mL solution of the anti-TAG72 diabody AVP0458 in degassed 100 mM phosphate buffer pHI 6.8 containing 2 mM EDTA (EDTA-PBS) was combined with freshly dissolved 100 mM DTT in EDTA-PBS (6 mM final DTT concentration) and incubated at room temperature for 1 h. The reduced diabody was then loaded on a PD-10 column and eluted from the column with EDTA-PBS, and immediately afterwards added with a solution of 5.5 (ca. 7.5 equiv. per SH) in DMSO (ca. 15% DMSO v/v % in the final mixture) and incubated overnight at 4° C. Subsequently the ADC (AVP0458-TCO-MMAE, tc-ADC) was purified by gel filtration on a AKTA system equipped with a Superdex 75 26/60 prep-grade column which was eluted with EDTA-PBS at 2.5 mL/min. The purified fractions were combined and mixed with 5% DMSO. The solution was then concentrated using Amicon Ultra-15 centrifugal filters and the tc-ADC concentration was measured by NanoDrop. tc-ADC was analyzed and characterized by SEC (FIG. 1*a*), SDS-PAGE (FIG. 1*b*) and ESI-TOF MS (FIG. 1*c,d*) confirming the identity of the conjugate with DARs of 4 in the presence of only trace amounts of aggregates.

Maleimide-TCO($PEG_{24}$)-MMAE Conjugation to Diabody AVP06

In the same manner as for tc-ADC, the anti-PSMA diabody AVP06 was conjugated with 5.5, affording AVP06-TCO-MMAE, nb-ADC) with a MMAE DAR of 4. For full characterization, see Rossin et al Nature Communications 2018, 9, 1484.

Maleimide-PEG4-TCO-Dox, Maleimide-PEG24-TCO-Dox and Maleimide-TCO (PEG24)-Dox Conjugation to Diabody AVP0458

Conjugation of compounds 5.8, 5.9, and 5.10 to AVP0458 was carried out as described for tc-ADC. The crude diabody-Dox conjugates were purified by gel filtration on an AKTA system equipped with a Superdex200 10/300 column eluted with 1% DMSO in PBS at 0.8 ml/min. The purified fractions were pooled and concentrated using Amicon Ultra-4 centrifugal devices. The final ADC concentration and a DAR of 4 were measured by NanoDrop (280 nm for protein and 480 nm for Dox). The DAR was also confirmed via a tetrazine titration followed by SDS-PAGE.

Example 7: In Vitro Tc-ADC Stability and MMAE Release

Figure 2:
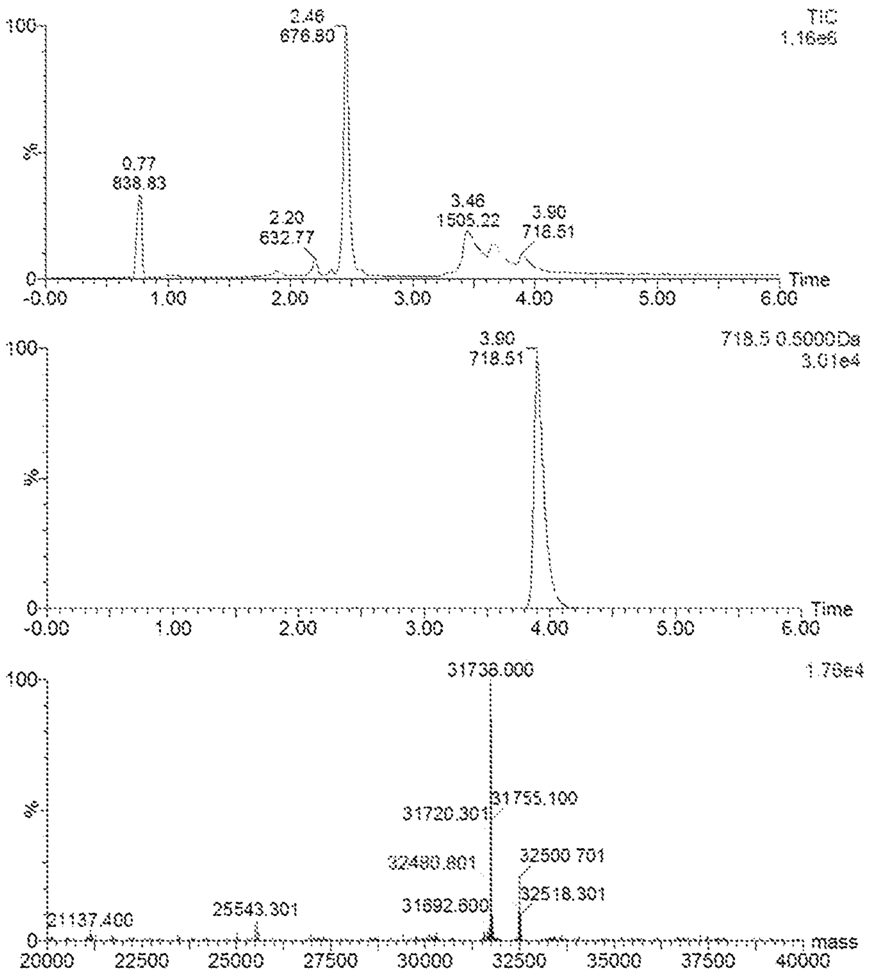
FIG. 2. shows HPLC-QTOF-MS analysis of tc-ADC activation with 2.12 in PBS; top: HPLC chromatogram (peak at 2.46 min is excess activator and at 3.90 min is free MMAE); middle: HPLC chromatogram filtered for m/z=718.51 Da (free MMAE); bottom: MS spectrum of the diabody conjugate after summation of the range from 3.2-4.2 min and subsequent deconvolution, showing fully reacted tc-ADC with 2×MMAE release (31720 Da) and a minor amount of fully reacted tc-ADC with 1×MMAE release (32481 Da).

The stability of stock solutions of diabody conjugate at 4° C. was monitored by QTOF-MS. An aliquot of the stock solution (10 μL 2 μg/μl tc-ADC in EDTA-PB containing 5% DMSO) was diluted with PBS (90 μL), and analysed with HPLC-QTOF-MS. This procedure was repeated over the course of 6 months and no tc-ADC degradation was observed in this time frame. Aliquots of the t-ADC stock solution (10 μL 2 μg/μl in 5% DMSO/EDTA-PB) were diluted with PBS (90 μL), mixed with activator 2.12 (5 μL 2.5 mM in PBS) and incubated at 37° C. for 1 h. Subsequent HPLC-QTOF-MS analysis demonstrated the formation of free MMAE (m/z=+718.51 Da) and the diabody reaction products without MMAE (FIG. 2).

Another aliquot of the stock solution was ten-fold diluted with PBS. Subsequently 50 μL of this solution was two-fold diluted with mouse serum and activator 2.12 was added (6.5 μL, 5 mM) followed by incubation at 37° C. After 10 min, 1 h, and 20 h proteins were precipitated by adding two parts of ice-cold acetonitrile. After vortexing, 10 min standing at −20° C. and centrifugation, the supernatants were separated from the protein pellets, diluted with five parts of PBS and analysed by HPLC-QTOF-MS (Table 2). MMAE recovery was quantified using calibration curves in 50% mouse serum, which were processed in the same manner. Reactions were performed in triplicate.

TABLE 2

| MMAE release from tc-ADC after activation with 2.12 in PBS and serum | | | |
|---|---|---|---|
| | 10 min | 1 h | 20 h |
| PBS | | ca. 90% | |
| 50% serum | 26 ± 3% | 51 ± 3% | 80 ± 2% |

Example 8: Stability of Activator 2.12 in Mouse Serum In Vitro

Precursor 2.10 was labeled with $^{177}$Lu following a standard procedure (Rossin et al. *Bioconjug. Chem.* 2016, 27, 1697-1706) thus obtaining a radioactive version of activator 2.12. [$^{177}$Lu]Lu-2.12 (11 nmol, ca. 20 MBq) was incubated in 50% mouse serum in PBS (0.7 mL) at 37° C. (n=3). At t=0, 30 min, 1, 2 and 3 h, 100 μL aliquots of the mixture were added with 100 μL ice-cold acetonitrile, mixed and centrifuged for 5 min at 13,000 rpm. Greater than 90% of the radioactivity was recovered in the supernatant at all time points. The supernatant was filtered through a 0.22 μm filter, 2.5-fold diluted with PBS and analyzed by radio-HPLC. Linear regression of the % intact activator over time afforded an extrapolated half-life of ca. 54 h.

Example 9: In Vitro Stability, Reactivity and Triggered Release of a Range of TZ Activators The stability of tetrazines was evaluated by dissolving them in 10% MeCN/PBS at 37° C. and following the decrease of the tetrazine UV absorbance at 520 nm in time (Table 2).

The second-order reaction rate constant of the reaction of axial (E)-cyclooct-2-en-1-yl N-methyl benzylcarbamate with a range of tetrazines was determined in 25% MeCN/PBS at 20° C. by UV spectroscopy. A cuvette was filled with 3 mL of a 83 μM solution of the appropriate TZ in 25% MeCN/PBS (0.25 μmol), and equilibrated at 20° C. Subsequently, a stock-solution of the TCO derivative was added (10 μL 25 mM in DMSO; 0.25 μmol). The second-order reaction rate constants were calculated from the rate at which the absorption at 520 nm (specific for the TZ moiety) decreased (Table 2).

The reaction kinetics between a diabody-based TCO-linked ADC according to this invention (AVP0458-TCO-MMAE) and activators 2.12 and 4.11 were determined as published in Rossin et al. *Angew. Chem.* 2010, 49, 3375-3378. Compounds 2.10 and 4.11 were radiolabeled with no-carrier added lutetium-177 and indium-111, respectively. The obtained radioactive activators were then reacted with increasing concentrations of AVP0458-TCO-MMAE (DAR=4) in PBS at 37° C. in pseudo-first order conditions. The obtained [$^{177}$Lu]Lu-2.12 ca. 0.2 μM was reacted with 0.6-1.8 μM ADC while [$^{111}$In]In-4.11 (ca.93 nM) was reacted with 0.2-0.8 μM ADC. In these conditions $k_2$ values of 54.7±2.2 $M^{-1}$ $s^{-1}$, and 375.9±43.2 $M^{-1}$ $s^{-1}$ were calculated for activators 2.12, and 4.11 respectively.

MMAE release from diabody ADC (AVP0458-TCO-MMAE) was determined by using a deuterated internal standard D8-MMAE. ADC ($1.1\times10^{-10}$ moles bound MMAE) and D8-MMAE ($1.1\times10^{-10}$ moles) and 10 equiv of tetrazine were incubated in 100 μL PBS/plasma (1/1) at 37° C. After 24 h the samples (n=3) were taken and proteins were precipitated by adding two parts of ice-cold acetonitrile. After vortexing, 10 min standing at −20° C. and centrifugation, the supernatants were separated from the protein pellets, diluted with five parts of PBS and the ratio MMAE/D8-MMAE was measured with LC-SIM-MS, affording the release yields (Table 3).

TABLE 3

In vitro tetrazine stability ($t_{1/2}$ in 10% MeCN/PBS at 37° C.), reactivity ($k_2$ ($M^{-1}$ $s^{-1}$) in 25% MeCN/PBS at 20° C.), and induced MMAE release from AVP0458-TCO-MMAE at 37° C. after 24 h.

| Compound | stability (h) | reactivity($k_2$) | release (%) |
|---|---|---|---|
| 2.1 | 14 | 14 | 95 ± 0.4 |
| 2.11 | n.d. | n.d. | 72 ± 0.5 |
| 2.12 | n.d. | n.d. | 88 ± 0.1 |
| 3.4 | n.d. | n.d. | 47 ± 0.3 |
| 4.1 | 10 | 250 | 69 ± 0.0 |
| 4.2 | 14 | n.d. | 56 ± 0.2 |
| 4.3 | 18 | 275 | 62 ± 0.5 |
| 4.4 | 15 | n.d. | 61 ± 0.4 |
| 4.11 | n.d. | n.d. | 56 ± 0.3 |
| 4.12 | n.d. | n.d. | 67 ± 0.4 |
| 4.13 | n.d. | n.d. | 61 ± 0.1 |
| 4.15 | n.d. | n.d. | 55 ± 0.4 |
| 4.17 | 12 | 412 | 70 ± 0.1 |
| 4.18 | 16 | 150 | 55 ± 0.8 |
| 4.19 | 1 | 290 | 60 ± 0.1 |
| 4.20 | 15 | 28 | 59 ± 0.3 |
| 4.23 | 6 | 246 | 69 ± 0.5 |
| 4.24 | 13 | n.d. | n.d. |
| 4.26 | 13 | 135 | 59 ± 0.6 |
| 4.27 | n.d. | n.d. | 66 ± 0.5 |
| 4.33 | n.d. | n.d. | 53 ± 0.6 |
| 4.35 | n.d. | n.d. | 67 ± 0.1 |
| 5.5 | n.d. | n.d. | 81 ± 0.4 |
| 5.8 | n.d. | n.d. | 80 ± 0.5 |

Example 10: Cell Proliferation Assay

The cell lines used in this study were obtained from ATCC and were maintained at 37° C. in a humidified atmosphere with 5% $CO_2$. The human colon cancer LS174T cell line was cultured in RPMI-1640 medium supplemented with 2 mM glutamine and 10% heat inactivated fetal calf serum. The human ovary carcinoma NIH: OVCAR-3 cell line was cultured in RPMI-1640 medium supplemented with 1 mM sodium pyruvate, 10 mM HEPES, 2 mM glutamine, 10 μg/mL bovine insulin and 20% fetal calf serum. The LS174T and NIH: OVCAR-3 cells were plated in 96-well plates at a 5000 cells/well density 24 h prior to the experiment. Activator 2.12 (52 mM in PBS containing 5% DMSO), tc-ADC (2.36 mg/mL in EDTA-PBS containing 5% DMSO) and MMAE (63 μM in DMSO) were serially diluted in pre-warmed culture medium immediately before the experiment and added to the wells (200 μL final volume per well). The tc-ADC was either added alone or followed by 3 μM 2.12 (5 eq. with respect to the highest TCO concentration). After 72 h incubation at 37° C., cell proliferation was assessed by an MTT assay. The proliferation assay was performed in triplicate. $EC_{50}$ values (Table 4) were derived from normalized cell growth curves generated with GraphPad Prism. In both cell lines the activator alone was not toxic while tc-ADC alone only exhibited a relatively moderate toxicity with $EC_{50}$ values of respectively 71 nM and 29 nM. However, when a fixed dose of 3 μM activator 2.12 was combined with the tc-ADC, the cytotoxicity increased 1000-fold, affording $EC_{50}$ values of 185 μM and 35 μM, matching the toxicity of the parent drug MMAE.

TABLE 4

In vitro cytotoxicity assay: $EC_{50}$ (half-maximal effective concentration) values in NIH:OVCAR-3 and LS174T tumor cells.

| Compound | EC50[a] NIH:OVCAR-3 | | EC50[a] LS174T | |
|---|---|---|---|---|
| tc-ADC+ 2.12 [3 μM] | 35 pM | (28-47 pM) | 185 pM | (16-22 pM) |
| tc-ADC | 29 nM | (18-48 nM) | 71 nM | (51-98 nM) |
| 2.12 | 0.79 mM | (0.48-1.29 mM) | 1.08 mM | (0.31-3.67 mM) |
| MMAE | 39 pM | (30-50 pM) | 277 pM | (236-325 pM) |

[a]95% confidence interval is given in parentheses (n = 3)

Figure 10:
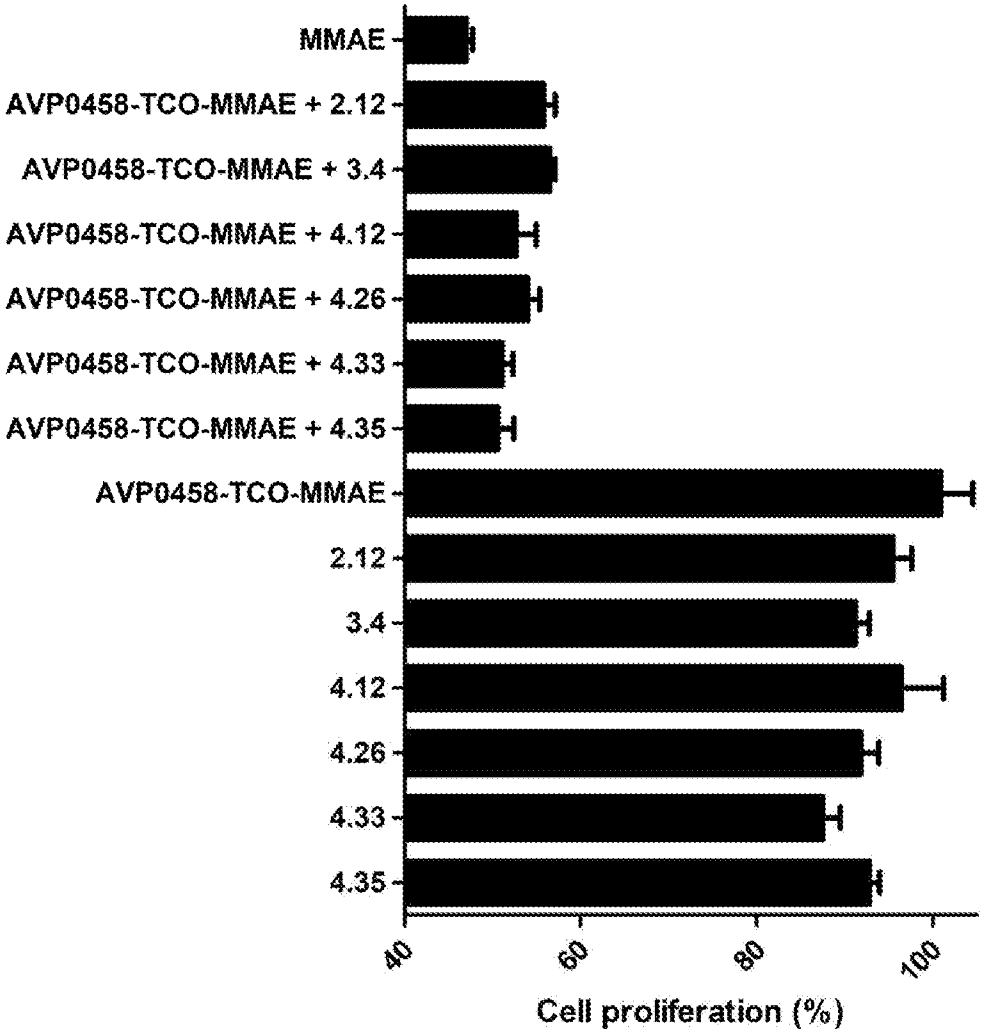
FIG. 10 depicts the results of a cell proliferation assay (LS174T cells) performed with a combination of tc-ADC (AVP0458-TCO-MMAE) and activators 2.12, 4.4, 4.12, 4.26, 4.33, 4.35, or with tc-ADC and activators alone; free MMAE is used as control.

To evaluate the combination of the -ADC with a range of tetrazines, LS174T human colon carcinoma cells were plated at a 5000 cells/well density in RPMI-1640 medium containing 2 mM glutamine and 10% FCS in 96-well plates 24 h prior to the experiment. The wells (n=4) were then added with AVP0458-TCO-MMAE (1 nM, DAR=4), alone or in combination with TZ activators 2.12, 3.4, 4.12, 4.26, 4.33 and 4.35 (1 μM). Control experiments were performed with the activators alone or MMAE (4 nM). Cell proliferation was assessed after a 3-day incubation by means of an MTT assay and was expressed as the % of that obtained without treatment. The results of this assay (FIG. 10) showed minimal cell growth inhibition in the wells added with the ADCs or with the activators alone, while in the wells treated with a combination of ADC and activator the growth inhibition approached that achieved with the corresponding amount of free drug, signifying effective drug release in the experimental conditions.

Figure 3:
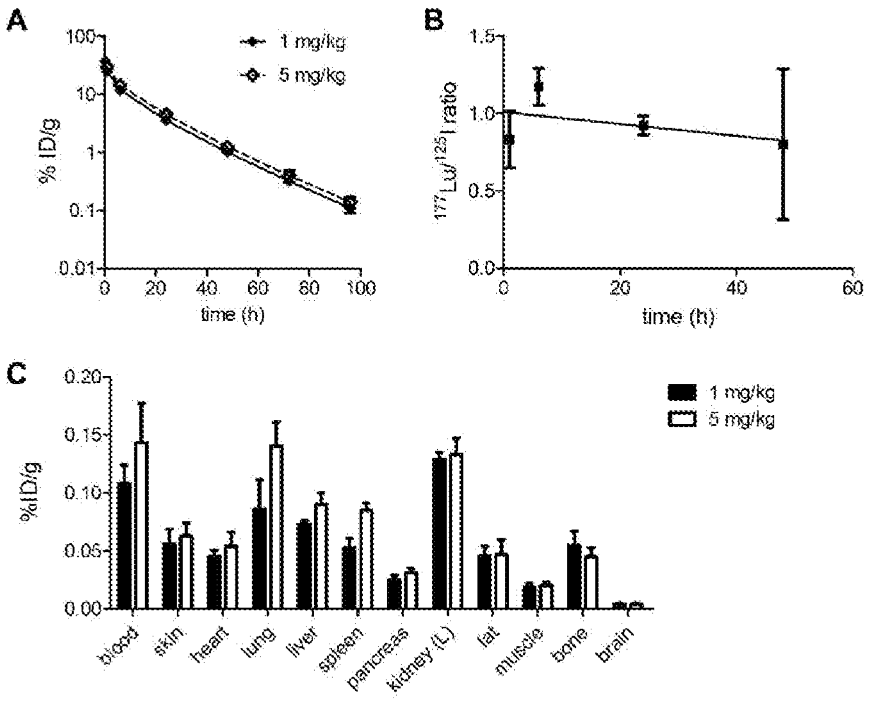
FIG. 3 shows in (A) Blood levels of $^{125}$I-labeled tc-ADC administered at two different doses; in (B) in vivo isomerization of ADC-bound TCO linker; in (C) biodistribution of $^{125}$I-labeled tc-ADC 4 days post-injection. Data represent the mean with SD (n=4).

Example 11: Biodistribution of Diabody ADCs and In Vivo Isomerization of ADC-Bound TCO The animal studies were performed in accordance with the principles established by the revised Dutch Act on Animal Experimentation (1997) and were approved by the institutional Animal Welfare Committee of the Radboud University Nijmegen. Female BALB/c nude mice (7-9 week old, 18-22 g body weight; Charles River Laboratories and Janvier) were used for blood kinetics and biodistribution studies. tc-ADC was labeled with $^{125}I$ as reported in van Duijnhoven et al., *J. Nucl. Med.* 2015, 56, 1422-1428. Two groups of tumour-free mice (n=4) were injected with $^{125}I$-labeled tc-ADC at 1 and 5 mg/kg dose. The mice were serially bled via the vena saphena (ca. 20 μL samples) at various times between 5 min and 72 h post-injection. Four days post-injection the mice were euthanized, one last blood sample was obtained via cardiac puncture, selected organs and tissues were harvested and the radioactivity was measured by γ-counting along with standards to determine the % injected dose per gram (% ID/g). The blood values (FIG. 3A) were fit to a two-exponential curve and the pharmacokinetics parameters were calculated. At both doses the tc-ADC showed fast elimination from blood (Table 5) and very low retention in non-target tissues 96 h post-injection (FIG. 3C).

Blood samples obtained from the mice injected with 5 m/kg tc-ADC were used also to monitor the in vivo TCO deactivation by reacting them ex vivo with an excess of [$^{177}$Lu]Lu-BisPy-TZ, as described in Rossin et al., *Bioconjug. Chem.* 2013, 24, 1210-1217. The change in $^{177}Lu/^{125}I$ cpm ratio over time (FIG. 3B) was used to estimate the amount of intact TCO in each blood sample and linear fitting of the data afforded a ca. 5.5 days half-life for the TCO deactivation in vivo. This value is in good agreement with the 5 days isomerization half-life that was previously measured for the same TCO linker conjugated to an intact mAb (CC49-TCO-Dox) without PEG (Rossin et al., *Bioconjug. Chem.* 2016, 27, 1697-1706).

TABLE 5

Blood half-life of $^{125}I$-labeled tc-ADC administered at two different doses.

| | $t_{1/2,\alpha}$ (%) | $t_{1/2,\beta}$ | $t_{1/2}$[a] | AUC |
|---|---|---|---|---|
| 1 mg/kg | 0.71 h (55) | 10.15 h | 5.95 h | 336.4 |
| 5 mg/kg | 1.94 h (54) | 12.55 h | 7.17 h | 374.3 |

[a] Calculated as $t_{1/2} = \ln 2 \times AUC/C_0$

Figure 11:
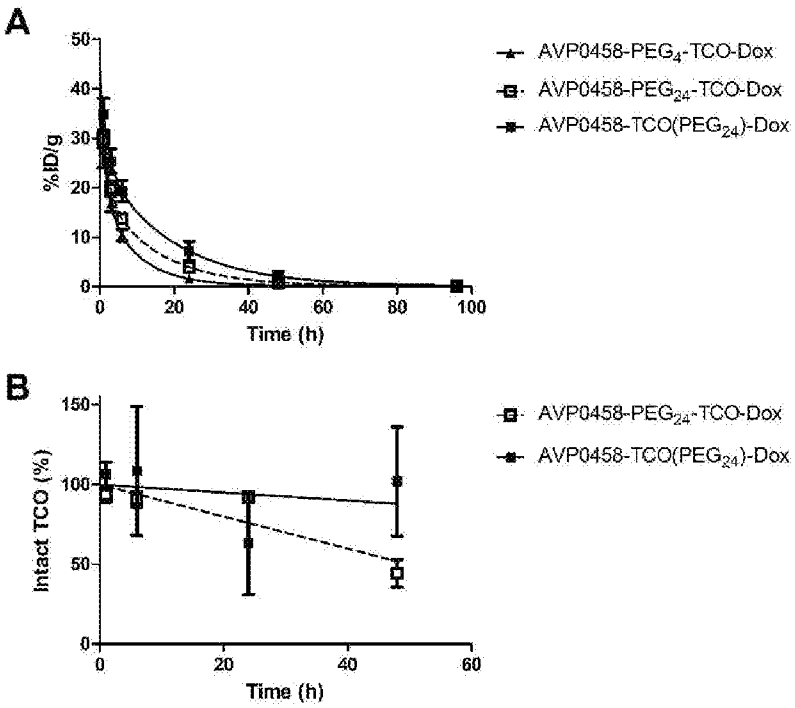
FIG. 11 depicts the in vivo evaluation of three TCO-linked doxorubicin ADCs. (A) Blood levels of $^{125}$I-labeled ADCs; (B) in vivo isomerization of ADC-bound TCO linker.

Three more groups of mice were injected $^{125}I$-labeled AVP0458-$PEG_4$-TCO-Dox (ca. 2.2 mg/kg), AVP0458-$PEG_{24}$-TCO-Dox (ca. 2.2 mg/kg), and AVP0458-TCO($PEG_{24}$)-Dox (ca. 1.3 mg/kg). Blood samples were collected at various times between 1 and 48 h p.i. and 4 days p.i. the mice were euthanized and the activity in blood and selected tissues was measured. All ADCs showed similar low retention in non-target tissues 4 days p.i. but different circulation profiles in blood based on the Dox-TCO linker (Table 6 and FIG. 11A). As expected, the ADC containing the short $PEG_4$ linker showed the fastest elimination from circulation within the ADC series. Between the two ADCs containing a $PEG_{24}$ chain in the linker, the one with TCO-Dox at the end of the chain, far from the protein, showed significantly shorter circulation in vivo than the analogue with TCO-Dox closer to the antibody. Blood samples from these two groups of mice were also reacted ex vivo with [$^{111}$In]In-BisPy-Tz and the changes in $^{111}In/^{125}I$ ratio over time revealed a markedly slower deactivation when the TCO linker was conjugated close to the protein (8.3 days extrapolated half-life), protected by the PEG chain, with respect to TCO exposed to the solvent (2.1 d extrapolated half-life) (FIG. 11B).

TABLE 6

| Blood half-lives of diabody-TCO-Dox constructs | | | | |
|---|---|---|---|---|
| | $t_{1/2,\alpha}$ (%) | $t_{1/2,\beta}$ | $t_{1/2}{}^{a}$ | AUC |
| AVP0458-PEG$_4$-TCO-Dox | 1.12 h (52.1) | 6.54 h | 4.14 h | 229.4 |
| AVP0458-PEG$_{24}$-TCO-Dox | 1.25 h (50.9) | 10.24 h | 6.03 h | 346.2 |
| AVP0458-TCO(PEG$_{24}$)-Dox | 1.28 h (41.7) | 13.05 h | 8.50 h | 536.6 |

[a]Calculated as $t_{1/2} = \ln 2 \times AUC/C_0$

Example 12: Blood Kinetics and Biodistribution of Activator 2.12

Figure 4:
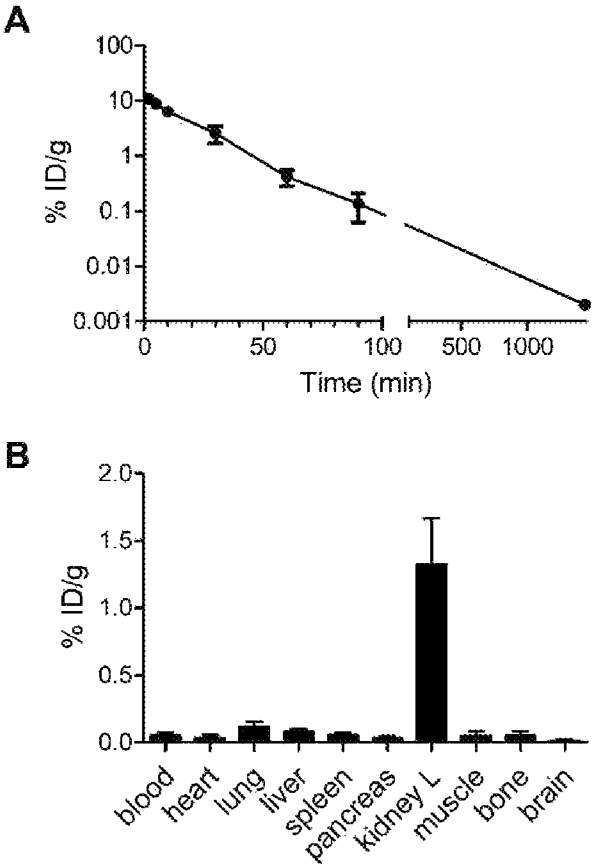
FIG. 4 shows in (A) Blood circulation of $^{177}$Lu-labeled activator 2.12 up to 24 h post-injection.

The activator precursor 2.10 was radiolabelled with $^{177}$Lu at ca. 1 MBq/nmol molar activity and the resulting product was used to spike the nonradioactive activator 2.12. Two groups of 4 tumor-free mice were injected with [$^{177}$Lu]Lu-2.12 (0.335 mmol/kg, ca. 1.5 MBq per mouse). One group was euthanized 1 h post-injection. The second group was serially bled at various times between 2 and 90 min post-injection via the vena saphena and euthanized 24 h post-injection. Selected organs and tissues were harvested for γ-counting. A 12.0 min half-life in blood was calculated by fitting the radioactivity levels (FIG. 4A) to a one-phase decay (GraphPad Prism) and complete lack of retention in tissues except some for the kidney, the organ of excretion, was found (FIG. 4B).

Example 13: Tumor Targeting of ADCs

Figure 5:
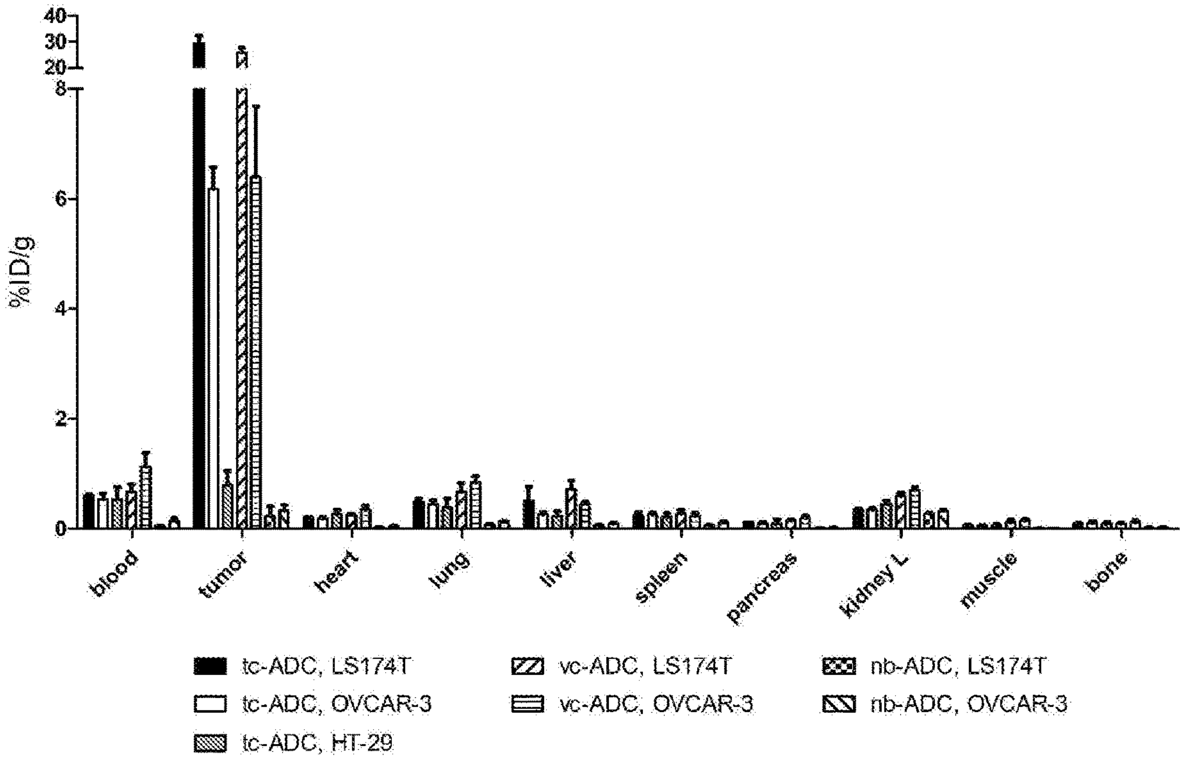
FIG. 5 shows the biodistribution of $^{125}$I-labeled ADCs in mice bearing TAG72 positive LS174T and OVCAR-3 xenografts or TAG72-negative HT-29 xenografts.

Female BALB/c nude mice (7-9 week old, 18-22 g body weight; Charles River Laboratories and Janvier) were subcutaneously inoculated ca. $3\times10^6$ LS174T cells (in 100 μL complete culture medium), ca. $5\times10^6$ NIH: OVCAR-3 cells (in 100 μL 1:1 RPMI-1640: matrigel) or $5\times10^6$ HT-29 cells (in 100 μL complete culture medium) in the hind limb. When the tumors reached a 0.1-0.2 cm$^3$ size the mice were randomly allocated to the treatment groups and the biodistribution experiments were started. tc-ADC and the control diabody-conjugates vc-ADC (anti-TAG72, containing the valine-citrulline enzymatically cleavable linker) and nb-ADC (anti-PSMA, functionalized with 5.5) and were labeled with iodine-125. Groups of mice bearing subcutaneous LS174T, OVCAR-3 or HT-29 xenografts (n=3-4) were injected with the $^{125}$I-labelled ADCs at 2 mg/kg dose. All mice were euthanized 48 h post-ADC injection, blood was obtained by cardiac puncture and, tumors and other organs were harvested for γ-counting. The anti-TAG72 ADCs, tc-ADC and vc-ADC, showed high and specific uptake in LS174T xenografts (25-30% ID/g) and, to a lower extent, in OVCAR-3 xenografts (ca. 6% ID/g), reflecting the different expression of TAG72 antigen in these tumor models. Significantly lower tc-ADC uptake was found in the TAG72 negative HT-29 tumor model. Similarly, the non-binding nb-ADC showed no uptake in both LS174T and OVCAR-3 xenografts (FIG. 5). Very low ADC retention was also found in blood and non-target organs and tissues 2 days post-ADC injection. These findings suggest that the combined use of tc-ADC followed by activator 2.12 48 h later should lead to tumor-specific ADC activation with low systemic exposure.

Example 14: Tumor Blocking and Antibody Dosing

To assess the in vivo reaction between tc-ADC and activator 2.12, a tumor blocking experiment was carried out as previously described (Rossin et al., Bioconjug. Chem. 2016, 27, 1697-1706). Briefly, the highly reactive probe BisPy-TZ was used as a reporter to show the presence of residual (unreacted) TCO moieties in the tumors of mice treated with tc-ADC followed by activator 2.12, in comparison to mice that did not receive the activator.

Figure 6:
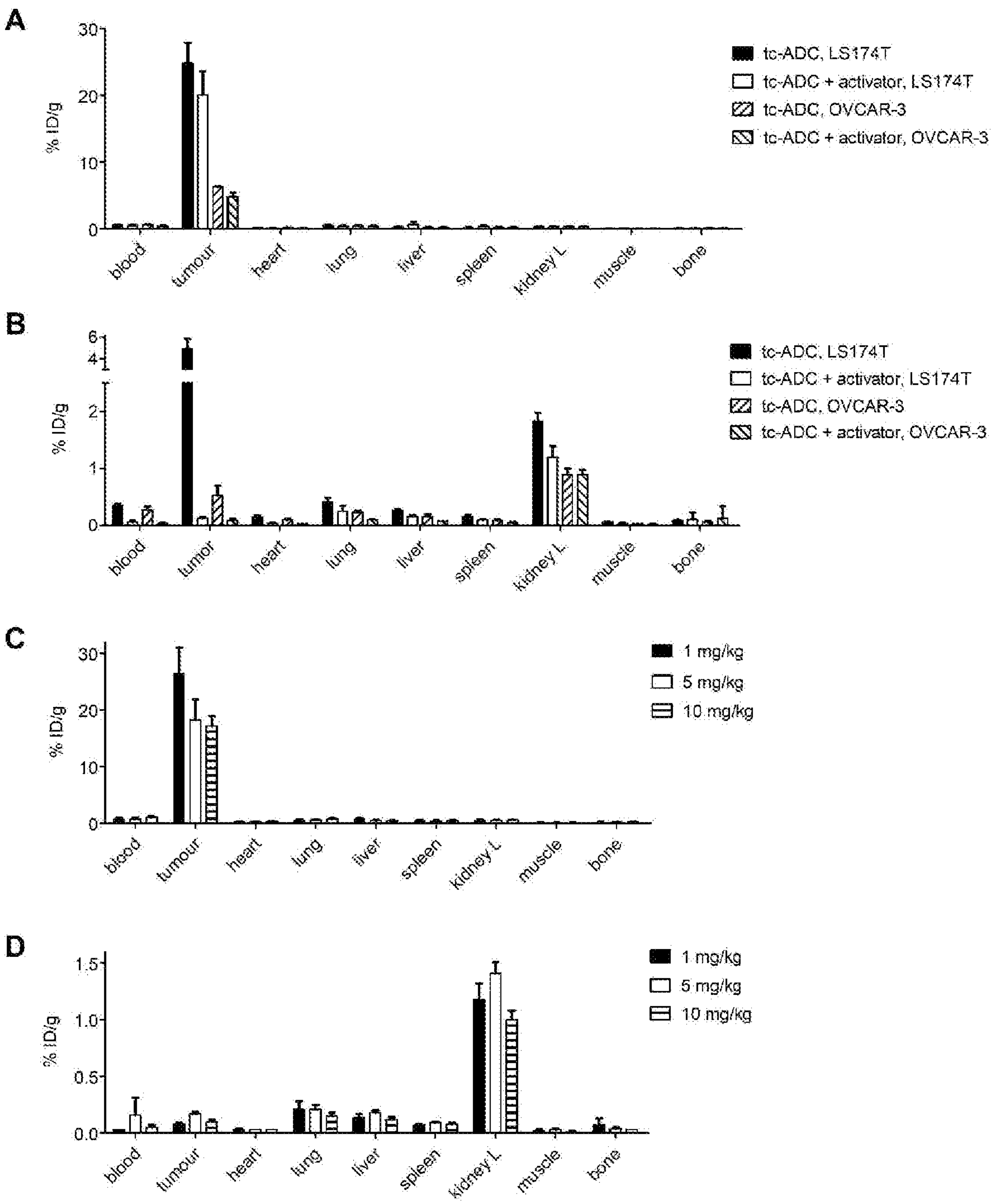
FIG. 6 shows tumor blocking experiments. (A) $^{125}$I uptake and (B) $^{177}$Lu uptake in mice bearing LS174T or OVCAR-3 xenografts, injected with $^{125}$I-labeled tc-ADC with and without activator 2.12, followed by $^{177}$Lu-BisPy-TZ probe. (C) $^{125}$I uptake and (D) $^{177}$Lu uptake in mice injected with different doses of $^{125}$I-labeled tc-ADC followed by activator 2.12 and $^{177}$Lu-probe.

Two groups of mice (n=4) bearing LS174T or OVCAR-3 xenografts were injected with $^{125}$I-labeled tc-ADC (2 mg/kg) followed 48 h later by activator 2.12 (ca. 0.335 mmol/kg) and, after 1 h, by [$^{177}$Lu]Lu-BisPy-TZ (ca. 0.335 μmol/kg). Two more groups of mice (n=4 for LS174T and n=3 for OVCAR-3) were injected with the same amount of $^{125}$I-labeled ADC followed only by BisPy-TZ 49 h later. All mice were euthanized 3 h post-probe injection and the $^{125}$I/$^{177}$Lu uptake in tumors and other organs and tissues was measured by γ-counting with dual-isotope protocol with cross contamination correction (FIGS. 6A and 6B). In both tumor models a significant decrease in probe uptake was observed in tumors of mice that received the ADC followed by the activator with respect to mice that received only the ADC. The tumor uptake levels were as low as previously found in tumor-bearing mice that were not administered any TCO-containing antibody construct (Rossin et al., Bioconjug. Chem. 2016, 27, 1697-1706). These findings demonstrate that the reaction between the tumor-bound tc-ADC and activator 2.12 was complete.

Then a dosing experiment was carried out to assess whether a 0.335 mg/kg dose of activator 2.12 is sufficient to completely activate TCO in the tumor of mice treated with >2 mg/kg tc-ADC. As in the previous study, [$^{177}$Lu]Lu-BisPy-TZ was used as reporter probe.

Three groups of mice bearing LS174T xenografts were injected with $^{125}$I-labeled tc-ADC at 1, 5, and 10 mg/kg dose followed by 0.335 mmol/kg activator 2.12 at 48 h post-injection and, 1 h later, by [$^{177}$Lu]Lu-BisPy-TZ probe (ca. 0.335 μmol/kg). All mice were euthanized 3 h post-probe injection and organs and tissues were harvested for dual-isotope γ-counting. In all groups a bolus injection of 0.335 mmol/kg activator 2.12 effectively blocked the subsequent uptake of BisPy-TZ (FIGS. 6C and 6D) demonstrating complete on-tumor reaction between activator and tc-ADC injected at doses as high as 10 mg/kg.

Figure 12:
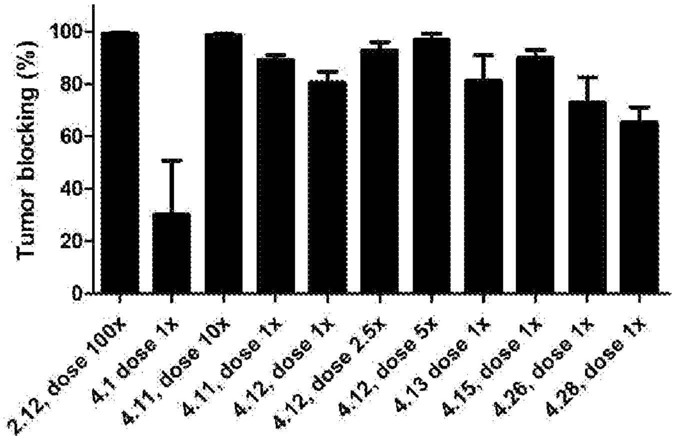
FIG. 12 depicts the tumor blocking (signifying on tumor reaction between TCO and activator) obtained in tumor-bearing mice injected with tc-ADC (2 mg/kg) followed by various doses of activators 2.12, 4.1, 4.11, 4.12, 4.13, 4.15, 4.26, and 4.28.

Following the same method the in vivo reaction of a range of TZ activators was evaluated in LS174T-bearing mice (n=3-5) pretreated with a diabody-based ADC (AVP0458-TCO-MMAE, tc-ADC; DAR=4). The mice were injected the ADC at a ca. 2 mg/kg dose followed 48 h later by the activator (dose 1×: ca. 3.35 μmol/kg; dose 2.5×: ca. 8.37 μmol/kg; dose 5×: ca. 0.017 mmol/kg; dose 10×: ca. 0.033 mmol/kg; dose 100×: ca. 0.335 mmol/kg) and, 1 h post-activator, by the [$^{111}$In]In-BisPy-TZ. Three hours (2.12, 4.1, 4.11, 4.12, 4.3, 4.15) or 24 h (4.26, 4.28) post-probe injection the mice were euthanized and the tumor blocking capacity of the various activators at the administered dose (FIG. 12) was calculated as reported above.

Example 15: MMAE Concentration in Tumors Following Tc-ADC Activation with 2.12

Groups of 3 mice bearing LS174T xenografts were injected with tc-ADC (2 mg/kg) followed by 0.335 mmol/kg activator 2.12 or vehicle 48 h later. Seventy-two or 96 h post-ADC administration, the mice were euthanized. One extra group of mice was injected vc-ADC (2 mg/kg) and euthanized 24 h post-injection. Tumour, liver and plasma samples were harvested from all groups, weighed and the MMAE concentration in tumour and liver samples was evaluated as described by Burke et al. (Mol. Cancer Ther. 2017, 16, 116-123) usind d8-MMAE as internal standard. All samples were then analysed by LC-QTOF-MS to quantify the amount of free MMAE based on the ratios with d8-MMAE. Tumour, liver and plasma samples from non-treated mice added with tc-ADC and/or d8-MMAE were used as controls. The limit of detection for MMAE in this assay was 0.2 nM.

Figure 7:
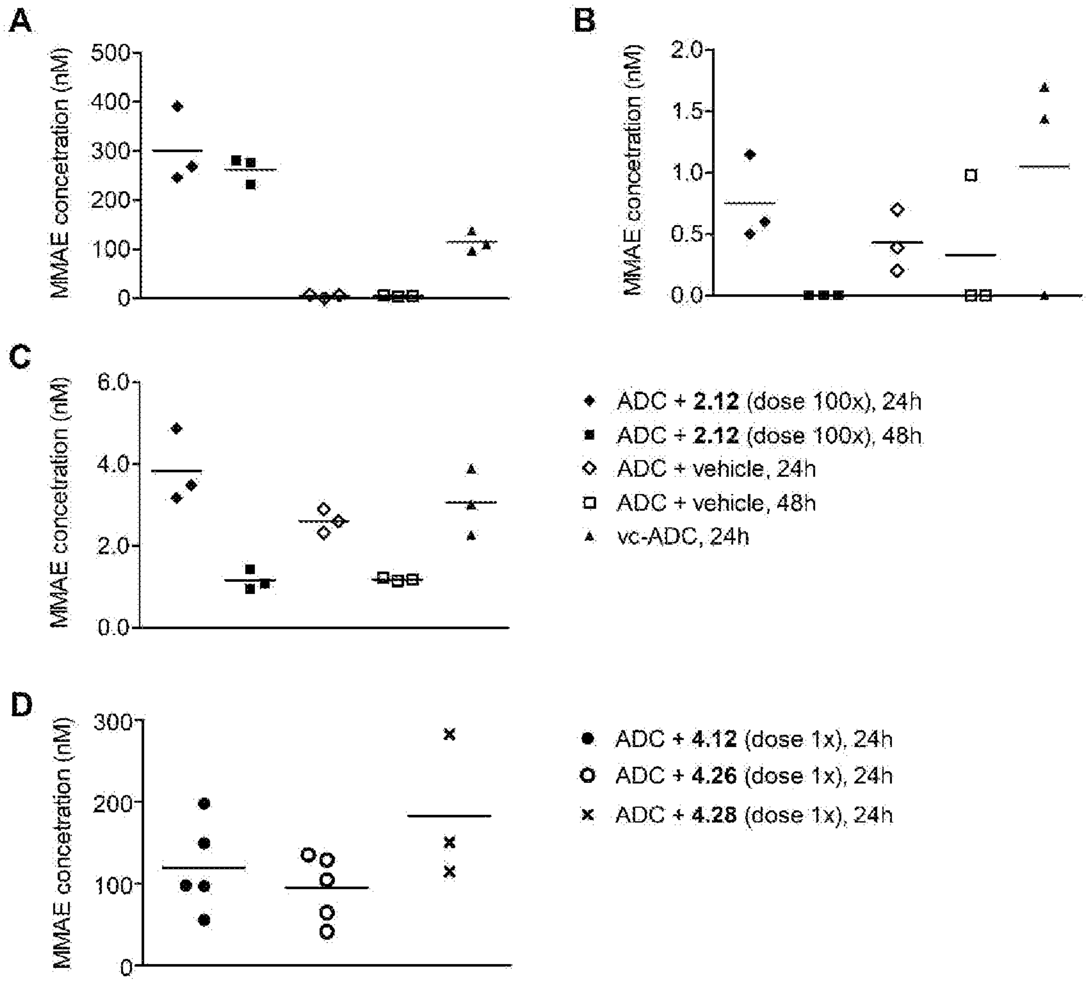
FIG. 7 shows the MMAE concentration in (A) tumors, (B) plasma, and (C) livers of mice injected with the -ADC (2 mg/kg) followed by activator 2.12 (0.335 mmol/kg) or vehicle and euthanized 24 or 48 h after the activator/vehicle administration, or in mice euthanized 24 h after the administration of vc-ADC (2 mg/kg). (D) MMAE concentration in tumors of mice injected tc-ADC (2 mg/kg) followed by low dose (3.35 μmol/kg) of activators 4.12, 4.26 and 4.28 and euthanized 24 h post activator injection.

The activation of tumor-bound tc-ADC indeed gave high and sustained MMAE tumor levels 24 h and 48 h after injection of 2.12, indicating that tumor washout of MMAE, if any, is minimal (FIG. 7A). In comparison, a 2-3 fold lower MMAE concentration was detected in the tumors of mice 24 h after the administration of the enzymatically cleavable vc-ADC. Furthermore, the MMAE levels were more than 100-fold lower in liver and plasma and in tumors that only received the ADC and not 2.12, underlining the very favorable biodistribution of the ADC, its stability and its TZ-dependent release (FIGS. 7B and 7C).

Three more groups of LS174T tumor bearing mice (n=3-5) were pre-treated with AVP0458-TCO-MMAE (ca. 2 mg/kg) followed 48 h later by a low dose of activator 4.12, 4.26 or 4.28 (ca. 3.35 μmol/kg). Twenty-four hours post-activation the tumors were harvested and the content of free MMAE was determined as described above. Despite the 100-fold lower dose of activator used in these experiments, a high amount of free MMAE was found in tumors (100-180 nM, FIG. 7D).

Example 16: Therapy Studies in a Colorectal Cancer Model with TZ 2.12

Figure 8:
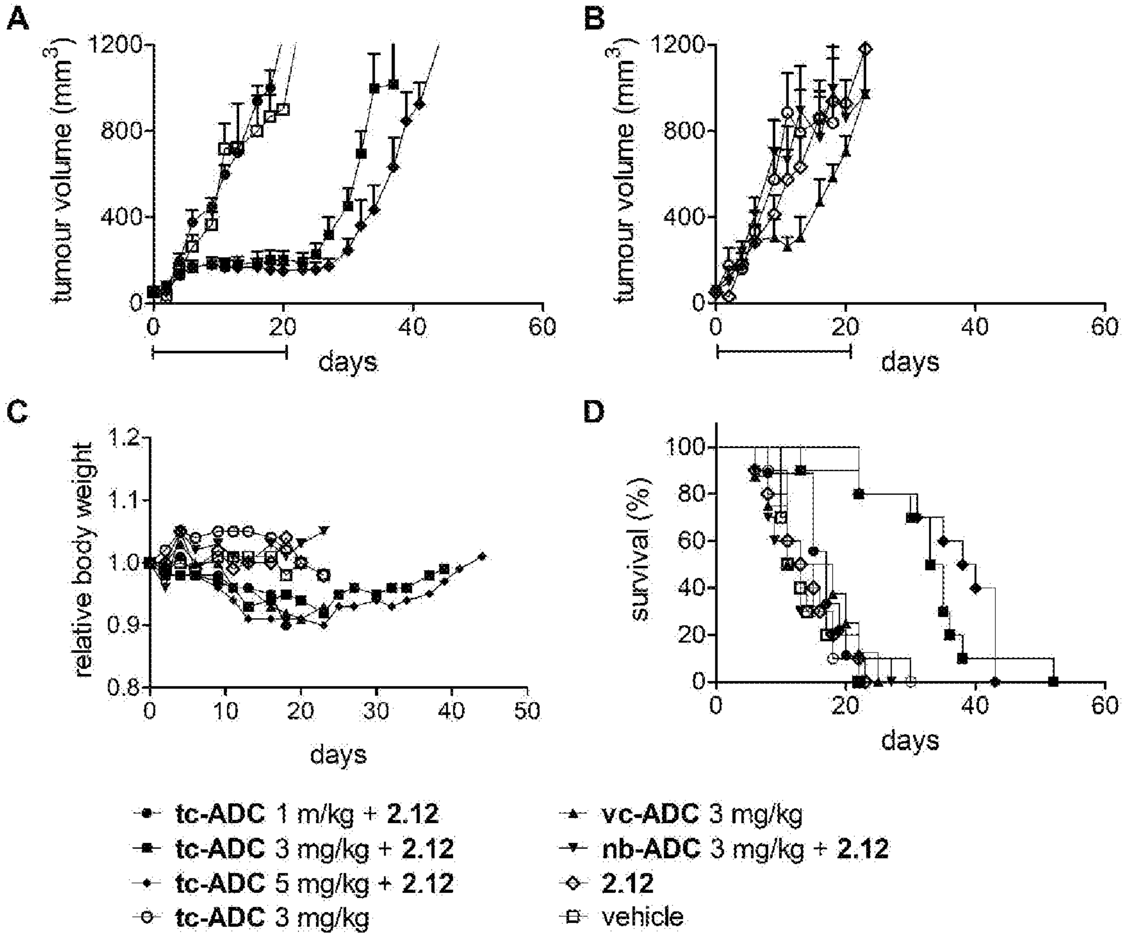
FIG. 8 depicts the results from therapy studies in mice bearing LS174T xenografts. (A, B) Mean tumor volumes (with SEM) in mice injected with 4 cycles of tc-ADC followed by 2.12, non-binding nb-ADC followed by 2.12, enzymatically cleavable vc-ADC followed by vehicle; control mice received vehicle, 2.12 or tc-ADC alone; the bars below the x axis indicate the treatment period. (C) Mean body weight of the mice during the therapy study (error bars omitted for clarity). (D) Survival curves for the therapy groups in A, B.

These studies were carried out by administering LS174T tumor bearing mice 4 cycles of ADC followed by activator (or vehicle) 48 h later. The cycle was repeated every 4 days. Four groups of LS174T tumor-bearing mice (n=8-10) were injected with increasing doses of tc-ADC (1, 3, and 5 mg/kg) or with nb-ADC (3 mg/kg) followed by activator 2.12 (0.335 mmol/kg). Two groups of mice (n=10) were administered 3 mg/kg vc-ADC or tc-ADC followed by vehicle and two more groups of mice (n=10) received either the activator or vehicle only. In this study a dose-dependent tumor growth inhibition was observed (FIG. 8A). The mice that received four cycles of 1 mg/kg doses of tc-ADC followed by activator did not respond to the therapy and their tumors grew as fast as those in the vehicle group (no differences in tumor sizes, 17 days median survival vs. 12 days for the vehicle, Table 7). On the contrary four cycles of 3 and 5 mg/kg tc-ADC followed by activator afforded a pronounced tumor growth delay (P<0.01 at day 16 with respect to 1 mg/kg dose and vehicle) and an extended median survival time of 34 and 39 days, respectively. In contrast, the vc-ADC, the tc-ADC without activator, the activator alone, and the nb-ADC all failed to control tumor growth (FIG. 8B), leading to similar survival outcomes as found for the vehicle.

Overall tc-ADC and activator 3 were generally well tolerated by the mice. In general all mice bearing this very aggressive tumour line experienced an approx. 10% weight loss (not considering tumor growth) during the study (FIG. 8C), most likely due to the tumour burden, but showed no signs of discomfort. On the contrary, most of the mice treated with repeated 3 mg/kg doses of vc-ADC were euthanized in the first month due to poor physical health.

TABLE 7

Number of LS174T bearing mice removed from the multi-dose efficacy study (based on pre-defined criteria) and median survival times.

| | Tumor >1 $cm^3$ | Body weight loss | Poor physical condition | Median survival (days) |
|---|---|---|---|---|
| tc-ADC 1 mg/kg + 2.12 | 7/9 | 0/9 | 2/9 | 17 |
| tc-ADC 3 mg/kg + 2.12 | 8/10 | 2/10 | 0/10 | 34 |
| tc-ADC 5 mg/kg + 2.12 | 8/10 | 1/10 | 1/10 | 39 |
| tc-ADC 3 mg/kg | 9/10 | 0/10 | 1/10 | 13 |
| vc-ADC 3 mg/kg | 1/8 | 1/8 | 6/8 | 14.5 |
| nb-ADC 3 mg/kg + activator | 7/10 | 0/10 | 3/10 | 13 |
| vehicle | 9/10 | 0/10 | 1/10 | 12 |
| 2.12 | 7/10 | 0/10 | 3/10 | 14 |

Example 17: Therapy Studies in an Ovarian Cancer Tumor Model with TZ 2.12

Figure 9:
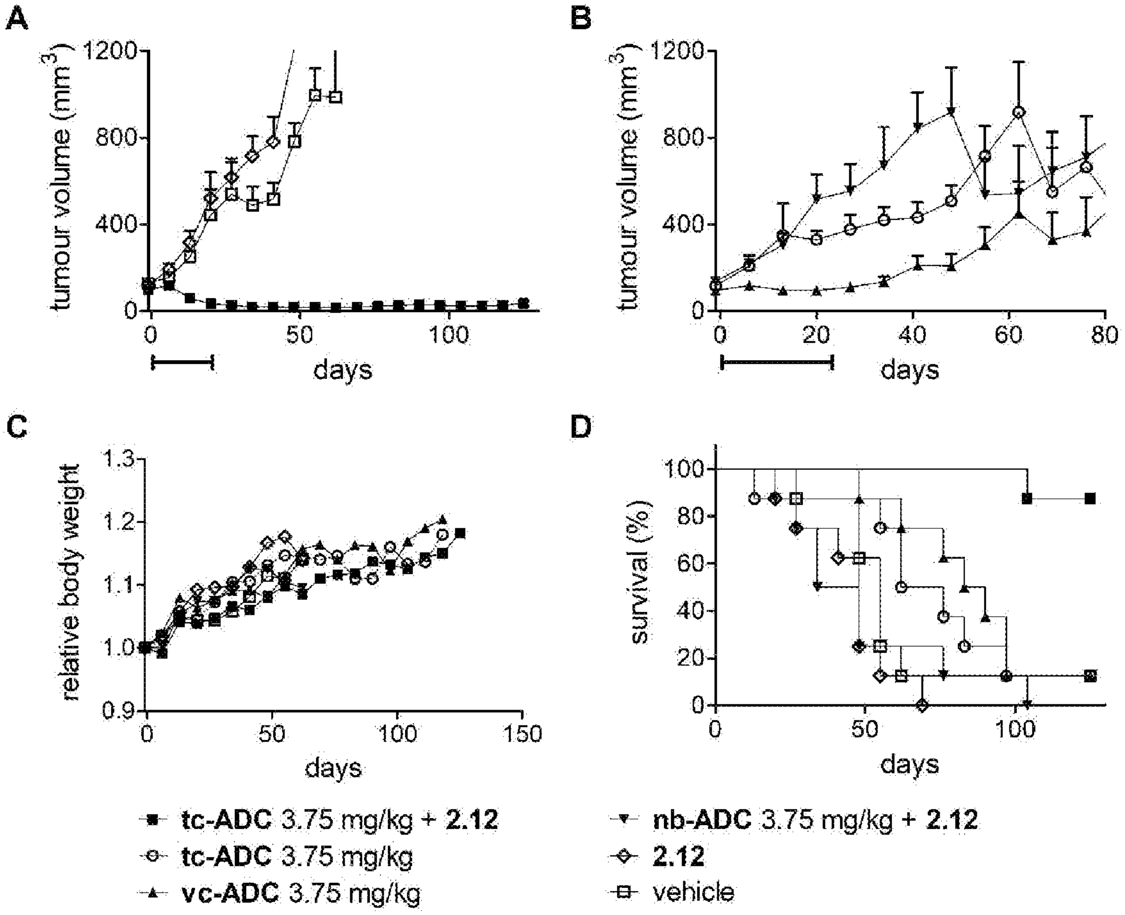
FIG. 9 depicts the results from therapy studies in mice bearing OVCAR-3 xenografts. (A, B) Mean tumor volumes (with SEM) in mice injected with 4 cycles of tc-ADC or non-binding nb-ADC followed by 2.12 (0.335 mmol/kg) or enzymatically cleavable vc-ADC followed by vehicle; control mice received vehicle, 2.12 or tc-ADC alone; the bars below the x axis indicate the treatment period. (C) Mean body weight of the mice during the therapy study (error bars omitted for clarity). (D) Survival curves for the therapy groups in A,B.

These studies were carried out by administering OVCAR-3 tumor bearing mice 4 cycles of ADC followed by activator (or vehicle) 48 h later. The cycle was repeated every 4 days. Two groups of tumor bearing mice (n=8) received 4 cycles of TCO-containing ADC (tc-ADC or nb-ADC) at a 3.75 mg/kg dose followed by activator 2.12 (0.335 mmol/kg). Two groups of mice (n=8) were injected either with the enzymatically cleavable vc-ADC or tc-ADC at the same dose followed by vehicle and, finally, two more groups of mice (n=8) received either 2.12 or vehicle only. The group of mice that received tc-ADC and 2.12 showed significant tumor regression in the first weeks after treatment (117±46 $mm^3$ and 18±9 $mm^3$ tumor volumes at 6 and 34 days, respectively; P-0.0004) followed by 3 months with barely palpable residual tumor masses (FIG. 9A). On the contrary, most of the mice that received vehicle, 2.12 or nb-ADC developed significantly larger tumors (P<0.05 at day 20; FIGS. 9A and 9B) and were removed from the study within two months (41-55 days median survival, Table 7). Four cycles of the -ADC alone or ve-ADC followed by vehicle produced very heterogeneous tumor response with significantly larger mean tumor sizes in the second half of the study. Despite the partial therapeutic effect, these groups of mice exhibited a limited median survival (72-86 days) and only one mouse per group reached the end of the study. Overall, repeated doses of tc-ADC and activator were well tolerated by the mice and only one mouse was removed from the study during the last month because of poor health. On the contrary, 4/8 mice treated with vc-ADC were euthanized in the second half of the study due to poor general health or extreme weight losses (Table 8).

TABLE 8

Number of OVCAR-3 bearing mice removed from the multi-dose efficacy study (based on pre-defined criteria) and median survival times.

| | Tumor >1 $cm^3$ | Body weight loss | Poor physical condition | Median survival (days) |
|---|---|---|---|---|
| tc-ADC + 2.12 | 0/8 | 0/8 | 1/8 | NA |
| tc-ADC | 5/8 | 0/8 | 2/8 | 69 |
| vc-ADC | 3/8 | 1/8 | 3/8 | 86.5 |
| nb-ADC + 2.12 | 8/8 | 0/8 | 0/8 | 41 |
| vehicle | 7/8 | 0/8 | 0/8 | 55 |
| 2.12 | 8/8 | 0/8 | 0/8 | 48 |

Example 18 ADC Therapy with Activator 4.12

One group of LS174T tumor bearing mice (n=8) was treated with 4 cycles (one every 4 days) of AVP0458-TCO-MMAE (ca. 3 mg/kg) followed by activator 4.12 (ca. 0.017 mmol/kg) 48 h later. Three more groups of mice (n=8-10) were treated with ADC alone, activator alone or vehicle. The mice were monitored daily and body weight and tumor sizes were recorder at least twice per week up to 50 days from the beginning of the treatment or until a humane end point was reached (>1.5 gr tumor, >20% weight loss, discomfort, etc). Blood samples were collected from 4 mice per group before (day-1) and after the treatment (day 14) and haemoglobin, thrombocytes and leukocytes levels were measured.

Figure 13:
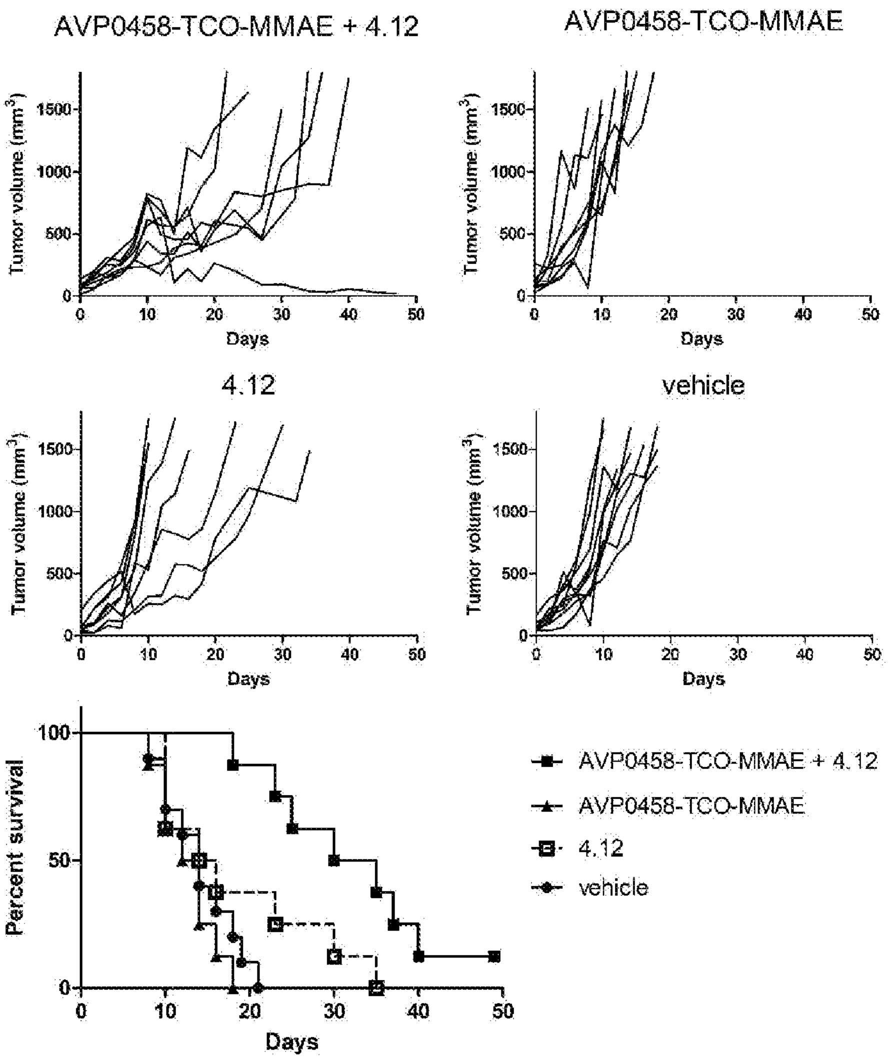
FIG. 13 depicts the results (single tumor growth curves and combined survival) from a therapy study in mice bearing LS174T xenografts injected with 4 cycles of tc-ADC (3 mg/kg) and activator 4.12 (16.7 μmol/kg), or with tc-ADC and activator alone, and with vehicle.

Most of the mice treated with ADC or activator alone were euthanized immediately before or shortly after completion of the fourth treatment cycle due to rapid tumor growth, similar to the group that received the vehicle (13-15 days median survival). On the contrary, despite heterogeneous tumor growth, the mice treated with four cycles of AVP0458-TCO-MMAE and activator 4.12 showed a pronounced response to therapy with a 32.5-day median survival (FIG. 13). Overall ADC and activator were well tolerated by the mice.

The invention claimed is:

1. A compound according to Formula (1):

Formula (1)

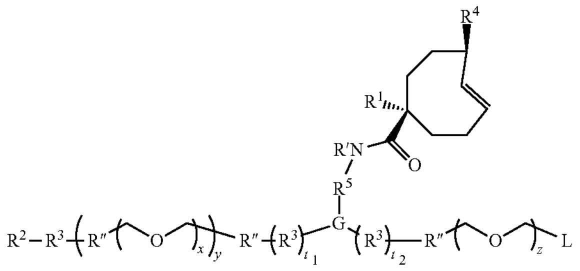

wherein $t_1$ is 0 or 1, wherein $t_2$ is 0 or 1, wherein x is an integer in a range of from 1 to 12, wherein y is 0 or 1, wherein z is an integer in a range of from 6 to 48, wherein L is selected from the group consisting of —$CH_2$—$OCH_3$, —$CH_2$—OH, —$CH_2$-C(O)OH, —C(O)OH, wherein when at least one of $t_1$ or $t_2$ is 0, then G is selected from the group consisting of CR', $C_5$-$C_6$ arenetriyl, $C_4$-$C_5$ heteroarenetriyl, $C_3$-$C_6$ cycloalkanetriyl, and $C_4$-$C_6$ cycloalkenetriyl, wherein when both $t_1$ and $t_2$ are 1, then G is selected from the group consisting of CR', N, $C_5$-$C_6$ arenetriyl, $C_4$-$C_5$ heteroarenetriyl, $C_3$-$C_6$ cycloalkanetriyl, and $C_4$-$C_6$ cycloalkenetriyl, wherein for G, the arenetriyl, heteroarenetriyl, cycloalkanetriyl, and cycloalkenetriyl are optionally further substituted with groups selected from the group consisting of —Cl, —F, —Br, —I, —OR', —$N(R')_2$, —SR', —$SO_3H$, —$PO_3H$, —$PO_4H_2$, —$NO_2$, —$CF_3$ and —$R_1$, and optionally contain one or more heteroatoms selected from the group consisting of —O—, —S—, —NR'—, —P—, and —Si—, wherein the N, S, and P atoms are optionally oxidized, wherein the N atoms are optionally quaternized, wherein $R^1$ is selected from the group consisting of hydrogen, $C_1$-$C_6$ alkyl groups, $C_6$ aryl groups, $C_4$-$C_5$ heteroaryl groups, $C_3$-$C_6$ cycloalkyl groups, $C_5$-$C_{12}$ alkyl(hetero)aryl groups, $C_5$-$C_{12}$ (hetero)arylalkyl groups, $C_4$-$C_{12}$ alkylcycloalkyl groups, —$N(R')_2$, —OR', —SR', —$SO_3H$, —C(O)OR', and $Si(R')_3$, wherein for $R_1$ the alkyl groups, (hetero)aryl groups, cycloalkyl groups, alkyl(hetero)aryl groups, (hetero) arylalkyl groups, alkylcycloalkyl groups are optionally substituted with a moiety selected from the group consisting of —Cl, —F, —Br, —I, $NO_2$, $SO_3H$, $PO_3H$, —$PO_4H_2$, —OR', —$N(R')_2$, —$CF_3$, =O, =NR', —SR', and optionally contain one or more heteroatoms selected from the group consisting of —O—, —S—, —NR'—, —P—, and —Si—, wherein the N, S, and P atoms are optionally oxidized, wherein the N atoms are optionally quaternized, wherein $R^2$ is selected from the group consisting of N-maleimidyl groups, halogenated N-alkyl-amido groups, sulfonyloxy N-alkylamido groups, vinyl sulfone groups, activated carboxylic acids, benzenesulfonyl halides, ester groups, carbonate groups, sulfonyl halide groups, thiol groups, $C_{2-6}$ alkenyl groups, $C_{2-6}$ alkynyl groups, $C_7$-18 cycloalkynyl groups, $C_{5-18}$ heterocycloalkynyl groups, bicyclo[6.1.0]non-4-yn-9-yl] groups, $C_{4-12}$ cycloalkenyl groups, azido groups, phosphine groups, nitrile oxide groups, nitrone groups, nitrile imine groups, isonitrile groups, diazo groups, ketone groups, (O-alkyl) hydroxylamino groups, hydrazine groups, halogenated N-maleimidyl groups, aryloxymaleimides, dithiophenol-maleimides, bromo- and dibromopyridazinediones, 2,5-dibromohexanediamide groups, alkynone groups, 3-arylpropiolonitrile groups, 1,1-bis(sulfonylmethyl)-methylcarbonyl groups, carbonyl halide groups, allenamide groups, 1,2-quinone groups, isothiocyanate groups, aldehyde groups, triazine groups, squaric acids, 2-imino-2-methoxyethyl groups, (oxa)norbornene groups, (imino) sydnones, methylsulfonyl phenyloxadiazole groups, aminooxy groups, and 2-amino benzamidoxime groups, wherein each individual $R^3$ is selected from the group consisting of $C_1$-$C_{12}$ alkylene groups, $C_2$-$C_{12}$ alkenylene groups, $C_2$-$C_{12}$ alkynylene groups, $C_6$ arylene groups, $C_4$-$C_5$ heteroarylene groups, $C_3$-$C_8$ cycloalkylene groups, $C_5$-$C_8$ cycloalkenylene groups, $C_5$-$C_{12}$ alkyl(hetero)arylene groups, $C_5$-$C_{12}$ (hetero)arylalkylene groups, $C_4$-$C_{12}$ alkylcycloalkylene groups, $C_4$-$C_{12}$ cyclo-alkylalkylene groups, wherein each individual $R^5$ is selected from the group consisting of $C_1$-$C_8$ alkylene groups, $C_2$-$C_8$ alkenylene groups, $C_2$-$C_8$ alkynylene groups, $C_6$ arylene groups, $C_4$-$C_5$ heteroarylene groups, $C_3$-$C_6$ cycloalkylene groups, $C_5$-$C_8$ cycloalkenylene groups, $C_5$-$C_{12}$ alkyl (hetero)arylene groups, $C_5$-$C_{12}$ (hetero)arylalkylene groups, $C_4$-$C_{12}$ alkylcycloalkylene groups, $C_4$-$C_{12}$ cyclo-alkylalkylene groups, wherein for $R^3$ and $R^5$ the alkylene groups, alkenylene groups, alkynylene groups, (hetero)arylene groups, cycloalkylene groups, cycloalkenylene groups, alkyl (hetero)arylene groups, (hetero)arylalkylene groups, alkylcycloalkylene groups, cycloalkylalkylene groups, are optionally substituted with a moiety selected from the group consisting of —Cl, —F, —Br, —I, —OR', —$N(R')_2$, —O, =NR', —SR', —$SO_3H$, —$PO_3H$, —$PO_4H_2$, —$NO_2$ and —$Si(R')_3$, and optionally contain one or more heteroatoms selected from the group consisting of —O—, —S—, —NR'—, —P—, and —Si—, wherein the N, S, and P atoms are optionally oxidized, wherein the N atoms are optionally quaternized, wherein each R' is independently selected from the group consisting of hydrogen, $C_1$-$C_6$ alkylene groups, $C_2$-$C_6$ alkenylene groups, $C_2$-$C_6$ alkynylene groups, $C_6$ arylene, $C_4$-$C_5$ heteroarylene, $C_3$-$C_6$ cycloalkylene groups, $C_5$-$C_8$ cycloalkenylene groups, $C_5$-$C_{12}$ alkyl (hetero)arylene groups, $C_5$-$C_{12}$ (hetero)arylalkylene groups, $C_4$-$C_{12}$ alkylcycloalkylene groups, and $C_4$-$C_{12}$ cycloalkyl-alkylene groups, wherein for R' the alkylene groups, alkenylene groups, alkynylene groups, (hetero)arylene groups, cycloalkylene groups, cycloalkenylene groups, alkyl(hetero) arylene groups, (hetero)arylalkylene groups, alkylcycloalkylene groups, cycloalkylalkylene groups are optionally substituted with a moiety selected from the group consisting of —Cl, —F, —Br, —I, —OH, —$NH_2$, =O, —SH, —$SO_3H$, —$PO_3H$, —$PO_4H_2$, —$NO_2$, and optionally contain one or more heteroatoms selected from the group consisting of —O—, —S—, —NH—, —P—, and —Si, wherein the N, S, and P atoms are optionally oxidized, wherein each R" is independently selected from the group consisting of

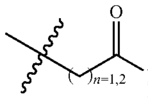
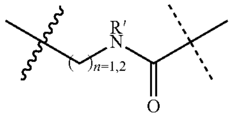
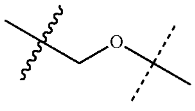
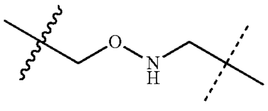
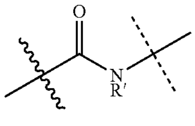
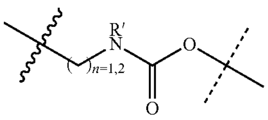
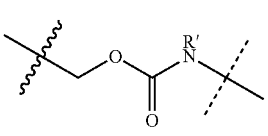
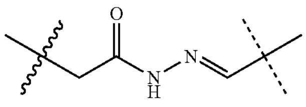
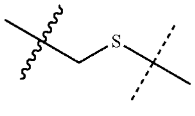
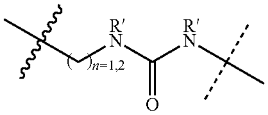
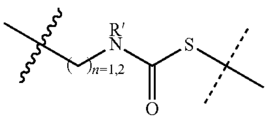
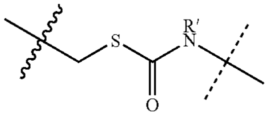
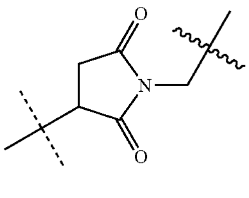
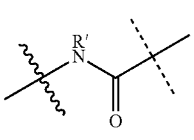
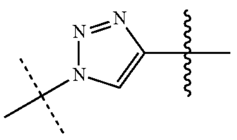
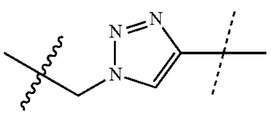

-continued

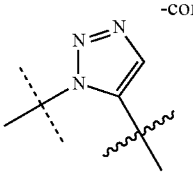
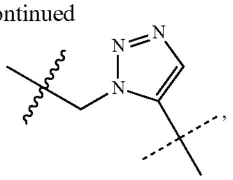

wherein the wiggly line depicts a bond to an ethylene glycol group or optionally to the $R^3$ adjacent to $R^2$ when y is 0, and the dashed line depicts a bond to $R^3$ or G, wherein $R^4$ is selected from the group consisting of —OH, —OC(O)Cl, —OC(O)O—N-succinimidyl, —OC(O)O-4-nitrophenyl, —OC(O)O-tetrafluorophenyl, —OC(O)O-pentafluorophenyl, —OC(O)—$C^A$, —OC(S)—$C^A$, —O-($L^C(C^A)_s(C^A)_s)_q$—$C^A$, and —$C^A$, wherein q is an integer in range of from 0 to 2, wherein each s is independently 0 or 1, wherein $L^C$ is a self-immolative linker, wherein $C^A$ denotes a Construct A, wherein said Construct A is a drug, wherein, when $R^4$ is —OC(O)—$C^A$ or —OC(S)—$C^A$, $C^A$ is bound to the —OC(O)— or —OC(S)— of $R^4$ via an atom selected from the group consisting of O, S, N, a secondary N and a tertiary N, wherein this atom is part of $C^A$, wherein, when $R^4$ is —O-($L^C(C^A)_s(C^A)_s)_q$—$C^A$ and q is 0, $C^A$ is bound to the —O— moiety of $R^4$ on the allylic position of the trans-cyclooctene ring of Formula (1) via a group selected from the group consisting of —C(O)—, and —C(S)—, wherein this group is part of $C^A$, wherein, when $R^4$ is —O-($L^C(C^A)_s(C^A)_s)_q$—$C^A$ and q is 1, $L^C$ is bound to the —O— moiety on the allylic position of the trans-cyclooctene ring of Formula (1) via a group selected from the group consisting of —C($Y^{C2}$)$Y^{C1}$—, and a carbon atom, which is optionally an aromatic carbon, wherein this group is part of Lc, wherein $Y^{C1}$ is selected from the group consisting of —O—, —S—, and —$NR^6$—, wherein $Y^{C2}$ is selected from the group consisting of O and S, wherein, when $R^4$ is —O-($L^C(C^A)_s(C^A)_s)_q$—$C^A$, and q is 1, then $C^A$ is bound to $L^C$ via a moiety selected from the group consisting of —O—, —S—, —N—, a secondary N and a tertiary N, wherein said moiety is part of $C^A$, wherein, when $R^4$ is —$C^A$, then $C^A$ is bound to the allylic position of the trans-cyclooctene of Formula (1) via an-O-atom, wherein this atom is part of $C^A$, wherein $R^6$ is selected from the group consisting of hydrogen, $C_1$-$C_4$ alkyl groups, $C_2$-$C_4$ alkenyl groups, and $C_{4-6}$ (hetero)aryl groups, wherein for $R^6$ the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$ and —$NO_2$ and optionally contain at most two heteroatoms selected from the group consisting of —O—, —S—, —NH—, —P—, and —Si—, wherein the N, S, and P atoms are optionally oxidized, and pharmaceutically accepted salts thereof.

2. The compound according to claim 1, wherein $R^2$ is an N-maleimidyl group linked to the remaining part of the compound according to Formula (1) via the amine of the N-maleimidyl group.

3. The compound according to claim 1 selected from the group consisting of
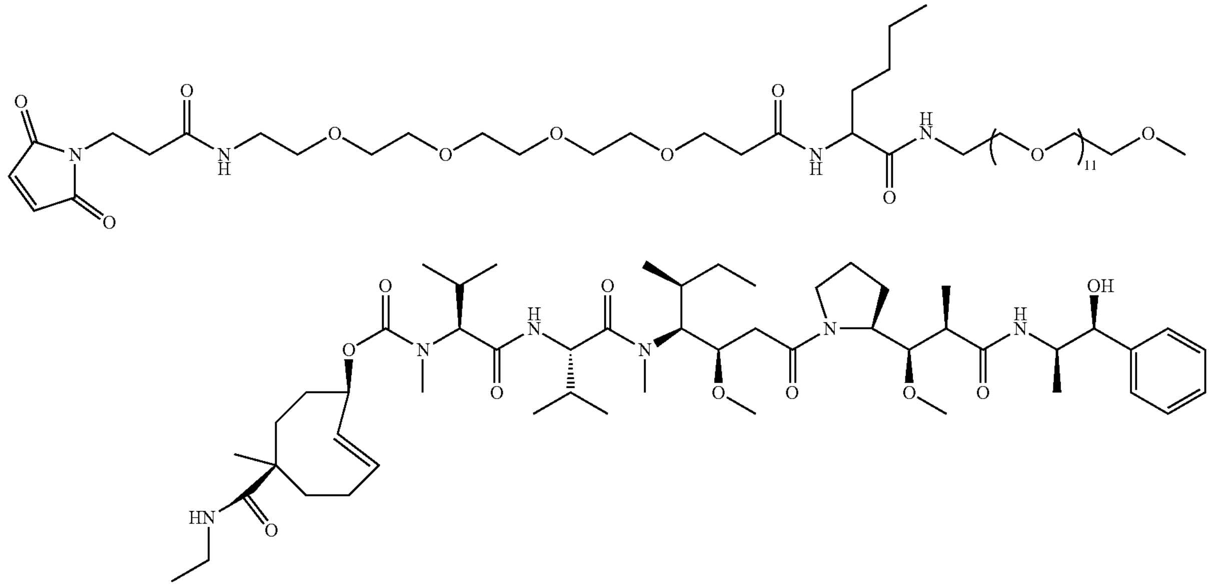
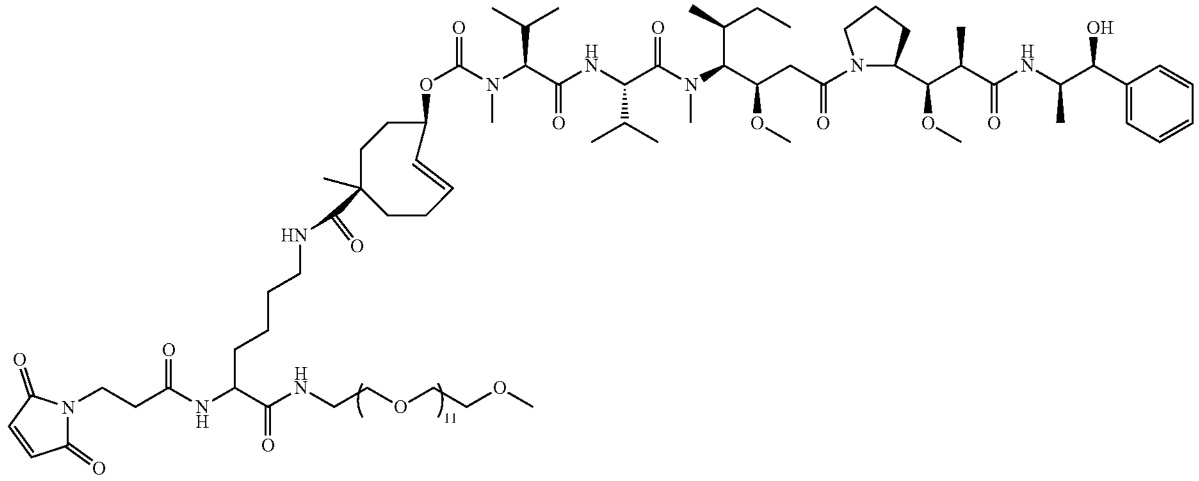
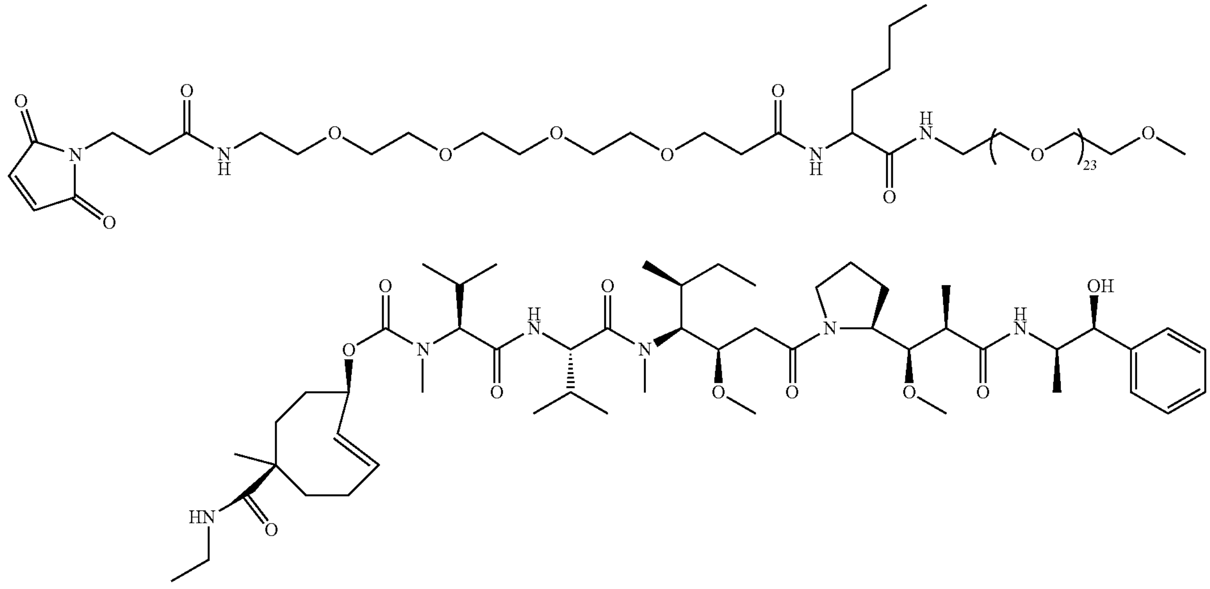

-continued
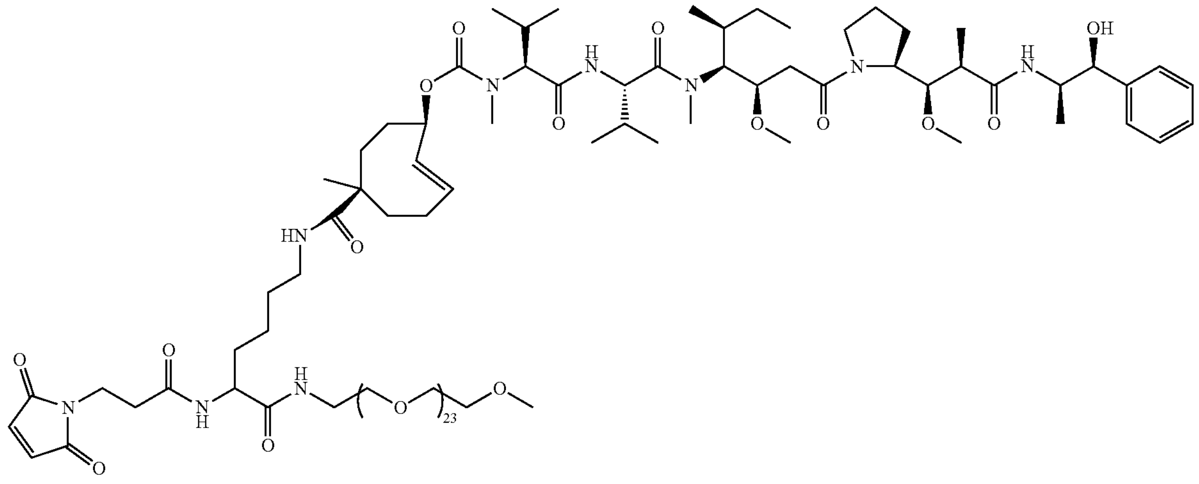
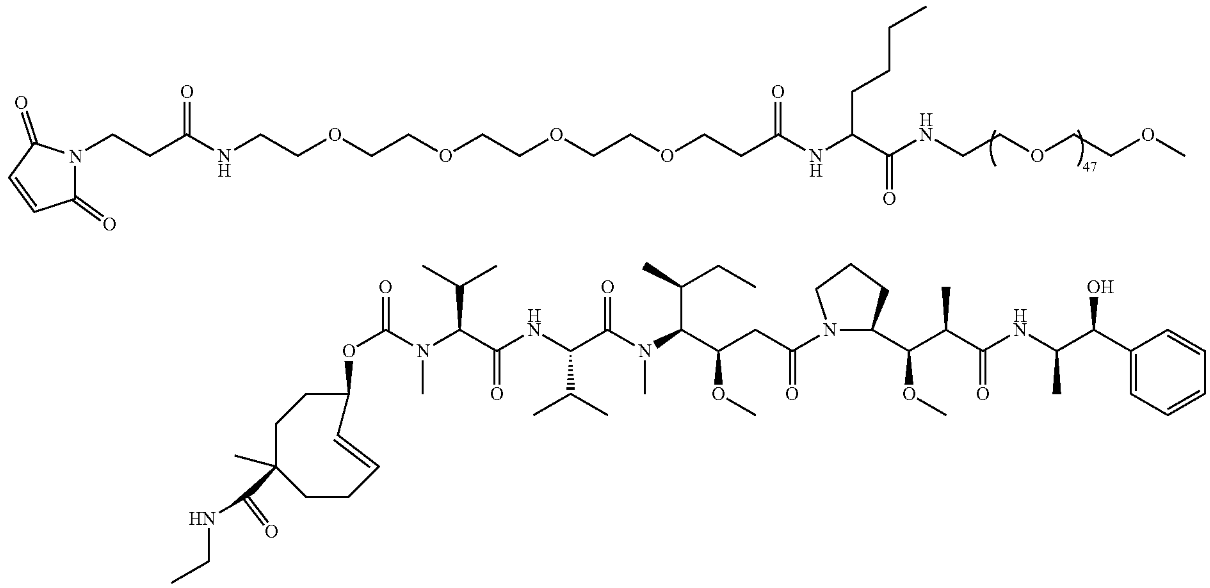
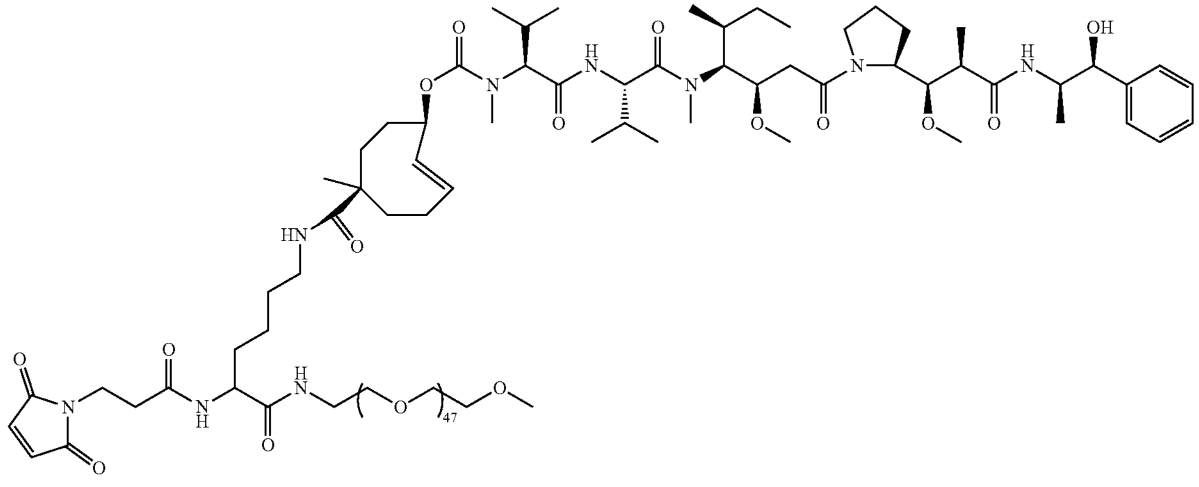

-continued
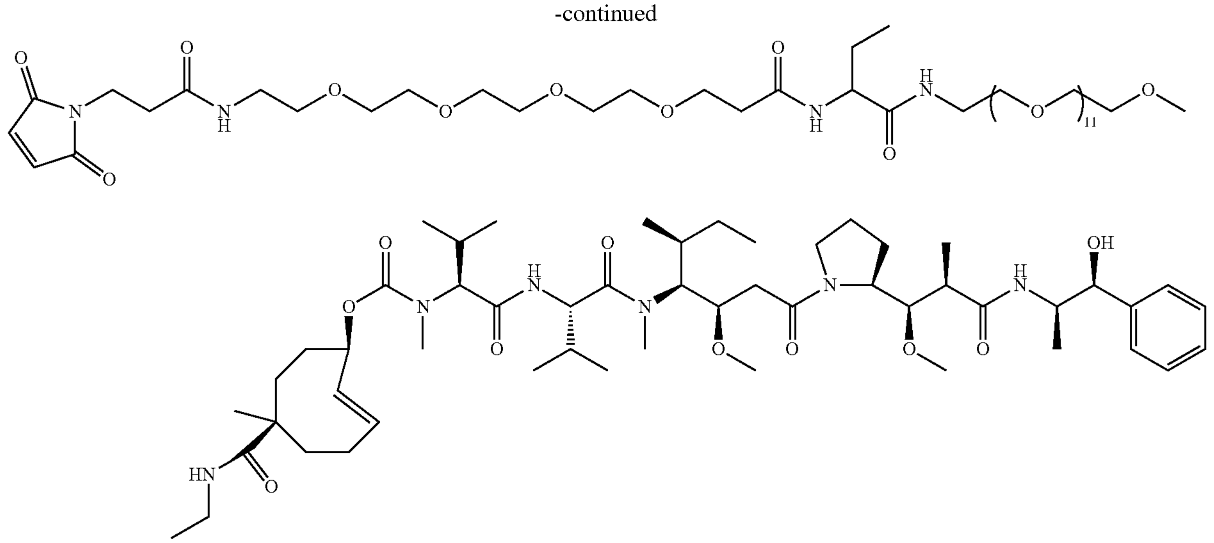
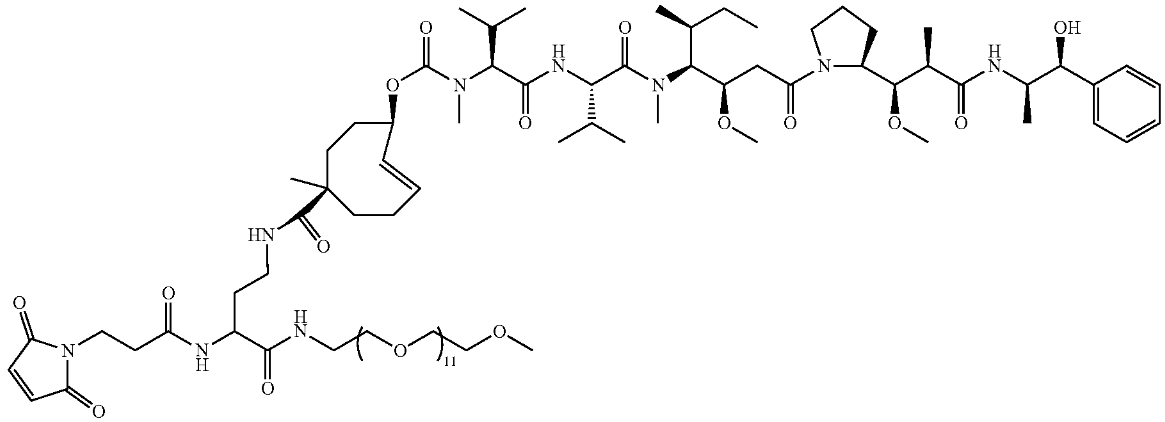
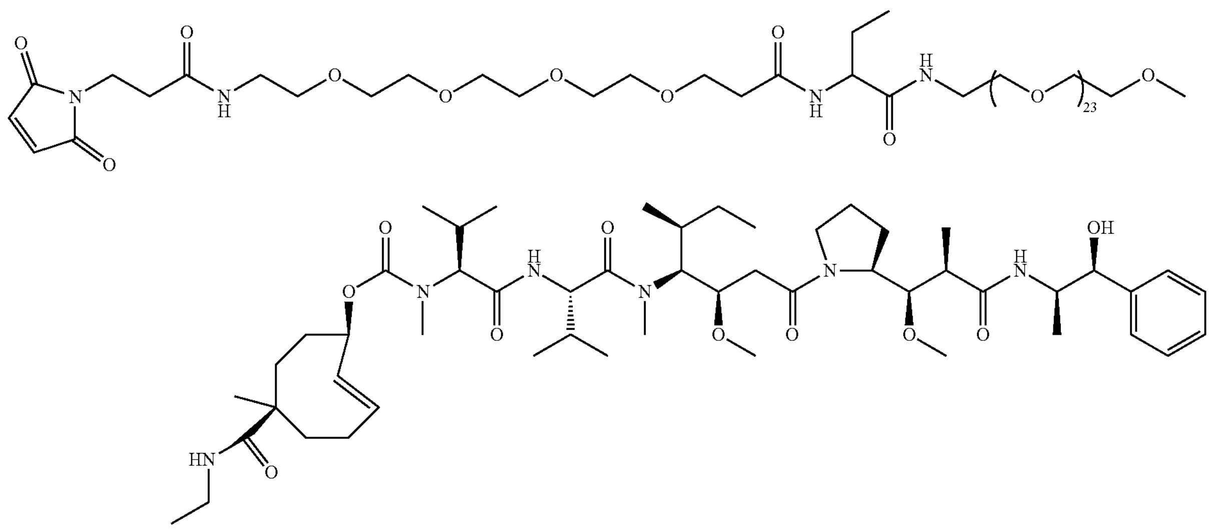

-continued
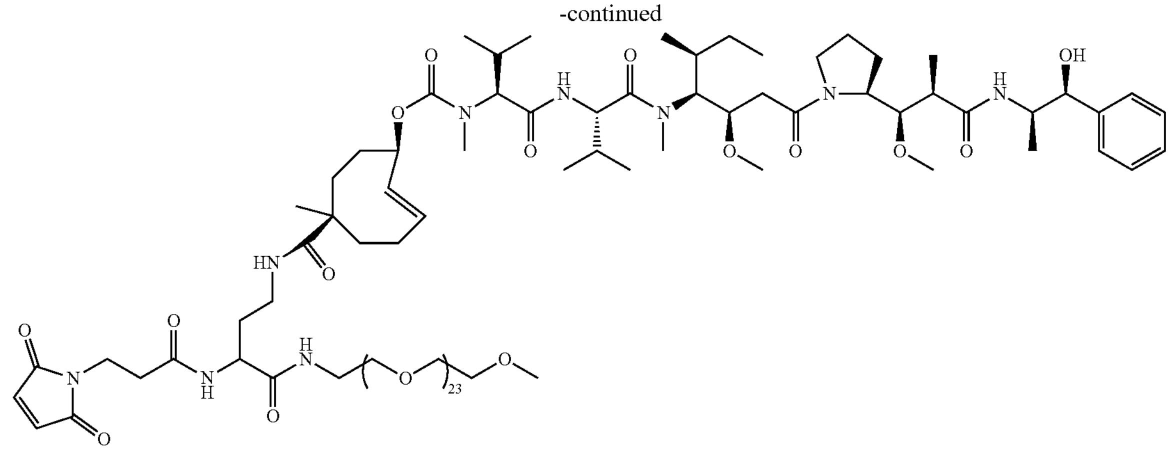
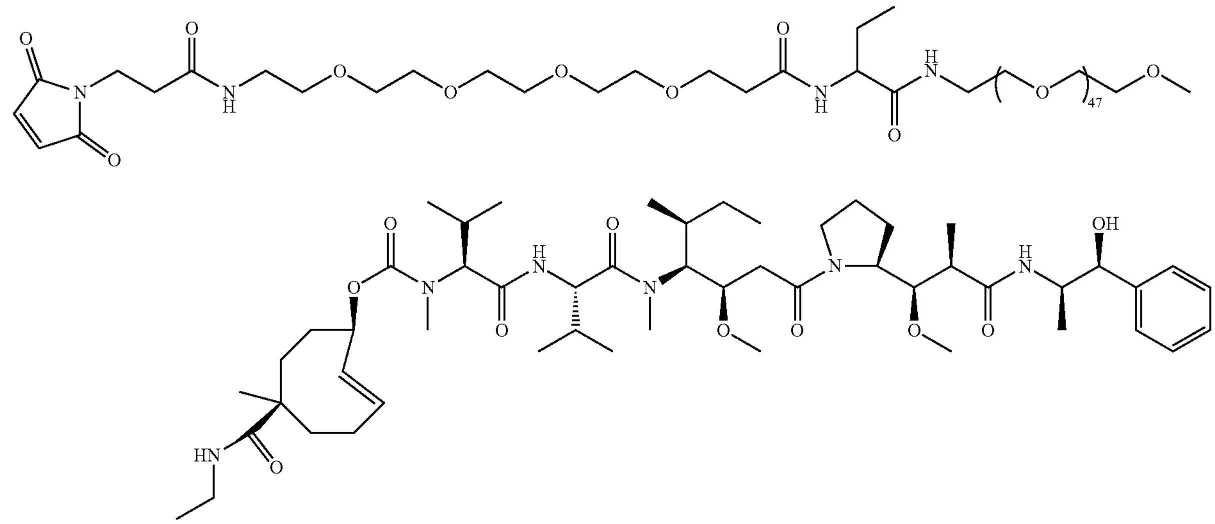
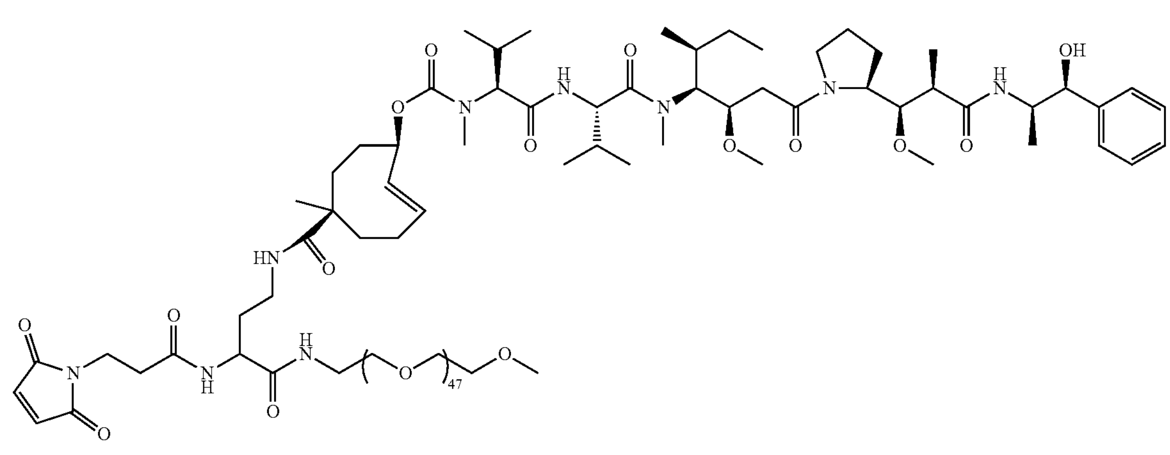

-continued
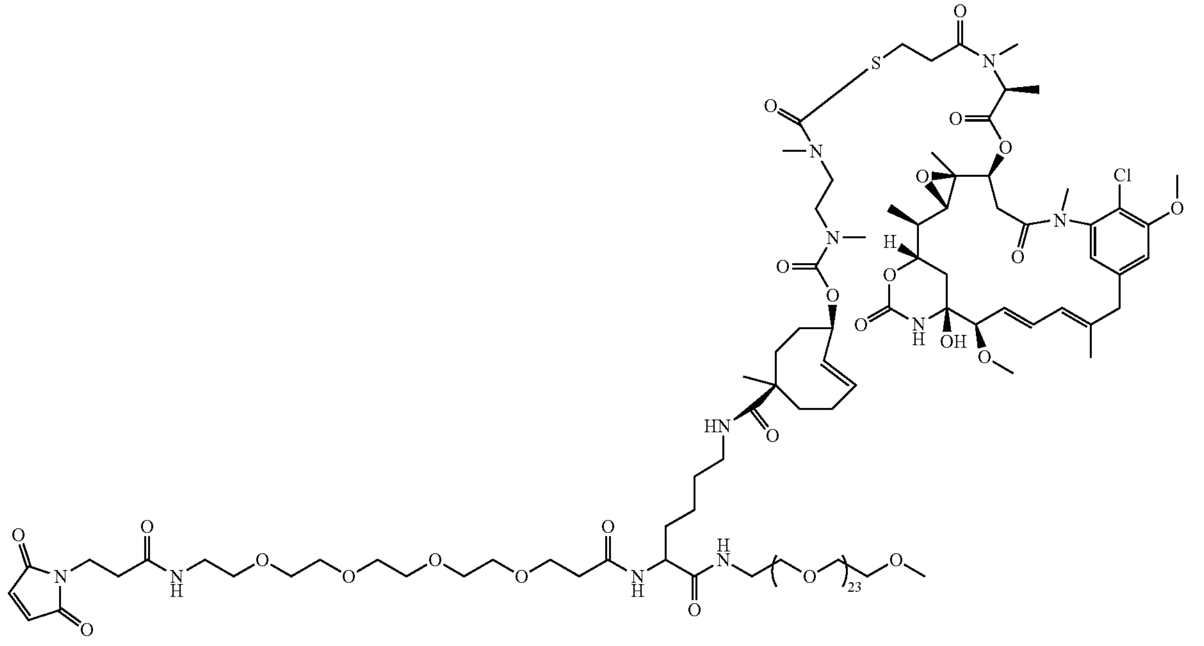
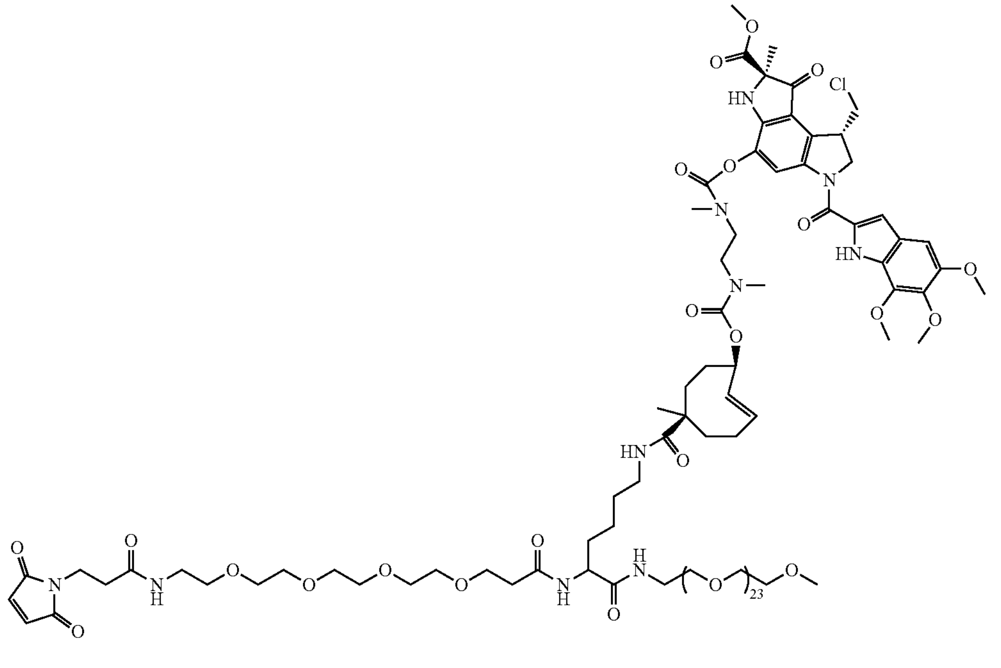

-continued
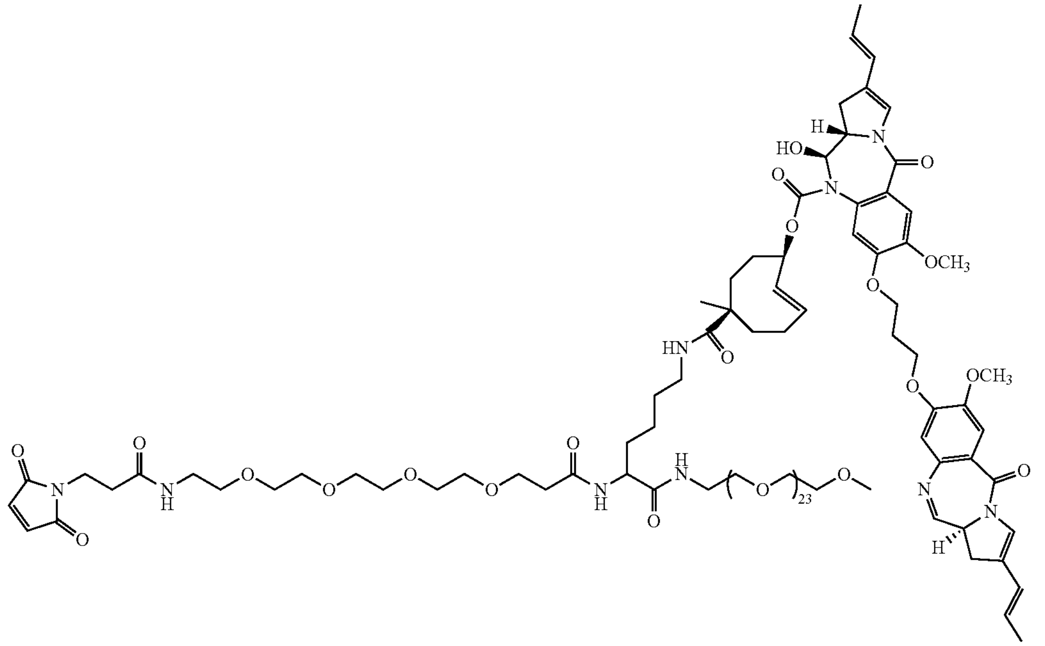
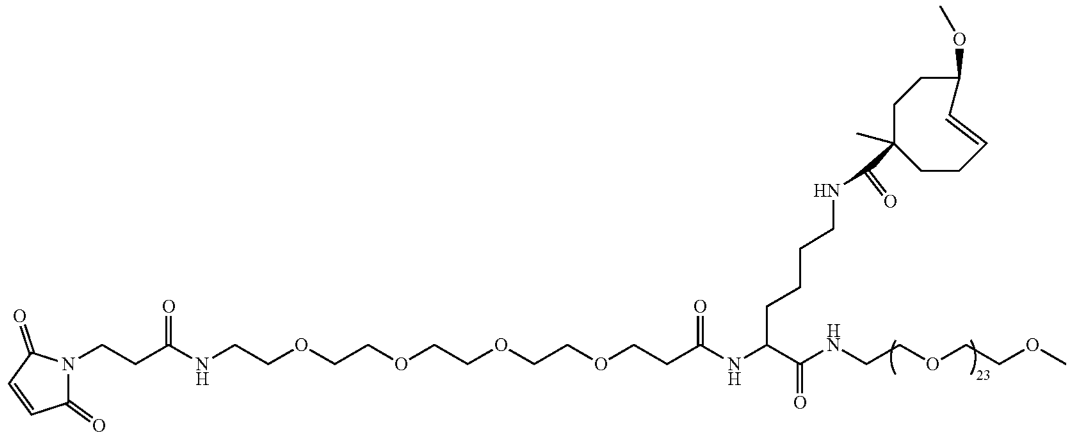

-continued

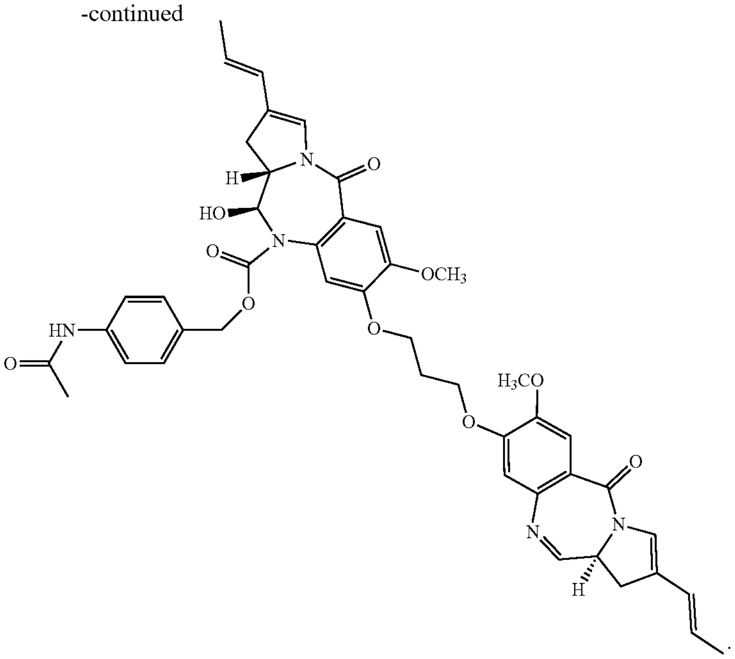

4. A compound selected from the group consisting of antibodies, proteins, peptoids, and peptides, modified with at least one compound according to claim 1, wherein the compound selected from the group consisting of antibodies, proteins, peptoids, and peptides comprises at least one moiety M selected from the group consisting of —OH, —NHR', —$CO_2$H, —SH, —S—S—, —$N_3$, terminal alkynyl, terminal alkenyl, —C(O)R', —C(O)R'—, $C_8$-$C_{12}$ (hetero)cycloalkynyl, nitrone, nitrile oxide, (imino)sydnone, isonitrile, (oxa)norbornene before modification with a compound according to claim 1, wherein R' is as defined in claim 1, wherein the compound selected from the group consisting of antibodies, proteins, peptoids and peptides satisfies Formula (2) after modification with at least one compound according to claim 1:

Formula (2)

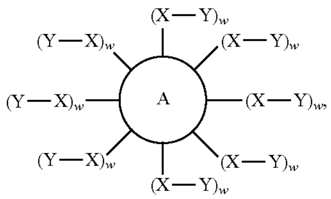

wherein moiety A is selected from the group consisting of antibodies, proteins, peptoids, and peptides, wherein each individual w is 0 or 1, wherein at least one wis 1, wherein each moiety Y is independently selected from moieties according to Formula (3), wherein at least one moiety Y satisfies said Formula (3):

Formula (3)

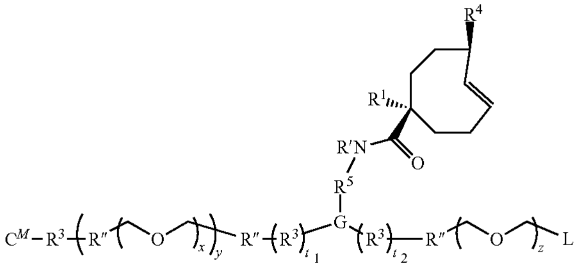

wherein n, $t_1$, $t_2$, x, y, z, G, L, $R^1$, $R^3$, $R^4$, $R^5$, R', and R" are as defined in claim 1 for Formula (1), wherein moiety X is part of moiety A and was a moiety M before modification of moiety A, wherein moiety $C^M$ is part of moiety Y and was a moiety $R^2$ as defined in claim 1 for Formula (1) before modification of moiety A, wherein when moiety X is —S—, then $C^M$ is selected from the group consisting of

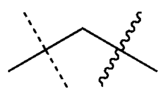 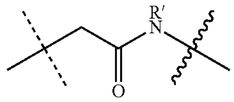

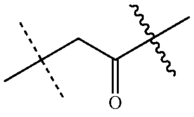 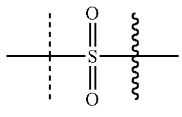

-continued

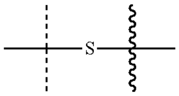
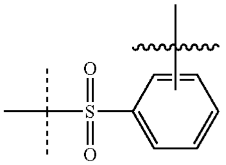
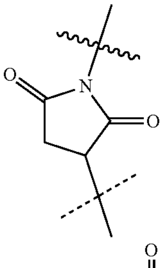
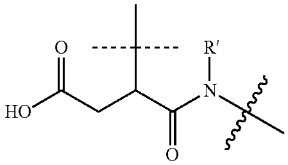
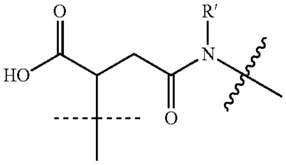
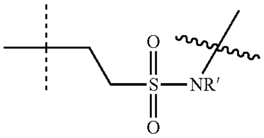
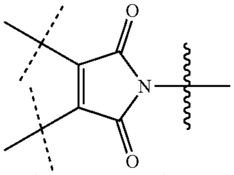
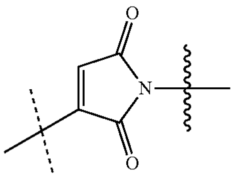
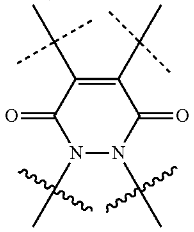
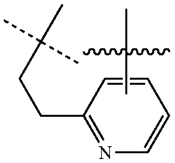
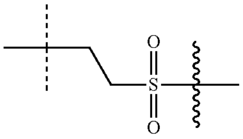
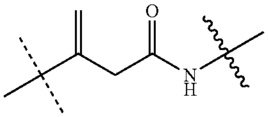
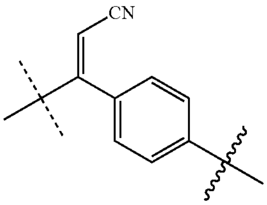
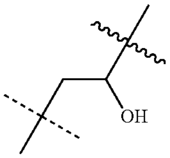
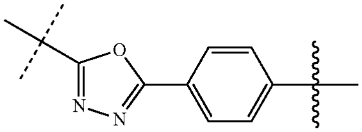

wherein the wiggly line denotes a bond to the remaining part of moiety Y, and wherein the dashed line denotes a bond to moiety X, wherein when moiety X is —NR'—, then $C^M$ is selected from the group consisting of

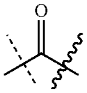
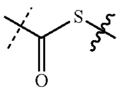
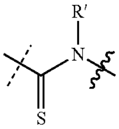
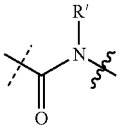
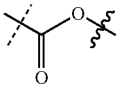
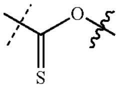

wherein the wiggly line denotes a bond to the remaining part of moiety Y, and wherein the dashed line denotes a bond to moiety X, wherein when moiety X is —C— derived from a moiety M that was —C(O)R' or —C(O)R'—, then $C^M$ is selected from the group consisting of

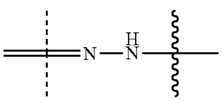
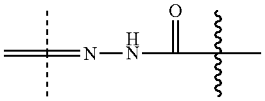
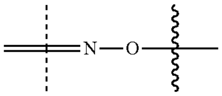
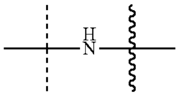

wherein the wiggly line denotes a bond to the remaining part of moiety Y, and wherein the dashed line denotes a bond to moiety X, wherein when moiety X is —C(O)— derived from a moiety M that was —C(O)OH, then CM is selected from the group consisting of

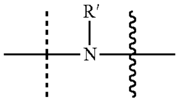

wherein the wiggly line denotes a bond to the remaining part of moiety Y, and wherein the dashed line denotes a bond to moiety X, wherein when moiety X is —O—, then $C^M$ is selected from the group consisting of

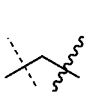
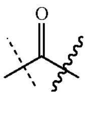
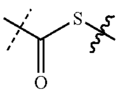
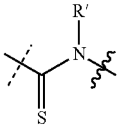
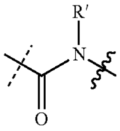
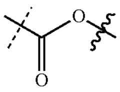
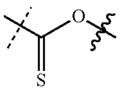

wherein the wiggly line denotes a bond to the remaining part of moiety Y, and wherein the dashed line denotes a bond to moiety X, wherein when moiety X is derived from a moiety M that was $—N_3$ and that was reacted with an $R^2$ that comprised an alkyne group, then X and $C^M$ together form a moiety $C^X$, wherein CX comprises a triazole ring.

5. The compound according to claim 4, wherein each $C^X$ is independently selected from the group consisting of

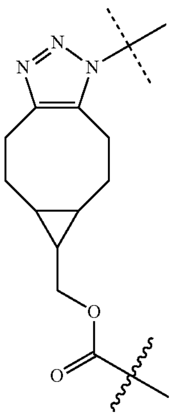

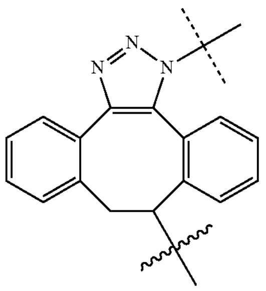

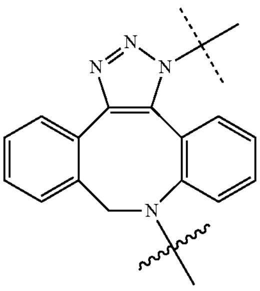

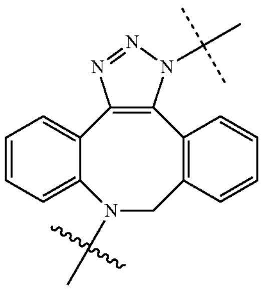

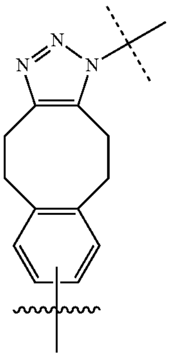

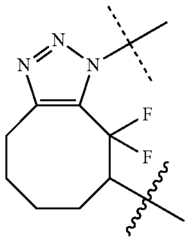

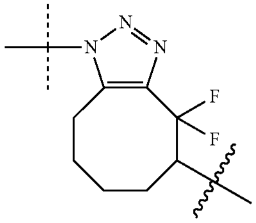

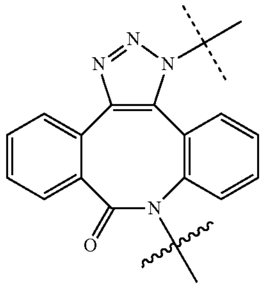

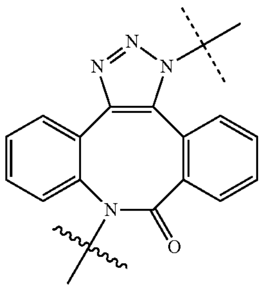

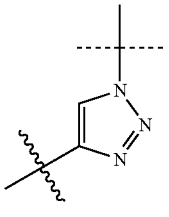

-continued

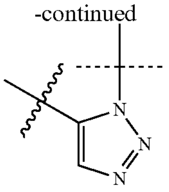

wherein the wiggly line denotes a bond to the remaining part of moiety Y, and wherein the dashed line denotes a bond to moiety X.

6. The compound according to claim 4, wherein moiety A is selected from the group consisting of antibodies, antibody fragments, diabodies, single chain variable fragment antibodies, and single domain antibodies.

7. The compound according to claim 1, wherein $C^A$ is selected from the group consisting of cytotoxins, antiproliferative agents, antitumor agents, antiviral agents, antibiotics, anti-inflammatory agents, chemosensitizing agents, radiosensitizing agents, immunosuppressants, immunostimulants, immunomodulators, and anti-angiogenic factors.

8. The compound according to claim 1, wherein $C^A$ is selected from the group consisting of colchinine, vinca alkaloids, anthracyclines, doxorubicin, epirubicin, idarubicin, daunorubicin, camptothecins, taxanes, taxols, vinblastine, vincristine, vindesine, calicheamycins, tubulysins, tubulysin M, cryptophycins, methotrexate, methopterin, aminopterin, dichloromethotrexate, irinotecans, enediynes, amanitins, deBouganin, dactinomycines, CC1065 and its analogs, duocarmycins, maytansines, maytansinoids, dolastatins, auristatins, pyrrolobenzodiazepines and dimers, indolinobenzodiazepines and dimers, pyridinobenzodiazepines and dimers, mitomycins, melphalan, leurosine, leurosideine, actinomycin, tallysomycin, lexitropsins, bleomycins, podophyllotoxins, etoposide, etoposide phosphate, staurosporin, esperamicin, SN-38, platinum-based drugs, and cytotoxic nucleosides.

9. The compound according to claim 1, wherein $C^A$ is an auristatin.

10. The compound according to claim 1, wherein $C^A$ is selected from the group consisting of dolastatin 10, monomethyl auristatin E, auristatin F, monomethyl auristatin F, auristatin F hydroxypropylamide, auristatin F phenylene diamine, monomethyl auristatin D, auristatin PE, auristatin EB, auristatin EFP, auristatin TP, and auristatin AQ.

11. The compound according to claim 1, wherein $C^A$ is monomethyl auristatin E.

12. The compound according to claim 1, wherein $L^C$ is selected from the group consisting of linkers according to Group I, Group II, and Group III, wherein linkers according to Group I are

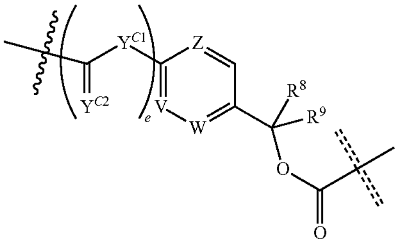

-continued

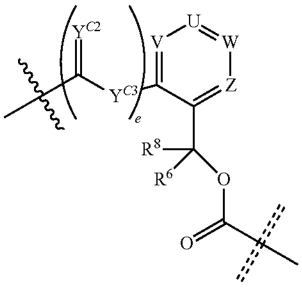

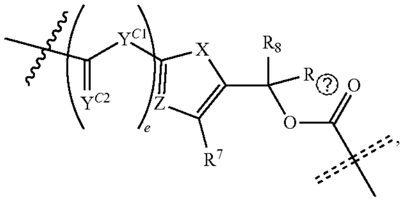

indicates bond to -O- on the allylic position of the trans-cyclooctene ring indicates bond to $C^A$ wherein U, V, W, Z are each selected from the group consisting of —$CR^7$—, and —N—, wherein e is either 0 or 1, wherein X is selected from the group consisting of —O—, —S— and —$NR^6$—, wherein each $R^8$ and $R^9$ are as defined for $R^6$ in claim 1, wherein for linkers according to Group I $C^A$ is linked to $L^C$ via a moiety selected from the group consisting of —O—, —N—, —C—, —S—, secondary amines and tertiary amines, wherein said moieties are part of $C^A$, wherein the linker according to Group II is

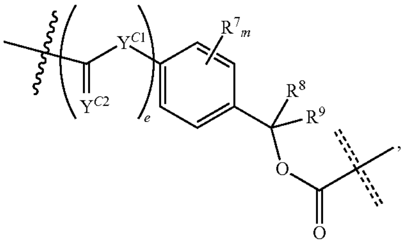

indicates bond to -O- on the allylic position of the trans-cyclooctene ring indicates bond to $C^A$ wherein m is an integer between 0 and 2, wherein e is either 0 or 1, wherein for linkers according to Group II $C^A$ is linked to $L^C$ via a moiety selected from the group consisting of —O—, —N—, —C—, —S—, secondary amines and tertiary amines, wherein said moieties are part of $C^A$, wherein linkers according to Group III are

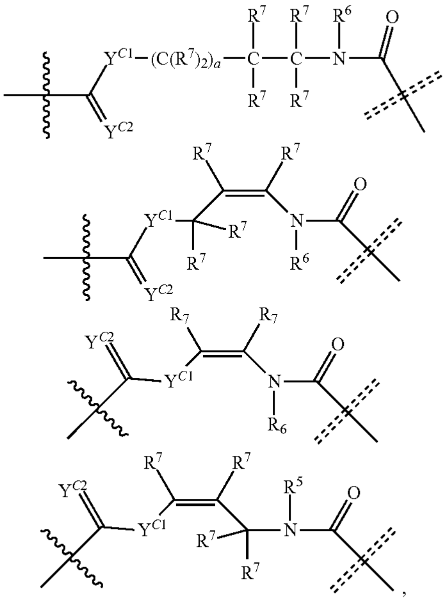

indicates bond to -O- on the allylic position of the trans-cyclooctene ring indicates bond to $C^A$ wherein for linkers according to Group III $C^A$ is linked to $L^C$ via a moiety selected from the group consisting of —O— and —S—, wherein —O— or —S— are optionally bound to a $C_{4-6}$ (hetero)aryl group, wherein said moieties are part of $C^A$, wherein $R^6$ is selected from the group consisting of hydrogen, $C_1$-$C_4$ alkyl groups, $C_2$-$C_4$ alkenyl groups, and $C_{4-6}$ (hetero)aryl groups, wherein each $R^7$ is independently selected from the group consisting of hydrogen and $C_1$-$C_3$ alkyl groups, $C_2$-$C_3$ alkenyl groups, and $C_{4-6}$ (hetero)aryl groups, wherein for $R^7$ the alkyl groups, alkenyl groups, and (hetero)aryl groups are optionally substituted with a moiety selected from the group consisting of —Cl, —F, —Br, —I, —OH, —$NH_2$, =O, =NH, —$N(CH_3)_2$, —$S(O)_2CH_3$, and —SH, and are optionally interrupted by at most one heteroatom selected from the group consisting of —O—, —S—, —NH—, —P—, and —Si—, wherein the N, S, and P atoms are optionally oxidized, wherein the N atoms are optionally quaternized, wherein $R^7$ is optionally selected from the group consisting of hydrogen, methyl, —$CH_2$—$CH_2$—$N(CH_3)_2$, and —$CH_2$—$CH_2$—$S(O)_2$—$CH_3$, wherein for all linkers according to Group I and Group II $Y^{C1}$ is selected from the group consisting of —O—, —S—, and —$NR^6$—, wherein for all linkers according to Group III, $Y^{C1}$ is —$NR^6$—, wherein for all linkers according to Group I, Group II, and Group III, $Y^{C2}$ is selected from the group consisting of O and S, wherein when q as defined in claim 1 is two, then the $L^C$ attached to the —O— at the allylic position of the trans-cyclooctene is selected from the group consisting of linkers according to Group I and Group II, and the $L^C$ between the $L^C$ attached to the —O— at the allylic position of the trans-cyclooctene and $C^A$ is selected from Group III, and that the wiggly line in the structures of Group III then denotes a bond to the $L^C$ attached to the —O— at the allylic position of the trans-cyclooctene instead of a bond to the allylic-O-on the trans-cyclooctene ring, and that the double dashed line in the structures of Groups I and II then denotes a bond to the $L^C$ between the LC attached to the —O— at the allylic position of the trans-cyclooctene and the $C^A$ instead of a bond to $C^A$.

13. The compound according to claim 1, wherein $L^C$ is selected from the group consisting of linkers according to Group IV, Group V, Group VI, and Group VII, wherein linkers according to Group IV are

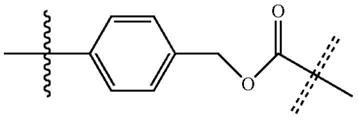

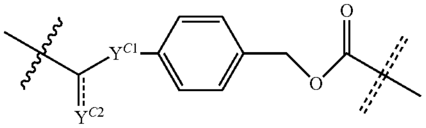

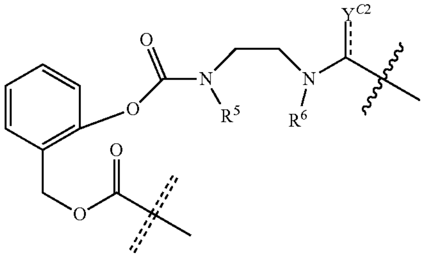

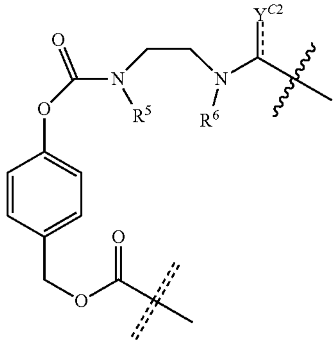

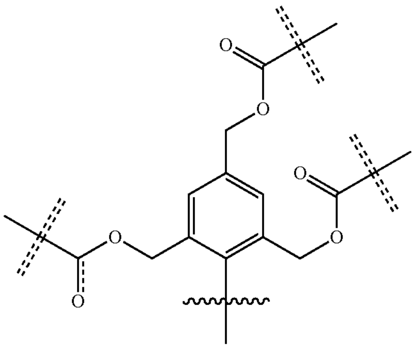

-continued

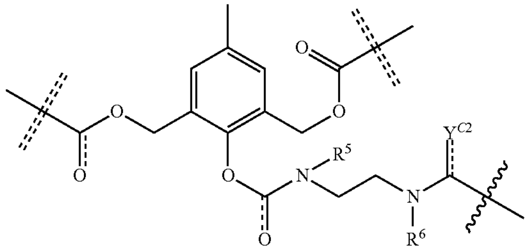

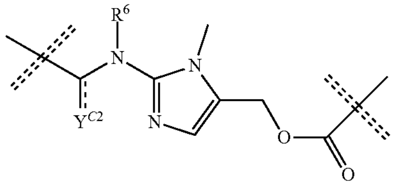

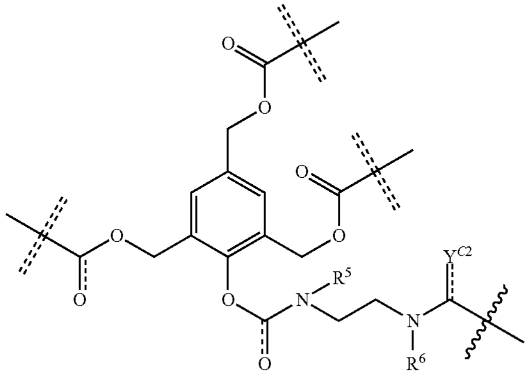

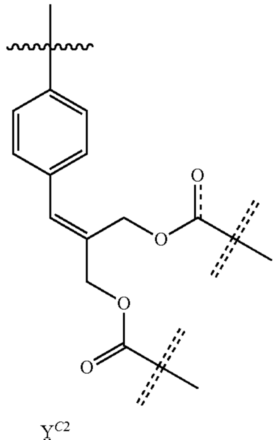

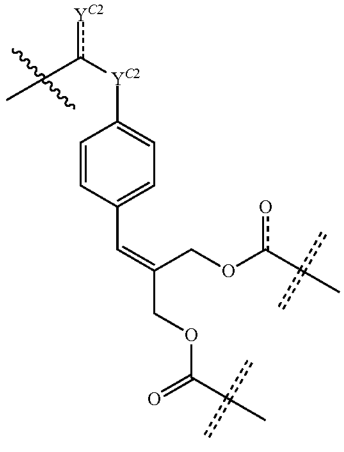

-continued

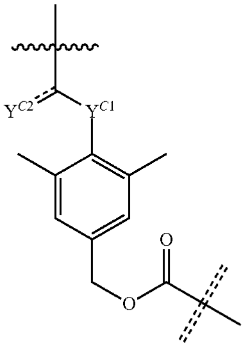

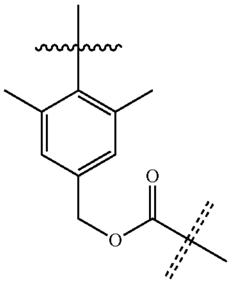

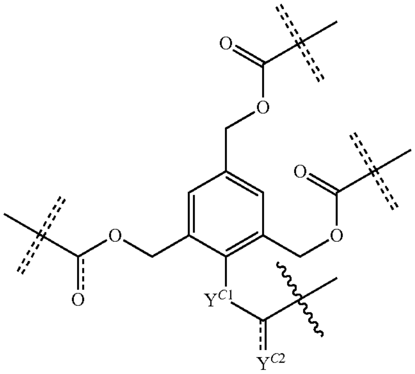

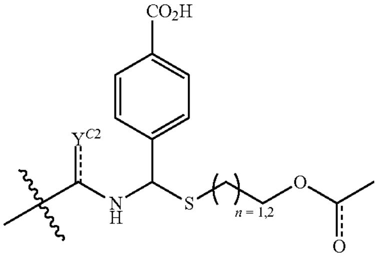

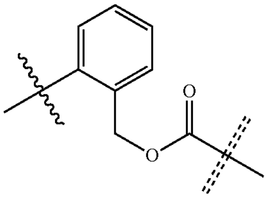

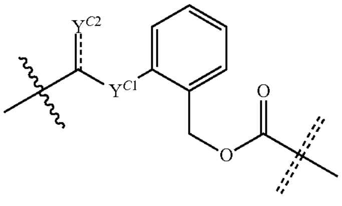

-continued

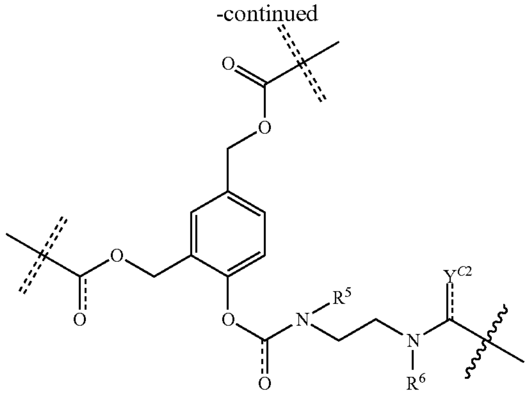

indicates bond to —O— group on allylic position of the transcyclooctene indicates bond to $C^A$ wherein for linkers according to Group IV $C^A$ is linked to $L^C$ via a moiety selected from the group consisting of —O—, —N—, and —S—, optionally from the group consisting of secondary amines and tertiary amines, wherein said moieties are part of $C^A$, wherein when multiple double dashed lines are shown within one $L^C$, each $C^A$ moiety is selected, wherein linkers according to Group V are

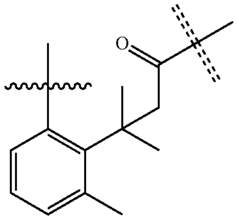

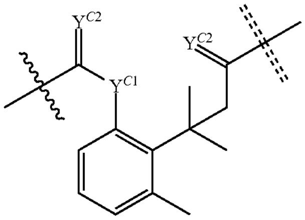

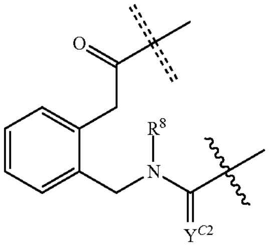

indicates bond to -O- on the allylic position of the transcyclooctene indicates bond to $C^A$ wherein for linkers according to Group V $C^A$ is linked to $L^C$ via a moiety selected from the group consisting of —O—, —N—, and —S—, wherein said moieties are part of $C^A$, wherein linkers according to Group VI are

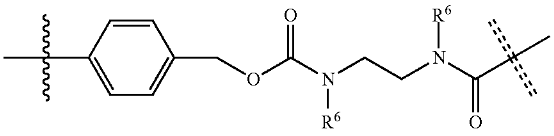

-continued

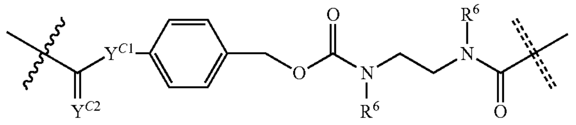

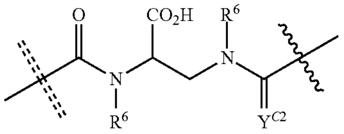

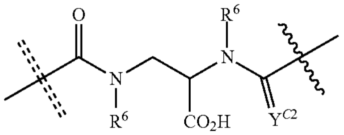

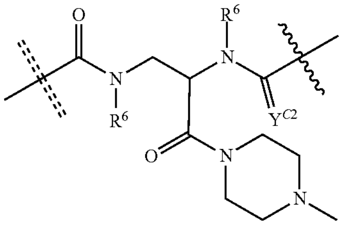

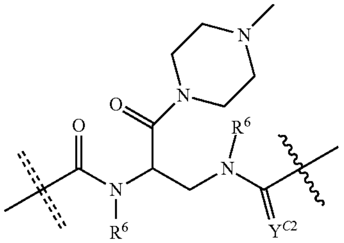

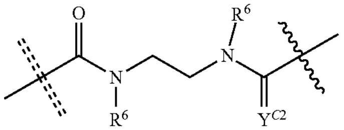

indicates bond to -O- on the allylic position of the transcyclooctene indicates bond to $C^A$ wherein for linkers according to Group VI $C^A$ is linked to $L^C$ via a moiety selected from the group consisting of —O— and —S—, —O— or —S— bound to a $C_{4-6}$ (hetero)aryl group, wherein said moieties are part of $C^A$, wherein linkers according to Group VII are

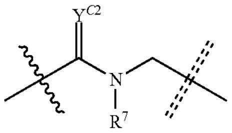

-continued

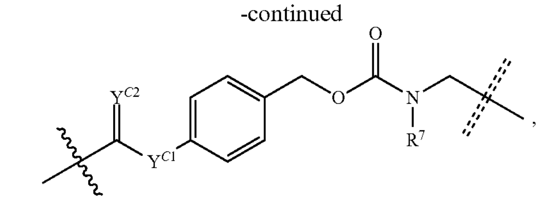

indicates bond to -O- on the allylic position of the transcyclooctene indicates bond to $C^A$ wherein for linkers according to Group VII $C^A$ is linked to $L^C$ via a moiety selected from the group consisting of —O—, —N—, and —S—, wherein said moieties are part of $C^A$, wherein for all linkers according to Group IV, Group V, Group VI, and Group VII, $Y^{C1}$ is selected from the group consisting of —O—, —S—, and —$NR_6$—, wherein for all linkers according to Group IV, Group V, Group VI, and Group VII, $Y^{C2}$ is selected from the group consisting of O and S, wherein each $R^6$ and each $R^7$ is independently selected, wherein each $R^7$ is independently selected from the group consisting of hydrogen and $C_1$-$C_3$ alkyl groups, $C_2$-$C_3$ alkenyl groups, and $C_{4-6}$ (hetero)aryl groups, wherein for $R^7$ the alkyl groups, alkenyl groups, and (hetero)aryl groups are optionally substituted with a moiety selected from the group consisting of —Cl, —F, —Br, —I, —OH, —$NH_2$, =O, =NH, —$N(CH_3)_2$, —$S(O)_2CH_3$, and —SH, and are optionally interrupted by at most one heteroatom selected from the group consisting of —O—, —S—, —NH—, —P—, and —Si—, wherein the N, S, and P atoms are optionally oxidized, wherein the N atoms are optionally quaternized, wherein $R^7$ is optionally selected from the group consisting of hydrogen, methyl, —$CH_2$—$CH_2$—$N(CH_3)_2$, and —$CH_2$—$CH_2$—$S(O)_2$—$CH_3$.

14. The compound according to claim 4, wherein moiety A is a diabody.

15. The compound according to claim 4, wherein moiety A is TAG72-binding diabody derived from the CC49 antibody.

16. The compound according to claim 1, wherein R" is

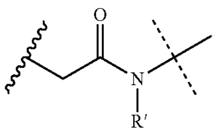

or

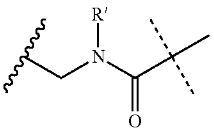

.

17. The compound according to claim 1, wherein $R^4$ is selected from the group consisting of —OC(O)—$C^A$, —OC(S)—$C^A$, —O-$(L^C(C^A)_s(C^A)_s)_q$—$C^A$, and —$C^A$.

18. A kit comprising a compound according to claim 1, said kit further comprising a diene.

* * * * *

SEQUENCE LISTING

```
<160> NUMBER OF SEQ ID NOS: 1

<210> SEQ ID NO 1
<211> LENGTH: 234
<212> TYPE: PRT
<213> ORGANISM: Artificial Sequence
<220> FEATURE:
<223> OTHER INFORMATION: TAG72-binding diabody derived from the CC49
      antibody

<400> SEQUENCE: 1

Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Cys
        115                 120                 125

Ser Ser Cys Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg
225                 230
```